US006395478B1

(12) United States Patent
Nandabalan et al.

(10) Patent No.: US 6,395,478 B1
(45) Date of Patent: *May 28, 2002

(54) IDENTIFICATION AND COMPARISON OF PROTEIN-PROTEIN INTERACTIONS THAT OCCUR IN POPULATIONS AND INDENTIFICATION OF INHIBITORS OF THESE INTERACTORS

(75) Inventors: Krishnan Nandabalan; Jonathan Marc Rothberg, both of Branford, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/231,303

(22) Filed: Jan. 12, 1999

Related U.S. Application Data

(63) Continuation of application No. 08/663,824, filed on Jun. 14, 1996, now Pat. No. 6,083,693.

(51) Int. Cl.$^7$ .......................... C12Q 1/68; C12P 21/02; C12N 1/15; C12N 15/63; G01N 33/566

(52) U.S. Cl. ......................... 435/6; 435/69.1; 435/69.7; 435/70.1; 435/71.1; 435/254.11; 436/501

(58) Field of Search .............................. 435/6, 5, 69.1, 435/252.3, 254.21, 320.1, 69.7, 70.1, 71.1, 254.11; 436/501, 94; 530/350

(56) References Cited

U.S. PATENT DOCUMENTS

| | | | |
|---|---|---|---|
| 4,593,002 A | | 6/1986 | Dulbecco .................. 435/172.3 |
| 5,198,346 A | | 3/1993 | Ladner et al. .............. 435/69.1 |
| 5,223,409 A | | 6/1993 | Ladner et al. .............. 435/69.7 |
| 5,270,170 A | | 12/1993 | Schatz et al. ............... 435/7.37 |
| 5,283,173 A | | 2/1994 | Fields et al. .................... 435/6 |
| 5,322,801 A | * | 6/1994 | Kingston et al. ........... 436/501 |
| 5,403,712 A | | 4/1995 | Crabtree et al. ................ 435/6 |
| 5,468,614 A | | 11/1995 | Fields et al. .................... 435/6 |
| 5,482,835 A | | 1/1996 | King et al. ...................... 435/6 |
| 5,512,473 A | | 4/1996 | Brent et al. ..................... 435/6 |
| 5,525,490 A | | 6/1996 | Erickson et al. .............. 435/29 |
| 5,580,721 A | | 12/1996 | Brent et al. ..................... 435/6 |
| 5,580,736 A | | 12/1996 | Brent et al. ..................... 435/6 |
| 5,965,368 A | * | 10/1999 | Vidal et al. ..................... 435/6 |
| 6,083,693 A | * | 7/2000 | Nandabalan et al. ........... 435/6 |

OTHER PUBLICATIONS

Bartel, et al. A protein linkage map of *Escherichia coli* bacteriophage T7. Nature Genetics, vol. 12, pp. 72–77, Jan. 1996.*
Chattoo et al. Selection of Lys–2 Mutant of the yeast Saccharomyces–Cerevisiae by Utilization of Alpha amino adipate. Genetics, vol. 93, No. 1, Abstract only, Feb. 1980.*
Fearson et al. Karyoplasmic interaction selection strategy: A general strategy to detect protein–protein interactions in mammalian cells. Proc. Natl. Acad. Sci. USA. vol., pp. 7958–7962, Sep. 1992.*
Bartel et al. A protein linkage map of *E coli* bacteriophage T7. Nature Genetics, vol. 12, pp. 72–77, Jan. 1996.*
Le Douarin et al. A new version of the two–hybrid assay for detection of protein–protein interactions. Nucleic Acids Research. vol. 23, No. 5, pp. 876–878, Mar. 1995.*
Mendelsohn et al. Applications of interaction traps/two–hybrid systems to biotechnology research. Current opinion in biotechnology vol. 5, pp. 482–486, Feb. 1980.*
Alam and Cook, 1990, Anal. Biochem. 188:245–254.
Allen et al., 1995, TIBS 20:511–516.
Alvarez et al., 1996, Nature Biotech. 14:335–335–338.
Bartel et al., 1993, Oxford University Press, NY, (Hartley, ed.), pp. 153–179.
Bartel et al., 1993, BioTechniques 14(6):920–924.
Bartel et al., 1996, Nature Genetics 12:72–77.
Bendixen et al., 1994, Nucl. Acids Res. 22(9):1778–1779.
Bonner et al., 1986, Nucl. Acids Res. 14(2):1009–1015.
Bustos and Schleif, 1993, Proc. Natl. Acad. Sci. USA 90:5638–5642.
Celenza and Carlson, 1986, Science 233:1175–1180.
Chaudhuri and Stephan, 1995, Biochem. Biophys. Res. Comm. 215(2):781–790.
Chaudhuri et al., 1995, FEBS Lett. 357:221–226.
U.S. application No. 08/874,825, Nandabalan et al., filed May 2, 2000.
U.S. application No. 08/663,824, Nandabalan et al., filed Jul. 4, 2000.

(List continued on next page.)

Primary Examiner—Stephanie W. Zitomer
Assistant Examiner—Cynthia B. Wilder
(74) Attorney, Agent, or Firm—Pennie & Edmonds LLP

(57) ABSTRACT

Methods are described for detecting protein-protein interactions, among two populations of proteins, each having a complexity of at least 1,000. For example, proteins are fused either to the DNA-binding domain of a transcriptional activator or to the activation domain of a transcriptional activator. Two yeast strains, of the opposite mating type and carrying one type each of the fusion proteins are mated together. Productive interactions between the two halves due to protein-protein interactions lead to the reconstitution of the transcriptional activator, which in turn leads to the activation of a reporter gene containing a binding site for the DNA-binding domain. This analysis can be carried out for two or more populations of proteins. The differences in the genes encoding the proteins involved in the protein-protein interactions are characterized, thus leading to the identification of specific protein-protein interactions, and the genes encoding the interacting proteins, relevant to a particular tissue, stage or disease. Furthermore, inhibitors that interfere with these protein-protein interactions are identified by their ability to inactivate a reporter gene. The screening for such inhibitors can be in a multiplexed format where a set of inhibitors will be screened against a library of interactors.

6 Claims, 33 Drawing Sheets

OTHER PUBLICATIONS

Chien et al., 1991, Proc. Natl. Acad. Sci. USA 88:9578–9582.
Chuang et al., 1994 Mol. Cell. Biol. 14(8):5318–5325.
Claffey et al., 1995, Biochim. et Biophys. Acta 1246:1–9.
Coney and Roeder, 1988, Mol. Cell. Biol. 8(10):4009–4017.
Colas et al., 1996, Nature 380:848–850.
Dingwall and Laskey, 1991, TIBS 16:479–481.
Dower, 1992, Current Biol. 2(5):251–253.
Durfee et al., 1993, Genes & Dev. 7:555–569.
Elledge and Davis, 1988, Gene 70:303–312.
Estojak et al., 1995, Mol. Cell. Biol. 15(10):5820–5829.
Fearon et al., 1992, Proc. Natl. Acad. Sci. USA 89:7958–7962.
Fields and Song, 1989, Nature 340:245–246.
Fields and Sternglanz, 1994, TIB 10(8):286–292.
Finley and Brent, 1994, Proc. Natl. Acad. Sci. USA 91:12980–12984.
Finley and Brent, in Gene Probes: A Practical Approach, Hames and Glover (eds.), Oxford University Press, Oxford, pp. 169–203.
Flam, 1994, Science 266:1324–1325.
FluoReporter® lacZ/Galactosidase Quantitation Kit (F–2905), 1995, Molecular Probes, Inc., pp. 1–4.
Franzén et al., 1993, Cell 75:681–692.
Fleig et al., 1986, Gene 46:237–245.
Galacto–Light™, Galacto–Light Plus™, 1995, Tropix, Inc., pp. 1–6.
Germino et al., 1993, Proc. Natl. Acad. Sci. USA 90:933–937.
Green et al., 1995, Chem. & Biol. 2:683–695.
Guarente, 1993, Proc. Natl. Acad. Sci. USA 90:1639–1641.
Gyuris et al., 1993, Cell 75:791–803.
Harper et al., 1993, Cell 75:805–816.
Heil, 1993, Gen. Engin. News 13(14):1–2.
Herskowitz and Jensen, 1991, Meth. Enzymol. 194:132–146.
Hong et al., 1994, Yeast 10:1083–1092.
Hu et al., 1990, Science 250:1400–1403.
Hu, 1995, Structure 3:431–433.
Hutchinson, 1994, Bio/Technology 12:375–380.
HybriZAP™ Two–Hybrid cDNA Gigapack® Cloning Kit, Instruction Manual, 1995, Stratagene, pp. 1–73.
Ito et al., 1983, J. Bacteriol. 153(1):163–168.
Jain and Magrath, 1991, Anal. Biochem. 199:119–124.
Jellinek et al., 1994, Biochemistry 33:10450–10456.
Johnston, 1987, Microbiol. Rev. 51(4):458–476.
Kato, 1996, Nucl. Acids Res. 24(2):394–395.
Keegan et al., 1986, Science 231:699–703.
Kishore and Shah, 1988, Ann. Rev. Biochem. 57:627–663.
Leung et al., 1989, Science 246:1306–1309.
Li and Herskowitz, 1993, Science 262:1870–1874.
Milosavljevic et al., 1996, Genome Res. 6:132–141.
Miura et al., 1986, Jpn. J. Cancer Res. (Gann) 77:45–51.
Murray et al., 1993, Gene 134:123–128.
Nallur et al., 1993, Nucl. Acids. Res. 21(16)3867–3873.
Nature Biotechnology, 1996, 14:247.
Pötgens et al., 1994, J. Biol. Chem. 269(52):32879–32885.
Prashar and Weissman, 1996, Proc. Natl. Acad. Sci. USA 93:659–663.
Rose and Botstein, 1983, Meth. Enzymol. 101:167–180.
Rothstein, 1991, Meth. Enzymol. 194:281–301.
Schneider and Guarente, 1991, Meth. Enzymol. 194:373–388.
Schmidt–Dörr et al., 1991, Biochem. 30:9657–9664.
Sherman et al., 1986, Laboratory course manual for Methods in Yeast Genetics, Cold Spring Harbor Laboratory, Table of Contents.
Sikorski and Boeke, 1991, Meth. Enzymol. 194:302–318.
Stratford, 1994, Yeast 10:1741–1752.
Struhl et al., 1979, Proc. Natl. Acad. Sci. USA 76:1035–1039.
Terman et al., 1992, Biochem Biophys. Res. Comm. 187(3):1579–1586.
Wang et al., 1994, Science 265:674–676.
Wang et al., 1996, Science 271:1120–1122.
Vasavada et al., 1991, Proc. Natl. Acad. Sci. USA 88:10686–10690.
Velculescu et al., 1995, Science 270:484–487.
Yang et al., 1995, Nucl. Acids. Res. 23(7):1152–1156.
Yocum et al., 1984, Mol. Cell. Biol. 4(10):1985–1998.
Mendelsohn et al., 1994, Curr. Opin. Biotech. 5:482–486.

* cited by examiner

CONSTRUCT DNA-BINDING & ACTIVATION DOMAIN FUSION LIBRARIES FROM
DIFFERENT POPULATIONS (TISSUE/DEVELOPMENT STAGE/DISEASE STAGE)

PERFORM YEAST MATING SCREENS TO IDENTIFY INTERACTING PAIRS OF
PROTEINS IN EACH POPULATION - ARRIVE AT "INTERACTIVE POPULATIONS"

CHARACTERIZE INTERACTIVE POPULATIONS BY A COMBINATION OF POOLING
STRATEGIES, QEA & SEQ-QEA

ARRIVE AT PAIRS OF INTERACTIVE PROTEINS UNIQUE TO A POPULATION

SCREEN FOR INHIBITORS OF THESE UNIQUE INTERACTORS USING
A YEAST-BASED SELECTION OF INHIBITION OF INTERACTIONS

ARRIVE AT LEAD DRUG COMPOUNDS THAT ARE SPECIFICALLY TARGETED
AGAINST PAIRS OF INTERACTING PROTEINS UNIQUE TO A
PARTICULAR POPULATION

FIG.1

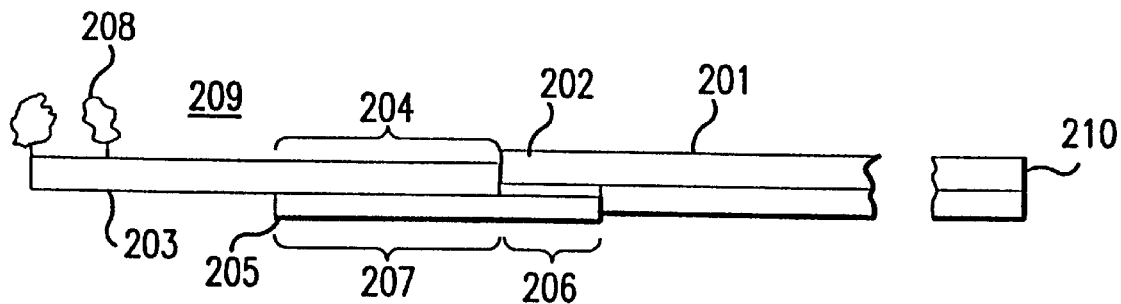
FIG.10A
5'-AGC ACT CTC CAG CCT CTC ACC GAA-3' (SEQ ID NO:1)
250     3'- AG TGG CTT CTAG-5' (SEQ ID NO:7)
5'-ACC GAC GTC GAC TAT CCA TGA AGC-3' (SEQ ID NO:42)
251     3'-GT ACT TCG TCGA-5' (SEQ ID NO:44)
FIG.10B
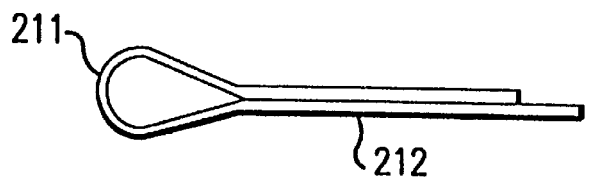
FIG.10C

5'-AGCACTCTCCAGCCTCTCACCGAGCATG (SEQ ID NO.55)
3'-AGTGGCTC

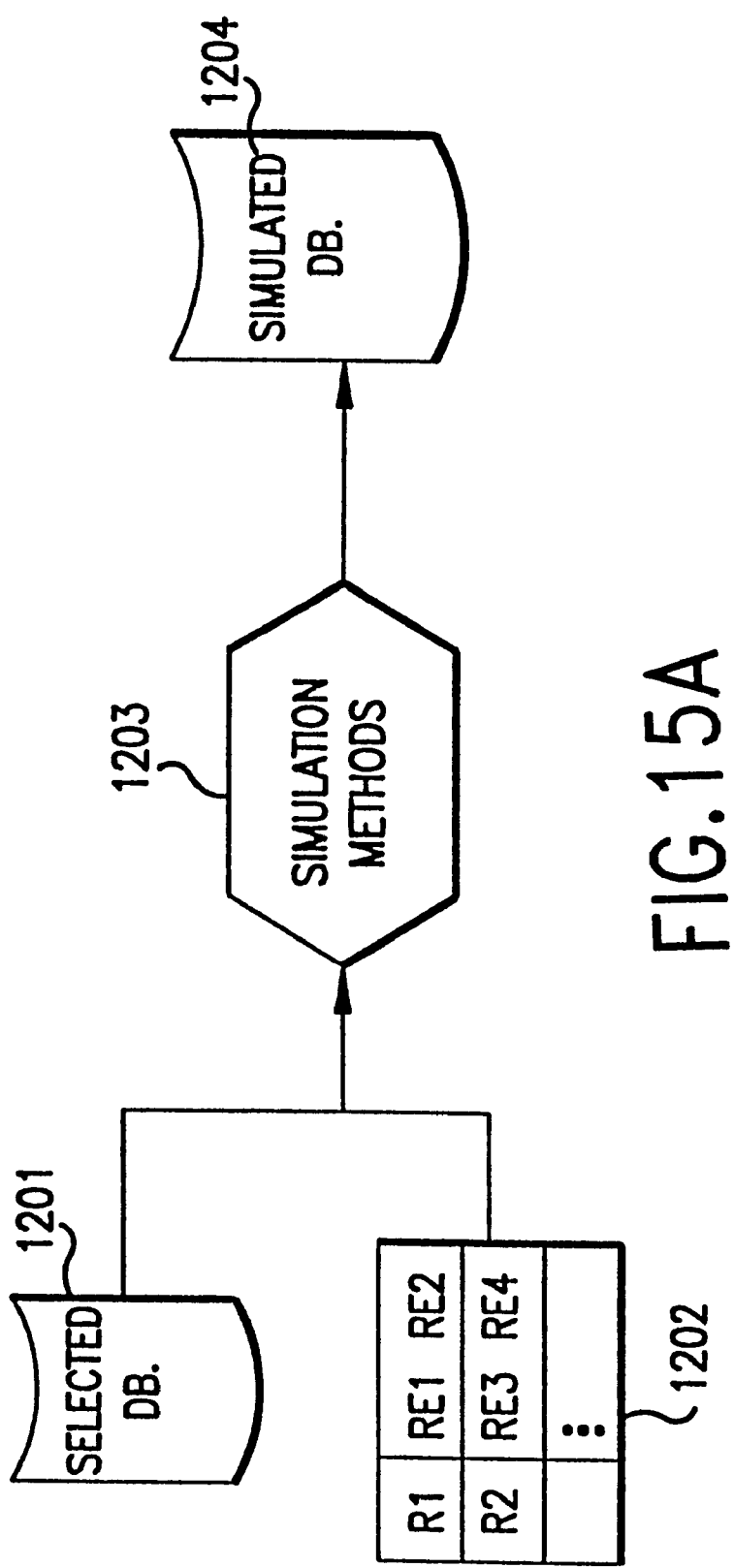

| L | (RE1, RE1)$_{R1}$ | (RE1, RE2)$_{R1}$ | (RE2, RE2)$_{R2}$ | (RE3, RE3)$_{R2}$ | (RE3, RE4)$_{R2}$ | ... |
|---|---|---|---|---|---|---|
| ... | | | | | | |
| 52 | A01 | | | | | |
| ... | | | | | | |
| 151 | T163 | | | | | |
| ... | | | | | | |
| 175 | | A01,T163 | | | | |
| ... | | | | | | |
| 222 | | T163,Q012 | | | | |
| ... | | | | | | |
| 402 | | | | A01,S003 | | |
| ... | | | | | | |
| 532 | | | | | Q012,S003 | |
| ... | | | | | | |

FIG. 15B $$1401 \diagdown V1 = ([10,14]_{RE1}, [62,66]_{RE1}, [610,614]_{RE1})$$
$$1402 \diagdown V2 = ([237,241]_{RE2}, [388,392]_{RE2})$$

1403 points to [10,14]

VECTORS OF CUTS

MERGED AND SORTED VECTORS OF CUTS

FRAGMENTS

FRAGMENTS SEQUENCES

FIG.17D 1411
([RE1,RE1,N,52] , [RE2,RE2,y,151] ,
 [RE1,RE2,N,175] , [RE1,RE2,N,222])
                    1412

SORTED FRAGMENT VECTOR

FIG.17E

| ℓ ↓ | [RE1,RE1] | [RE1,RE2] | [RE2,RE2] | |
|---|---|---|---|---|
| ⋮ | | | | |
| 52 | +A01 | | 1412 | |
| ⋮ | | | | |
| 151 | | | +A01 | |
| ⋮ | | | | |
| 175 | | +A01 | | |
| ⋮ | | | | |
| 222 | | +A01 | | |

DIGEST TABLE

FIG.17F

ISOLATION OF INTERACTING PROTEINS FROM AN M X N ANALYSIS

- ISOLATATE URA+,HIS+,lacZ+, CELLS: POSITIVE FOR PROTEIN-PROTEIN INTERACTION e.g., VEGF-VEGF, R4-FKBP-12, RAS-RAF etc., SELECTING INHIBITION OF NOVEL PROTEIN-PROTEIN INTERACTIONS BY CANDIDATE
INHIBITORS USING THE 5-FOA ASSAY

- POOL ALL INTERACTANTS FROM AN M X N ANALYSIS e.g., R4-FKBP12 IN A POOL OF INTERACTANTS

- SCREEN AGAINST INHIBITORS USING THE 5-FOA ASSAY e.g., FK506 AGAINST R4-FKBP12 IN A POOL OF INTERACTANTS

- SELECTION OF THOSE PROTEIN-PROTEIN INTERACTION EVENTS
  WHERE INHIBITION OCCURRED e.g., SELECTION OF R4-FKBP12 AS 5-FOA RESISTANT CELLS AMONG A POOL
    OF INTERACTANTS WHEN EXPOSED TO FK506

ISOLATION AND PROTEIN-PROTEIN INTERACTIONS AND INHIBITORS OF THESE
INTERACTIONS

- CHARACTERIZATION OF THE GENES ENCODING THE INTERACTING PROTEINS
  BY SEQUENCE ANALYSIS

- CONFIRMATION OF INHIBITION BY ENZYMATIC ASSAYS e.g., $\beta$-GALACTOSIDASE ASSAYS

FIG.25

IDENTIFICATION AND COMPARISON OF PROTEIN-PROTEIN INTERACTIONS THAT OCCUR IN POPULATIONS AND INDENTIFICATION OF INHIBITORS OF THESE INTERACTORS

This application is a continuation of application Ser. No. 08/663,824, filed Jun. 14, 1996 now U.S. Pat. No. 6,083,693, which is incorporated by reference herein in its entirety.

This invention was made with United States Government support under award number 70NANB5H1066 awarded by the National Institute of Standards and Technology. The United States Government has certain rights in the invention.

1. INTRODUCTION

The present method relates to the identification of protein-protein interactions and inhibitors of these interactions that, preferably, are specific to a cell type, tissue type, stage of development, or disease state or stage.

2. BACKGROUND OF THE INVENTION

Proteins and protein-protein interactions play a central role in the various essential biochemical processes. For example, these interactions are evident in the interaction of hormones with their respective receptors, in the intracellular and extracellular signalling events mediated by proteins, in enzyme substrate interactions, in intracellular protein trafficking, in the formation of complex structures like ribosomes, viral coat proteins, and filaments, and in antigen-antibody interactions. These interactions are usually facilitated by the interaction of small regions within the proteins that can fold independently of the rest of the protein. These independent units are called protein domains. Abnormal or disease states can be the direct result of aberrant protein-protein interactions. For example, oncoproteins can cause cancer by interacting with and activating proteins responsible for cell division. Protein-protein interactions are also central to the mechanism of a virus recognizing its receptor on the cell surface as a prelude to infection. Identification of domains that interact with each other not only leads to a broader understanding of protein-protein interactions, but also aids in the design of inhibitors of these interactions.

Protein-protein interactions have been studied by both biochemical and genetic methods. The biochemical methods are laborious and slow, often involving painstaking isolation, purification, sequencing and further biochemical characterization of the proteins being tested for interaction. As an alternative to the biochemical approaches, genetic approaches to detect protein-protein interactions have gained in popularity as these methods allow the rapid detection of the domains involved in protein-protein interactions.

An example of a genetic system to detect protein-protein interactions is the "Two-Hybrid" system to detect protein-protein interactions in the yeast Saccharomyces cerevisiae (Fields and Song, 1989, Nature 340:245–246; U.S. Pat. No. 5,283,173 by Fields and Song). This assay utilizes the reconstitution of a transcriptional activator like GAL4 (Johnston, 1987, Microbiol. Rev. 51:458–476) through the interaction of two protein domains that have been fused to the two functional units of the transcriptional activator: the DNA-binding domain and the activation domain. This is possible due to the bipartite nature of certain transcription factors like GAL4. Being characterized as bipartite signifies that the DNA-binding and activation functions reside in separate domains and can function in trans (Keegan et al., 1986, Science 231:699–704). The reconstitution of the transcriptional activator is monitored by the activation of a reporter gene like the lacZ gene that is under the influence of a promoter that contains a binding site (Upstream Activating Sequence or UAS) for the DNA-binding domain of the transcriptional activator. This method is most commonly used either to detect an interaction between two known proteins (Fields and Song, 1989, Nature 340:245–246) or to identify interacting proteins from a population that would bind to a known protein (Durfee et al., 1993, Genes Dev. 7:555–569; Gyuris et al., 1993, Cell 75:791–803; Harper et al., 1993, Cell 75:805–816; Vojtek et al., 1993, Cell 74:205–214).

Another system that is similar to the Two-Hybrid system is the "Interaction-Trap system" devised by Brent and colleagues (Gyuris et al., 1993, Cell 75:791–803). This system is similar to the Two-Hybrid system except that it uses a LEU2 reporter gene and a lacz reporter gene. Thus protein-protein interactions leading to the reconstitution of the transcriptional activator also allow cells to grow in media lacking leucine and enable them to express β-galactosidase. The DNA-binding domain used in this system is the LexA DNA-binding domain, while the activator sequence is obtained from the B42 transcriptional activation domain (Ma and Ptashne, 1987, Cell 51:113–119). The promoters of the reporter genes contain LexA binding sequences and hence will be activated by the reconstitution of the transcriptional activator. Another feature of this system is that the gene encoding the DNA-binding domain fusion protein is under the influence of an inducible GAL promoter so that confirmatory tests can be performed under inducing and non-inducing conditions.

In yet another version of this system developed by Elledge and colleagues, the reporter genes HIS3 and lacz (Durfee et al., 1993, Genes Dev. 7:555–569) are used. The transcriptional activator that is reconstituted in this case is GAL4 and protein-protein interactions allow cells to grow in media lacking histidine and containing 3-aminotriazole (3-AT) and to express β-galactosidase. 3-AT inhibits the growth of his3 auxotrophs in media lacking histidine (Kishore and Shah, 1988, Annu. Rev. Biochem. 57:627–663).

In a different two-hybrid assay, a URA3 reporter gene under the control of Estrogen Response Elements (ERE) has been used to monitor protein-protein interactions. Here, the DNA-binding domain is derived from the human estrogen receptor. The authors of the ERE assay propose that inhibition of the protein-protein interactions can be identified by negative selection on 5-FOA medium (Le Douarin et al., 1995, Nucleic Acids Res. 23:876–878), but do not provide any details.

A version of the two-hybrid approach called the "Contingent Replication Assay" that is applicable in mammalian cells has also been reported (Nallur et al., 1993, Nucleic Acids Res. 21:3867–3873; Vasavada et al., 1991, Proc. Natl. Acad. Sci. USA 88:10686–10690). In this case, the reconstitution of the transcription factor in mammalian cells due to the interaction of the two fusion proteins leads to the activation of the SV40 T antigen. This antigen allows the replication of the activation domain fusion plasmids. Another modification of the two-hybrid approach using mammalian cells is the "Karyoplasmic Interaction Selection Strategy" that also uses the reconstitution of a transcriptional activator (Fearon et al., 1992, Proc. Natl. Acad. Sci. USA 89:7958–7962). Reporter genes used in this case have included the gene encoding the bacterial chloramphenicol acetyl transferase, the gene for cell-surface antigen CD4, and the gene encoding resistance to Hygromycin B. In both of the mammalian systems, the transcription factor that is reconstituted is a hybrid transcriptional activator in which the DNA-binding domain is from GAL4 and the activation domain is from VP16.

In all of the assays described above, the identity of one (or both) of the proteins being tested for interaction is known. All of the assays mentioned above can be used to identify novel proteins that interact with a known protein of interest. In a variation of the "Interaction Trap" system, a "mating-grid" strategy has been used to characterize interactions between proteins that are thought to be involved in the Drosophila cell cycle (Finley and Brent, 1994, Proc. Natl. Acad. Sci. USA 91:12980–12984). This strategy is based on a technique first established by Rothstein and colleagues (Bendixen et al., 1994, Nucleic Acids Res. 22:1778–1779) who used a yeast-mating assay to detect protein-protein interactions. Here, the DNA-binding and activation domain fusion proteins were expressed in two different haploid yeast strains, a and α, and the two were brought together by mating. Thus, interactions between proteins can be studied in this method. However, even in this method, the identities of at least one of the proteins in the interacting pairs of proteins was known prior to analyzing the interactions between pairs of proteins.

Stanley Fields and coworkers have recently performed an analysis of all possible protein-protein interactions that can take place in the *E. coli* bacteriophage T7 (Bartel et al., 1996, Nature Genet. 12:72–77). Randomly sheared fragments of T7 DNA were used to make libraries in both the DNA-binding domain and the activation domain plasmids and a genome-wide two-hybrid assay was performed by use of a mating strategy. The DNA-binding and the activation domain fusions were transformed into separate yeast strains of opposite mating type. The DNA-binding domain hybrids containing yeast transformants were then divided into groups of 10. The groups were screened (by the mating strategy outlined above) against a library of activation domain hybrids numbering around 105 transformants. By this method, 25 interactions were characterized among the proteins of T7. While this study provides a method to screen more than one DNA-binding domain hybrid against more than one activation domain hybrid, it does not address the issues involved in screening complex libraries against each other. This is an important limitation due to the value of enabling the detection and isolation of interactants from cDNA libraries prepared from complex organisms like human beings. Indeed, the prior art has taught away from using complex populations of proteins as hybrids to the DNA-binding domain, since random hybrids to the DNA binding domain produce a large percentage of false positives (hybrids that have transcriptional activity in the absence of an interacting protein) (Bartel et al., 1993, "Using the two hybrid system to detect protein-protein interactions," in *Cellular Transduction in Development*, Ch. 7, Hartley, D. A. (ed.), Practical Approach Series xviii, IRL Press at Oxford University Press, New York, N.Y., pp. 154–179 at 171; Ma and Ptashne, 1987, Cell 51:113).

None of the prior art systems provides a method that not only isolates and catalogues all possible protein-protein interactions within a population, be it a tissue/cell-type, disease state, or stage of development, but also allows the comparison of such interactions between two such populations thereby allowing the identification of protein-protein interactions unique to any particular tissue/cell-type, disease state, or stage of development. In contrast, such a method is provided by the present invention.

Accordingly, it is one of the objectives of this invention to devise a genetic method to identify and isolate preferably all possible protein-protein interactions within a population of proteins, or between two different populations of proteins, be it a tissue/cell-type, disease state or stage of development.

It is another objective of the present invention to perform a comparative analysis of the protein-protein interactions that occur two or more different tissue/cell-types, disease states, or stages of development.

It is also an objective of this invention to identify and isolate in a rapid manner the genes encoding the proteins involved in interactions that are specific to a tissue/cell-type, disease state, or stage of development.

It is yet another objective of this invention to. provide a method for the concurrent identification of inhibitors of the protein-protein interactions that characterize a given population, be it a tissue/cell type, disease state, or stage of development. These inhibitors may have therapeutic value.

Citation of a reference herein shall not be construed as an admission that such is prior art to the present invention.

3. SUMMARY OF THE INVENTION

The present invention provides methods and means to detect and isolate the genes encoding the proteins that interact with each other between two populations of proteins, using the reconstitution of a selectable event. This selectable event is the formation of a transcription factor. In contrast to the prior art, in which problems with false positives and low throughput limited the complexity of the populations that could be analyzed, each of the two populations of proteins has a complexity of greater than 10, and preferably has a complexity of at least 1,000. The reconstitution of a transcription factor occurs by interaction of fusion proteins expressed by chimeric genes. In a preferred embodiment, the types of fusion proteins used are DNA-binding domain hybrids and activation domain hybrids of transcriptional activators. Libraries of genes encoding hybrid proteins are preferably constructed in both a DNA-binding domain hybrid plasmid vector and in an activation domain hybrid plasmid vector. In a preferred embodiment, two types of haploid yeast strains, a and a respectively, are each transformed with a different one of the two libraries to create two yeast libraries. The two yeast libraries are then mated together to create a diploid yeast strain that contains both the kinds of fusion genes encoding the hybrid proteins. If the two hybrid proteins can interact (bind) with each other, the transcriptional activator is reconstituted due to the proximity of the DNA-binding and the activation domains of the transcriptional activator. This reconstitution causes transcription of reporter genes that, by way of example, enable the yeast to grow in selective media. In a preferred aspect, the activity of a reporter gene is monitored enzymatically. The isolation of the plasmids that encode these fusion genes leads to the identification of the genes that encode proteins that interact with each other.

Thus, in a specific embodiment, the invention is directed to a method of detecting one or more protein-protein interactions comprising (a) recombinantly expressing within a population of host cells (i) a first population of first fusion proteins, each said first fusion protein comprising a first protein sequence and a DNA binding domain in which the DNA binding domain is the same in each said first fusion protein, and in which said first population of first fusion proteins has a complexity of at least 1,000; and (ii) a second population of second fusion proteins, each said second fusion protein comprising a second protein sequence and a transcriptional regulatory domain of a transcriptional regulator, in which the transcriptional regulatory domain is the same in each said second fusion protein, such that a first fusion protein is co-expressed with a second fusion protein in host cells, and wherein said host cells contain at least one nucleotide sequence operably linked to a promoter driven by one or more DNA binding sites recognized by said DNA binding domain such that interaction of a first fusion protein with a second fusion protein results in regulation of transcription of said at least one nucleotide sequence by said regulatory domain, and in which said second population of second fusion proteins has a complexity of at least 1,000; and (b) detecting said regulation of transcription of said at least one nucleotide sequence, thereby detecting an interaction between a first fusion protein and a second fusion protein.

The present invention also provides a method to isolate concurrently inhibitors of such protein-protein interactions that occur in, are characteristic of or are specific to a given population of proteins. By way of example, preferably all the yeast diploids that harbor fusion proteins that interact with each other are pooled together and exposed to candidate inhibitors. Exemplary candidate inhibitors include chemically synthesized molecules and genetically encoded peptides. After treatment with candidate inhibitors, the yeast cells harboring interacting hybrid proteins are selected for the inactivation of the reporter gene, preferably by transfer to appropriate selective media. Preferably, the same media also selects for the presence of the plasmids that encode the interacting proteins, and the peptide-encoding peptides in the case of the screening for peptide inhibitors expressed from expression plasmids. Successful inhibition events are thus monitored by the inactivation of the reporter gene.

The major advantages of these methods are as follows. From a population of proteins characteristic of a particular tissue or cell-type, all possible detectable protein-protein interactions that occur can be identified and the genes encoding these proteins can be isolated. Thus, parallel analyses of two cell types enumerates the protein-protein interactions that are common to both and those that are specific to both (differentially expressed in one cell type and not the other). Such an analysis has value since protein-protein interactions specific to a disease state can serve as therapeutic points of intervention.

Furthermore, inhibitors of such protein-protein interactions can be isolated in a rapid fashion. Such inhibitors can be of therapeutic value or serve as lead compounds for the synthesis of therapeutic compounds. This system can also be used to identify novel peptide inhibitors of protein-protein interactions. One advantage of this method over existing methods is that peptides or chemicals are identified by an ability to block protein-protein interactions. In many existing methods, molecules are identified by an ability only to bind to one of a pair of interacting proteins; such binding does not necessarily imply that the protein-protein interaction will be blocked by the same agent. Another advantage of the method is that multiple protein-protein interactions can be screened against a prospective inhibitor in a single assay.

4. DESCRIPTION OF THE FIGURES

These and other features, aspects, and advantages of the present invention will become better understood by reference to the accompanying drawings, following description, and appended claims, where the drawings are described briefly as follows:

FIG. 1. An overview of an exemplary strategy to identify pairs of interacting proteins that are specific to a particular population and to identify inhibitors of these interactors in a high throughput fashion.

FIG. 2. A yeast interaction mating assay for the detection of protein-protein interactions. The two test proteins are indicated as X and Y. X=DNA binding domain fusion protein; Y=activation domain fusion protein. The activation and DNA-binding domains are indicated as A and D respectively. The two yeast cell types are a and a, while the diploid is marked as a/α. A blue color (not shown) indicates expression of β-galactosidase by conversion of the clear X-gal substrate into an insoluble blue precipitate.

FIG. 3. Exemplary scheme for the isolation of stage-specific pairs of interacting proteins. M and N are two populations of proteins expressed in a particular state (e.g., cancer). The mating of two populations M and N results in the creation of an interactive population that contains all possible pairs of interacting proteins in the two populations. The reporter genes are URA3, HIS3, and lacZ. The interactive population is further characterized by methods such as the QEA™ method, the SEQ-QEA™ method, and sequencing which aid in the identification of the pairs of interacting proteins. A comparison of two such interactive populations leads to the identification of stage-specific or disease state-specific pairs of interacting proteins.

FIGS. 4A–C. Pooling strategies to characterize the interactive populations. PCR reactions are performed on pooled yeast cells and the PCR products are either analyzed directly by electrophoresis or by the QEA™ method and SEQ-QEA™ method. These methods lead to the characterization of an interactive population. (A) 2-dimensional pooling and deconvolution. (B) 3-dimensional pooling and deconvolution. In order to determine the location of each clone, wells are pooled along planes (as opposed to lines in the 2-dimensional strategy). The location of a specific gene can be determined by finding which pool from each axis contains it. (C) 3-dimensional pooling from 96 well plates. 1152 positive colonies are arrayed into individual wells of twelve microtiter plates. A total of 32 pools are produced: 12 pooled along the columns axis (each from all 12 plates), 8 pooled along rows (A–H), and 12 pooled plates (p1–p12). These pools contain genes from 96, 144, and 96 wells, respectively. Two-dimensional pooling and deconvolution requires 36+24 pools, but no pool is from more than 36 wells (genes), so it is easier to get clearly separate bands from a seqQEA™ method reaction of pools than with the three-dimensional strategy.

FIG. 5. Isolation of stage-specific pairs of interacting proteins by probing interactive grids. M and N are two populations of proteins expressed in a particular state (e.g., cancer). The PCR products corresponding to M and N partners from an M×N analysis are spotted onto a solid support like a nitrocellulose membrane to create an interactive grid. The interactive grids are then probed with DNA that is unique to a specific stage to isolate pairs of interacting proteins that are unique to a specific stage.

FIG. 6. Integration of the expression linkage analysis and inhibitor screen. Exemplary steps in an integrated isolation of inhibitors of protein-protein interactions are depicted. The interactive populations that arise from an M×N analysis are screened against many inhibitors such that only successful inhibition events are selected. Thus, from an M×N analysis not only are obtained stage-specific pairs of interacting proteins, but also inhibitors of such interactions.

FIG. 7. Peptide expression vector polylinker. The polylinker region of the peptide expression vector (PEV) is depicted. ADC1-P and ADC1-T refer to the ADC1 promoter and terminator, respectively. This is a yeast promoter that promotes transcription of genes downstream of it. Sfi I and Asc I sites demarcate the region within which the peptide-coding regions will be inserted. UAG refers to the termination codon and NLS refers to the Nuclear Localization Signal that provides transport of the peptides into the nucleus.

FIG. 8. A QEA™ Method Analysis. A comparison is depicted of a QEA™ method pattern from an M×N analysis. conducted in duplicate (Section 6.5). The PCR products that were pAS-like vector-specific were pooled and subjected to a QEA™ method analysis. I and II refer to duplicate M×N analyses. The dotted peaks correspond to the molecular weight markers and the solid peaks are the QEA™ method products.

FIG. 9. The QEA™ Method Comparison. A comparison is shown of the QEA™ method patterns from an M×N analysis conducted wherein one of the interactive populations had the RAS-RAF interaction. The RAF peak obtained in the QEA™ method is shown in solid black.

FIGS. 10A, 10B, 10C, and 10D show DNA adapters for. an RE/ligation implementation of a Quantitative Expression Analysis ("QEA™") method, where the restriction endonucleases generate 5' overhangs, open blocks indicating strands of DNA;

FIGS. 11A and 11B show the DNA adapters for an RE/ligation implementation of a QEA™ method, where the restriction endonucleases generate 3' overhangs;

FIGS. 12A, 12B, and 12C show an exemplary biotin alternative embodiment of the QEA™ method;

FIGS. 15A and 15B show an overview of a method for determining a simulated database of experimental results for an embodiment of a QEA™ method;

Figure 16:
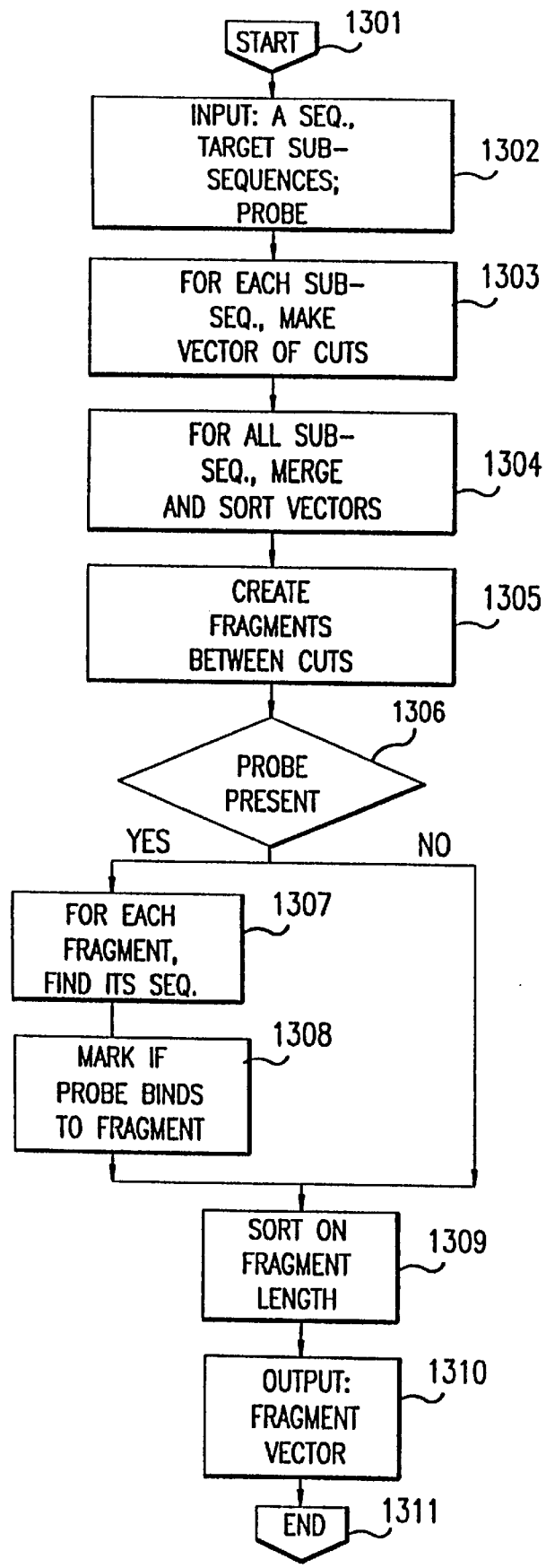
FIG. 16 shows the detail of a method for simulating a QEA™ reaction.
Figure 18:
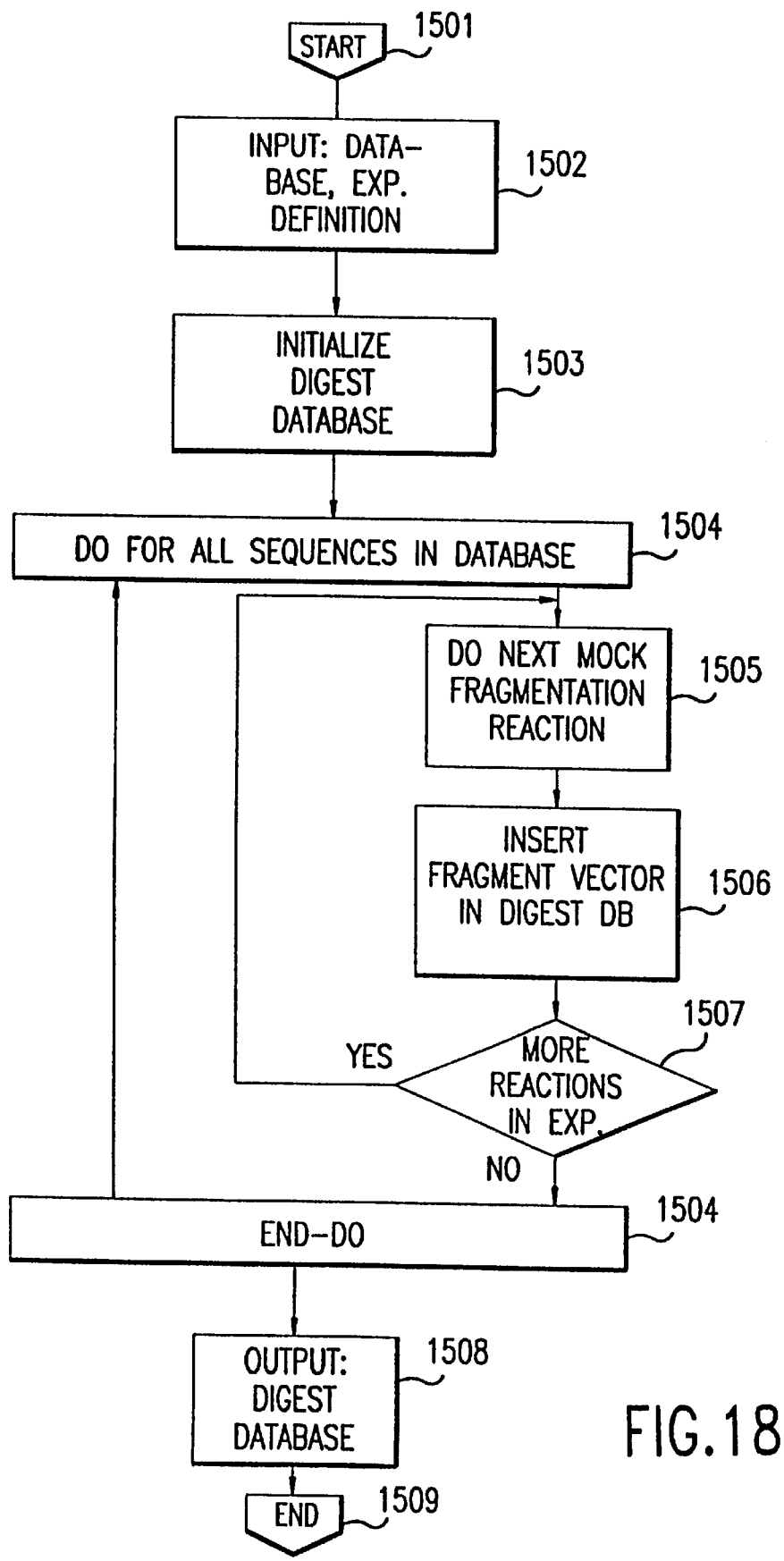
Figure 19A:
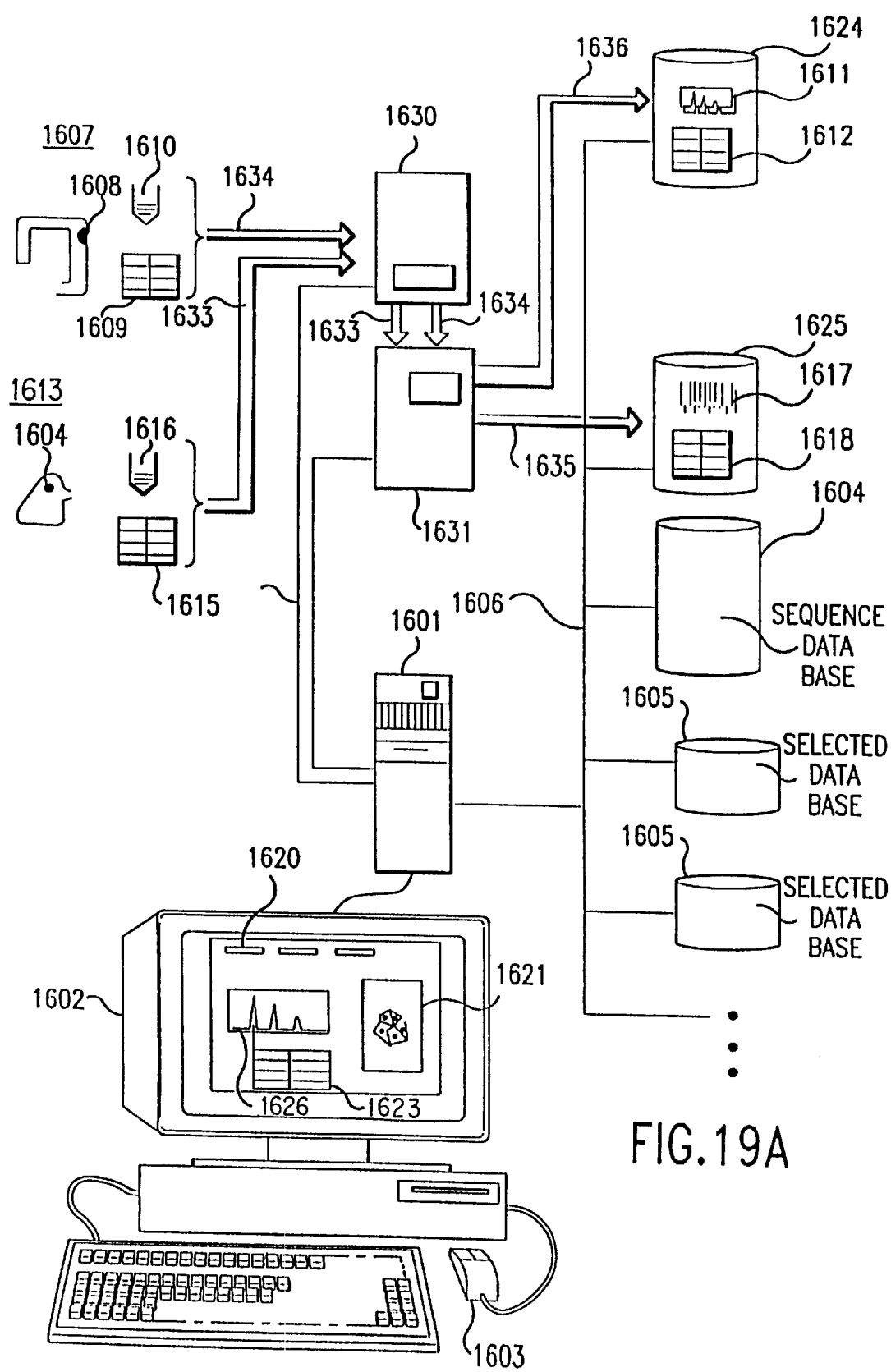
Figure 19B:
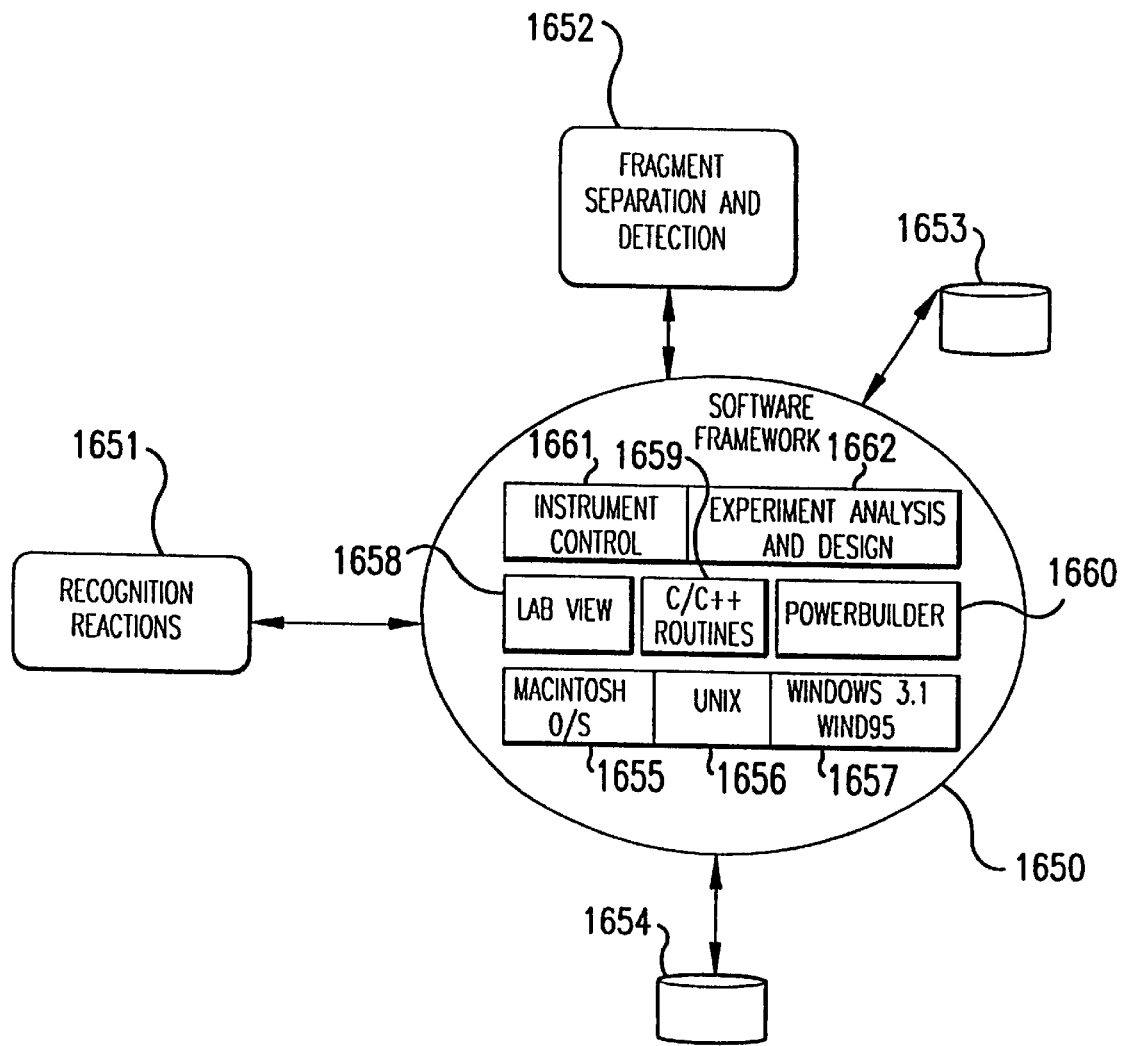
Figure 20A:
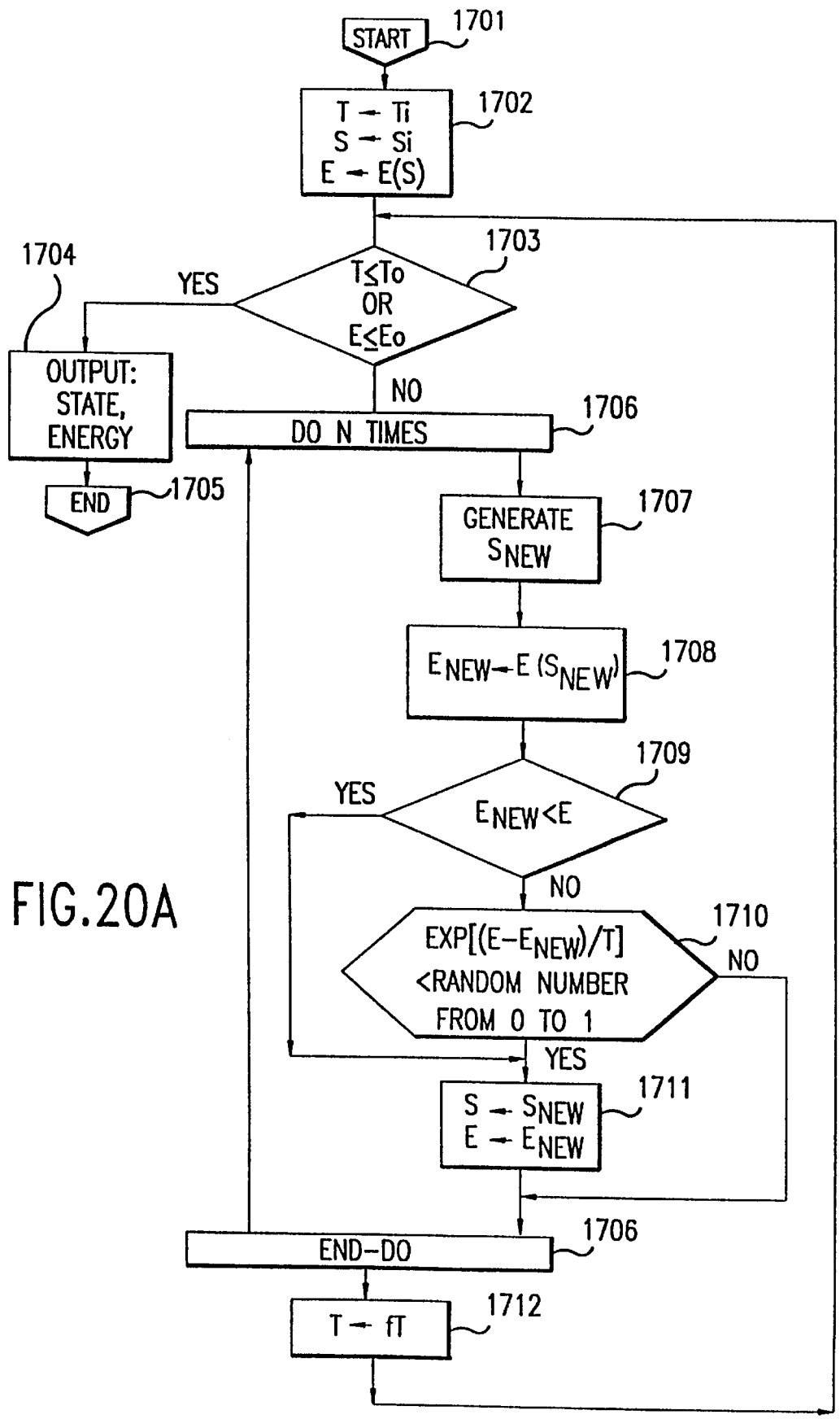
Figure 20B:
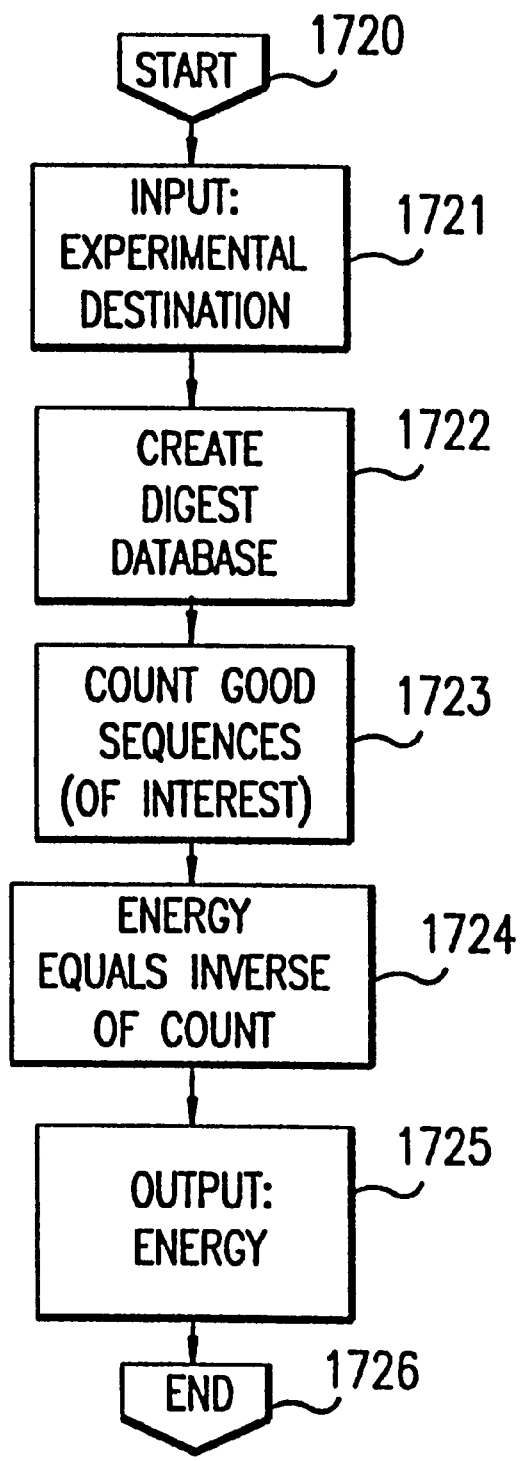
Figure 21:
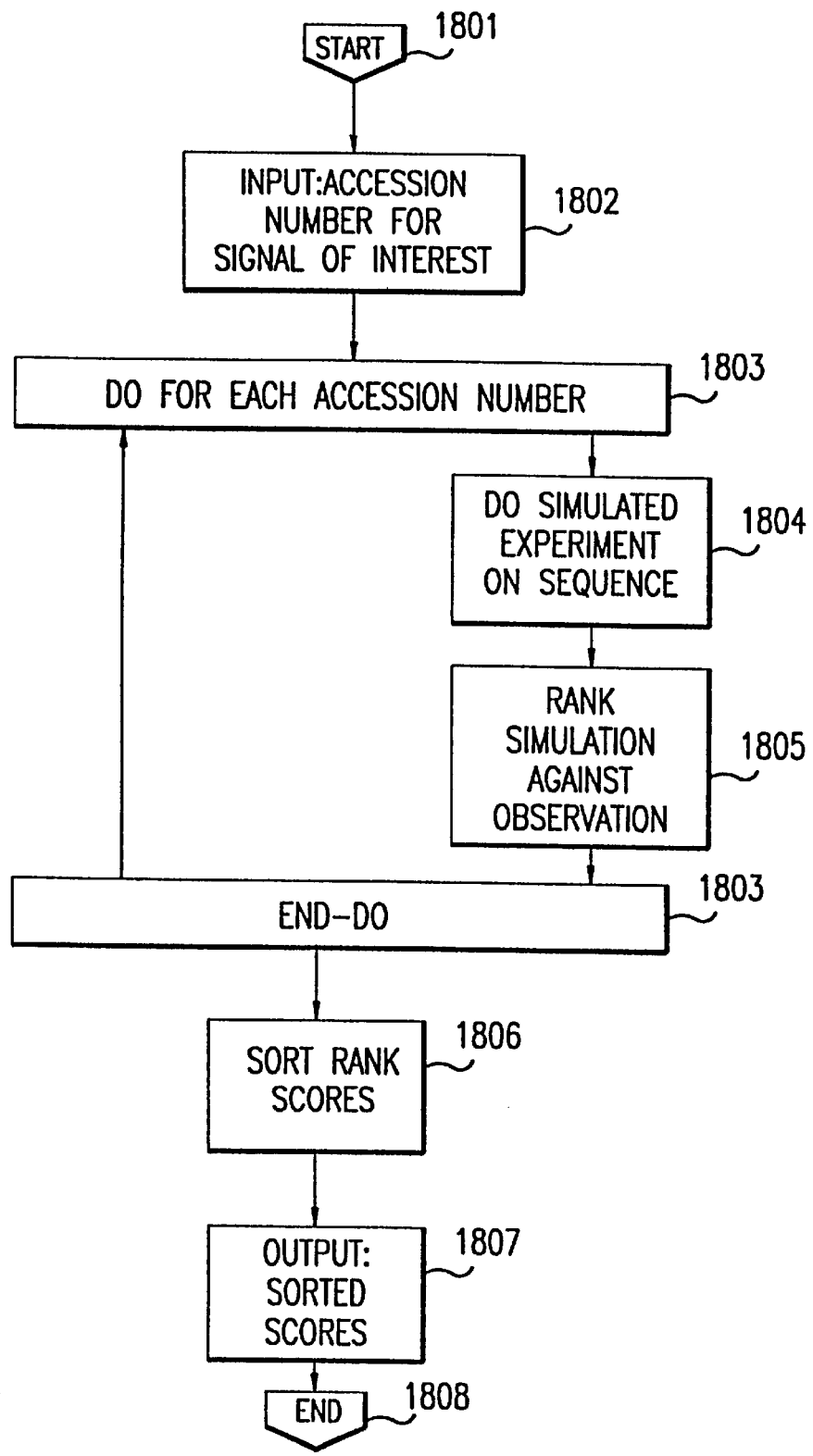

FIGS. 17A–F show exemplary results of the action of the method of FIG. 16;

FIG. 18 shows the detail of a method for determining a simulated database of experimental results for a QEA™ embodiment;

FIGS. 19A and 19B show an exemplary computer system apparatus implementing the QEA™ methods;

FIG. 20A shows exemplary detail of an experimental design method for a QEA™ method, and FIG. 20B shows exemplary detail of an experimental design method for an embodiment of a QEA™ method;

FIG. 21 shows an exemplary method for ordering the DNA sequences found to be likely causes of a QEA™ method signal in the order of their likely presence in the sample;

FIGS. 22A, 22B, 22C, and 22D show exemplary reaction temperature profiles for preferred manual and automated implementations of a preferred RE embodiment of a QEA™ method; and FIGS. 23A–23E show details of a SEQ-QEA™ embodiment of a QEA™ method.

Figure 24:
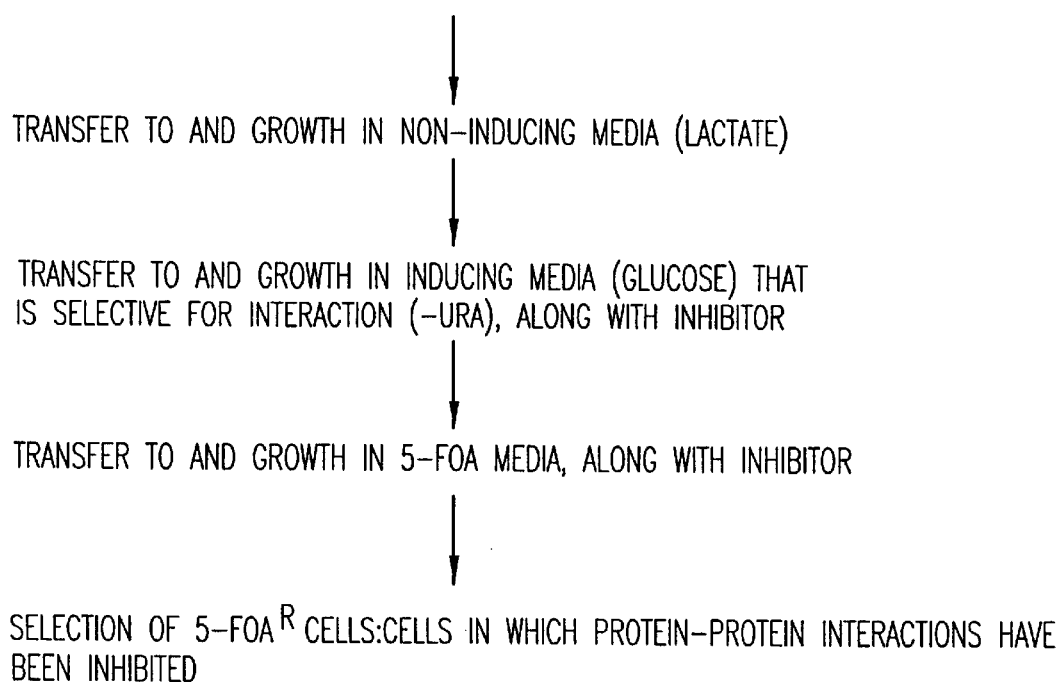

FIG. 24. Exemplary protocol for selection of inhibitors of protein-protein interactions.

FIG. 25. Exemplary protocol for selection of novel interacting proteins and inhibitors of these interacting proteins.

5. DETAILED DESCRIPTION OF THE INVENTION

In contrast to prior art methods of detecting protein-protein interactions between two protein populations, wherein the number of false positives and low throughput limited the applicability of such prior art methods to situations in which the complexity of at least one of the populations was no more than 10, the present invention allows detection of protein-protein interactions (and isolation and characterization of the interacting proteins) between populations in which both populations can have complexities of orders of magnitude significantly greater than 10, e.g., 1,000, 100,000, or in the range of 50,000–100,000 as is found in mammalian cDNA populations. Methods for detecting, isolating, and characterizing inhibitors of such interactions are also provided.

For purposes of convenience of description and not by way of limitation, the detailed description is divided into the subsections set forth below.

5.1. DETECTING INTERACTING PROTEINS

The present invention provides methods for detecting interacting proteins (including peptides). Interacting proteins are detected based on the reconstitution of a transcriptional regulator in the presence of a reporter gene ("Reporter Gene") whose transcription is then regulated by the reconstituted regulator. In contrast to prior art methods, the protein-protein interactions can be detected, and the interacting pairs of proteins isolated and identified, between two populations of proteins wherein both. of the populations have a complexity of at least 10 (i.e., both populations contain more than ten distinct proteins). The populations are expressed as fusion proteins to a DNA binding domain, and to a transcriptional regulatory domain, respectively. In various specific embodiments, one or both of the populations of proteins has a complexity of at least 50, 100, 500, 1,000, 5,000, 10,000, or 50,000; or has a complexity in the range of 25 to 100,000, 100 to 100,000, 50,000 to 100,000, or 10,000 to 500,000. For example, one or both populations can be mammalian cDNA populations, generally having a complexity in the range of 50,000 to 100,000; in such populations from total mRNA, the detection of a protein in an interacting pair that is expressed to a particular level can be optimized by the statistical considerations described in Section 5.2.7 below. In a specific embodiment, the invention is capable of detecting substantially all detectable interactions that occur between the component proteins of two populations, each population having a complexity of at least 50, 100, 500, 1000, 5000, 10,000 or 50,000. In a specific embodiment, the two populations are samples (aliquots) of at least 100 or 1000 members (e.g., expressed in host yeast cells) of a larger population (e.g., a mammalian cDNA library) having a complexity of at least 100, 1000, 5,000, 10,000, or 50,000; in a particular embodiment, the sample is uncharacterized in that the particular identities of all or most of its member proteins are not known.

The populations can be the same or different populations. If it is desired to detect interactions between proteins encoded by a particular DNA population, both protein populations are expressed from chimeric genes comprising DNA sequences representative of that particular DNA population. In another embodiment, one protein population is expressed from chimeric genes comprising cDNA sequences of diseased human tissue, and the other protein population is expressed from chimeric genes comprising cDNA sequences of non-diseased human tissue. In a specific embodiment, one or more of the populations can be uncharacterized in that the identities of all or most of the members of the population are not known. Preferably, the populations are proteins encoded by DNA, e.g., cDNA or genomic DNA or synthetically generated DNA. For example, the populations can be expressed from chimeric genes comprising cDNA sequences from an uncharacterized sample of a population of cDNA from mammalian RNA. Preferably, a cDNA library is used. The cDNA can be, e.g., a normalized or subtracted cDNA population. The cDNA of one or both populations can be cDNA of total mRNA or polyA$^+$ RNA or a subset thereof from a particular species, particular cell type, particular age of individual, particular tissue type, disease state or disorder or stage thereof, or stage of development. Accordingly, the invention provides methods of identifying and isolating interacting proteins that are present in or specific to particular species, cell type, age, tissue type, disease state, or disease stage, and also provides methods for comparing the protein-protein interactions present in such particular species, cell type, age, tissue type, disease state, or disease stage (by e.g., using a cDNA library of total mRNA particular to such species, cell type, age, tissue type, disease state, or disease stage, respectively, as both the populations between which interactions are detected) with the protein-protein interactions present in a different species, cell type, age, tissue type, non-diseased state or a different disease stage, or different state of development, respectively. For example, in one embodiment, interactions are detected between identical populations of proteins in which the population of proteins is from cDNA of cancerous or pre-cancerous (e.g., hyperplastic, metaplastic, or dysplastic cells), e.g., of prostate cancer, breast cancer, stomach cancer, lung cancer, ovarian cancer, uterine cancer, etc.; these interactants are then compared to interacting proteins detected between two other identical populations of proteins in which the population of proteins is from cDNA of cells not having the cancer or precancerous condition, as the case may be. In a specific embodiment, cDNA may be obtained from a preexisting cDNA sample or may be prepared from a tissue sample. When cDNA is prepared from tissue samples, methods commonly known in the art can be used. For example, these can consist of largely conventional steps of RNA preparation from the tissue sample, preferably total poly(A) purified RNA is used but less preferably total cellular RNA can be used, RNase extraction, DNase treatment, mRNA purification, and first and second strand cDNA synthesis.

Preferably, the populations of proteins between which interactions are detected are provided by recombinant expression of nucleic acid populations (e.g., cDNA or genomic libraries). Also preferably, the interactions occur intracellularly. In another specific embodiment, recombinant biological libraries expressing random peptides can be used as the source nucleic acid for one or both of the nucleic acid populations.

In a specific embodiment, presented by way of example and not limitation, the method of the invention comprises the steps schematically depicted in FIG. 1.

In a preferred aspect, the present invention provides a method for detecting unique protein-protein interactions that characterize a population or library of proteins by comparing all detectable protein-protein interactions that occur in a population or library with those interactions that occur in another population or library. Furthermore, the method also enables the identification of inhibitors of such protein-protein interactions.

Protein-protein interactions are detected according to the invention by detecting transcriptional regulation (preferably activation) which occurs upon interaction of proteins between the two populations being tested (referred to hereinafter merely for purposes of convenience as the M population and the N population). Proteins of each population (M, N) are provided as fusion (chimeric) proteins (preferably by recombinant expression of a chimeric coding sequence) containing each protein contiguous to a preselected sequence. For one population, the preselected sequence is a DNA binding domain. The DNA binding domain can be any available, as long as it specifically recognizes a DNA sequence within a promoter. For example, the DNA binding domain is of a transcriptional activator or inhibitor. For the other population, the preselected sequence is an activator or inhibitor domain of a transcriptional activator or inhibitor, respectively.

In a preferred embodiment, each protein in one population (e.g., M) is provided as a fusion to a DNA binding domain of a transcriptional regulator (e.g., activator). Each protein in the other population (N) is provided as a fusion to an activator domain of a transcriptional activator. The regulatory domain alone (not as a fusion to a protein sequence) and the DNA-binding domain alone (not as a fusion to a protein sequence) preferably do not detectably interact (so as to avoid false positives in the assay). When binding occurs of a fusion protein in M to a fusion protein in N, reconstitution of a transcriptional activator occurs such that transcription is increased of a gene ("Reporter Gene") responsive to (whose transcription is under the control of) the transcriptional activator. Thus, the Reporter Gene comprises a nucleotide sequence operably linked to a promoter regulated by a DNA binding site for the DNA binding domain of the transcriptional activator. The activation of transcription of the Reporter Gene occurs intracellularly, e.g., in prokaryotic or eukaryotic cells, preferably in cell culture.

The Reporter Gene comprises a nucleotide sequence operably linked to a promoter that is operably linked to one or more nucleic acid binding sites that are specifically bound by the DNA binding domain of the fusion protein that is employed in the assay of the invention, such that binding of a reconstituted transcriptional activator or inhibitor to the one or more DNA binding sites increases or inhibits, respectively, transcription of the nucleotide sequence under the control of the promoter. The promoter that is operably linked to the nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native. Thus, for example, one or more tandem copies (e.g., 4 or 5 copies) of the appropriate DNA binding site can be introduced upstream of the TATA box in the desired promoter (e.g., in the area of position −100 to −400). In a preferred aspect, 4 or 5 tandem copies of the 17 bp UAS (GAL4 DNA binding site) are introduced upstream of the TATA box in the desired promoter, that is in turn upstream of the desired coding sequence that encodes a selectable or detectable marker. In a preferred embodiment, the GAL1-10 promoter is operably fused to the desired nucleotide sequence; the GAL1-10 promoter already contains 5 binding sites for GAL4. Thus, in a particular embodiment, the transcriptional activation binding site of the desired gene(s) can be deleted and replaced with GAL4 binding sites (Bartel et al., 1993, BioTechniques 14(6): 920–924; Chasman et al., 1989, Mol. Cell. Biol. 9:4746–4749). Referring to use of a particular gene as a Reporter Gene herein thus means that, if the native promoter is not driven by binding site(s) recognized by the DNA binding domain used in the interaction assay of the invention, such DNA binding site(s) have been introduced into the gene.

The Reporter Gene preferably comprises a nucleotide sequence, whose transcription is regulated by the transcriptional activator, that is a coding sequence that encodes a detectable marker or selectable marker, facilitating detection of transcriptional activation, thereby detecting a protein-protein interaction. Preferably, the assay is carried out in the absence of background levels of the transcriptional activator (e.g., in a cell that is mutant or otherwise lacking in the transcriptional activator). Preferably, more than one different Reporter Gene is used to detect transcriptional activation, e.g., one encoding a detectable marker, and one or more encoding different selectable markers. The detectable marker can be any molecule that can give rise to a detectable signal, e.g., an enzyme or fluorescent protein. The selectable marker can be any molecule which can be selected for its expression, e.g., which gives cells a selective advantage over cells not having the selectable marker under appropriate (selective) conditions. In preferred aspects, the selectable marker is an essential nutrient in which the cell in which the interaction assay occurs is mutant or otherwise lacks or is deficient, and the selection medium lacks such nutrient. The Reporter Gene used need not be a gene containing a coding sequence whose native promoter contains a binding site for the DNA binding protein, but can alternatively be a chimeric gene containing a sequence that is transcribed under the control of a promoter that is not the native promoter for the transcribed sequence.

In a specific embodiment, to make the fusion constructs (encoding the fusion proteins such that the fusion proteins are expressed in the desired host cell) from each population (e.g., library), the activation domain and DNA binding domain of a wide variety of transcriptional activator proteins can be used, as long as these transcriptional activators have separable binding and transcriptional activation domains. For example, the GAL4 protein of S. cerevisiae, the GCN4 protein of S. cerevisiae (Hope and Struhl, 1986, Cell 46:885–894); the ARD1 protein of S. cerevisiae (Thukral et al., 1989, Mol. Cell. Biol. 9:2360–2369), and the human estrogen receptor (Kumar et al., 1987, Cell 51:941–951) have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg et al., 1988, Genes Dev. 2:730–742) activation domain is employed. In a specific embodiment, amino acids 1–147 of GAL4 (Ma et al., 1987, Cell 48:847–853; Ptashne et al., 1990, Nature 346:329–331) is the DNA binding domain, and amino acids 411–455 of VP16 (Triezenberg et al., 1988, Genes Dev. 2:730–742; Cress et al., 1991, Science 251:87–90) is the activation domain.

Figure 2:
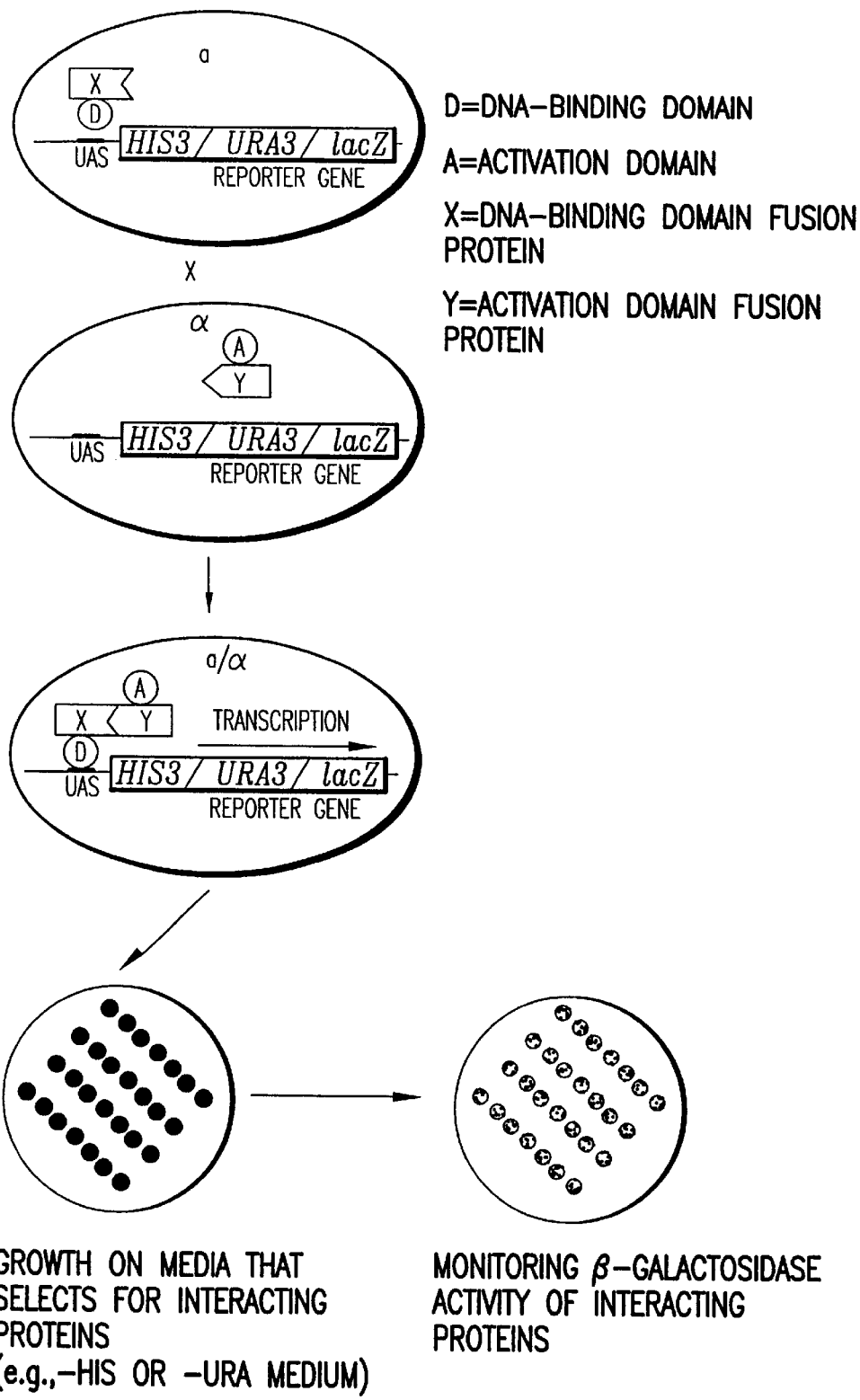

In a preferred embodiment, the transcriptional activator that is reconstituted in the manner described above is the yeast transcription factor GAL4 (FIG. 2). The host strain bears a mutant GAL4 gene (e.g., having a deletion or point mutation) and as such cannot express the GAL4 transcriptional activator.

In another embodiment, the DNA-binding domain is Ace1N, the DNA binding domain of the Ace1 protein. In another embodiment, the activation domain is Ace1C, the activation domain of Ace1. Ace1 is a yeast protein that activates transcription from the CUP1 operon in the presence of divalent copper. CUP1 encodes metallothionein, which chelates copper; thus, CUP1 gene expression is Reporter Gene expression suitable for use with Ace1N, in which selection is carried out by using copper in the media of the growing host cells which would otherwise be toxic to the cells. Alternatively or additionally, the Reporter Gene can comprise a CUP1-lacZ fusion such that the enzyme β-galactosidase is expressed upon binding of a transcriptional activator reconstituted with Ace1N (see Chaudhuri et al., 1995, FEBS Letters 357:221–226).

In another specific embodiment, the DNA binding domain of the human estrogen receptor is used, with a Reporter Gene driven by one or three estrogen receptor response elements (see Le Douarin et al., 1995, Nucl. Acids. Res. 23:876–878).

In an embodiment in which the interaction assay is carried out in a prokaryotic cell and in which fusion proteins to a transcriptional inhibition domain are used as one of the populations of proteins, both the DNA binding domain fusion population and the inhibition domain fusion population can be fusions to the λ cI repressor. In this embodiment, interaction of two fusion proteins via the non-cI protein portions promotes oligomerization of the λ cI DNA binding domain sufficient to cause DNA binding and inhibition of transcription from the two phage major early promoters, preventing lytic growth and rendering the host bacterial cells immune to superinfection by λ (Hu et al., 1995, Structure 3:431–433). Alternatively, the DNA binding domains of the LexA repressor (Schmidt-Dörr et al., 1991, Biochemistry 30:9657–9664), 434 repressor (Pu et al., 1993, Nucl. Acids Res. 21:4348–4355), or AraC protein (Bustos et al., 1993, Proc. Natl. Acad. Sci. USA 90:5638–5642) can be used in both the DNA binding domain and the transcription inhibition fusion populations.

The DNA binding domain and the transcription activator/inhibitor domain each preferably comprises a nuclear localization signal (see Ylikomi et al., 1992, EMBO J. 11:3681–3694; Dingwall and Laskey, 1991, TIBS 16:479–481) functional in the cell in which the fusion proteins are to be expressed.

In another embodiment, the fusion constructs further comprise sequences encoding affinity tags such as glutathione-S-transferase or maltose-binding protein or an epitope of an available antibody, so as to facilitate isolation of the encoded proteins by affinity methods (e.g., binding to glutathione, maltose, or antibody, respectively) (see Allen et al., 1995, TIBS 20:511–516). In another embodiment, the fusion constructs further comprise bacterial promoter sequences operably linked to the fusion coding sequences to facilitate the production of the fusion proteins also in bacterial cells (see Allen et al., 1995, TIBS 20:511–516).

The host cell in which the interaction assay occurs can be any cell, prokaryotic or eukaryotic, in which transcription of the Reporter Gene can occur and be detected, including but not limited to mammalian (e.g., monkey, chicken, mouse, rat, human, bovine), bacteria, and insect cells, and is preferably a yeast cell. Expression constructs encoding and capable of expressing the binding domain fusion proteins, the transcriptional activation domain fusion proteins, and the Reporter Gene product(s) are provided within the host cell, by mating of cells containing the expression constructs, or by cell fusion, transformation, electroporation, microinjection, etc. For example, GAL4 and VP16 are functional in animal cells and thus the desired binding or activation domain thereof can be used in, e.g., yeast or mammalian cells. In a specific embodiment in which the assay is carried out in mammalian cells (e.g., hamster cells), the DNA binding domain is the GAL4 DNA binding domain, the activation domain is the herpes simplex virus VP16 transcriptional activation domain, and the Reporter Gene contains the desired coding sequence operably linked to a minimal promoter element from the adenovirus E1B gene driven by several GAL4 DNA binding sites (see Fearon et al., 1992, Proc. Natl. Acad. Sci. USA 89:7958–7962). As will be apparent, other DNA binding domains, activation domains, promoters, and/or DNA binding sites can be used, as long as the DNA binding sites are recognized by the DNA binding domains, and the promoter is operative in the cells chosen in which to carry out the assay of the invention. The host cell used should not express an endogenous transcription factor that binds to the same DNA site as that recognized by the DNA binding domain fusion population. Also, preferably, the host cell is mutant or otherwise lacking an endogenous, functional form of the Reporter Gene(s) used in the assay.

In a specific embodiment, transcription of the Reporter Gene is detected by a linked replication assay. For example, as described by Vasavada et al. (1991, Proc. Natl. Acad. Sci. USA 88:10686–10690), for use in animal cells, a Reporter Gene under the control of the E1B promoter, which promoter in turn is controlled by GAL4 DNA binding sites, encodes the SV40 T antigen. In the presence of reconstituted GAL4 DNA binding domain-activation domain (composed of two interacting fusion proteins), SV40 T antigen is produced from the Reporter Gene. If a plasmid is present that contains the SV40 origin of replication, this plasmid will replicate only upon the production of SV40 T antigen. Thus, replication of such a plasmid is used as an indicator of protein-protein interaction. Constructing one or both of the plasmids encoding the fusion proteins of the assay to contain an SV40 origin of replication means that replication of these plasmids will be an indication of Reporter Gene activity. Sensitivity to DpnI can be used to destroy unreplicated plasmids according to the methods described in Vasavada et al. (1991, Proc. Natl. Acad. Sci. USA 88:10686–10690). In an alternative embodiment, alternatively to an SV40 origin of replication, a polyoma virus replicon can be employed (id.)

Preferably, the protein-protein interactions are assayed according to the method of the invention in yeast cells, e.g., *Saccharomyces cerevisiae* or *Schizo-saccharomyces pombe*. Various vectors for producing the two fusion protein populations and host strains for conducting the assay are known and can be used (see, e.g., Fields et al., U.S. Pat. No. 5,468,614 dated Nov. 21, 1995; Bartel et al., 1993, "Using the two-hybrid system to detect protein-protein interactions," in *Cellular Interactions in Development*, Hartley, D. A. (ed.), Practical Approach Series xviii, IRL Press at Oxford University Press, New York, N.Y., pp. 153–179; Fields and Sternglanz, 1994, TIG 10:286–292). By way of example but not limitation, yeast strains or derivative strains made therefrom which can be used are (see Section 6.3 and its subsections) N105, N106, N105', N106', and YULH; the respective genotypes of these strains are set forth in Section 6.3, infra. Exemplary strains that can be modified to create reporter strains (containing the desired Reporter Gene for use in the assay of the invention) also include the following:

Y190: MATa, ura3-52, his3-200, lys2-801, ade2-101, trp1-901, leu2-3,112, gal4Δ, gal80Δ, cyh'2, LYS2::GAL1$_{UAS}$-HIS3$_{TATA}$-HIS3, URA3::GAL1$_{UAS}$-GAL1$_{TATA}$-lacZ (available from Clontech, Palo Alto, Calif.; Harper et al., 1993, Cell 75:805–816). Y190 contains HIS3 and lacZ Reporter Genes driven by GAL4 binding sites.

CG-1945: MATa, ura3-52, his3-200, lys2-801, ade2-101, trp1-901, leu2-3,112, gal4-542, gal80-538, cyhr2, LYS2::GAL1$_{UAS}$-GAL1$_{TATA}$-HIS3, URA3::GAL1$_{UAS\ 17\ mers\ (x3)}$-CYC1$_{TATA}$-lacZ (available from Clontech). CG-1945 contains HIS3 and lacZ Reporter Genes driven by GAL4 binding sites.

Y187: MATα, ura3-52; his3-200, ade2-101, trp1-901, leu2-3,112, gal4Δ, gal80Δ, URA3::GAL1$_{UAS}$-GAL1$_{TATA}$-lacZ (available from Clontech). Y187 contains a lacZ Reporter Gene driven by GAL4 binding sites.

SFY526: MATa, ura3-52, his3-200, lys2-801, ade2-101, trp1-901, leu2-3,112, gal4-542, gal80-538, can', URA3::GAL1-lacz (available from Clontech). SFY526 contains HIS3 and lacZ Reporter Genes driven by GAL4 binding sites.

HF7c: MATa, ura3-52, his3-200, lys2-801, ade2-101, trp1-901, leu2-3,112, gal4-542, gal80-538, LYS2::GAL1-HIS3, URA3::GAL1$_{UAS\ 17\ MERS\ (x3)}$-CYC1-lacZ (available from Clontech). HF7c contains HIS3 and lacZ Reporter Genes driven by GAL4 binding sites.

YRG-2: MATα, ura3-52, his3-200, lys2-801, ade2-101, trp1-901, leu2-3,112, gal4-542, gal80-538, LYS2::GAL1$_{UAS}$-GAL1$_{TATA}$-HIS3, URA3::GAL1$_{UAS\ 17\ mers\ (x3)}$-CYC1-lacZ (available from Stratagene). YRG-2 contains HIS3 and lacZ Reporter Genes driven by GAL4 binding sites.

Many other strains commonly known and available in the art can be used.

Consistent with convention in the art, wild-type gene names throughout this application are all capitalized and italicized; mutant gene names are lower case and italicized—except for lacz for which the functional, non-mutant gene is written lower case, italicized.

If not already lacking in endogenous Reporter Gene activity, cells mutant in the Reporter Gene may be selected by known methods, or the cells can be made mutant in the target Reporter Gene by known gene-disruption methods prior to introducing the Reporter Gene (Rothstein, 1983, Meth. Enzymol. 101:202–211).

In a specific embodiment, plasmids encoding the different fusion protein populations can be both introduced into a single host cell (e.g., a haploid yeast cell) containing one or more Reporter Genes, by cotransformation, to conduct the assay for protein-protein interactions. As a preferred alternative to cotransformation of expression constructs, mating (e.g., of yeast cells) or cell fusion (e.g., of mammalian cells) can be employed for delivery of a binding domain fusion expression construct and an activation domain fusion expression construct into a single cell. In a mating-type assay, conjugation of haploid yeast cells of opposite mating type that have been transformed with a binding domain fusion expression construct (preferably a plasmid) and an activation (or inhibitor) domain fusion expression construct (preferably a plasmid), respectively, delivers both constructs into the same diploid cell. The mating type of a strain may be manipulated as desired, by transformation with the HO gene (Herskowitz and Jensen, 1991, Meth. Enzymol. 194:132–146).

In a preferred embodiment, a yeast interaction mating assay is employed, using two different types of host cells, strain-types a and α, of the yeast *Saccharomyces cerevisiae* (FIG. 2). The host cell preferably contains at least two Reporter Genes, containing a binding site for the DNA-binding domain (e.g., of a transcriptional activator), such that the Reporter Gene is transcriptionally activated when the DNA-binding domain is in proximity to an activator domain of a transcriptional activator. The activator domain and DNA binding domain are each parts of chimeric proteins formed from the two respective populations of proteins.

One type of host cell, for example the a strain, hosts a library of chimeric genes that encode hybrid proteins that are all fusions of different nucleotide sequences (e.g., gene sequences) to the DNA-binding domain of a transcriptional activator like GAL4 (see by way of example Section 6.1.7). These hybrid proteins are capable of recognizing the DNA-binding site on the Reporter Gene. In a preferred embodiment of this invention, the library of DNA-binding domain chimeric genes is introduced into the host cell as a set of plasmids. These plasmids are preferably capable of autonomous replication in a host yeast cell and preferably can also be propagated in *E. coli*. The plasmid contains a promoter directing the transcription of the DNA binding domain fusion gene, and a transcriptional termination signal. The plasmid preferably also contains a selectable marker gene, the expression of which in the host cell permits selection of cells containing the marker gene from cells that do not contain the selectable marker, upon incubation of the cells in an environment in which substantial death of the cells occurs in the absence of expression of the selectable marker. The plasmid can be single-copy or multi-copy. Single-copy yeast plasmids that have-the-yeast centromere in them may also be used to express the activation and DNA-binding domain fusions (Elledge et al., 1988, Gene 70:303–312). In another embodiment of the invention, the DNA-binding chimeric genes are introduced directly into the yeast chromosome via homologous recombination. The homologous recombination for these purposes is mediated through yeast sequences that are not essential for vegetative growth of yeast, e.g., MER2, MER1, ZIP1, REC102, or ME14 gene.

In yet another embodiment of the invention, alternatively to plasmids, bacteriophage vectors such as λ vectors are used as the DNA binding domain vectors and/or activation domain vectors to make, e.g., the respective cDNA libraries. The use of λ vectors generally makes it faster and easier to generate such libraries than with the use of plasmid vectors.

The second type of yeast host, for example the strain α, hosts a library of chimeric genes encoding hybrid proteins that are all fusions of different genes to the activation domain of a transcriptional activator (see by way of example Section 6.1.7). Preferably, this library is plasmid-borne, and the plasmids are capable of replication in both *E. coli* and yeast. The plasmid contains a promoter directing the transcription of the activation domain fusion gene, and a transcriptional termination signal. The plasmid preferably also contains a selectable marker gene, the expression of which in the host cell permits selection of cells containing the marker gene from cells that do not contain the selectable marker. In another embodiment of the invention the DNA-binding chimeric genes are introduced directly into the yeast chromosome via homologous recombination. The homologous recombination for these purposes is mediated through yeast sequences that are not essential for vegetative growth of yeast.

In one embodiment of the invention, the DNA-binding domain and the activation domain arise from the same transcriptional activator where these functions reside in separate domains. In another embodiment, the DNA-binding and the activation domains may be from different transcriptional activators. Preferably, the two chimeric gene libraries are made from cDNA from various sources, for example, different human tissues, fused to the DNA-binding or the activation domains, respectively (see by way of example Section 6.1.6). These cDNA libraries may be derived from subtracted or normalized cDNA populations. In other specific embodiments, the fusions are of genomic, synthetic, viral or bacterial DNA fused to the DNA-binding domains or the activation domains of the transcriptional activator.

In a specific embodiment, the invention provides a method of detecting one or more protein-protein interactions comprising (a) recombinantly expressing in a first population of yeast cells of a first mating type, a first population of first fusion proteins, each first fusion protein comprising a first protein sequence and a DNA binding domain, in which the DNA binding domain is the same in each said first fusion protein; wherein said first population of yeast cells contains a first nucleotide sequence operably linked to a promoter driven by one or more DNA binding sites recognized by said DNA binding domain such that an interaction of a first fusion protein with a second fusion protein, said second fusion protein comprising a transcriptional activation domain, results in increased transcription of said first nucleotide sequence, and in which said first population of first fusion proteins has a complexity of at least 1,000; (b) negatively selecting to eliminate those yeast cells expressing said first population of first fusion proteins in which said increased transcription of said first nucleotide sequence occurs in the absence of said second fusion protein; (c) recombinantly expressing in a second population of yeast cells of a second mating type different from said first mating type, a second population of said second fusion proteins, each second fusion protein comprising a second protein sequence and an activation domain of a transcriptional activator, in which the activation domain is the same in each said second fusion protein, and in which said second population of second fusion proteins has a complexity of at least 1,000; (d) mating said first population of yeast cells with said second population of yeast cells to form a population of diploid yeast cells, wherein said population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (e) detecting said increased transcription of said first and/or second nucleotide sequence, thereby detecting an interaction between a first fusion protein and a second fusion protein.

In a preferred embodiment, the two libraries of chimeric genes are combined by mating the two yeast strains on solid media for a period of approximately 6–8 hours (see Section 6.1.1). In a less preferred embodiment, the mating is performed in liquid media. The resulting diploids contain both the kinds of chimeric genes,. i.e., the DNA-binding domain fusion and the activation domain fusion. The interaction between the two hybrid proteins within a diploid cell causes the activation domain to be in close proximity to the DNA-binding domain of the transcriptional activator. This in turn causes reconstitution of the transcriptional activator and is monitored by the activity of the Reporter Gene. Thus, when two libraries M and N are mated together, an M×N screen for interacting proteins is performed.

In a preferred embodiment, the two host strains are preferably of the mating type a and α of the yeast *Saccharomyces cerevisiae*. Each mating type of the host preferably has at least two Reporter Genes that each contain one or more recognition sites for the DNA-binding domain. Preferably, the Reporter Gene(s) are the URA3, HIS3 and/or the lacz (see, e.g., Rose and Botstein, 1983, Meth. Enzymol. 101:167–180) gene that have been manipulated so as to contain recognition sites (preferably at least two) in the promoter for the DNA-binding domain of GAL4 (see by way of example Section 6.3.5) (FIG. 2). In other embodiments, Reporter Genes comprising the functional coding sequences of genes, including but not limited to, Green Fluorescent Protein (GFP) (Cubitt et al., 1995, Trends Biochem. Sci. 20:448–455), luciferase, LEU2, LYS2, ADE2, TRP1, CAN1, CYH2, GUS, CUP1 (encoding metallothionein which confers resistance to copper) or chloramphenicol acetyl transferase (CAT) may be used, operatively linked to a promoter driven by DNA binding site(s) recognized by the DNA binding domain being employed in the assay to form a fusion population. LEU2, LYS2, ADE2 and TRP1 are selectable markers, i.e., their activity results in prototrophic growth in media lacking the nutrients encoded by these genes, while the activity of luciferase, GUS and CAT are preferably monitored enzymatically. Preferably, CAN1 and CYH2 Reporter Genes are used to carry out negative selection in the presence of canavanine and cyloheximide, respectively (see infra), rather than to detect an interacting pair of proteins. With respect to GFP, the natural fluorescence of the protein is detected. In another embodiment, the expression of Reporter Genes that encode proteins can be detected by immunoassay, i.e., by detecting the immunospecific binding of an antibody to such protein, which antibody can be labeled, or alternatively, which antibody can be incubated with a labeled binding partner to the antibody, so as to yield a detectable signal. Alam and Cook (1990, Anal. Biochem. 188:245–254) disclose non-limiting examples of detectable marker genes that can be constructed so as to be operably linked to a transcriptional regulatory region responsive to a reconstituted transcriptional activator used in the method of the invention, and thus used as Reporter Genes. As will be apparent, use of a particular Reporter Gene should be conducted in cells mutant or otherwise lacking in functional versions of the Reporter Gene. Thus, for example, for (positive or negative) selection for URA3 Reporter Gene activity, the host cell should be homozygous mutant (point mutation or deleted or otherwise lacking function of the gene in both alleles) so as to lack endogenous URA3 activity. Similarly, in the use of a LYS2 Reporter Gene., the host cell should be homozygous mutant for LYS2, in the use of a CAN1 Reporter Gene for negative selection, the host cell should be homozygous mutant for CAN1, in the use of a CYH2 Reporter Gene for negative selection, the host cell should be homozygous mutant for CYH2, etc., in cases in which the host cell has an endogenous form of the Reporter Gene.

Figure 3:
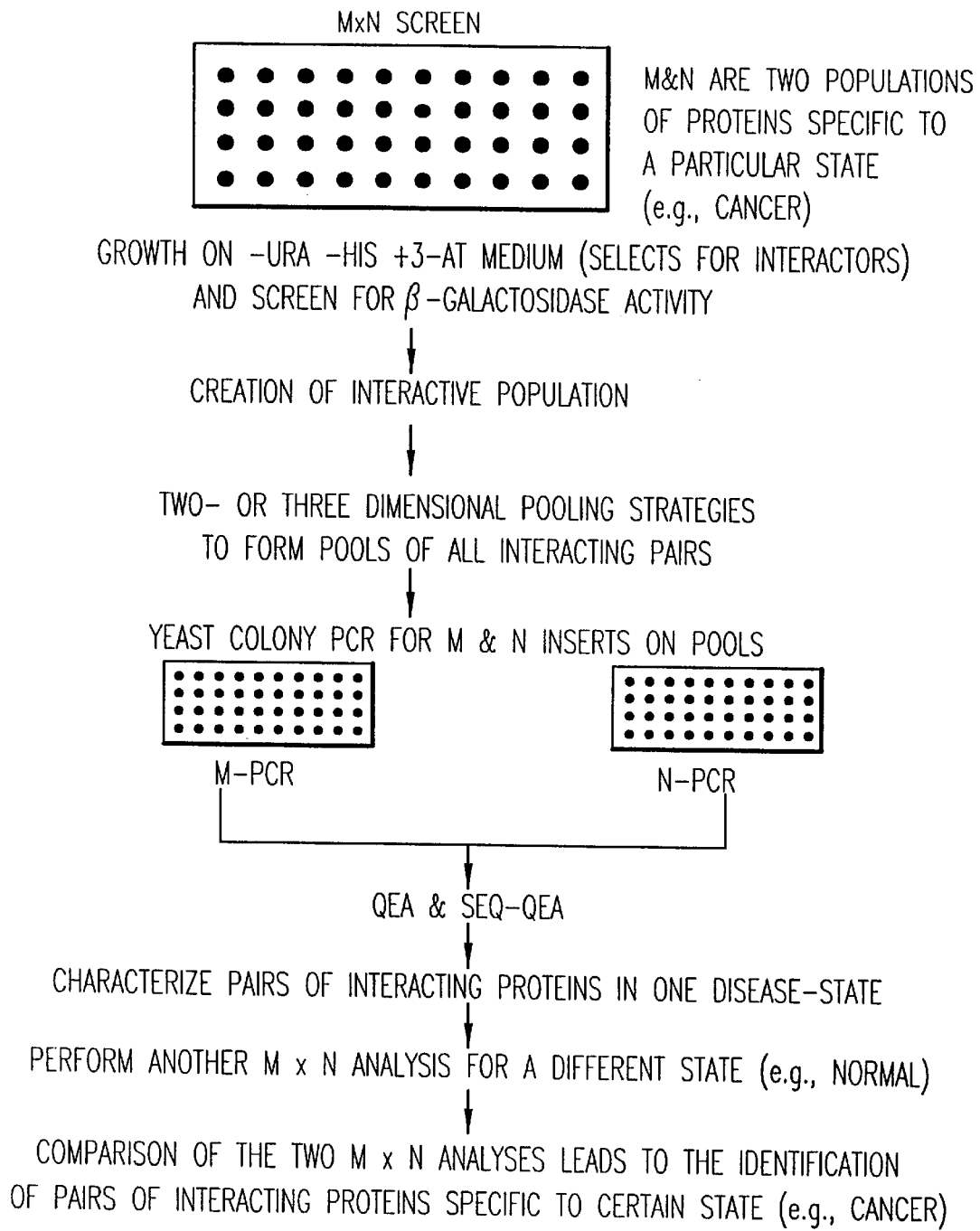

The activation of Reporter Genes like URA3 or HIS3 enables the cells to grow in the absence of uracil or histidine, respectively, and hence serves as a selectable marker. Thus, after mating, the cells exhibiting protein-protein interactions are selected by their abilities to grow in media lacking the requisite ingredient like uracil or histidine, respectively (referred to as -URA (minus URA) and -HIS medium, respectively) (see by way of example Section 6.3–6.5). In a specific embodiment, -HIS medium preferably contains 3-amino-1,2,4-triazole (3-AT), which is a competitive inhibitor of the HIS3 gene product and thus requires higher levels of transcription in the selection (see Durfee et al., 1993, Genes Dev. 7:555–569). Similarly, 6-azauracil, which is an inhibitor of the URA3 gene product, can be included in -URA medium (Le Douarin et al., 1995, Nucl. Acids Res. 23:876–878). Alternatively to detecting URA3 gene activity by selecting in -URA medium, URA3 gene activity can be detected and/or measured by determining the activity of its gene product, orotidine-5'-monophosphate decarboxylase (Pierrat et al., 1992, Gene 119:237–245; Wolcott et al., 1966, Biochem. Biophys. Acta 122:532–534). In other embodiments of the invention, the activities of the reporter genes like lacZ or GFP are monitored by measuring a detectable signal (e.g., fluorescent or chromogenic) that results from the activation of these Reporter Genes. For example, lacZ transcription can be monitored by incubation in the presence of a chromogenic substrate, such as X-gal (5-bromo-4-chloro-3-indolyl-β-D-galactoside), for its encoded enzyme, β-galactosidase. The pool of all interacting proteins isolated by this manner from mating the two libraries is termed the "interactive population" (see by way of example FIG. 3).

In a preferred embodiment of the invention, false positives arising from transcriptional activation by the DNA binding domain fusion proteins in the absence of a transcriptional activator domain fusion protein are prevented or reduced by negative selection for such activation within a host cell containing the DNA binding fusion population, prior to exposure to the activation domain fusion population. By way of example, if such cell contains URA3 as a Reporter Gene, negative selection is carried out by incubating the cell in the presence of 5-fluoroorotic acid (5-FOA, which kills URA+ cells (Rothstein, 1983, Meth. Enzymol. 101:167–180). Hence, if the DNA-binding domain fusions by themselves activate transcription, the metabolism of 5-FOA will lead to cell death and the removal of self-activating DNA-binding domain hybrids. By way of another example, if LYS2 is present as a Reporter Gene in the cell, negative selection is carried out by incubating the cell in the presence of a-amino-adipate (Chatoo et al., 1979, Genetics 93:51), which kills $LYS^+$ cells. In another embodiment, if CAN1 is present as a Reporter Gene in the cell, negative selection is carried out by incubating the cell in the presence of canavanine (CAN1 encodes an arginine permease that renders the cell sensitive to the lethal effects of canavanine) (Sikorski et al., 1991, Meth. Enzymol. 194:302–318). In yet another embodiment, if CYH2 is present as a Reporter Gene in the cell, negative selection is carried out by incubating the cell in the presence of cycloheximide (CYH2 encodes the L29 protein of the yeast ribosome; the wild-type L29 protein is sensitive to cycloheximide which thus blocks protein synthesis, resulting in cell death) (Sikorski et al., 1991, Meth. Enzymol. 194:302–318). Such negative selection with the DNA-binding domain fusion population helps to avoid false positives that become amplified through the preferred processing steps of the invention, and which becomes more troublesome as the complexity of the assayed populations increases. In another embodiment, the DNA-binding domain fusion population can be subjected to negative immunoselection by use of antibodies specific to the expressed protein product of a Reporter Gene; in this embodiment, cells expressing a protein that is recognized by the antibody are removed and the fusion constructs from the remaining cells are kept for use in the interaction assay. In yet another embodiment, negative selection can be carried out by plating the DNA-binding domain fusion population on medium selective for interaction (e.g., minus URA or minus HIS medium if the Reporter Gene is URA3 or HIS3, respectively), following which all the surviving colonies are physically removed and discarded. Negative selection involving the use of a selectable marker as a Reporter Gene and the presence in the cell medium of an agent toxic or growth inhibitory to the host cells in the absence of Reporter Gene transcription is preferred, since it allows high throughput, i.e., a much greater number of cells to be processed much more easily than alternative methods.

As will be apparent, negative selection can also be carried out on the activation domain fusion population prior to interaction with the DNA binding domain fusion population, by similar methods, alone or in addition to negative selection of the DNA binding fusion population.

In another embodiment, negative selection can also be carried out on the recovered pairs of protein interactants, by known methods (see, e.g., Bartel et al., 1993, BioTechniques 14(6):920–924) although pre-negative selection (prior to the interaction assay), as described above, is preferred. For example, each plasmid encoding a protein (peptide or polypeptide) fused to the activation domain (one-half of a detected interacting pair) can be transformed back into the original screening strain, either without any other plasmid, or with a plasmid encoding only the DNA-binding domain, the DNA-binding domain fusion to the detected interacting protein (the second half of the detected interacting pair), or the DNA-binding domain fusion to an irrelevant protein; a positive interaction detected with any plasmid other than that encoding the DNA-binding domain fusion to the detected interacting protein is deemed a false positive and eliminated from further use.

In a preferred embodiment of the invention, the DNA-binding domain library is introduced into a host strain that has URA3 as a reporter gene. This library should not activate transcription by itself. To weed out DNA-binding domain fusions that activate transcription by themselves (carry out negative selection), the yeast transformants containing the DNA-binding domain library are plated out on media that contain the chemical 5-fluoroorotic acid (5-FOA). In order to easily detect the protein-protein interactions between proteins in complex populations as provided by the methods of the present invention, it is preferred to use a host cell containing at least two, preferably three, Reporter Genes (e.g., HIS3, URA3, lacZ operably linked to a DNA binding site of a transcription activator that is recognized by the DNA binding domain part of the fusion protein, in a yeast host cell), and to carry out negative selection among the DNA binding domain-fusion protein population (e.g., by use of 5-FOA and a URA3 Reporter Gene); and to use a yeast mating assay in which the mating is performed on a solid phase, which increases the percentage of productive mating events that can be recovered.

In a specific embodiment, a DNA binding domain fusion library is expressed from a first plasmid population, and a transcription activation domain fusion library is expressed from a second plasmid population, and each plasmid contains a selectable marker. For example, the first plasmid population can express TRP1, and the second plasmid population can express LEU2, or some other gene encoding an essential amino acid so that the presence of the plasmid can be selected for in medium lacking the amino acid. In a preferred embodiment, the first plasmid population is expressed in a yeast strain of a first mating type (selected from between a and α), and which yeast strain is deficient in endogenous URA3 and HIS3, and contains URA3 as a Reporter Gene and optionally also lacZ as a Reporter Gene. In a preferred embodiment, the second plasmid population is expressed in a yeast strain of a second mating type different from the first mating type, which yeast strain is deficient in endogenous URA3 and HIS3, and contains HIS3 as a Reporter Gene and optionally also lacZ as a Reporter Gene. Yeast cells of the first mating type are transformed with the first plasmid population, and are positively selected for the plasmids and are negatively selected for false positive transcriptional activation by incubating the cells in an environment (e.g., liquid medium, and/or solid phase plates) lacking the selectable marker (e.g., tryptophan) and containing 5-FOA. Selected cells are pooled. Yeast cells of the second mating type are transformed with the second plasmid population, and are positively selected for the plasmids by incubating the cells in an environment lacking the appropriate selectable marker, e.g., leucine. Selected cells are pooled. Both groups of pooled cells are mixed together and mating is allowed to occur on a solid phase. The resulting diploid cells are then transferred to selective media, that selects for the presence of each plasmid and for activation of Reporter Genes, i.e., in this embodiment, medium lacking uracil, histidine, tryptophan and leucine, and optionally, also containing 3-amino-1,2,4-triazole.

In specific embodiments, the invention also provides purified cells of a single yeast strain of mating type a, that is mutant in endogenous URA3 and HIS3, and contains functional URA3 coding sequences under the control of a promoter containing GAL4 binding sites, and contains functional lacZ coding sequences under the control of a promoter containing GAL4 binding sites; and also provides purified cells of a single yeast strain of mating type α, that is mutant in endogenous URA3 and HIS3, and contains functional URA3 coding sequences under the control of a promoter containing GAL4 binding sites, and contains functional lacz coding sequences under the control of a promoter containing GAL4 binding sites. A kit is also provided, comprising in one or more containers cells of the foregoing strains. In a specific embodiment, the kit further comprises in one or more containers (a) a first vector comprising (i) a promoter; (ii) a nucleotide sequence encoding a DNA binding domain, operably linked to the promoter; (iii) means for inserting a DNA sequence encoding a protein into the vector in such a manner that the protein is capable of being expressed as part of a fusion protein containing the DNA binding domain; (iv) a transcription termination signal operably linked to the nucleotide sequence; (v) a means for replicating in the cells of the above-described yeast strains; and (c) a second vector comprising (i) a promoter; (ii) a nucleotide sequence encoding an activation domain of a transcriptional activator, operably linked to the promoter; (iii) means for inserting a DNA sequence encoding a protein into the vector in such a manner that the protein is capable of being expressed as part of a fusion protein containing the activation domain of a transcriptional activator; (iv) a transcription termination signal operably linked to the nucleotide sequence; and (v) a means for replicating in the cells of the above-described yeast strains. The means for inserting a DNA sequence can be one or more restriction endonuclease recognition sites suitably located within the vector.

In a preferred embodiment of the invention, after an interactive population is obtained, the DNA sequences encoding the pairs of interactive proteins are isolated by a method wherein either the DNA-binding domain hybrids or the activation domain hybrids are amplified specifically in an individual reaction (see by way of example Section 6.9). Preferably, both the DNA-binding fusion sequences and the activation domain fusion sequences are amplified, in separate respective reactions. Preferably, the amplification is carried out by polymerase chain reaction (PCR) (U.S. Pat. Nos. 4,683,202. 4,683,195 and 4,889,818; Gyllenstein et al., 1988, Proc. Natl. Acad. Sci. USA 85:7652–7656; Ochman et al., 1988, Genetics 120:621–623; Loh et al., 1989, Science 243:217–220; Innis et al., 1990, PCR Protocols, Academic Press, Inc., San Diego, Calif.), using pairs of oligonucleotide primers that are specific to either the DNA-binding domain hybrids or the activation domain hybrids in the PCR reaction (see by way of example Section 6.1.8). This PCR reaction can also be performed on pooled cells expressing interacting protein pairs, preferably pooled arrays of interactants. Other amplification methods known in the art can be used, including but not limited to ligase chain reaction (see EP 320,308) use of Qβ replicase, or methods listed in Kricka et al., 1995, Molecular Probing, Blotting, and Sequencing, chap. 1 and table IX, Academic Press, New York.

In another embodiment of the invention, the plasmids encoding the DNA-binding domain hybrid and the activation domain hybrid proteins are isolated from yeast cells by transforming the yeast DNA into *E. coli* and recovering the plasmids from *E. coli* (see e.g., Hoffman et al., 1987, Gene 57:267–272). This is possible when the plasmid vectors used for both the DNA-binding domain and the activation domain hybrids are shuttle vectors that can replicate both in *E. coli* and in yeast. Many such shuttle vectors are known in the art and can be used. Alternatively, if a shuttle vector is not used, the yeast vector can be isolated, and the insert encoding the fusion protein subcloned into a bacterial expression vector for growth in bacteria. Growing up the interacting clones in bacteria yields large quantities without the use of amplification reactions such as PCR.

5.2. CHARACTERIZATION OF INTERACTIVE POPULATIONS THAT ARE DIFFERENTIALLY EXPRESSED BY A PARTICULAR TISSUE TYPE, DISEASE STATE OR STAGE OF DEVELOPMENT, AND CREATION OF "PROTEIN INTERACTION MAPS"

An important object of the present invention is to provide a method to identify protein-protein interactions that are unique to particular disease states, stages of development, or tissue type. An analysis of the interacting proteins between two populations of proteins ("M×N analysis") performed in parallel on two types of tissue or disease states, wherein both the M and N populations are preferably identical and are derived from the same type of tissue or disease state, will yield the respective interactive protein populations for each type. The differences between the two interactive populations will yield the protein-protein interactions that are characteristic of or unique to a particular tissue type or disease state. Hence, it is desired to identify and isolate the protein-protein interactions that are unique to a complex population. This is preferably achieved by coding, pooling and arraying strategies for the interactants as described below and deconvolution of the arrayed interactants by sequencing a Quantitative Expression Analysis (QEA™ method), SEQ-QEA™ method, and/or other methods that facilitate analysis of the interactants (e.g., SAGE (velculescu et al., 1995, Science 270:484–487). Alternatively, sequencing of individual interactants provides a method for identifying the interacting genes that does not necessarily use pooling or require deconvolution. Thus, in this alternative embodiment, clones of interactants can be recovered, e.g., from the interactant-positive yeast cells, amplified or grown up in bacteria, and subjected to sequence analysis. Sequencing can be carried out by any of numerous methods known in the art (see e.g., Sanger et al., 1977, Proc. Natl. Acad. Sci. USA 74(12):5463–5467). In a specific embodiment, to enhance throughput, a multiplex sequencing analysis can be conducted. For example, in a multiplex sequencing analysis, one can carry out dideoxy sequencing reactions with just one of the dideoxynucleotides, e.g., ddT, using a different dye on the dideoxynucleotide in the reaction with DNA of each of four separate interactant pairs, which reaction products are then pooled together and subjected to electrophoresis. Comparing the pattern of bands formed by DNA of interactant pairs from different populations identifies differences, indicating an interacting protein specific to that population. The DNA for such a protein can then be sequenced fully. Moreover, identical patterns of bands for a single dye between pooled groups identifies interactions which share the same partners, thus saving sequencing DNA encoding a common interacting protein over and over again. This method would raise throughput four-fold.

5.2.1. DETERMINATION OF ALL THE DETECTABLE PROTEIN-PROTEIN INTERACTIONS

Cells containing interacting protein pairs are identified as described above, by detecting Reporter Gene expression. Determining all the detectable pairs of interactions then employs pooling and two sets of deconvolution reactions. The first set characterizes all the "M" interacting partners; the second set characterizes the "N" interacting partners. Preferably, DNA of cells containing interacting proteins is subjected to an amplification reaction that specifically amplifies the DNA-binding fusion sequences and, in a separate reaction, the activation domain fusion sequences. In a preferred embodiment, the characterizations of interacting partners are performed by "the SEQ-QEA™ method" (see infra) on PCR products that were generated with "M" or "N" specific amplification primers, respectively (see by way of example FIG. 3). The. "M"-specific amplification primers hybridize specifically to and amplify sequences from one type of fusion construct, e.g., the DNA binding fusion construct (e.g., by hybridization to vector sequences flanking the inserted variant protein coding sequences of population M that are fused to the DNA binding domain sequences). The "N"-specific amplification primers hybridize specifically to and amplify sequences from the other type of fusion construct, the activation domain fusion construct (e.g., by hybridization to vector sequences flanking the inserted variant protein coding sequence of population N that are fused to the activation domain sequences). The PCR is preferably performed wherein DNA-binding and activation domain fusion specific primers are used to amplify the genes encoding the two interacting proteins directly from yeast (see by way of example Section 6.1.8). This PCR product serves as a reservoir for further analysis, including the QEA™ method, the SEQ-QEA™ method (see infra) and sequencing, that leads to the identification of interacting proteins, in particular, those that are differentially expressed (e.g., stage-specific). The primers used in the PCR reaction may be labelled, e.g., by biotinylation or addition of fluorescent tags and may also serve to introduce specific restriction endonuclease sites.

The labels are useful tools in the subsequent QEA™ method and sequencing.

Thus, in a specific embodiment, DNA isolated from each cell containing each individual pair of interactants is, in separate reactions, subjected to PCR to amplify the DNA encoding the DNA-binding domain fusion protein, and DNA encoding the activation domain fusion protein, respectively. The DNA encoding the DNA-binding domain fusion protein and the DNA encoding the activation domain fusion protein are each subjected to sequencing analysis to determine its sequence and thus the sequence of the interacting protein that formed a part of the fusion protein. In this manner, each individual pair of interactants is identified. Alternative methods that can be used to identify individual pairs of interactants are described in Sections 5.2.2 to 5.2.6.2.

5.2.2. CLASSIFICATION OF THE ARRAYED POOLS OF INTERACTANTS BY THE QEA™ METHOD AND THE SEQ-QEA™ METHOD

A Quantitative Expression Analysis method (QEA™ method) produces signals comprising target subsequence presence and a representation of the length in base pairs along a nucleic acid between adjacent target subsequences by measuring the results of recognition reactions on DNA (e.g., cDNA or genomic DNA) mixtures. A QEA™ method provides an economical, quantitative, and precise classification of DNA sequences, either in arrays of single sequence clones or in mixtures of sequences, without actually sequencing the DNA. Preferably, all the signals taken together have sufficient discrimination and resolution so that each particular DNA sequence in a sample may be individually classified by the particular signals it generates, and with reference to a database of DNA sequences possible in the sample individually determined. These signals are preferably optical, generated by fluorochrome labels and detected by automated optical detection technologies. The signals are generated by detecting the presence or absence of short DNA subsequences within a nucleic acid sequence of the sample analyzed. The subsequences are detected by use of recognition means, or probes for the subsequences. A detailed description of the QEA™ methods is provided in the U.S. patent applications Ser. No. 08/547,214 filed on Oct. 24, 1995, and Serial No. to be assigned, filed on even date herewith, both by Rothberg et al. and entitled "Method and apparatus for classifying, identifying, or quantifying DNA sequences in a sample without sequencing", which are incorporated by reference herein in their entireties. QEA™ methods that can be used are also described in Section 5.4, infra, and, by way of example, in Section 6.1.12.

A QEA™ method reveals the distribution (both qualitative and quantitative) of genes within a population. Thus when comparing two interactive populations to which a QEA™ method is applied, the differential presence of genes between two interactive populations is identified as unique or increased or decreased intensity bands after size separation such as in a denaturing polyacrylamide gel (see by way of example Section 6.1.12). In a preferred embodiment of the invention, the identity of the gene producing each band is determined by a modification of the QEA™ method called the SEQ-QEA™ method (see by way of example Sections 6.1.12.2 and 6.1.12.5). The SEQ-QEA™ method (for Sequencing QEA™) provides a method to identify the 4 terminal nucleotides next to a subsequence that was used as a recognition site in the QEA™ method. Thus, by combining the information from the QEA™ method and the SEQ-QEA™ method, it is possible to classify and identify precisely the DNA sequences present in an interactive population without sequencing. A description of SEQ-QEA™ methods is provided in Section 5.4.4 and, by way of example, in Sections 6.1.12.2 (and its subsections) and 6.1.12.5.

5.2.3. ARRAYING AND CODING STRATEGIES FOR AN INTERACTIVE POPULATION

In a preferred embodiment, "interactive colonies" are arrayed into wells on microtiter plates. "Interactive colonies" are those colonies that emerge as a result of the selection of interacting proteins. A deconvolution strategy allows for a characterization of both members of each pair of interacting proteins (from all the individual wells) without sequencing each pair individually. In this way, the proteins expressed in each well are characterized and statistics can be gathered as to the frequency of the types of interactions. We refer to the catalog of interacting proteins as a "protein interaction map". This characterization can be further used to identify the genes of interest directly or to indicate the specific physical locations in the array of clones that should be sequenced to determine (or confirm) the identities. Thus, this process provides information on protein-protein interactions characterizing a population of interest.

The differences between the patterns of protein interactions in different types of tissue (e.g., diseased versus normal, different stages of development, etc.) provide information that can be much more valuable than the knowledge of the interactions in a single tissue alone. Similarly, expression levels (e.g., as determined by the QEA™ method) yield greater value when they can be correlated with fundamental differences in various tissue samples. A protein interaction map of any given tissue or cell type will contain many non-biological or unimportant interactions. However, a comparison of the interactions taking place between a disease state, and a "normal" state will be very informative, as this process of comparison tends to eliminate the unimportant interactions. Identifying the genes encoding interacting proteins may also provide information on the putative biological functions of the genes of interest, which will help assess which of the interactions detected are likely to take place physiologically (some interactions in the protein interaction map might be artifacts of the method) and be of heightened interest. It can also be valuable to review the differences in protein interaction maps with the results of a QEA™ method or other method of analyzing expression levels (e.g., SAGE (Velculescu et al., 1995, Science 270:484–487; Northern analysis) performed on a cDNA population prior to performing an interaction screen according to the invention. For instance, the appearance of a new interaction in diseased tissue that is not present in normal tissue can be correlated with the QEA™ method or SAGE or Northern analysis measurements of the expression levels of the genes involved in the interaction. Upregulation or co-regulation of the genes would serve to corroborate the protein interaction maps.

5.2.4. MAINTAINING LINKAGE BETWEEN PAIRS OF INTERACTING PROTEINS

The most preferable QEA™ method on the amplified products derived from a pool of interactive colonies identifies the interactions that take place in a sample and identifies the differences between samples while retaining the linkage between a specific gene and the corresponding interacting partner gene of the interacting pair. If the QEA™ method is done on the entire pooled, interacting population and this is compared to another entire population, the linkage between interacting partners in each individual sample (i.e., from each individual colony containing a separate interacting pair) is lost. Preferable pooling strategies are coupled with deconvolution strategies that maintain linkage between the interacting partners and allow identification of the interactive colony that gives rise to each set of interacting partners. The invention provides a method of determining one or more characteristics of or the identities of nucleic acids encoding an interacting pair of proteins from among a population of cells containing a multiplicity of different nucleic acids encoding different pairs of interacting proteins, said method comprising (a) designating each group of cells containing nucleic acids encoding an identical pair of interacting proteins as one point of a multidimensional array in which the intersection of axes in each dimension uniquely identifies a single said group; (b) pooling all groups along a simple axis to form a plurality of pooled groups; (c) amplifying from a first aliquot of each pooled group a plurality of first nucleic acids, each first nucleic acid comprising a sequence encoding a first protein that is one-half of a pair of interacting proteins; (d) amplifying from a second aliquot of each pooled group a plurality of second nucleic acids, each second nucleic acid comprising a sequence encoding a second protein that is the other half of the pair of interacting proteins; (e) subjecting said first nucleic acids from each pooled group to size separation; (f) subjecting said second nucleic. acids from each pooled group to size separation; (g) identifying which at least one of said first nucleic acids are present in samples of first nucleic acids from a pooled group from each axes in each dimension, thereby indicating that said at least one first nucleic acid is present in said array in the group designated at the intersection of said axes in each dimension; and (h) identifying which at least one of said second nucleic acids are present in samples of a second nucleic acid from a pooled group from axes in each dimension, thereby indicating that the said at least one second nucleic acid is present in said array in the group designated at the intersection of said axes in each dimension; in which the first and second nucleic acids that are indicated to be present in said array in a group designated at the same intersection are indicated to encode interacting proteins. In preferred aspects, such a method is applied to colonies of yeast cells, each colony containing nucleic acids encoding a different pair or interacting proteins identified according to a method of the invention. Exemplary pooling and deconvolution strategies are described below.

Pooling and deconvolution strategies can be characterized by the dimensionality of the pooling array. We assume that N distinct colonies containing interacting pairs of proteins have been identified. Sequencing of each pair of interactors individually corresponds formally to a 1-dimensional strategy in which each pool draws from one of the N samples. This yields N pools in total. In higher dimensions, the number of pools required is $$D \times N^{1/D},$$

where D is the number of dimensions. (This assumes a square grid). The maximum number of genes in each pool is the number of colonies contributing to each of the pools. Again assuming a square grid, the maximum number is $$(\text{max genes/pool}) = N^{(D-1)/D},$$

where N is the total number of colonies used in a D-dimensional pooling strategy.

Increasing the dimensionality D reduces the total number of pools but increases the total number of genes that can be in each pool. It is preferable to choose the largest value for D such that the genes in a pool can still be identified. Thus, the optimal pooling strategy, i.e., the preferred choice for D, depends on the number of individual genes that can be identified in a single pool as well as on the total number of interactive colonies.

In order to standardize the pooling and deconvolution strategy, it can be preferable to use a 2-dimensional pooling and deconvolution strategy exclusively. If the size of the interactive population is in the hundreds, then a simple two-dimensional pooling strategy suffices.

Further details of preferred pooling and deconvolution strategies are provided below. In a specific embodiment, strategies are automated.

5.2.5. POOLING STRATEGIES 2-dimensional Pools

Figure 4A:
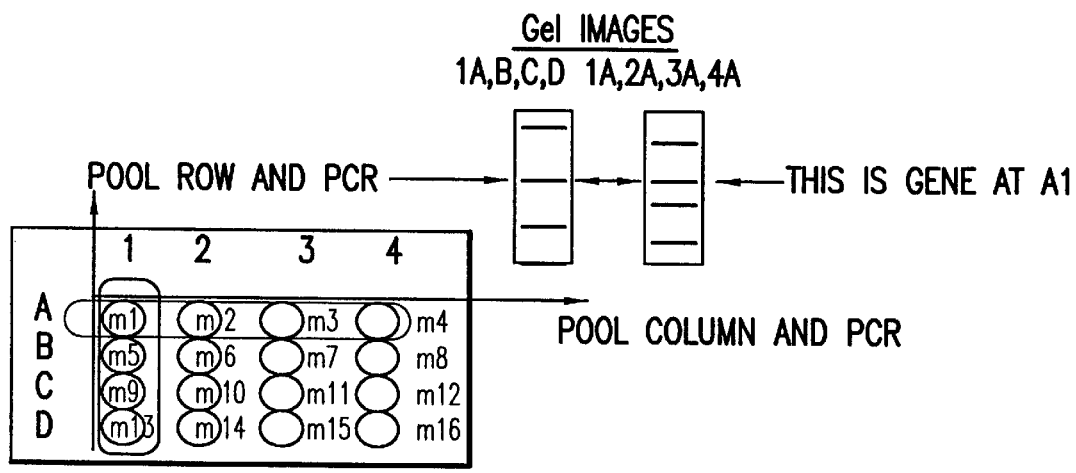

In a preferred embodiment of a 2-dimensional strategy, the interactive colonies are arrayed in a 12×8 grid representing 96 different interactive colonies (as shown in FIG. 4A). The cells from the rows and columns are then pooled together and amplification (preferably PCR) is performed on the pools of interactants. Two sets of amplification (e.g., PCR) reactions, one specific for one kind of the fusion protein (or M) and the other specific for the second kind of fusion protein (or N), are then performed. If the total number of interactants is small (<20), then electrophoretic separation (e.g., by polyacrylamide or agarose gel electrophoresis) of the amplified (e.g., PCR) products is generally sufficient to distinguish the interactants from one another (see FIG. 4A). In that case, comparison of the amplified products from each row and column identifies the interactive colony from which the amplified product originated. That is, the presence of a band in both a sample from a pooled row and a sample from a pooled column indicates that the band is present in the interactive colony present at the intersection of the row and colony. A perfect symmetry (the same PCR product in two rows and columns) indicates either the same pair of interactants repeating or two pairs of interactants that have insert DNAs of identical lengths.

When the number of interactants is greater than 20 and within a few hundred, a 2-dimensional strategy is still sufficient. However, distinct inserts may have the same lengths and may not be separated to adequate resolution, for example, by electrophoresis of PCR products. Therefore, in a preferred embodiment, to aid in the deconvolution, the QEA™ method applied to cDNA populations is performed with a 4-mer or 6-mer recognition subsequence. The length of the recognition subsequence is adjusted to provide a resolvable number of the QEA™ method bands. Because the size of the inserts in interactive populations tends to be in the range of 0.5 to 3 kb when using mammalian cDNA libraries as source of the populations, the use of 6-mer subsequences can necessitate that a large number of reactions be performed in order to ensure that every insert DNA contains two such subsequences and thus has been included in the QEA™ method. The use of 4-mer recognition subsequences provides more frequent cutting and can alleviate this problem. As 4-mer subsequence "hits" occur more frequently than with 6-mer subsequences, the probability of including each interactant in the QEA™ method increases. Furthermore, by limiting the number of interactants in a given pool to 10 to 15, the number of "bands" or genes in a QEA™ method can be limited to about 40, and thus provide an easily analyzable QEA™ method readout that can be used to deconvolute the pools. Exemplary protocols for a QEA™ method that can be used are described in Section 6.1.12 and its subsections (particularly 6.1.12.2).

In a preferred embodiment, the addition of the SEQ-QEA™ method to the above analysis further refines the deconvolution process by imparting more information to each band (see, by way of example, Section 6.1.12.2). Furthermore, the SEQ-QEA™ method aids in uniquely identifying the bands from the QEA™ method reaction. This often is not possible using a the 4-mer QEA™ method alone as the information from such a QEA™ method reaction is generally not sufficient to uniquely identify genes within a eukaryotic cDNA population made from total mRNA. The ability to identify unambiguously the bands in each pool and those in common between pools is the desired outcome of deconvolution. The methods of QEA™ method (preferably 4-mer), preferably in combination with the SEQ-QEA™ method, resolve the identity of the bands in each pool, thus identifying the proteins that appear in an interacting pair, and in common between pools without the need for sequencing of the bands. By such methods, the identified bands that appear, or appear at increased level, after the interaction assay of the invention is carried out wherein a first cDNA population forms both N and M populations, compared to the bands that appear after the interaction assay is carried out with a second cDNA population forming both N and M, identifies differentially expressed proteins between the first and second cDNA populations that mediate protein-protein interactions.

3-dimensional Pools

In the case of large interactive populations, a 3-dimensional coding and pooling strategy (FIGS. 4B–4C) is used. In the illustrated example of FIGS. 4B–4C, a total of 32 pools are used: 12 (pooled columns, 8×12 wells each)

Figure 4B:
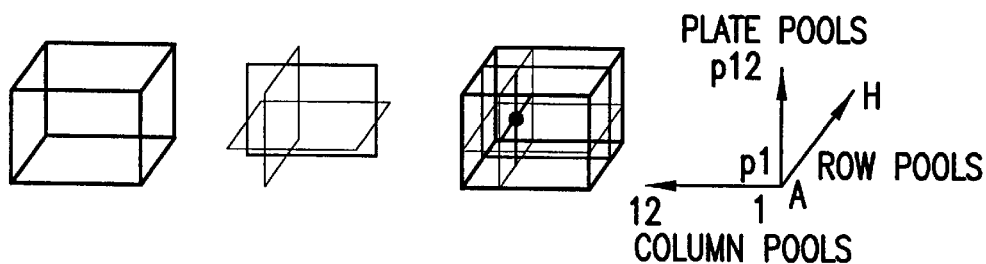
Figure 4C:
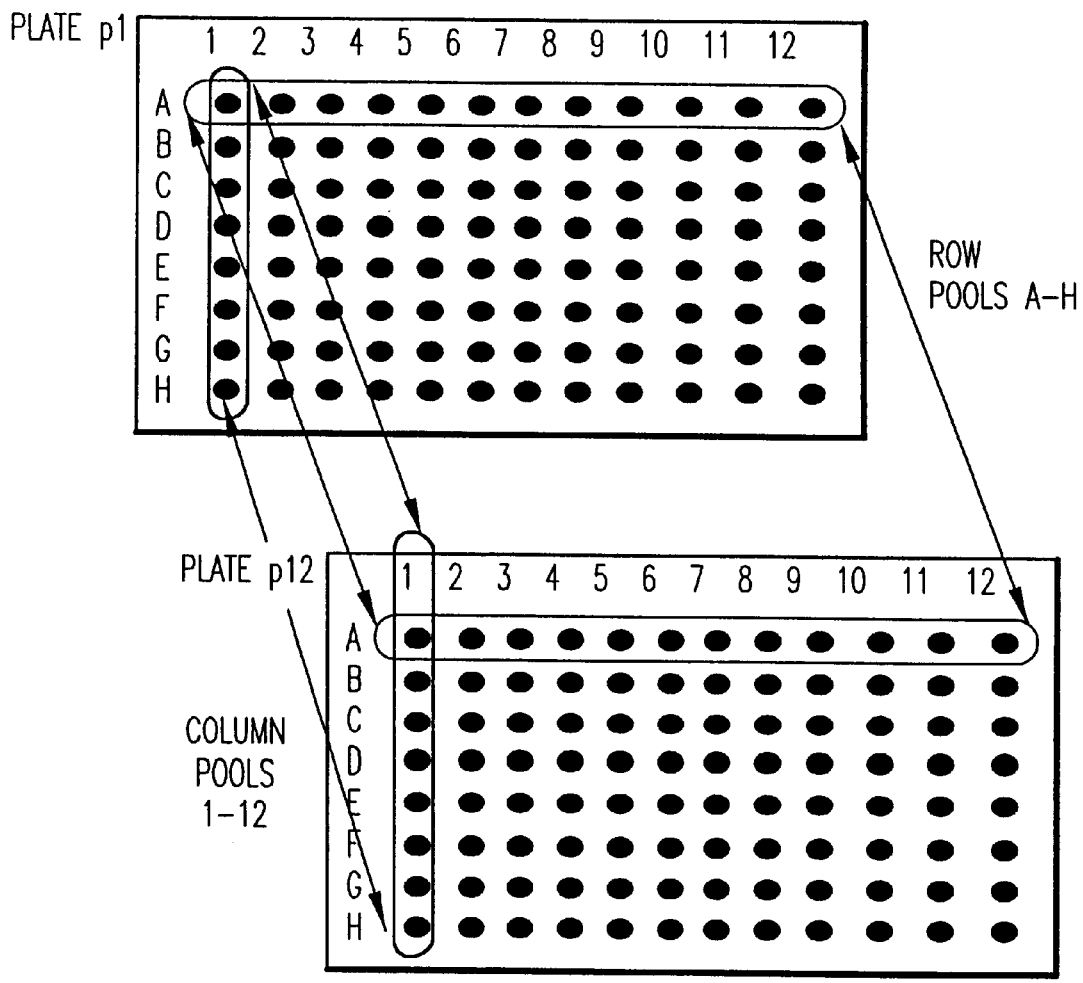

+8 (pooled rows, 144 wells)+12 (pooled plates, 96). Each pool will have a maximum of 144 genes (FIGS. 4B–4C). The QEA™ method and SEQ-QEA™ method are performed on the PCR products derived from each pool (separately for the DNA-binding fusions, and the activation fusions, respectively), and the intersection of three pooling dimensions is used to identify the gene at each location. The SEQ-QEA™ method based on 4-mer subsequences may not be easy to interpret due to the large number of bands (genes) in each pool. Therefore, it can be preferable to use a large number of less common subsequence pairs (6-mers instead of 4-mers) to discriminate between all the genes present.

5.2.6. ALTERNATIVE STRATEGIES TO CHARACTERIZE INTERACTIVE POPULATIONS

5.2.6.1. SEQUENCE-BASED STRATEGIES TO IDENTIFY PAIRS OF INTERACTING PROTEINS

An alternative strategy involving gene-specific PCR provides means to identify the pair of genes coding for each set of interacting proteins, as described hereinbelow. The QEA™ method performed on the interactive populations identifies 'difference' bands (bands that differentiate one interactive population from the other). In a pooling strategy, in which different colonies are pooled together before the QEA™ method, it is preferable to have means to indicate which colony gave rise to each band. This section describes means for performing sequencing studies to identify which colony gives rise to each band. The methods in this section are based on sequencing, which also provides the identity of the sequence generating each QEA™ method band in question, the same sequences that encode the proteins responsible for the interactions.

A QEA™ method band includes knowledge of specific sub-sequences (which the recognition means, used in the QEA™ method reaction, detect). Specific PCR primers are designed based on these sub-sequences so as to be able to hybridize to and thus amplify only those bands in a pooled population that contain these sub-sequences. Thus, these PCR primers are used to screen by PCR the entire interactive population. This is done by performing PCR with gene-specific primers, preferably on the original stored PCR products (both the DNA-binding domain-specific and activation domain-specific PCR products), when pooled according to the two-dimensional or three-dimensional pooling strategies described above. A specific PCR product will be observed only if the particular PCR pool contains the gene that gives rise to the QEA™ method band. Deconvolution strategies can be carried out as described above. Thus, e.g., a PCR product appearing at the intersection of a pooled row and pooled column (or pooled plate, in a three-dimensional strategy) indicates that such PCR product arose from the colony situated at such intersection, and indicates that such PCR product contains the subsequences to which the primers were designed to hybridize. By this method, the original mating pair that gives rise to the QEA™ method band can be identified and the sequence of the two genes that encode the interacting proteins can be confirmed by sequencing the respective DNA-binding domain and activation domain plasmids after isolating these plasmids from the relevant colony.

5.2.6.2. CREATION OF INTERACTIVE-GRIDS

Figure 5:
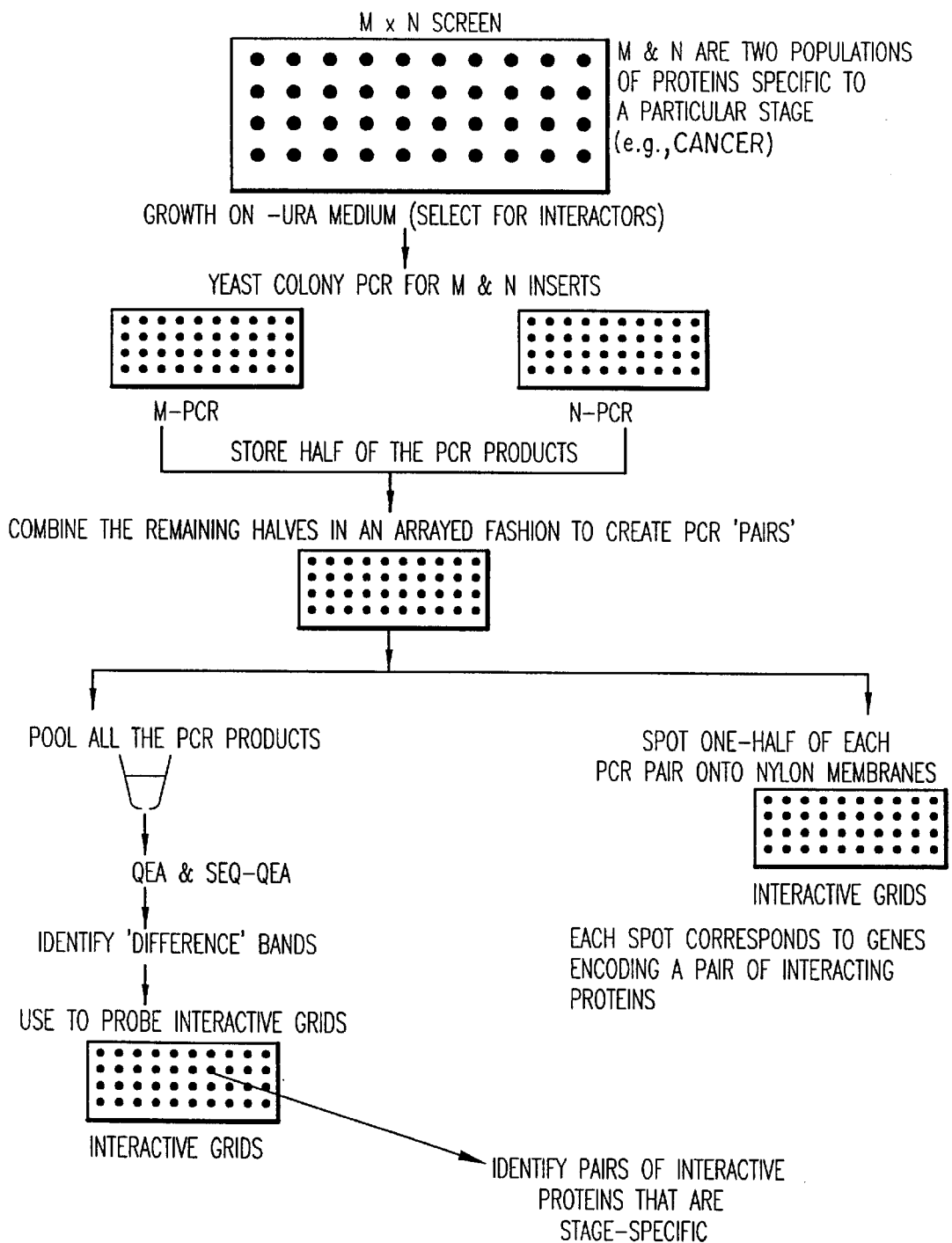

As a variation of the PCR-based strategy, a hybridization-based strategy can also be used to identify interacting proteins that are in an interactive population, or that are unique to such population. The PCR products from each of the interactive colonies (the DNA-binding domain-specific amplified products and the activation domain-specific amplified products, respectively) are spotted onto a membrane thus creating an "interactive grid". Preferably, the DNA binding domain-specific products and the DNA activation domain specific products from a single colony are spotted together in a single spot. This interactive grid is then probed with a band of interest that has been identified and isolated through the QEA™ method process. If the band of interest is a band that, through the QEA™ method, has been identified as an interacting band that is present only in one population and not another, this method yields the identity of interacting proteins unique to the population in which such band is present. Probes for this purpose can be prepared by labeling the QEA™ method band(s) of interest with radioisotopes, degoxigenin, biotin (detectable by its ability to bind to streptavidin, e.g., conjugated to an enzyme), fluorescent tags, or other detectable labels known in the art. The spots on the interactive grid are contacted with the probe under conditions conducive to hybridization. Spots that hybridize thus pinpoint the pair of interacting proteins that are unique to an interactive population (FIG. 5). A sequence analysis of these genes yields the identities of the interacting proteins.

5.2.7. STATISTICAL CONSIDERATIONS FOR DETECTING ALL POSSIBLE INTERACTIONS AMONG GENES THAT ARE EXPRESSED AT DIFFERENT LEVELS

In a library of $1 \times 10^6$ individual clones, taking into account that only sense strand cDNAs are cloned and thus one in every three will be in the proper reading frame, and that each gene has approximately 4 domains, there will be about 80 copies of each domain of a gene that is expressed at the high level of 1 in a 1000 transcripts within a cell $[(\frac{1}{3} \times \frac{1}{4} \times \frac{1}{1000} \times 10^6)]$. After transformation into yeast, if there are $5 \times 10^5$ individual transformants, then there will be 40 copies of each domain of a gene that was originally expressed at a 1 in a 1000 level $[80 \times (5 \times 10^5) \div (1 \times 10^6)]$. These guidelines can be used to calculate the number of copies of genes expressed at other levels. For instance, if a gene is expressed at a 1 in 5000 level, a library of $2.5 \times 10^6$ transformants in yeast will be contain roughly $2.5 \times 10^6 \times (\frac{1}{3} \times \frac{1}{4} \times \frac{1}{5000}) = 40$ copies of each gene.

For a given sample size, it is possible to calculate the number of matings that are expected to yield a pair of interacting proteins. Suppose that gene X and gene Y are expressed at a level of 1 in 1000, and that domains of these two genes interact. The fractions of cells bearing the proper domain of each protein are Fraction of cells bearing Gene X=$1/(3 \times 4 \times 1000)=\frac{1}{12,000}$;
Fraction of cells bearing Gene Y=1/12,000.

The number of matings that bring together the interacting domains of gene X and gene Y is X-Y matings=(total number of matings)×(mating efficiency)×(fraction bearing gene X)×(fraction bearing gene Y).

Assuming a mating efficiency of 25%, this yields the number of X-Y matings as:

X-Y matings=(total number of matings)/$5.8 \times 10^8$

Therefore, the total number of matings that must be performed to expect to see one productive X-Y mating is, on average, total number of matings=$5.8 \times 10^8$. This is a statistical estimate of the number of matings; performing this number of matings will result in a productive X-Y mating roughly 50% of the time. To raise the probability of obtaining a productive mating, it is preferable to perform even more matings. An exemplary goal is a 95% confidence level that an interaction will be retrieved, which requires 3X over-sampling according to probability theory arguments. For genes expressed at a level of 1 in 1000, the number of matings for 95% confidence is $1.7 \times 10^9$.

For genes that are expressed at moderate to low levels, by calculations similar to those described above, the snumber of matings for 95% confidence is as follows:

TABLE 1

| Expression Level | Number of Matings |
| --- | --- |
| 1 in 5000 | $8.5 \times 10^9$ |
| 1 in 10,000 | $1.7 \times 10^{10}$ |
| 1 in 50,000 | $8.5 \times 10^{10}$ |
| 1 in 100,000 | $1.7 \times 10^{11}$ |

Thus, in a preferred embodiment, to detect all detectable interactions that occur between genes that are highly expressed in mammalian cells, by assaying interactions between two populations that are cDNA of substantially total mRNA from a cell, at least $5.8 \times 10^8$, or more preferably at least $1 \times 10^9$, or $1.7 \times 10^9$ matings between yeast cells in the preferred yeast interaction mating assays are done. (By way of clarification, $1.7 \times 10^9$ matings means mixing $1.7 \times 10^9$ cells together of each fusion population for a total of $3.4 \times 10^9$ cells.) The methods described herein allow achievement and selection of these numbers of matings, as well as the increased number of matings shown in Table 1. In various specific embodiments, at least $1 \times 10^8$, $1.7 \times 10^9$, $8.5 \times 10^9$, $1.7 \times 10^{10}$, $8.5 \times 10^{10}$, or $1.7 \times 10^{11}$ matings are carried out and Reporter Gene activity is tested for in the mated cells, per interaction assay.

5.3. INTEGRATED ISOLATION OF INHIBITORS OF AN INTERACTIVE POPULATION

The present invention also provides methods for identifying inhibitors or enhancers of protein-protein interactions. The method of identifying inhibitors provided by the invention provides for greater ease and higher throughput than prior art methods, inter alia, through the ability to select for inhibitors based on cell survival. The present invention is particularly valuable in that it enables one to identify not only the interacting proteins that are unique to or characteristic of a particular situation, but also enables the identification of inhibitors of such interactions. The invention provides a method of detecting an inhibitor of a protein-protein interaction comprising (a) incubating a population of cells, said population comprising cells recombinantly expressing a pair of interacting proteins, said pair consisting of a first protein and a second protein, in the presence of one or more candidate molecules among which it is desired to identify an inhibitor of the interaction between said first protein and said second protein, in an environment in which substantial death of said cells occurs (i) when said first protein and second protein interact, or (ii) if said cells lack a recombinant nucleic acid encoding said first protein or a recombinant nucleic acid encoding said second protein; and (b) detecting those cells that survive said incubating step, thereby detecting the presence of an inhibitor of said interaction in said cells. In a preferred aspect, the population of cells comprises a plurality of cells, each cell within said plurality recombinantly expressing a different said pair of interacting proteins. In various embodiments, the plurality of cells consists of at least 10, at least 100, or at least 1000 cells (corresponding to different pairs of interacting proteins being assayed in a single assay). In a preferred embodiment, the pair(s) of interacting proteins in the cells being assayed consist of a first fusion protein and a second fusion protein, each said first fusion protein comprising a first protein sequence and a DNA binding domain; each said second fusion protein comprising a second protein sequence and a transcriptional activation domain of a transcriptional activator; and in which the cells contain a first nucleotide sequence operably linked to a promoter driven by one or more DNA binding sites recognized by said DNA binding domain such that an interaction of said first fusion protein with said second fusion protein results in increased transcription of said first nucleotide sequence, and in which the cells are incubated in an environment in which substantial death of the cells occurs (i) when increased transcription occurs of the first nucleotide sequence or (ii) if the cells lack a recombinant nucleic acid encoding the first fusion protein or a recombinant nucleic acid encoding the second fusion protein. The cells in which the assay is carried out are preferably (but need not be) yeast cells, which can be haploid or diploid.

In a specific embodiment, an assay for the presence of an interacting protein pair is carried out as described in the sections supra, except that it is done in the presence of one or more candidate molecules which it is desired to screen for the ability to affect an interaction between a protein-protein pair that results in transcription from the Reporter Gene. An increase or decrease in Reporter Gene activity relative to that present when the one or more candidate molecules are absent indicates that the candidate molecule has an effect on the interacting pair. For example, a decrease in (e.g., absence of) Reporter Gene activity that would otherwise occur in the absence of a candidate molecule, due to the presence of an interacting pair, indicates that the candidate molecule is an inhibitor of the interaction exhibited by the protein pair. In a preferred embodiment, selection of positive interactants (colonies) is carried out; these colonies are exposed to candidate inhibitor molecule(s) and are selected again, this time for lack of interaction (e.g., by selection for survival in medium containing 5-FOA wherein URA3 is a Reporter Gene, or by selection for survival in medium containing α-amino-adipate wherein LYS2 is a Reporter Gene, or the other methods of negative selection described in Section 5.1 above; selection of cells that do not display a signal generated by a Reporter Gene (e.g., in the case of lacZ, by activity on the β-gal substrate X-gal (5-bromo-4-chloro-3-indolyl-β-D-galactoside)). The environment in which selection is carried out preferably also selects for the presence of the recombinant nucleic acids encoding the interacting pair of proteins. Thus, for example, the proteins are expressed from plasmids also expressing a selectable marker, thus facilitating this selection.

For detecting an inhibitor, candidate inhibitor molecules can be directly provided to a cell containing an interacting pair, or, in the case of candidate protein inhibitors, can be provided by providing their encoding nucleic acids under conditions in which the nucleic acids are recombinantly expressed to produce the candidate proteins within the cell. The recombinantly expressed candidate inhibitors preferably comprise a nuclear localization signal to facilitate their import into the nucleus and exposure to the interacting protein pair.

Figure 6:
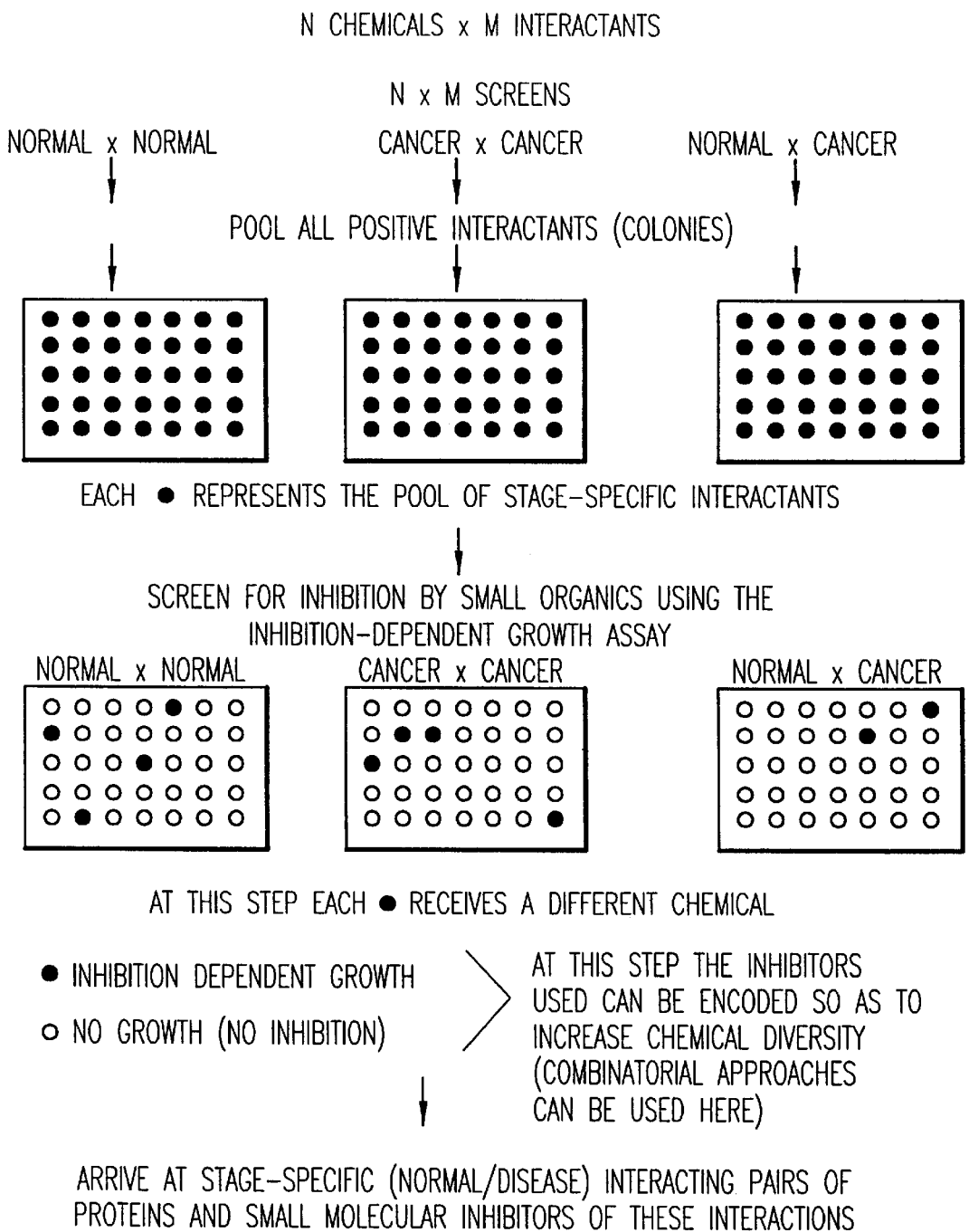

A preferred exemplary method for detecting the presence of inhibitors of protein-protein interactions is shown in FIG. 6. The interactive population is grown in a 96-well format with each well containing 200 μl of media. If the two interacting proteins are plasmid-borne then the media preferably selects for maintenance of the plasmids, e.g., the media lacks those markers, like tryptophan or leucine that allow selection for the plasmids bearing TRP1 or LEU2, respectively. (This maintenance of selective pressure is obviated if the genes encoding the two proteins are not plasmid-borne but have been integrated into the chromosome instead). Each well contains all the colonies that were identified as containing protein interactants from an N×M assay of protein interactions according to the invention. Thus, each well is representative of all the interactive proteins present in a particular population. In the preferred embodiment of the invention, the Reporter Gene used for selection of interaction and selection of inhibition of interaction is the URA3 gene. Interaction between the two fusion proteins causes the yeast to grow in the absence of uracil, allowing selection of the interacting colonies. However, activation of the URA3 gene causes the yeast to die in medium containing the chemical 5-fluoroorotic acid (5-FOA; (Rothstein, 1983, Meth. Enzymol. 101:167–180)). After a growth period that is sufficient for early log-phase growth (a cell density of about $1 \times 10^7$ cells/ml), the cells are exposed to inhibitor(s) for 1–2 hours. Then an appropriate dilution of the cells is transferred to a 96-well plate containing 200 μl media lacking uracil to activate the transcription of the URA3 gene as a result of interaction between the two hybrid proteins in the presence of inhibitor(s). After this, an appropriate dilution of the cells is transferred to a 96-well plate containing 200 ml media made up of 5-FOA and the inhibitor(s). At this step an alternative is to transfer 1 μl onto a 96-slot grid on solid media containing 5-FOA and the inhibitor(s) at the desired concentration.

Growth will be evident only in those instances where inhibition of the protein-protein interaction occurs. As a preferred control, all the cells should be able to grow in the absence of 5-FOA but in the presence of the inhibitor. Thus, in a single screen, the inhibitor and the pair of interacting proteins it inhibits are identified. The identities of the interacting proteins that are inhibited are revealed by characterizing the genes that encode these interacting proteins.

The presence of more than one inhibited pair in a well would be indicated, e.g., by sequence analysis. In such an instance, the cells surviving in -the presence of 5-FOA can be diluted, and the inhibition assay repeated. Ultimately, the cells are diluted and streak-purified so as to isolate single colonies representing a single pair of interacting proteins. Then the inhibition assay is repeated on these streak-purified isolates.

In the 96-well format of this assay, the activity of a lacZ Reporter Gene can also be assayed enzymatically. The activity of the lacZ gene can be determined by assaying the β-galactosidase levels. This can be done in a high through-put fashion as chemiluminescent assays or fluorescent assays using substrates that are chemiluminescent (Jain and Magrath, 1991, Anal. Biochem. 199:119–124) or fluorescent (Fluoreporter lacZ/β-galactosidase quantitation kit from Molecular Probes Inc.).

Use of a Reporter Gene that encodes a selectable marker (e.g., URA3 or LYS2) that can be negatively selected against is preferred over the sole use of a Reporter Gene that encodes a detectable marker (e.g., lacZ), since negative selection for a selectable marker can be carried out on each of multiple interacting pairs within a single well, thus allowing "multiplex" analysis (analysis of pools of cells containing interacting pairs in one well), thus increasing throughput. This is because in the use of negative selection, survival of any cells indicates that at least one inhibited pair is present; in contrast, lack of detection of a detectable marker occurs only if all interacting pairs in the well are inhibited, while detection of a detectable marker indicates that at least one interacting pair in the well is not inhibited but does not indicate whether or not any of the other potential pairs present are inhibited.

This embodiment of the invention is well suited to screen chemical libraries for inhibitors of protein-protein interactions.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective inhibitor. Thus, in many combinatorial approaches, the position on a plate of a compound specifies that compound's composition. Also, in one example, a single plate position may have from 1–20 chemicals that can be screened by administration to a well containing the interactions of interest. Thus, if positive inhibition is detected, smaller and smaller pools of interacting pairs can be assayed for inhibition. By such methods, many inhibitors can be screened against many interactors (see, e.g., FIG. 6).

Many diversity libraries suitable for use are known in the art and can be used to provide compounds to be tested as inhibitors according to the present invention. Alternatively, libraries can be constructed using standard methods. Chemical (synthetic) libraries, recombinant expression libraries, or polysome-based libraries are exemplary types of libraries that can be used.

The libraries can be constrained or semirigid (having some degree of structural rigidity), or linear or nonconstrained. The library can be a cDNA or genomic expression library, random peptide expression library or a chemically synthesized random peptide library. Expression libraries are introduced into the cells in which the inhibition assay occurs, where the nucleic acids of the library are expressed to produce their encoded proteins.

In one embodiment, the peptide libraries used in the present invention may be libraries that are chemically synthesized in vitro. Examples of such libraries are given in Houghten et al., 1991, Nature 354:84–86, which describes mixtures of free hexapeptides in which the first and second residues in each peptide were individually and specifically defined; Lam et al., 1991, Nature 354:82–84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709–710, which describes split synthesis and T-bag synthesis methods; and Gallop et al., 1994, J. Medicinal Chemistry 37(9): 1233–1251. Simply by way of other examples, a combinatorial library may be prepared for use, according to the methods of Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; or Salmon et al., 1993, Proc. Natl. Acad. Sci. USA 90:11708–11712. PCT Publication No. WO 93/20242 and Brenner and Lerner, 1992, Proc. Natl. Acad. Sci. USA 89:5381–5383 describe "encoded combinatorial chemical libraries," that contain oligonucleotide identifiers for each chemical polymer library member. Compounds synthesized so as to be immobilized on a substrate are released from the substrate prior to use in the inhibition assay.

Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708–4712) may be used.

Conformationally constrained libraries that can be used include but are not limited to those containing invariant cysteine residues which, in an oxidizing environment, crosslink by disulfide bonds to form cystines, modified peptides (e.g., incorporating fluorine, metals, isotopic labels, are phosphorylated, etc.), peptides containing one or more non-naturally occurring amino acids, non-peptide structures, and peptides containing a significant fraction of γ-carboxyglutamic acid.

Libraries of non-peptides, e.g., peptide derivatives (for example, that contain one or more non-naturally occurring amino acids) can also-be used. One example of these are peptoid libraries (Simon et al., 1992, Proc. Natl. Acad. Sci. USA 89:9367–9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, Proc. Natl. Acad. Sci. USA 91:11138–11142).

The members of the libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γ-Abu, ε-Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, Nα-methyl amino acids, fluoro-amino acids and amino acid analogs in general. Furthermore, the amino acid can be D (dextrorotary) or L (levorotary).

A specific embodiment of this invention uses mutant strains of yeast that have a mutation in at least one gene coding for a cell wall component, thereby having modified cell walls that are more permeable to exogenous molecules than are wild-type cell walls, thus facilitating the entry of chemicals into the cell, and rendering such yeast cells preferred for an inhibition assay in which exogenous candidate inhibitor compounds are provided directly to the cell. In one embodiment, mutations in the gene KNR4 in *Saccharomyces cerevisiae* cause the cell wall to be more permeable to chemicals like X-gal, while not affecting general growth (Hong et al., 1994, Yeast 10:1083–1092). The reporter strains are made mutant with respect to gene KNR4 to facilitate entry of inhibitor compounds. Similarly, in other embodiments, mutations in genes that influence the cell wall integrity (reviewed in Stratford, 1994, Yeast 10:1741–1752) are incorporated into the reporter strain so as to make the cell wall more permeable.

In a specific embodiment of the invention, the prospective inhibitors are peptides that are genetically encoded and either plasmid-borne or are introduced into the chromosome through homologous recombination. The peptides to be screened are thus provided by recombinant expression within the cell in which the inhibition assay occurs. The peptides are preferably expressed as a fusion to a nuclear localization sequence. The interactive population (preferably the entire population) from an M×N screen is pooled together and then transformed with a library of plasmids encoding peptides to be tested as potential inhibitors. Alternatively, genes encoding the peptides are introduced directly into the chromosome by first cloning the genes into an integration plasmid containing the yeast sequences that donate the site necessary for homologous recombination. The transformed yeast cells are then plated on media that selects for inhibition events. In the preferred embodiment of the invention, the reporter gene for interaction and inhibition of the interaction will be the URA3 gene. Thus, transformants that emerge in media containing 5-FOA represent peptide inhibitors that inhibit specific protein-protein interactions.

In another embodiment, DNA from a microorganism that reconstitutes synthetic pathways for a compound (see Hutchinson, 1994, Bio/Technology 12:375–380; Alvarez et al., 1996, Nature Biotechnology 14:335–338) can be introduced into the cell in which the inhibition assay takes place, so as to be recombinantly expressed by the cell such that the compound is synthesized within the cell. If the synthesized compound blocks the protein interactants, such cells containing an inhibitor of the interacting pair can be detected by methods as described above. By sequencing the DNA in the cells in which inhibition of the interactants has thus occurred, a novel inhibitory compound can be identified.

The identities of the peptide inhibitors are deciphered by the isolation and sequencing of the plasmids that encode these peptides. The identities of the pair of interacting proteins, whose interaction has been inhibited by the peptide, are identified by isolation and sequencing the plasmids that encode these two proteins. The sequences of the inhibitor peptide and those of the interacting proteins can also be obtained by amplifying the protein and peptide encoding region by PCR or other methods and sequencing of the same. Specific primers can be used to amplify the peptide or the DNA-binding fusion protein or the activation domain fusion protein.

In a particular embodiment of the invention, cells are incubating in the presence of candidate inhibitor molecules by expressing such molecules within the cell from recombinant nucleic acids comprising the following operably linked components (a) an ADC1 promoter; (b) a nucleotide sequence encoding a candidate molecule fused to a nuclear localization signal; and (c) an ADC1 transcription termination signal (see e.g., Section 6.8). In a particular embodiment, the candidate molecules are expressed from purified expression vectors comprising the following components: (a) a promoter active in yeast; (b) a first nucleotide sequence encoding a peptide of 20 or fewer amino acids fused to a nuclear localization signal, said first nucleotide sequence being operably linked to the promoter; (c) a transcription termination signal active in yeast, operably linked to said first nucleotide sequence; (d) means for replicating in a yeast cell; (e) means for replicating in *E. coli*; (f) a second nucleotide sequence encoding a selectable marker for selection in a yeast cell, operably linked to a transcriptional promoter and transcription termination signal active in yeast; and (g) a third nucleotide sequence encoding a selectable marker for selection in *E. coli*, operably linked to a transcriptional promoter and transcription termination signal active in *E. coli*. The means for inserting is preferably one or more suitably located restriction endonuclease recognition sites; the means for replicating in a yeast cell can be any suitable origin of replication; the means for replicating in *E. coli* can be any suitable origin of replication. The invention provides expression vectors which can be used for expression of candidate inhibitor molecules, such as a purified expression vector comprising the following components: (a) an ADC1 promoter; (b) a first nucleotide sequence encoding a nuclear localization signal, operably linked to the promoter; (c) means for inserting a DNA sequence into the vector in such a manner that a protein encoded by the DNA sequence is capable of being expressed as part of a fusion protein containing the nuclear localization signal; (d) an ADC1 transcription termination signal, operably linked to the first nucleotide sequence; (e) means for replicating in a yeast cell; (f) means for replicating in *E. coli*; (g) a second nucleotide sequence encoding a selectable marker for selection in a yeast cell, operably linked to a transcriptional promoter and transcription termination signal active in yeast; and (h) a third nucleotide sequence encoding a selectable marker for selection in *E. coli*, operably linked to a transcriptional promoter and transcription termination signal active in *E. coli*.

5.4. THE QEA™ METHOD

5.4.1. QUANTITATIVE EXPRESSION ANALYSIS METHOD, GENERALLY

According to a Quantitative Expression Analysis ("QEA™") method, to uniquely identify an expressed gene sequence, full or partial, and many components of genomic DNA, it is not necessary to determine actual, complete nucleotide sequences of samples. Full sequences provide far more information than is needed to merely classify or determine a gene according to the QEA™ method.

In a QEA™ method, expressed sequences are recognized by codes which are constructed from signals which represent the presence of short nucleic acid (preferably DNA) subsequences (hereinafter called "target subsequences") in the sample sequence and include a representation of the length along the sample sequence between adjacent target subsequences. The presence of these subsequences is recognized by subsequence recognition means, including, but not limited to, restriction endonucleases (hereinafter called "REs"), DNA binding proteins, and oligomers ("probes") hybridizable to DNA made of, for example, peptide nucleic acids (hereinafter called "PNAs") (See, e.g., Egholm et al., 1993, Nature 365:566–67) or DNAS. The subsequence recognition means allow recognition of specific DNA subsequences by the ability to specifically bind to or react with such subsequences. A QEA™ method, and particularly its computer methods, are adaptable to any subsequence recognition means available in the art. Acceptable subsequence recognition means preferably precisely and reproducibly recognize target subsequences and generate a recognition signal of adequate signal to noise ratio for all genes, however rare, in a sample, and can also provide information on the length between target subsequences.

In some QEA™ embodiments, the presence of target subsequences is directly recognized by direct subsequence recognition means, including, but not limited to, REs and other DNA binding proteins, which bind and/or react with target subsequences, and oligomers of, for example, PNAs or DNAs, which hybridize to target subsequences. In other embodiments, the presence of effective target subsequences is recognized indirectly as a result of applying protocols, such as a SEQ-QEA™ method, or e.g., involving multiple DNA binding proteins together with hybridizing oligomers. In this latter case, each of the multiple proteins or oligomers recognizes a separate subsequence and an effective target subsequence is the combination of the separate subsequences. A preferable combination is subsequence concatenation in the situation where all the separately recognized subsequences are adjacent. Such effective target subsequences can have advantageous properties not achievable by, for example, REs or PNA oligomers alone. However, the QEA™ method, and particularly its computer methods, are adaptable to any acceptable subsequence recognition means available in the art. The computer implemented analysis and design methods treat target subsequences and effective target subsequences in the same manner.

The signals contain representations of target subsequence occurrences and a representation of the length between target subsequence occurrences. In various embodiments of the QEA™ method these representations may differ. In embodiments where the target subsequences are exactly recognized, as where REs are used, subsequence representation may simply be the actual identity of the subsequences. In other embodiments where subsequence recognition is less exact, as where short oligomers are used, this representation may be "fuzzy". It may, for example, consist of all subsequences which differ by one nucleotide from the target, or some other set of possible subsequences, perhaps weighted by the probability that each member of the set is the actual subsequence in the sample sequence. Further, the length representation may depend on the separation and detection means used to generate the signals. In the case of electrophoretic separation, the length observed electrophoretically may need to be corrected, perhaps up to 5 to 10%, for mobility differences due to average base composition differences or due to effects of any labeling moiety used for detection. As these corrections may not be known until target sequence recognition, the signal may contain the electrophoretic length in base pairs (hereinafter called "bp") and not the true physical length in bp. For simplicity and without limitation, in most of the following description unless otherwise noted the signals are presumed to represent the information conveyed exactly, as if generated by exact recognition means and error or bias free separation and detection means. However, in particular embodiments, target subsequences may be represented in a fuzzy fashion and length, if present, with separation and detection bias present.

Target subsequences recognized are typically contiguous. This is required for all known REs. However, oligomers recognizing discontinuous subsequences can be used and can be constructed by inserting degenerate nucleotides in any discontinuous region.

A QEA™ method is adaptable to analyzing any DNA sample for which exists an accompanying database listing possible sequences in the sample. More generally, a QEA™ method is adaptable to analyzing the sequences of any biopolymer, built of a small number of repeating units, whose naturally occurring representatives are far fewer that the number of possible, physical polymers and in which small subsequences can be recognized. Thus, it is applicable to not only naturally occurring DNA polymers but also to naturally occurring RNA polymers, proteins, glycans, etc. Typically and without limitation, however, a QEA™ method is applied to the analysis of cDNA samples from any in vivo or in vitro sources.

A QEA™ method probes a sample with recognition means, the recognition means generating signals, a preferred signal being a triple comprising an indication of the presence of a first target subsequence, an indication of the presence of a second target subsequence, and a representation of the length between the target subsequences in the sample nucleic acids sequence. Each pair of target subsequences may occur more than once in a sample nucleic acid, in which case the associated lengths are between adjacent target subsequence occurrences.

The QEA™ method is preferred for classifying and determining sequences in cDNA mixtures, but is also adaptable to samples with only one sequence. It is preferred for mixtures because it affords the relative advantage over prior art methods that cloning of sample nucleic acids is not required. Typically, enough distinguishable signals are generated from pairs of target subsequences to recognize a desired sequence in a sample mixture. For example, first, any pair of target subsequences may hit more than once in a single DNA molecule to be analyzed, thereby generating several signals with differing lengths from one DNA molecule. Second, even if the pair of target subsequences hits only once in two different DNA molecules to be analyzed, the lengths between the hits may differ and thus distinguishable signals may be generated.

The target subsequences used in the QEA™ method are preferably optimally chosen by computer methods from DNA sequence databases containing sequences likely to occur in the sample to be analyzed. Efforts of the Human Genome Project in the United States, efforts abroad, and efforts of private companies in the sequencing of the human genome sequences, both expressed and genetic, are being collected in several available databases (listed in Section 5.4.2).

In a specific embodiment, a QEA™ method comprises (a) probing a sample comprising a plurality of nucleic acids having different nucleotide sequences with one or more recognition means, each recognition means causing recognition of a target nucleotide subsequence or a set of target nucleotide subsequences, (b) generating one or more signals from said sample probed by said recognition means, each generated signal arising from a nucleic acid in said sample and comprising a representation of (i) the identities of effective subsequences, each said effective subsequence comprising a said target nucleotide subsequence, or the identities of sets of effective subsequences, each said set having member effective subsequences each of which comprises a different one or more member target nucleotide subsequences from one of said sets of target nucleotide sequences, and (ii) the length between occurrences of effective subsequences in said nucleic acid or between one occurrence of one effective subsequence and the end of said nucleic acid; and (c) searching a nucleotide sequence database to determine sequences that match or the absence of any sequences that match said one or more generated signals, said database comprising a plurality of known nucleotide sequences of nucleic acids that may be present in the sample, a sequence from said database matching a generated signal when the sequence from said database has both (i) the same length between occurrences of effective subsequences or the same length between one occurrence of one effective subsequence and the end of the sequence as is represented by the generated signal, and (ii) the same effective subsequences as are represented by the generated signal, or effective subsequences that are members of the same sets of effective subsequences as are represented by the generated signal, whereby said one or more nucleic acids in said sample are identified, classified, or quantified. In a preferred embodiment, the method comprises (a) digesting said sample with one or more restriction endonucleases, each said restriction endonuclease recognizing a subsequence recognition site and digesting DNA at said recognition site to produce fragments with 5' overhangs; (b) contacting said produced fragments with shorter and longer oligodeoxynucleotides, each said shorter oligodeoxynucleotide hybridizable with a said 5' overhang and having no terminal phosphates, each said longer oligodeoxynucleotide hybridizable with a said shorter oligodeoxynucleotide; (c) ligating said longer oligodeoxynucleotides to said 5' overhangs on said fragments to produce ligated DNA fragments; (d) extending said ligated DNA fragments by synthesis with a DNA polymerase to produce blunt-ended double stranded DNA fragments; (e) amplifying said blunt-ended double stranded DNA fragments by a method comprising contacting said blunt-ended double stranded DNA fragments with a DNA polymerase and primer oligodeoxynucleotides, each said primer oligodeoxynucleotide having a sequence comprising that of one of the longer oligodeoxynucleotides; (f) determining the length of the amplified DNA fragments produced in step (e); and (g) searching a DNA sequence database, said database comprising a plurality of known DNA sequences that may be present in the sample, for sequences matching one or more of said fragments of determined length, a sequence from said database matching a fragment of determined length when the sequence from said database comprises recognition sites of said one or more restriction endonucleases spaced apart by the determined length, whereby DNA molecules in said sample are identified, classified, or quantified.

A QEA™ method can be conducted in a "query" mode or a "tissue" mode. "In a QEA™ method "query mode" experiment, the focus is on determining the expression of several genes, perhaps 1–100, of interest and of known sequence. A minimal number of target subsequences is chosen to generate signals, with the goal that each of the several genes is discriminated by at least one unique signal, which also discriminates it from all the other genes likely to occur in the sample. In other words, the experiment is designed so that each gene generates at least one signal unique to it (a "good" gene, see infra). In a QEA™ method "tissue mode" experiment, the focus is on determining the expression of as many as possible, preferably a majority, of the genes in a sample, without the need for any prior knowledge or interest in their expression. Target subsequences are optimally chosen to discriminate the maximum number of sample DNA sequences into classes comprising one or preferably at most a few sequences. Signals are generated and detected as determined by the threshold and sensitivity of a particular experiment. Some important determinants of threshold and sensitivity are the initial amount of mRNA and thus of cDNA, the amount of molecular amplification performed during the experiment, and the sensitivity of the detection means. Preferably, enough signals are produced and detected so that the QEA™ computer methods can uniquely determine the expression of a majority, or more preferably most, of the genes expressed in a tissue.

QEA™ method signals are generated by methods utilizing recognition means that include, but are not limited to, REs in a preferred RE/ligase method or in a method utilizing a removal means, preferably contacting streptavidin linked to a solid phase with biotin-labeled DNA, for removal of unwanted DNA fragments.

A preferred embodiment of an RE/ligase QEA™ method is as follows. The method employs recognition reactions with a pair (or more) of REs which recognize target subsequences with high specificity and cut the sequence at the recognition sites leaving fragments with sticky ends characteristic of the particular RE. To each sticky end, special primers are ligated which are distinctively labeled with fluorochromes identifying the particular RE making the cut, and thus the particular target subsequence. A DNA polymerase is used to form blunt-ended DNA fragments. The labeled fragments are then PCR amplified using the same special primers a number of times, preferably just sufficient to detect signals from all sequences of interest while making relatively small signals from the linearly amplifying singly cut fragments. The amplified fragments are then separated by length using electrophoresis, and the length and labeling of the fragments is optically detected. In order to improve the quality of the QEA™ method signals, it is preferable to conjugate a capture moiety with one or more of the primers and then to separate unwanted reaction products by a method comprising contacting the reaction products with a binding partner of the capture moiety, washing away unbound products, and then separating by length those single strands which are denatured from the bound products. See Sec. 6.1.12.2.1 ("QEA™ Method Preferred For Use In A SEQ-QEA™ Method"). Optionally, single stranded fragments can be removed by a binding hydroxyapatite, or other single strand specific, column or by digestion by a single strand specific nuclease. Also, the QEA™ method is adaptable to other functionally equivalent amplification and length separation means. In this manner, the identity of the REs cutting a fragment, and thereby the subsequences present, as well as the length between the cuts is determined.

In an exemplary QEA™ method utilizing a removal means, which has improved quantitative characteristics and is also adapted to highly sensitive detection systems, cDNA is amplified using at least one internally biotinylated primer. The cDNA is then cyclized, cut with a pair of REs, and specifically labeled primers are ligated to the cut ends, as discussed in § 5.4.3.2 (entitled "Second Alternative RE Embodiment"). The singly cut ends attached to the biotinylated synthesis primers are removed with streptavidin or avidin beads leaving highly pure labeled double cut cDNA fragments without any singly cut and labeled background fragments. With a sufficiently sensitive optical detection system, these pure doubly cut and labeled fragments can be separated by length (e.g., by electrophoresis or column chromatography) and directly detected without amplification. If amplification is needed, absence of the DNA singly cut fragment background improves signal to noise ratio permitting fewer amplification steps and, thereby, decreased PCR amplification bias.

Optional alternatives can provide increased discrimination in a QEA™ method. Two sequences producing two fragments of identical end subsequences and length can be discriminated by recognizing a third subsequence present in one of the fragments but not in the other. In one alternative, a labeled probe recognizing this third subsequence can be added before detection to generate unique signals from the fragment containing that subsequence. In another alternative, a probe can be added before amplification which prevents amplification of the fragment with the third subsequence and which thereby removes (suppresses) its signal. By way of example, such a probe can be either an RE for recognizing and cutting the fragment with the third subsequence, or a PNA, or modified DNA probe which will hybridize with the third subsequence and prevent its PCR amplification.

Further RE/ligase alternative methods increase sample sequence discrimination in QEA™ experiments, for example, by recognizing target subsequences longer or less limited than those recognized by REs; such target subsequences are termed herein effective target subsequences or effective subsequences. This added information can often discriminate two sample sequences producing fragments having identical original end subsequences and lengths. The effective subsequences are used in the computer implemented database lookup methods of this invention in a manner similar to the use of target subsequences. In one alternative, termed herein a SEQ-QEA™ method, the target subsequences recognized are effectively lengthened by using an amplification primer with an internal Type IIS RE recognition site so positioned that the Type IIS RE cuts the amplified fragments in a manner producing a second overhang contiguous with the recognition site of the initial RE. The sequence of the second overhang concatenated with the initial target end subsequence produces an effective subsequence that comprises, and is longer than, the target subsequence recognized by the RE. Alternatively, an effectively longer target subsequence can be recognized by using phasing primers during PCR amplification. The PCR amplification step can be divided into several pools with each pool using one phasing amplification primer constructed so as to recognize one or more additional nucleotides beyond the original RE recognition site. These additional nucleotides then contribute to an effective subsequence that comprises the target subsequence recognized by the RE.

In a SEQ-QEA™ method embodiment, an additional 4–8 bp subsequence is recognized at the end of a fragment by digestion of a primer by a type IIS RE. This resulting overhang is precisely contiguous with the RE cut end and is sequenced in a standard manner, as by conventional Sanger reactions. The additional subsequence information is combined with the RE recognition subsequence to generate an effective longer end target subsequence that is used as the effective subsequence.

The signals generated from the recognition reactions of a QEA™ method experiment are analyzed by computer methods. The analysis methods simulate a QEA™ method experiment using a database either of substantially all known DNA sequences or of substantially all, or at least a majority of, the DNA sequences likely to be present in a sample to be analyzed and a description of the reactions to be performed. The simulation results in a digest database which contains for all possible signals that can be generated the sample sequences responsible. Thereby, finding the sequences that can generate a signal involves a look-up in the simulated digest database. Computer implemented design methods optimize the choice of target subsequences in the QEA™ method reactions in order to maximize the information produced in an experiment. For the tissue mode, the methods maximize the number of sequences having unique signals by which their quantitative presence can be unambiguously determined. For the query mode, the methods maximize only the number of sequences of interest having unique signals, ignoring other sequences that might be present in a sample.

In QEA™ method embodiments wherein high stringency hybridization is specified, such conditions generally comprise a low salt concentration, equivalent to a concentration of SSC (173.5 g. NaCl, 88.2 g. Na Citrate, $H_2O$ to 1 l.) of less than approximately 1 mM, and a temperature near or above the $T_m$ of the hybridizing DNA. In contrast, conditions of low stringency generally comprise a high salt concentration, equivalent to a concentration of SSC of greater than approximately 150 mM, and a temperature below the $T_m$ of the hybridizing DNA.

In QEA™ method embodiments wherein DNA oligomers are specified for performing functions, including hybridization and chain elongation priming, alternatively oligomers can be used that comprise those of the following nucleotide mimics which perform similar functions. Nucleotide mimics are subunits (other than classical nucleotides) which can be polymerized to form molecules capable of specific, Watson-Crick-like base pairing with DNA. The oligomers can be DNA or RNA or chimeric mixtures or derivatives or modified versions thereof. The oligomers can be modified at the base moiety, sugar moiety, or phosphate backbone. The oligomers may include other appending groups such as peptides, hybridization-triggered cleavage agents (see, e.g., Krol et al., 1988, *BioTechniques* 6:958–976), or intercalating agents (see, e.g., Zon, 1988, *Pharm. Res.* 5:539–549). The oligomers may be conjugated to another molecule, e.g., a peptide, hybridization triggered cross-linking agent, transport agent, hybridization-triggered cleavage agent, etc.

The oligomers may also comprise at least one nucleotide mimic that is a modified base moiety which is selected from the group including, but not limited to, 5-fluorouracil, 5-bromouracil, 5-chlorouracil, 5-fodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. The oligomers may comprise at least one modified sugar moiety selected from the group including, but not limited to, arabinose, 2-fluoroarabinose, xylulose, and hexose. The oligomers may comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The oligomer may be an α-anomeric oligomer. An α-anomeric oligomer forms specific double-stranded hybrids with complementary RNA in which, contrary to the usual β-units, the strands run parallel to each other (Gautier et al., 1987, *Nucl. Acids Res.* 15:6625–6641).

Oligomers for use in a QEA™ method can be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al., 1988, *Proc. Natl. Acad. Sci. USA* 85:7448–7451), etc.

In specific QEA™ method embodiments, it is preferable to use oligomers that can specifically hybridize to subsequences of a DNA sequence too short to achieve reliably specific recognition, such that a set of target subsequences is recognized. Further where PCR is used, since Taq polymerase tolerates hybridization mismatches, PCR specificity is generally less than hybridization specificity. Where such oligomers recognizing short subsequences are preferable, they can be constructed in manners including, but not limited to, the following. To achieve reliable hybridization to shorter DNA subsequences, degenerate sets of DNA oligomers can be used which are constructed of a total length sufficient to achieve specific hybridization with each member of the set containing a shorter sequence complementary to the common subsequence to be recognized. Alternatively, a longer DNA oligomer can be constructed with a shorter sequence complementary to the subsequence to be recognized and with additional universal nucleotides or nucleotide mimics, which are capable of hybridizing to any naturally occurring nucleotide. Nucleotide mimics are sub-units which can be polymerized to form molecules capable of specific, Watson-Crick-like base pairing with DNA. Alternatively, the oligomers may be constructed from DNA mimics which have improved hybridization energetics compared to naturally occurring nucleotides.

A preferred mimic is a peptido-nucleic acid ("PNA") based on a linked N-(2-aminoethyl)glycine backbone to which normal DNA bases have been attached (Egholm et al., 1993, *Nature* 365:566–67). This PNA obeys specific Watson-Crick base pairing, that with greater free energy of binding and correspondingly higher melting temperatures. Suitable oligomers may be constructed entirely from PNAs or from mixed PNA and DNA oligomers.

In QEA™ method embodiments wherein DNA fragments are separated by length, any length separation means known in the art can be used one alternative separation means employs a sieving medium for separation by fragment length coupled with a force for propelling the DNA fragments though the sieving medium. The sieving medium can be a polymer or gel, such a polyacrylamide or agarose in suitable concentrations to separate 10–1000 bp DNA fragments. In this case the propelling force is a voltage applied across the medium. The gel can be disposed in electrophoretic configurations comprising thick or thin plates or capillaries. The gel can be non-denaturing or denaturing. Alternately, the sieving medium can be such as used for chromatographic separation, in which case a pressure is the propelling force. Standard or high performance liquid chromatographic ("HPLC") length separation means may be used. An alternative separation means employs molecular characteristics such as charge, mass, or charge to mass ratio. Mass spectrographic means capable of separating 10–1000 bp fragments may be used.

DNA fragment lengths determined by such a separation means represent the physical length in base pairs between target subsequences, after adjustment for biases or errors introduced by the separation means and length changes due to experimental variables (e.g., presence of a detectable label, ligation to an adopter molecule). A represented length is the same as the physical length between occurrences of target subsequences in a sequence from said database when both said lengths are equal after applying corrections for biases and errors in said separation means and corrections based on experimental variables. For example, represented lengths determined by electrophoresis can be adjusted for mobility biases due to average base composition or mobility changes due to an attached labeling moiety and/or adapter strand by conventional software programs, such as Gene Scan Software from Applied Biosystems, Inc. (Foster City, Calif.).

In QEA™ method embodiments wherein DNA fragments are labeled-and detected, any compatible labeling and detection means known in the art can be used. Advances in fluorochromes, in optics, and in optical sensing now permit multiply labeled DNA fragments to be distinguished even if they completely overlap in space, as in a spot on a filter or a band in a gel. Results of several recognition reactions or hybridizations can be multiplexed in the same gel lane or filter spot. Fluorochromes are available for DNA labeling which permit distinguishing 6–8 separate products simultaneously (Ju et al., 1995, *Proc. Natl. Acad Sci. USA* 92:4347–4351).

Exemplary fluorochromes adaptable to a QEA™ method and methods of using such fluorbchromes to label DNA are described in § 6.1.12.4 (entitled "Fluorescent Labels For QEA™ methods").

Single molecule detection by fluorescence (Eigen et al., 1994, *Proc. Natl. Acad Sci. USA* 91:5740–5747) can also be adapted for use.

In QEA™ method embodiments wherein intercalating DNA dyes are utilized to detect DNA, any suitable dye known in the art can be used. In particular such dyes include, but are not limited to, ethidium bromide, propidium iodide, Hoechst 33258, Hoechst 33342, acridine orange, and ethidium bromide homodimers. Such dyes also include POPO, BOBO, YOYO, and TOTO from Molecular Probes (Eugene, Oreg.).

Alternative sensitive detection means available include silver staining of polyacrylamide gels (Bassam et al., 1991, *Analytic Biochemistry* 196:80–83), and the use of intercalating dyes. In this embodiment, the gel can be photographed and the photograph scanned by scanner devices conventional in the computer art to produce a computer record of the separated and detected fragments. A further alternative is to blot an electrophoretic separating gel onto a filter (e.g., nitrocellulose) and then to apply any visualization means known in the art to visualize adherent DNA. See, e.g., Kricka et al., 1995, Molecular Probing, Blotting, and Sequencing, Academic Press, New York. In particular, visualization means utilizing secondary reactions with one or more reagents or enzymes can be used.

A preferred separation and detection apparatus for use in a QEA™ method is found in copending U.S. patent application Ser. No. 08/438,231 filed May 9, 1995, which is herein incorporated by reference in its entirety. Other detection means adaptable to a QEA™ method include the commercial electrophoresis machines from Applied Biosystems Inc. (Foster City, Calif.), Pharmacia (ALF), Hitachi, Licor. The Applied Biosystems machine is preferred among these as it is the only machine capable of simultaneous 4 dye resolution.

In the following subsections and the accompanying examples sections a QEA™ method embodiment is described in detail.

5.4.2. DETAILS OF A QUANTITATIVE EXPRESSION ANALYSIS METHOD

This embodiment of a QEA™ method preferably generates one or more signals unique to each cDNA sequence in a sample containing a mixture of cDNAs, and to quantitatively relate the strength of such a signal or signals to the relative amount of that cDNA sequence in the sample. Less preferably, the signals uniquely determine only sets of a small number of sequences, typically 2–10 sequences. QEA™ method signals comprise an indication of the presence of pairs of target subsequences and the length between pairs of adjacent subsequences in a DNA sample. Signals are generated in a manner permitting straightforward automation with existing laboratory robots. For simplicity of disclosure, and not by way of limitation, the detailed description of this method is directed to the analysis of samples. comprising a plurality of cDNA sequences. It is equally applicable to samples comprising a single sequence or samples comprising sequences of other types of DNA or nucleic acids generally.

While described in terms of cDNA hereinbelow, it will be understood that the DNA sample can be any DNA, e.g., cDNA and/or genomic DNA, and preferably comprises a mixture of DNA sequences. In specific embodiments, the DNA sample is an aliquot of cDNA of total cellular RNA or total cellular mRNA, most preferably derived from human tissue. The human tissue can be diseased or normal.

The cDNA, or the mRNA from which it is synthesized, should be present at some threshold level in order to generate signals, this level being determined to some degree by the conditions of a particular QEA™ method experiment. For example, such a threshold is that preferably at least 1000, and more preferably at least 10,000, mRNA molecules of the sequence to be detected be present in a sample. In the case where one or only a few mRNAs of a type of interest are present in each cell of a tissue from which it is desired to derive the sample mRNA, at least a corresponding number of such cells should be present in the initial tissue sample. In a specific embodiment, the mRNA detected is present in a ratio to total sample RNA of $1:10^5$ to $1:10^6$. With a lower ratio, more molecular amplification can be performed during a QEA™ method experiment.

The cDNA sequences occurring in a tissue derived pool include short untranslated sequences and. translated protein coding sequences, which, in turn, may be a complete protein coding sequence or some initial portion of a coding sequence, such as an expressed sequence tag. A coding sequence may represent an as yet unknown sequence or gene or an already known sequence or gene entered into a DNA sequence database. Exemplary sequence databases include those made available by the National Center for Biotechnology Information ("NCBI") (Bethesda, Md.) (GenBank) and by the European Bioinformatics Institute ("EMBL") (Hinxton Hall, UK).

A QEA™ method is also applicable to samples of genomic DNA in a manner similar to its application to cDNA. In gDNA samples, information of interest includes occurrence and identity of translocations, gene amplifications, loss of heterozygosity for an allele, etc. This information is of interest in cancer diagnosis and staging. In cancer patients, amplified sequences might reflect an oncogene, while loss of heterozygosity might reflect a tumor suppressor gene. Such sequences of interest can be used to select target subsequences and to predict signals generated by a QEA™ method experiment. Even without prior knowledge of the sequences of interest, detection and classification of the QEA™ method signal patterns is useful for the comparison of normal and diseased states or for observing the progression of a disease state.

Classification of QEA™ method signal patterns, in an exemplary embodiment, can involve statistical analysis to determine significant differences between patterns of interest. This can involve first grouping samples that are similar in one of more characteristics, such characteristics including, for example, epidemiological history, histopathological state, treatment history, etc. Signal patterns from similar samples are then compared, e.g., by finding the average and standard deviation of each individual signals. Individual signal which are of limited variability, e.g., for which the standard deviation is less than the average, then represent genetic constants of samples of this particular characteristic. Such limited variability signals from one set of tissue samples can then be compared to limited variability signals from another set of tissue samples. Signals which significantly differ in this comparison then represent significant differences in the genetic expression between the tissue samples and are of interest in reflecting the biological differences between the samples, such as the differences caused by the progression of a disease. For example, a significant difference in expression is detected with the difference in the genetic expression between two tissues exceed the sum of the standard deviation of the expressions in the tissues. Other standard statistical comparisons can also be used to establish level of expression and the significance of differences in levels of expressions.

Target subsequence choice is important in the practice of a QEA™ method. The two primary considerations for selecting subsequences are, first, redundancy, that is, that there be enough subsequence pair hits per gene that a unique signal is likely to be generated for each sample sequence, and second, resolution, that is, that there not be so many primer pairs hitting with very similar lengths in a sample that the signals cannot be discriminated. For sufficient redundancy, it is preferable that there be on average, approximately three pair hits per gene or DNA sequence in the sample. It is highly preferable that there be at least one pair hit per each gene In a test of a database of eukaryotic expressed sequences, it has been found that an average value of three hits per gene appears to be generally a sufficient guarantee of this minimum criterion.

Sufficient resolution depends on the separation and detection means chosen. For a particular choice of separation and detection means, a recognition reaction preferably should not generate more fragments than can be separated and distinguishably detected. In a preferred embodiment, gel electrophoresis is the separation means used to separate DNA fragments by length. Existing electrophoretic techniques allow an effective resolution of three base pair ("bp") length differences in sequences of up to 1000 bp length. Given knowledge of fragment base composition, effective resolution down to 1 bp is possible by predicting and correcting for the small differences in mobility due to differing base composition. However and without limitation, an easily achievable three bp resolution is assumed by way of example in the description of the QEA™ method. It is preferable for increased detection efficiency that the distinguishably labeled products from as many recognition reactions as possible be combined for separation in one gel lane. This combination is limited by the number of labels distinguishable by the employed detection means. Any alternative means for separation and detection of DNA fragments by length, preferably with resolution of three bp or better, can be employed. For example, such separation means can be thick or thin plate or column electrophoresis, column chromatography or HPLC, or physical means such as mass spectroscopy.

The redundancy and resolution criteria are probabilistically expressed in Eqns. 1 and 2 in an approximation adequate to guide subsequence choice. In these equations the number of genes in the cDNA sequence mixture is N, the average gene length is L, the number of target subsequence pairs is M (the number of pairs of recognition means), and the probability of each target subsequence hitting a typical gene is p. Since each target subsequences is preferably selected to independently hit each pooled sequence, the probability of an arbitrary subsequence pair hitting is then $p^2$. Eqn. 1 expresses the redundancy condition of three hits per gene, assuming the probabilities of target subsequence hits are independent.

$$Mp^2 = 3 \tag{1}$$

Eqn 2 expresses the resolution condition of having fragments with lengths: no closer on average than 3 base pairs. This equation approximates the actual fragment length distribution with a uniform distribution.

$$\frac{L}{Np^2} = 3 \tag{2}$$

Given expected values of N, the number of sequences in the library or pool to analyze (library complexity), and L, the average expressed sequence (or gene) length, Eqns 1 and 2 are solved for the subsequence hit probability and number of subsequences required. This solution depends on the particular redundancy and resolution criteria dictated by the particular experimental method chosen to implement the QEA™ method. Alternative values may be required for other implementations of a QEA™ method.

For example, it is estimated that the entire human genome contains approximately $10^5$ protein coding sequences with an average length of 2000. The. solution of Eqns. 1 and 2 for these parameters is p=0.082 and M=450. Thereby the gene expression of all genes in all human tissues can be analyzed with a tissue mode QEA™ method using 450 target subsequence pairs, each subsequence having an independent probability of occurrence of 8.2%. In an embodiment in which eight fluorescently labeled subsequence pairs can be optically distinguished and detected per electrophoresis lane, such as is possible when using the separation and detection apparatus described in copending U.S. patent application Ser. No. 08/438,231 filed May 9, 1995, 450 reactions can be analyzed in only 57 lanes. Thereby only one electrophoresis plate is needed in order to completely determine all human genome expression levels. Since the best commercial machines known to the applicants can discriminate only four fluorescent labels in one lane, a corresponding increase in the number of lanes is required to perform a complete genome analysis with such machines.

As a further example, it is estimated that a typically complex human tissue expresses approximately 15,000 genes. The solution for N=15000 and L=2000 is p=0.21 and M=68. Thus expression in a typical tissue can be analyzed with a tissue mode QEA™ method using 68 target subsequence pairs, each subsequence having an independent probability of occurrence of 21%. Assuming 4 subsequence pairs can be run per gel electrophoresis lane, the 68 reactions can be analyzed in 17 lanes in order to determine the gene expression frequencies in any human tissue. Thus it is clear that this method leads to greatly simplified quantitative gene expression analysis within the capabilities of existing electrophoretic systems.

These equations provide an adequate guide to picking subsequence pairs. Typically, preferred probabilities of target subsequence occurrence are from approximately 0.01 to 0.30. Probabilities of occurrence of subsequences and RE recognition sites can be determined from databases of DNA sample sequences. Appropriate target subsequences can be selected from these tables. Computer implemented, QEA™ method experimental design methods can then optimize this initial selection.

Another use of a QEA™ method is to compare directly the expression of only a few genes, typically 1 to 10, between two different tissues, the query mode, instead of seeking to determine the expression of all genes in a tissue, the tissue mode. In this query mode, a few target subsequences are selected to identify the genes of interest both among themselves and from all other sequences possibly present. The computer design methods described hereinbelow can make this selection. If 4 subsequence pairs are sufficient for identification, then the fragments from the 4 recognition reactions performed on each tissue are preferably separated and detected on two separate lanes in the same gel. If 2 subsequence pairs are sufficient for identification, the two tissues are preferably analyzed in the same gel lane. Such comparison of signals from the same gel improves quantitative results by eliminating measurement variability due to differences between separate electrophoretic runs. For example, expression of a few target genes in diseased and normal tissue samples can be rapidly and reliably analyzed.

A query mode of a QEA™ method is also useful even if the sequences of the particular genes of interest are not yet known. For example, fluorescent traces produced by subjecting separate samples to gel electrophoretic separation means and then fluorescent detection means are compared to identify feature differences. Such differentially expressed features created in a particular recognition reaction are then retrieved from the gel by methods known in the art (e.g. electro-elution from the gel) and their contained DNA fragments are analyzed by conventional techniques such as by sequencing. If partial, such sequences can then be used as probes (e.g., in PCR or Southern blot hybridization) to recover full-length sequences. In this manner, QEA™ method techniques can guide the discovery of new differentially expressed cDNA or of changes of the state of gDNA. The sequences of the newly identified genes, once determined, can then be used to guide QEA™ method target subsequence choice for further analysis of the differential expression of the new genes.

Two specific embodiments of a QEA™ method are described herein. The specific embodiments described herein use REs to recognize and cleave target subsequences in the sample DNA. In one implementation, the desired doubly cut fragments are amplified by an amplification means in order to dilute remaining, unwanted singly cut fragments. Alternatively, the singly cut fragments are removed by physical means (e.g., hydroxyapatite column separation) or enzymatic means (e.g., single strand specific nucleases) In another implementation, the unwanted singly cut ends are removed by a removal means from the desired doubly cut fragments without an amplification step, as described in § 5.4.3.2 (entitled "Second Alternative RE Embodiment"). For these implementations, RE recognition sites define the possible target subsequences and are selected in a manner similar to the above in order to meet the previous probability or occurrence and independence criteria. The probabilities of occurrence of various RE recognition sites are determined from a database of potential sample sequences, and those REs are chosen with recognition sequences whose probabilities of occurrence meet the criterion of Eqns. 1 and 2 as closely as possible. If multiple REs satisfy the selection criteria, a subset is selected by including only those REs with independently occurring recognition sequences, determined, for example, by using conditional probabilities. Checking for independence can be done, by, for example, checking that the conditional probability for a hit by any selected pair of subsequences is the product of the probabilities of the individual subsequence hit probabilities. An initial choice can be optionally optimized by the computer implemented experimental design methods.

A number, $R_e$, of REs are preferably selected so that the number of RE pairs is approximately M, where the relation between M and $R_e$ is given by Eqn. 3.

$$M = \frac{R_e(R_e + 1)}{2} \tag{3}$$

For example, a set a set of 20 acceptable REs results in 210 subsequence pairs.

There are numerous REs currently available whose recognition sequences have a wide range of occurrence probabilities, from which REs can be selected for the QEA™ method. A sample of these are presented in Example 6.1.12.3 (entitled "Preferred QEA™ Method Adapters And RE Pairs").

Restriction endonucleases ("RE") generally bind with specificity only to their short four to eight bp recognition sites, cleaving the DNA preferably with 4 bp complementary sequences. It is preferable that REs used in this embodiment produce overhangs characteristic of the particular RE. Thus REs, such as those known as class IIS restriction enzymes, which produce overhangs of unknown sequence are less preferable. Class IIS REs are adaptable to generate short subsequences which may be sequenced to increase QEA™ method resolution by extending initial target subsequences into longer effective target subsequences. This alternative-embodiment is known as the SEQ-QEA™ method (see Section 5.4.4). Phasing primers can also be used to recognize longer effective target subsequences. Further, ligases, which are used in a QEA™ method to ligate an adapter strand to a digested terminus, are highly specific in their hybridization requirements; even one bp mismatch near the ligation site will prevent ligation (U.S. Pat. No. 5,366,877, Nov. 22, 1994, to Keith et al.; U.S. Pat. No. 5,093,245, Mar. 3, 1992, to Keith et al.).

QEA™ method experiments are also adaptable to distinguish sequences into small sets, typically comprising 2 to 10 sequences, which require fewer target subsequence pairs. Such coarser grain analysis of gene expression or genomic composition requires fewer recognition reactions and analysis time. Alternatively, smaller numbers of target subsequence pairs can be optimally chosen to distinguish individually a specific set of genes of interest from all the other genes in the sample. These target subsequences can be chosen either from REs that produce fragments from the desired genes.

Detailed descriptions of exemplary implementations for practicing QEA™ method recognition reactions and related computer implemented experimental analysis and design methods are presented in the following subsections followed by detailed experimental protocols in the Examples subsections. The implementations are illustrative and not limiting, as a QEA™ method can be practiced by any method generating the previously described QEA™ method signals.

5.4.3. RE EMBODIMENTS OF A QEA™ METHOD

Restriction endonuclease ("RE") embodiments of a QEA™ method use implementations of simultaneous RE and ligase enzymatic reactions for generating labeled fragments of the genes or sequences to be analyzed. These fragments are then separated by length by a separation means and detected by a detection means to yield QEA™ method signals comprising the identity of the REs cutting each fragment together with each fragment's length. The recognition reactions can specifically and reproducibly generate QEA™ method signals with good signal to noise ratios and without any intermediate extractions or buffer exchanges, which would hinder automatic execution.

REs bind with specificity to short DNA target subsequences, usually 4 to 8 bp long, that are termed recognition sites and are characteristic of each RE. REs that are used cut the sequence at (or near) these recognition sites preferably producing characteristic. ("sticky") ends with single-stranded overhangs, which usually incorporate part of the recognition site.

Preferred REs have a 6 bp recognition site and generate a 4 bp 5' overhang. If more fragments are desired for the analysis of a particular sample, REs with shorter recognition sites can be used, for example with 4 or 5 bp recognition sites. The RE embodiments are also adaptable to a 2 bp 5' overhang, which is less preferred since 2 bp overhangs have a lower ligase substrate activity than 4 bp overhangs. All RE embodiments can be adapted to 3' overhangs of two and four bp. Further preferred REs have the following additional properties. Their recognition sites and overhang sequences are preferably such that an adapter can be designed whose ligation does not recreate the recognition site. They preferably have sufficient activity below 37° C. and are heat inactivated at 65° C. Heat inactivation is preferable so that RE inactivation can be performed prior to adding PCR reagents and conducting the PCR reaction in the same vial. They preferably have low non-specific cutting and nuclease activities and cut to completion. Of course, REs selected for a particular experiment preferably have recognition sites meeting the previously described occurrence and independence criteria. Preferred pair of REs for analyzing human and mouse cDNA are listed in § 6.1.12.3 (entitled "Preferred QEA™ Method Adapters and RE Pairs").

Only doubly cut sequence fragments are of interest, and thus in all RE QEA™ method embodiments the desired doubly cut fragments are distinguished from the unwanted singly cut fragments. Singly cut fragments have a non-specific and non-reproducible length distribution derived from the distribution of overall cDNA lengths, which depends strongly on cDNA synthesis conditions. Only the doubly cut fragments have a specific and reproducible length distribution dependent only on the DNA sequence analyzed and independent of cDNA synthesis conditions. To make this distinction, the preferred RE embodiment of a QEA™ method exponentially amplifies doubly cut fragments, so that their signals quickly overwhelm signals from singly cut fragments, which are at most linearly amplified. PCR is the preferred amplification means.

Alternative amplification means known in the art are adaptable to a QEA™ method. If a removal means for singly cut ends is not utilized in an embodiment, alternative amplification means should preferentially amplify doubly cut ends over singly cut ends in order that signals from singly cut ends be relatively suppressed. On the other hand, if a removal means for singly cut ends is utilized in an embodiment, then alternative amplification means need have no amplification preference, as no singly cut ends are present at the amplification step. Known alternative amplification means are listed in Kricka et al., 1995, Molecular Probing, Blotting, and Sequencing, chap. 1 and table IX, Academic Press, New York. Of these alternative means, those employing the T7 RNA polymerase are preferred.

Two other specific embodiments use a physical removal means to directly remove singly cut fragments, preferably before amplification. This can be accomplished, e.g., by labeling DNA termini with a capture moiety prior to digestion. After digestion, the singly cut fragments are removed by contacting the sample with a binding partner of the capture moiety, affixed to a solid phase. The preferred removal means is biotin-streptavidin. Other removal means adaptable to this embodiment of a QEA™ method include various haptens, which are removed by their corresponding antibodies. Exemplary haptens include digoxigenin, DNP, and fluorescein (Holtke et al., 1992, Sensitive chemiluminescent detection of digoxigenin labeled nucleic acids: a fast and simple protocol for applications, Biotechniques 12(1): 104–113 and Olesen et al., 1993, Chemiluminescent DNA sequencing with multiple labeling, Biotechniques 15(3):480–485). Alternatively, single stranded fragments can be removed by single stand specific column separation or single strand specific nucleases.

RE embodiments of a QEA™ method use recognition moieties which are specifically ligated to RE cut sticky ends so that in any one recognition reaction ends cut by a particular RE receive a unique moiety. Recognition moieties comprise oligomers capable of specifically hybridizing to the RE generated sticky ends. In the preferred RE embodiment, which uses PCR amplification, the recognition moieties also provide primer means for the PCR.

The recognition moieties also provide for labeling and recognition of RE cut ends. For example, using a pair of REs in one recognition reaction generates doubly cut fragments some with the recognition sequence of the first RE on both ends, some with the recognition sequence of the second RE on both ends, and the remainder with one recognition sequence of each RE on either end. Using more REs generates doubly cut fragments with all pairwise combinations of RE cut ends from adjacent RE recognition sites along the sample sequences. All these cutting combinations need preferably to be distinguished, since each provides unique information on the presence of different subsequences pairs present in the original DNA sequence. Thus the recognition moieties preferably have unique labels which label specifically each RE cut made in a reaction. As many REs can be used in a single reaction as labeled recognition moieties are available to uniquely label each RE cut. If the detectable labeling in a particular system is, for example, by fluorochromes, then fragments cut with one RE have a single fluorescent signal from the one fluorochrome associated with that RE, while fragments cut with two REs have mixed signals, one from the fluorochrome associated with each RE. Thus all possible pairs of fluorochrome labels are preferably distinguishable. Alternatively, if certain target subsequence information is not needed, the recognition moieties need not be distinctively labeled. In embodiments using PCR amplification, corresponding primers would not be labeled.

If silver staining is used to recognize fragments separated on an electrophoresis gel, no recognition moiety need be labeled, as fragments cut by the various RE combinations are not distinguishable. In this case, when PCR amplification is used, only primers are required.

The recognition reaction conditions are preferably selected, as described in § 6.1.12.1 (entitled "QEA™ Preferred RE Method"), so that RE cutting and recognition moiety ligation go to full completion: all recognition sites of all REs in the reaction are cut and ligated to a recognition moiety. It is more preferable, in general, to perform the recognition reactions according to Sec. 6.1.12.2.1 ("QEA™ Method Preferred For Use In A SEQ-QEA™ Method"). This more preferred protocol describes performing the RE/ligase and PCR reactions in a single reaction vessel, with at least one primer having a conjugated capture moiety, followed by cleanup of certain reaction products. In this manner, the fragments generated from a sequence analyzed lie only between adjacent recognition sites of any RE in that reaction. No fragments remain which include any RE recognition site, since such a site is cut. Multiple REs can be used in one recognition reaction. Too many REs in one reaction may cut the sequences too frequently, generating a compressed length distribution with many short fragments of lengths between 10 and a few hundred base pairs long. Such a distribution may not be resolvable by the separation means, for example gel electrophoresis, if the fragments are too close in length, for example less than 3 bp apart on the average. Too many REs also may generate fragments of the same length and end subsequences from different sample sequences, thereby leading to non-unique signals. Finally, where fragment labels are to be distinguished, no more REs can be used than can have distinguishably labeled sticky ends. These considerations limit the number of REs optimally useable in one recognition reaction. Preferably two REs are used, with one, three and four REs less preferable. Preferable pairs of REs for the analysis of human cDNA samples are listed in § 6.1.12.3 (entitled "Preferred QEA™ Method Adapters and RE Pairs").

An additional level of signal specificity is possible by selecting or suppressing fragments having a third internal target subsequence. Additional information on the presence or absence of specific internal subsequences can be used along with the two end subsequences and the length information to further distinguish between otherwise identically classified fragments.

Other methods of providing third subsequence information are described below which label or suppress fragments with third subsequences. To select fragments with a third internal subsequence, probes with distinguishable labels which bind to this target subsequence are added to the fragments prior to detection, and alternatively prior to separation and detection. On detection, fragments with this third subsequence present will generate a signal, preferably fluorescent, from the probe. Such a probe can be a labeled PNA or DNA oligomer. Short DNA oligomers may need to be exterded witb a universal nucleotide or degenerate-sets of natural nucleotides in order to provide for specific hybridization.

Fragments with a third subsequence can be suppressed in various manners in embodiments using PCR amplification. First, a probe hybridizing with this third subsequence which prevents polymerase elongation in PCR can be added prior to amplification. Then sequences with this subsequence will be at most linearly amplified and their signal thereby suppressed. Such a probe could be a PNA or modified DNA oligomer (with the last nucleotide being a ddNTP). Second, if the third subsequence is recognized by an RE, this RE can be added to the RE-ligase reaction without any corresponding specific primer. Fragments with the third subsequence will be at most linearly amplified.

Both these alternatives can be extended to multiple internal sequences by using multiple probes to recognize the sequences or to disrupt exponential PCR amplification.

Construction of the recognition moieties, also herein called adapters or linker-primers, is important and is described here in advance of further details of the individual recognition reaction steps. In the preferred embodiment, the adapters are partially double stranded DNA ("dsDNA"). Alternatively, the adapters can be constructed as oligomers of any nucleic acid, with corresponding properties to the preferred DNA polymers. In an embodiment employing an alternative amplification means, any polymer that can serve with a template as a primer for that amplification means can be used in that embodiment.

FIG. 10A illustrates the DNA molecules involved in the ligation reaction as conventionally indicated with the 5' ends of the top strands and the 3' ends of the bottom strands at left. dsDNA. 201 is a fragment of a sample cDNA sequence with an RE cut at the left end generating, preferably, a four bp 5' overhang 202. Adapter dsDNA 209 is a synthetic substrate provided by a QEA™ method.

The precise characteristics of adapter 209 are selected in order to ensure that RE digestion and adapter ligation preferably go to completion, that generation of unwanted products and amplification biases are minimized, and that unique labels are attached to cut ends (if needed). Adapter 209 comprises strand 203, called a primer, and a partially complementary strand 205, called a linker. The primer is also known as the longer strand of the adapter, and the linker is also known as the shorter strand of the adapter.

The linker, or shorter strand, links the end of a cDNA cut by an RE to the primer, or longer strand, by hybridization to the sticky overhang of the cut end and to the primer in order that the primer can be ligated to dsDNA 201. Therefore, linker 205 comprises sequence 206 complementary to the sticky RE overhang 202 and sequence 207 complementary to the 3' end of primer 203. Sequence 206 is preferably of the same length as the RE overhang. Sequence 207 is most preferably eight nucleotides long, less preferably from 4 to 12 nucleotides long, but can be of any length as long as the linker reliably hybridizes with only one top primer in any one recognition reaction and has an appropriate $T_m$ (preferably less than approximately 68° C.). Linker 205 also preferably has no 5' terminal phosphate so that it will not ligate to the bottom strand of dsDNA 201. Lack of terminal phosphate also prevents the annealed adapters from ligating to each other, forming dimers, and thereby competing with adapter ligation to RE cut sample fragments. Adapter dimers would also be amplified in a subsequent amplification step generating unwanted fragments. Terminal phosphates can be removed using phosphatases (e.g., alkaline phosphatase) known in the art, followed by separation of the enzyme.

Further, the linker, or shorter strand, $T_m$ should preferably be less than primer 203 self-annealing $T_m$. This ensures that subsequent PCR amplification conditions can be controlled so that linkers present in the reaction mixture will not hybridize and act as PCR primers, and, thereby, generate spurious fragment lengths. The preferable $T_m$ is less than approximately 68° C.

Primer, or longer strand, 203 further has a 3' end sequence 204 complementary to 3' end sequence 207 of bottom linker 205. In a preferred aspect, in order that all RE cuts are properly ligated to a unique top primer, in any single reaction, each primer should be complementary to and hybridize with only one linker 205. Consequently, all the linkers in any one reaction mixture preferably have unique sequences 207 for hybridizing with unique primers. In order that the ligation reaction go to completion, primer 203 preferably should not recreate the recognition sequence of any RE in the reaction mixture when it is ligated with cDNA end 202. Primer 203 has no 5' terminal phosphate in order to prevent any self-ligations. To minimize amplification of undesired sequences, termed amplification noise, in any subsequent PCR step it is preferred that primer 203 not hybridize with any sequence present in the original sample mixture. The $T_m$ of primer 203 is preferably high, in the range from 500 to 80° C., and more preferably above 68° C. This ensures that the subsequent PCR amplification can be controlled so that only primers and not linkers initiate new chains. For example, this $T_m$ can be achieved by use of a primer having a combination of a G+C content preferably from 40–60%, most preferably from 55–60%, and a primer length most preferably 24 nucleotides, and preferably from 18 to 30 nucleotides. Primer 203 is optionally labeled with fluorochrome 208, although any DNA labeling system that preferably allows multiple labels to be simultaneously distinguished is usable in the QEA™ method.

Generally, the primer, or longer strand, are constructed so that, preferably, they are highly specific, free of dimers and hairpins, and form stable duplexes under the conditions specified, in particular the desired $T_m$. Software packages are available for primer construction according to these principles, an example being OLIGO™ Version 4.0 For Macintosh from National Biosciences, Inc. (Plymouth, Minn.). In particular, a formula for $T_m$ can be found in the OLIGO™ Reference Manual at Eqn. I, page 2.

FIG. 10B illustrates two exemplary adapters and their component primers and linkers constructed according to the above description. Adapter 250 is specific for the RE BamHI, as it has. a 3' end complementary to the 5' overhang generated by BamHI. Adapter 251 is similarly specific for the RE HindIII.

Example 6.1.12.3 (entitled "Preferred QEA™ Method Adapters And RE Pairs") contains a more comprehensive, non-limiting list of adapters that can be used according to the QEA™ method. All synthetic oligonucleotides used in the QEA™ method are preferably as short as possible for their functional roles in order to minimize synthesis costs.

Alternatively, adapters can be constructed from hybrid primers which are designed to facilitate the direct sequencing of a fragment or the direct generation of RNA probes for in situ hybridization with the tissue of origin of the DNA sample analyzed. Hybrid primers for direct sequencing are constructed by ligating onto the 5' end of existing primers the M13–21 primer, the M13 reverse primer, or equivalent sequences. Fragments generated with such hybrid adapters can be removed from the separation means and amplified and sequenced with conventional systems. Such sequence information can be used both for a previously known sequence to confirm the sequence determination and for a previously unknown sequence to isolate the putative new gene. Hybrid primers for direct generation of RNA hybridization probes are constructed by ligating onto the 5' end of existing primers the phage T7 promoter. Fragments generated with such hybrid adapters can be removed using the separation means and transcribed into anti-sense RNA with conventional systems. Such probes can be used for in situ hybridization with the tissue of origin of the DNA sample to determine in precisely what cell types a signal of interest is expressed.

A further alternative illustrated in FIG. 10C is to construct an adapter by self hybridization of single stranded DNA in hairpin loop configuration 212. The subsequences of loop 212 would have similar properties to the corresponding subsequences of linker 205 and primer 203. Exemplary-hairpin loop 211 sequences are $C_4$ to $C_{10}$.

Figures 11A, 11B:
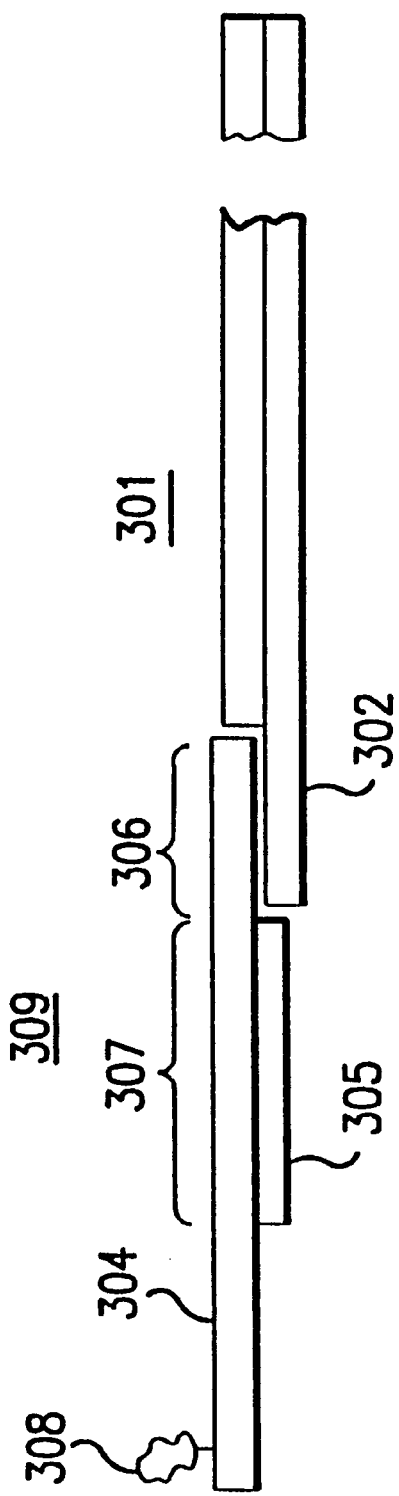

REs generating 3' overhangs are less preferred and require the different adapter structure illustrated in FIG. 11A. dsDNA 301 is a fragment of a sample cDNA cut with a RE generating 3' sticky overhang 302. Adapter 309 comprises primer, or longer strand, 304 and linker, or shorter strand, 305. Primer, or longer strand, 304 includes segment 306 complementary to and of the same length as 3' overhang 302 and section 307 complementary to linker 305. It also optionally has label 308 which distinctively labels primer 304. As in the case of adapters for 5' overhangs, primer 304 has no 5' terminal phosphate, in order to prevent self-ligations, and is such that no recognition site for any RE in one recognition reaction is created upon ligation of the primer with dsDNA 301. These condition ensure that the RE digestion and ligation reactions go to completion. Primer 304 should preferably not hybridize with any sequence in the initial sample mixture. The $T_m$ of primer 304 is preferably high, in the range from 50° to 80° C., and more preferably above 68° C. This ensures the subsequent PCR amplification can be controlled so that only primers and not linkers initiate new chains. For example, this $T_m$ can be achieved by using a primer having a G+C content preferably from 40–60%, most preferably from 55–60%, and a primer length most preferably of 24 nucleotide and less preferably of 18–30 nucleotides. Each primer 304 in a reaction can optionally have a distinguishable label 308, which is preferably a fluorochrome.

Linker, or shorter strand, 305 is complementary to and hybridizes with section 307 of primer 304 such that it is adjacent to 3' overhang 302. Linker 305 is most preferably 8 nucleotides long, less preferably from 4–16 nucleotides, and has no terminal phosphates to prevent any self-ligation. This linker serves only to promote ligation specificity and reaction speed. It does not perform the function of linking primer 304 to the cut dsDNA, as it did in the 5' case. Further, linker 305 $T_m$ should preferably be less than primer 304 self-annealing $T_m$. This insures that subsequent PCR amplification conditions can be controlled so that linkers present in the reaction mixture will not hybridize and act as PCR primers, and, thereby, generate spurious fragment lengths.

FIG. 11B illustrates an exemplary adapter with its primer and linker for the case of the RE NlaIII. As in the 5' overhang case, a 3' adapter can also be constructed from a hairpin loop configuration.

REs generating 5' and 3' overhangs are preferably not used in the same recognition reaction. This is in order that a complementary primer hybridization site can be presented on each of the two strands of the product of the RE/ligase recognition reaction.

Turning now to a detailed description of a preferred RE embodiment of the QEA™ method recognition reactions, the steps of this preferred embodiment comprise, first, simultaneously cleaving a mixed DNA sample (e.g., one of the populations of proteins being assayed for interaction by the method of the invention with another protein population, or a pooled group of cDNAs encoding interacting proteins identified in the assay) with one or more REs and ligating recognition moieties on the cut ends, second, amplifying the twice cut fragments, if necessary, and third, separating the fragments by length and detecting the lengths and labels, and the identities of the REs cutting each fragment. Following the amplification step, optional steps to remove unwanted singly stranded DNA fragments prior to detection can increase the signal to noise ratio of the following detection. Two alternative RE embodiments are described in following subsections. The number of REs and associated adapters preferably are limited so that both a compressed length distribution consisting of shorter fragments is avoided and enough distinguishable labels are available for all the REs used. Alternatively, REs can be used without associated adapters in order that the amplified fragments not have the associated recognition sequences. Absence of these sequences can be used to additionally differentiate genes that happen to produce fragments of identical length with particular REs.

A cDNA sample is prepared prior to carrying out a QEA™ method by removal of terminal phosphates from all the cDNA. This is important to improve the signal to noise ratio in the subsequent fragment length separation and detection by eliminating amplification of unwanted, singly cut fragments. Significant background signals arise from exponential amplification of singly cut fragments whose blunt ends have ligated to form a single dsDNA with two cut ends, an apparently doubly cut fragment, which is exponentially amplified like a normal doubly cut fragment. Since cDNA lengths vary depending on synthesis condition, these unwanted, apparently doubly cut fragments have a wide range of lengths and produce a diffuse background on gel electrophoresis which obscures sharp bands from the normally doubly cut fragments. This background can be eliminated by preventing blunt end ligation of singly cut fragments by initially removing all terminal phosphates from the cDNA sample, without otherwise disrupting the integrity of the cDNA.

Terminal phosphate removal is preferably done with a phosphatase. To prevent interference with the intended ligation of adapters to doubly cut fragments, the phosphatase activity preferably is removed prior to the RE digestion and adapter ligation step. To avoid any phosphatase separation or extraction step, the preferred phosphatase is a heat labile alkaline phosphatase which is heat inactivated prior to the RE/ligase step. A preferred phosphatase comes from cold living Barents Sea (arctic) shrimp (U.S. Biochemical Corp.) ("shrimp alkaline phosphatase" or "SAP"). Terminal phosphate removal need be done only once for each population of cDNA being analyzed.

In other embodiments additional phosphatases may be used for terminal phosphate removal, such as calf intestinal phosphatase-alkaline from Boehringer Mannheim (Indianapolis, Ind.). Those that are not heat inactivated require the addition of a step to separate the phosphatase from the cDNA before the recognition reactions, such as by phenol-chloroform extraction.

Preferably, the prepared cDNA is then separated into batches of from 1 picogram ("pg") to 200 nanograms ("ng") of cDNA each, and each batch is separately processed by the further steps of the method. For a tissue mode experiment, to analyze gene expression, preferably from a majority of expressed genes, from a single human tissue requires determination of the presence of about 15,000 distinct cDNA sequences. By way of example, one sample is divided into approximately 50 batches, each batch is then subject to the RE/ligase recognition reaction and generates approximately 200–500 fragments, and more preferably 250 to 350 fragments of 10 to 1000 bp in length, the majority of fragments preferably having a distinct length and being uniquely derived from one cDNA sequence. A preferable example analysis would entail 50 batches generating approximately 300 bands each.

For the query mode, fewer recognition reactions are employed since only a subset of the expressed genes are of interest, perhaps approximately from 1 to 100. The number of recognition reactions in an experiment may then number approximately from 1 to 10 and an appropriate number of cDNA batches is prepared.

Following cDNA preparation, the next step is simultaneous RE cutting of and adapter ligation to the sample cDNA sequences. The prepared sample is cut with one or more REs. The amount of RE enzyme in the reaction is preferably approximately a 10 fold unit excess. Substantially greater quantities are less preferred because they can lead to star activity (non-specific cutting) while substantially lower quantities are less preferred because they will result in less rapid and only partial digestion, and hence incomplete and inaccurate characterization of the subsequence distribution.

In the same reaction, adapters and ligase enzyme are present for simultaneous adapter ligation to the RE cut ends. The method is adaptable to any ligase that is active in the temperature range 10 to 37° C. T4 DNA ligase is the preferred ligase. In other embodiments, cloned T4 DNA ligase or T4 RNA ligase can also be used. In a further embodiment, thermostable ligases can be used, such as Ampligase™ Thermostable DNA Ligase from Epicenpre (Madison, Wis.), which has a low blunt end ligation activity. These ligases in conjunction with the repetitive cycling of the basic thermal profile for the RE-ligase reaction, described in the following, permit more complete RE cutting and adapter ligation.

Ligase activity can both generate unwanted products and also, if an RE recognition site is regenerated, can cause an endless cycle of further cutting and ligation. Terminal phosphate removal during cDNA preparation prevents spurious ligation of the blunt other ends of singly cut cDNA (and subsequent exponential amplification of the results). Other unwanted products are fragment concatamers formed when the sticky ends of cut cDNA fragments hybridize and ligate. Such fragment concatamers are removed by keeping the restriction enzymes active during ligation, thus cutting unwanted concatamers once they form. Further, adapters, once ligated, terminate further RE cutting, since adapters are selected such that RE recognition sites are not recreated. A high molar excess of adapters also is preferable since it limits concatamer formation by driving the RE and ligase reactions toward complete digestion and adapter ligation. Finally, unwanted adapter self-ligation is prevented since primers and linker also lack terminal phosphates (preferably due to synthesis without phosphates or less preferably due to pretreatment thereof with phosphatases).

The temperature profile of the RE/ligase reaction is important for achieving complete cutting and ligation. The preferred protocol has several stages. The first stage is at the optimum RE temperature to achieve substantially complete cutting, for example 37° C. for 30 minutes. The second stage is a ramp at $-1°$ C./min down to a third stage temperature for substantially compete annealing of adapters to the sticky cut ends and primer ligation. During this ramp, cutting and ligation continue. The third stage is at the optimum temperature for adapter annealing and ligation to the sticky ends, and is, for example, at 16° C. for 60 minutes. The fourth stage is again at the optimum RE to achieve complete cutting of all recognition sites, for example at 37° C. for 15 minutes. The fifth stage is to heat inactivate the ligase and, preferably, also the RE enzymes, and is, for example, 10 minutes at or above 65° C. If the PCR reaction is not to be immediately performed, the results are held at 4° C. If the PCR amplification is to be immediately performed, as in the preferred single tube protocol of Sec. 6.1.12.2.1 ("QEA™ Method Preferred For Use In A SEQ-QEA™ Method"), this fifth stage is at 72° C. for 20 minutes.

A less preferred profile involves repetitive cycling of the first four stages of the temperature protocol described above, that is from an optimum RE temperature to optimum annealing and ligation temperatures, and back to an optimum RE temperature. The additional cycles further drive the RE/ligase reactions to completion. In this embodiment, it is preferred to use thermostable ligase enzymes. The majority of restriction enzymes are active at the conventional 16° C. ligation temperature and hence prevent unwanted ligation events without thermal cycling. However, temperature profiles consisting of optimum ligation conditions interspersed with optimum RE cutting conditions cause both enzymatic reactions to proceed more rapidly than one constant temperature. An exemplary profile comprises periodically cycling between a 37° C. optimum RE temperature to a 16° C. optimum annealing and ligation temperature at a ramp of −1° C./min, and then back to the 37° C. optimum RE temperature. Following completion of approximately 2 to 4 of these temperature cycles, the RE and ligase enzymes are heat inactivated by a final stage at 65° C. for 10 minutes. This avoids the need for separation or extractions between steps. The results are held at 4° C.

These thermal profiles are easily controlled and automated by the use of commercially available computer controlled thermocyclers, for example from MJ Research (Watertown, Mass.) or Perkin Elmer (Norwalk, Conn.).

These reaction conditions are designed to achieve substantially complete cutting of all RE recognition sites present in the analyzed sequence mixture and complete ligation of reaction terminating adapters on the cut ends, each adapter being unique in one reaction for a particular RE cut end. The fragments generated are limited by adjacent RE recognition sites and no fragment includes internal undigested sites. Further, a minimum of unwanted self-ligation products and concatamers is formed.

Following the RE/ligase step is amplification of the doubly cut cDNA fragments. Although PCR protocols are described in the exemplary embodiment, any amplification method that selects fragments to be amplified based on end sequences is adaptable to a QEA™ method (see above). With high enough sensitivity of detection means, or even single molecule detection means, the amplification step can be dispensed with entirely. This is preferable as amplification inevitably distorts the quantitative response of the method.

The PCR amplification protocol is designed to have maximum specificity and reproducibility. First, the PCR amplification produces fewer unwanted products if the amplification steps occur at a temperature above the $T_m$ of the shorter linker so that it cannot initiate unwanted DNA strands. The linker is preferably melted by an initial incubation at 72° C. without the Taq polymerase enzyme or dNTP substrates present. A further incubation at 72° C. for 10 minutes with Taq polymerase and dNTPs is performed in order to complete partial double strands to complete double strands. Alternatively, linker melting and double strand completion can be performed by a single incubation at 72° C. for 10 minutes with Taq polymerase. Subsequent PCR amplification steps are carried out at temperatures sufficiently high to prevent re-hybridization of the bottom linker.

Second, primer strand 203 of FIG. 10A (and 304 of FIG. 11A) are typically used as PCR primers. They are preferably designed for high amplification specificity and not to hybridize with any native cDNA species to be analyzed. They have high melting temperatures, preferably above 50° C. and most preferably above 68° C., to ensure specific hybridization with a minimum of mismatches.

Third, the protocol's temperature profile is preferably designed for specificity and reproducibility. A preferred profile is 95° C. for 30 seconds, then 57° C. for 1 minute, and then 72° C. for 2 minutes. High annealing temperatures minimize primer mis-hybridizations. Longer extension times reduce PCR bias in favor of smaller fragments. Longer melting times reduces PCR amplification bias in favor of high G+C content. Further, large amplification volumes are preferred to reduce bias. Sufficient amplification cycles are performed, typically between 15 and 30 cycles.

Any other techniques designed to raise specificity, yield, or reproducibility of amplification are applicable to this method. One preferred technique is to include Betaine (Sigma) in both the RE/ligase reaction and in the PCR amplification. Another technique that can be used is the use of 7-deaza-2'-dGTP in the PCR reaction in place of dGTP. This has been shown to increase PCR efficiency for G+C rich targets (Mutter et al., 1995, Nuc. Acid Res. 23:1411–1418). As a further example, another technique that can be used is the addition of tetramethylammonium chloride to the reaction mixture, which has the effect of raising the $T_m$ (Chevet et al., 1995, Nucleic Acids Research 23(16): 3343–3344).

In a particular method of performing the PCR amplification, each RE/ligase reaction sample is sub-divided into multiple aliquots, and each aliquot is amplified with a different number of cycles. Multiple amplifications with an increasing number of amplification cycles, for example 10, 15, and 20 cycles, are preferable. Amplifications with a lower number of cycles detect more prevalent messages in a ore quantitative manner. Amplification with a higher number of cycles detect the presence of less prevalent genes but less quantitatively. Multiple amplifications also serve as controls for checking the reliability and quantitative response of the process by comparing the size of the same signal in each amplification.

Other methods of performing the PCR amplification are more suited to automation. For example, the content of a reaction vial can be configured as follows. First, 40 µl of the PCR mix without Mg ions is added followed by a wax bead that melts approximately at 72° C., such as Ampliwax beads (Perkin-Elmer, Norwalk, Conn.). This bead is melted at 75° C. for 5 minutes and solidified at 25° C. for 10 minutes. A preferred wax is a 90:10 mixture of Paraffin:Chillout™ 14. The paraffin is a highly purified paraffin wax melting between 58° C. and 60° C. such as can be obtained from Fluka Chemical, Inc. (Ronkonkoma, N.Y.) as Paraffin Wax cat. no. 76243. Chillout™ 14 Liquid Wax is a low melting, purified paraffin oil available from MJ Research. It is preferred to coat the upper sides of the reaction tubes with this solidified wax, carefully add the PCR mix, then melt this wax onto the PCR mix by the temperature protocol in Sec. 6.1.12.2.1, which beginning with a 2 min incubation at 72° C. then decreases the temperature by 5° C. every 2 min until 25° C. is reached. Then, the RE/ligase mix with Mg ions is added. The RE/ligase and PCR reactions are carried out by following the preferred temperature profile in FIG. 22D. In this arrangement in the same vial, the RE/ligase reactions can first be performed. The incubation at 72° C. for 20 minutes permits the wax layer separating the mixtures to melt, allows the RE/ligase mixture to mix with the PCR mix, and allows completion of the partial double strands to complete double strands. Then sufficient PCR cycles are performed, typically between 15 and 30 cycles. This single tube implementation is well adapted to automation. Other so called PCR "hot-start" procedures can be used, such as those employing heat sensitive antibodies (Invitrogen, Calif.) to initially block the activity of the polymerase.

Following the amplification step, optional steps prior to length separation and detection improve the method's signal to noise ratio. It is preferable to use the protocol of Sec. 6.1.12.2.1 referred to as "Biotin bead clean-up." This involves the use of a primer with a biotin (or capture moiety) in the PCR amplification followed by binding to streptavidin (or the capture moieties's binding partner) and washing to remove certain reaction products. The single strands denatured from the bound products are then further analyzed. Further, single strands produced as a result of linear amplification from singly cut fragments can be removed by the use of single strand specific exonucleases. Mung Bean exonuclease (Exo) or Exo I can be used, with Exo I preferred because of its higher specificity for single strands. Mung bean is less preferred and even less preferred is S1 nuclease.

Less preferably, the amplified products may be optionally concentrated by ethanol precipitation or column separation.

Figure 10D:
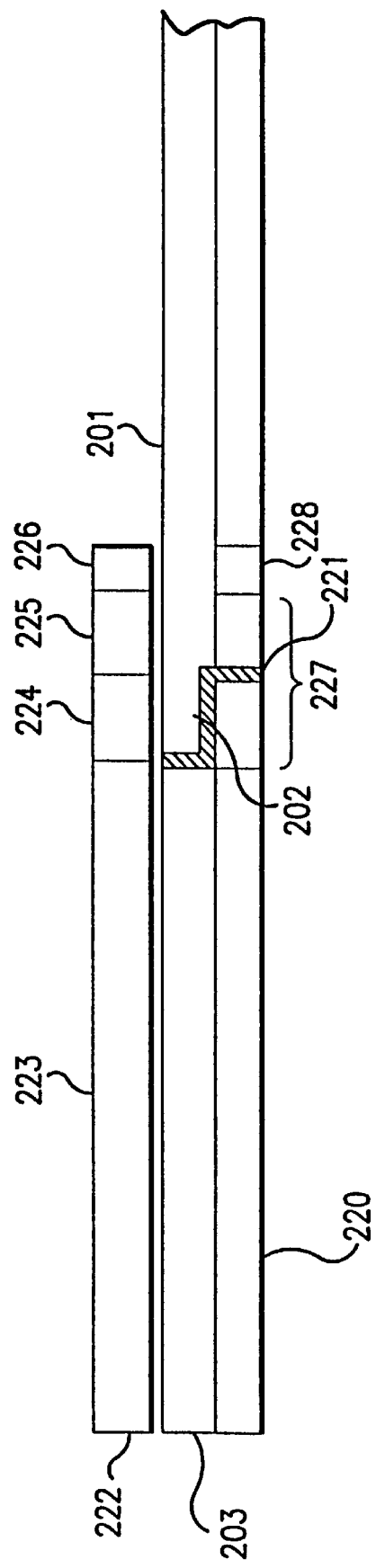

Alternate PCR primers illustrated in FIG. 10D can be advantageously used. In that figure, sample dsDNA 201 is illustrated after the RE/ligase reaction and after incubation at 72° C. for 10 minutes but just prior to the PCR amplification steps. dsDNA 201 has been cleaved by an RE recognizing subsequence 227 at position 221 producing overhang 202 and has been ligated to adapter primer strand 203. For definiteness and without limitation, a particular relative position between RE recognition subsequence 227 and overhang 202 is illustrated. Other relative positions are known. The resulting DNA has been completed to a blunt ended double strand by completing strand 220 by incubation at 72° C. for 10 minutes. Typically adapter primer strand 203 is used as the PCR primer.

Alternatively, strand 222, illustrated with its 5' end at the left, can be advantageously used. Strand 222 comprises subsequence 223, with the same sequence as strand 203; subsequence 224, with the same sequence as the RE overhang 202; subsequence 225, with a sequence consisting of a remaining portion of RE recognition subsequence 227, if any; and subsequence 226 of P nucleotides. Length P is preferably from 1 to 6 and more preferably either 1 or 2. Subsequences 223 and 224 hybridize for PCR priming with corresponding subsequences of dsDNA 201. Subsequence 225 hybridizes with any remainder of recognition subsequence 227. Subsequence 226 hybridizes only with fragments 201 having complementary nucleotides in corresponding positions 228. When P is 1, primer 223 selects for PCR amplification 1 of the 4 possible dsDNAs 201 which may be present; and when P is 2, 1 of the 16 is selected. If 4 (or 16) primers 223 are synthesized, each with one of the possible (pairs of) nucleotides, and if the RE/ligase reactions mix is separated in 4 (16) aliquots for use with one of these 4 (16) primers, the 4 (16) PCR reactions will select for amplification only one of the possible dsDNAs 201. Thus, these primers are similar to phasing primers (European Patent Publication No. 0 534 858 A1, published Mar. 31, 1993).

The joint result of using primers 223 with subsequence 226 in multiple PCR reactions after one RE/ligase reaction is to extend the effective target subsequence from the RE recognition subsequence by concatenating onto the recognition subsequence a subsequence which is complementary to subsequence 226. Thereby, many additional target subsequences can be recognized while retaining the specificity and exactness characteristic of the RE embodiment. For example, REs recognizing 4 bp subsequences can be used in such a combined reaction with an effective 5 or 6 bp target subsequence, which need not be palindromic. REs recognizing 6 bp sequences can be used in a combined reaction to recognize 7 or 8 bp sequences. Such effective sequences are then used in the computer implemented design and analysis methods subsequently described.

In a further enhancement, additional subsequence information can be generated from adapters comprising primers with specially placed Type IIS RE recognition subsequence followed by digestion with the Type IIS RE and sequencing of the generated overhang (in a SEQ-QEA™ embodiment). In a preferred alternative, the Type IIS recognition subsequence is placed so that the generated overhang is contiguous with the original recognition subsequence of the RE that cut the end to which the adapter hybridizes. In this embodiment, an effective target subsequence is formed by concatenating the sequence of the Type IIS overhang and the original recognition sequence. In another alternative, the Type IIS recognition sequence is placed so that the sequence of the generated overhang is not contiguous with the original recognition sequence. Here, the sequence of the overhang is used as an third internal subsequence in the fragment. In both cases, the additionally recognized subsequence is used in the computer implemented experimental analysis methods to increase the capability of determining the source sequence of a fragment. This enhancement is illustrated in FIGS. 23A–E and is described in detail in Sec. 5.4.4 ("A SEQ-QEA™ Embodiment of a QEA™ Method).

A subsequent QEA™ method step is the separation by length of the amplified, labeled, cut cDNA fragments and observation of the length distribution. Lengths of the sample of cut fragments will typically span a range from a few tens of bp to perhaps 1000 bp. For this range standard gel electrophoresis is capable of resolving separate fragments which differ by three or more base pairs. Knowledge of average fragment composition allows for correction of composition induced small mobility differences and permits resolution down to 1 bp. Any separation method with adequate length resolution, preferably at least to three base pairs in a 1000 base pair sequence, can also be used. The length distribution is detected with means sensitive to the primer labels. In the case of fluorochrome labels, since multiple fluorochrome labels can be typically be resolved from a single band in a gel, the products of one recognition reaction with several REs or other recognition means or of several separate recognition reaction can be analyzed in a single lane. The detection apparatus resolution for different labels limits the number of RE products that can be simultaneously detected.

Preferred protocols for the specific RE embodiments are described in detail in § 6.1.12.1 (entitled "The QEA™ Method Preferred RE Method").

5.4. FIRST ALTERNATIVE RE EMBODIMENT

An alternative QEA™ method protocol performs amplification prior to the RE/ligase step. After the RE/ligase step, further amplification is performed. Alternately, no further amplification is performed, and in this case unwanted singly cut ends are removed as they are not diluted by subsequent amplification.

Such removal is accomplished by first using primers that are labeled with a capture moiety. A capture moiety is a substance having a specific binding partner that can be affixed to a solid substrate. For example, suitable capture moiety-binding partner pairs include, but are not limited to, biotin-streptavidin, biotin-avidin, a hapten (such as digoxigenin) and a corresponding antibody, or other removal means known in the art. For example, double stranded cDNA is PCR amplified using a set of biotin-labeled, arbitrary primers with no net sequence preference. The result is partial cDNA sequences with biotin labels linked to both ends. The amplified cDNA is cut with REs and ligated to recognition moieties uniquely for each particular RE cut end. The RE/ligase step is performed by procedures identical to those of the prior section in order to drive the RE digestion and recognition moiety ligation to completion and to prevent formation of concatamers and other unwanted ligation products. The recognition moieties can be the adapters previously described.

Next the unwanted singly cut fragments labeled with the capture moiety are removed by contacting them with the binding partner for the capture moiety affixed to a solid phase, followed by removal of the solid phase. For example, where biotin is the capture moiety, singly cut fragments can be removed using streptavidin or avidin magnetic beads, leaving only doubly cut fragments that have RE-specific recognition moieties ligated to each end. These products are then analyzed, also as in the previous section, to determine the distribution of fragment lengths and RE cutting combinations.

Other direct removal means may alternatively be used in this embodiment of a QEA™ method. Such removal means include, but are not limited to, digestion by single strand specific nucleases or passage though a single strand specific chromatographic column, for example, containing hydroxyapatite.

5.4.3.2. SECOND ALTERNATIVE RE EMBODIMENT

A second alternative embodiment in conjunction with sufficiently sensitive detection means can eliminate altogether the amplification step. In the preferred RE protocol, doubly cut fragments ligated to adapters are exponentially amplified, while unwanted, singly cut fragments are at best linearly amplified. Thus amplification dilutes the unwanted fragments relative to the fragments of interest. After ten cycles of amplification, for example, signals from unwanted fragments are reduced to less than approximately 0.1% of the signals from the doubly cut fragments. Gene expression can then be quantitatively determined down to at least this level. A greater number of amplification cycles results in a greater relative dilution of signals from unwanted singly cut fragments and, thereby, a greater sensitivity. But amplification bias and non-linearities interfere with the quantitative response of the method. For example, certain fragments will be preferentially PCR amplified depending on such factors as length and average base composition.

For improved quantitative response, it is preferred to eliminate the bias accompanying the amplification steps. Then output signal intensity is linearly responsive to the number of input genes or sequences generating that signal. In the case of common fluorescent detection means, a minimum of $6 \times 10^{-18}$ moles of fluorochrome (approximately $10^5$ molecules) is required for detection. Since one gram of cDNA contains about $10^{-6}$ moles of transcripts, it is possible to detect transcripts to at least a 1% relative level from microgram quantities of mRNA. With greater mRNA quantities, proportionately rarer transcripts are detectable. Labeling and detection schemes of increased sensitivity permit use of less mRNA. Such a scheme of increased sensitivity is described in Ju et al., 1995, Fluorescent energy transfer dye-labeled primers for DNA sequencing and analysis, *Proc. Natl. Acad. Sci. USA* 92:4347–4351. Single molecule detection means are about $10^5$ times more sensitive than existing fluorescent means (Eigen et al., 1994, *Proc. Natl. Acad. Sci. USA* 91:5740–5747).

To eliminate amplification steps, a preferred protocol uses a capture moiety separation means to directly remove singly cut fragments from the desired doubly cut fragments. Only the doubly cut fragments have a discrete length distribution dependent only on the input gene sequences. The singly cut fragments have a broad non-diagnostic distribution depending on cDNA synthesis conditions. In this protocol, cDNA is synthesized using a primer labeled with a capture moiety, is circularized, cut with REs, and ligated to adapters. Singly cut ends are then removed by contact with a solid phase to which a specific binding partner of the capture moiety is affixed.

Figure 12A:
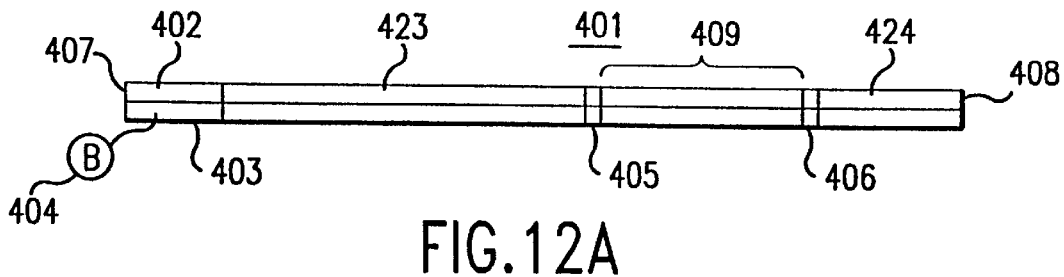
Figure 12B:
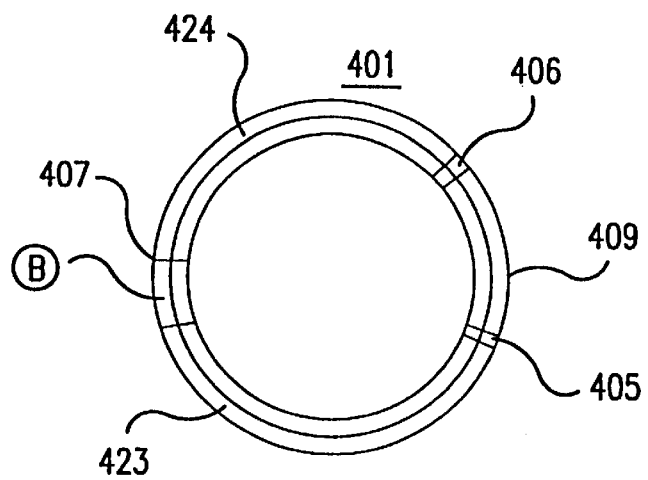
Figure 12C:
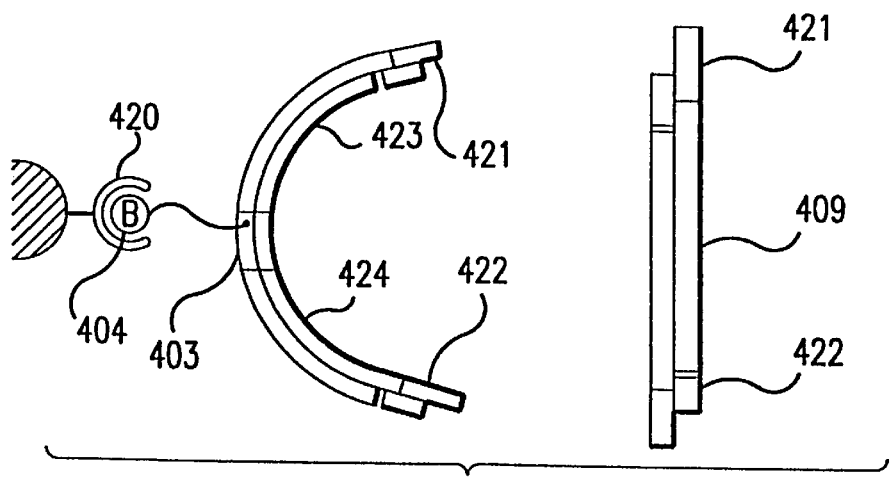

FIGS. 12A, 12B, and 12C illustrate a second alternative RE protocol, which uses biotin as such a capture moiety for direct removal of the singly cut 3' and 5' cDNA ends from the RE/ligase mixture. cDNA strands are amplified using, for example, a primer with a biotin molecule linked to one of the internal nucleotides as one of the two primers in PCR. Terminal phosphates are retained.

FIG. 11A illustrates such a cDNA 401 with ends 407 and 408, poly(da) sequence 402, poly(dT) primer 403 with biotin 404 attached. 405 is a recognition sequences for $RE_1$; 406 is a sequence for $RE_2$. Fragment 409 is the cDNA sequence defined by these adjacent RE recognition sequences. Fragments. 423 and 424 are singly cut fragments resulting from RE cleavages at sites 405 and 406.

FIG. 12B illustrates that, next, the cDNA is ligated into a circle. A ligation reaction using, for example, T4 DNA ligase is performed under sufficiently dilute conditions so that predominantly intramolecular ligations occur circularizing the cDNA, with a only a minimum of intermolecular, concatamer forming ligations. Reaction conditions favoring circularization versus concatamer formation are described in Maniatis, 1982, *Molecular Cloning A Laboratory Manual*, pp. 124–125, 286–288, Cold Spring Harbor, N.Y. Preferably, a DNA concentration of less than approximately 1 µg/ml has been found adequate to favor circularization. Concatamers can be separated from circularized single molecules by size separation using gel electrophoresis, if necessary. FIG. 12B illustrates the circularized cDNA. Blunt end ligation occurred between ends 407 and 408.

Then the circularized, biotin end labeled, cDNA is cut with REs and ligated to adapters uniquely recognizing and perhaps uniquely labeled for each particular RE cut. The RE/ligase step is performed by procedures as described in the section hereinabove in order to drive RE digestion and primer ligation to completion over formation of concatamers and other unwanted ligation products. Next, the unwanted singly cut ends are removed using streptavidin or avidin magnetic beads, leaving only doubly cut fragments that have RE-specific recognition sequences ligated to each end.

FIG. 12C illustrates these latter steps. Sequences 405 and 406 are cut by $RE_1$ and $RE_2$, respectively, and adapters 421 and 422 specific for cuts by $RE_1$ and $RE_2$, respectively are ligated onto the sticky ends. Thereby, fragment 409 is freed from the circularized cDNA and adapters 421 and 422 are ligated to it. The remaining segment of the circularized cDNA comprises singly cut ends 423 and 424 with ligated adapters 421 and 422. Both singly cut ends are joined to the primer sequence 403 with attached biotin 404. Removal is accomplished by contact with streptavidin or avidin 420 which is fixed to substrate 425, perhaps comprising magnetic beads. The doubly cut labeled fragment 409 can now be simply separated from the singly cut ends affixed to the substrate. Thereby, separation of the singly and doubly cut fragments is achieved.

Signals from the uniquely labeled doubly cut ends can be directly detected without any unwanted contamination from signals from labeled singly cut ends. Importantly, since signals originate only from cDNA sequences originally present in the sample, the detected signals will quantitatively reflect cDNA sequence content and thus gene expression levels. If the expression level is too low for direct detection, the sample can be subjected to just the minimum number of cycles of amplification, according to the methods of Example 6.1.12.1 (entitled "Preferred QEA™ RE Method"), to detect the gene or sequence of interest. For example, the number of cycles can be as small as four to eight without any concern of background contamination or noise. Thus, in this embodiment, amplification is not needed to suppress signals from singly cut ends, and preferred more quantitative response signal intensities result.

5.4.4. A SEQ-QEA™ EMBODIMENT OF A QEA™ METHOD

SEQ-QEA™ is an alternative embodiment to the preferred method of practicing a QEA™ method as described in Sec. 5.4.3 ("RE Embodiments Of a QEA™ Method"). By the use of recognition moieties, or adapters, comprising specially constructed primers bearing a recognition site for a Type IIS RE, a SEQ-QEA™ method is able to identify an additional 4–6 terminal nucleotides adjacent to the recognition site, or recognition subsequence, of the RE initially cutting a fragment. Thereby, the effective target subsequence is the concatenation of the initial RE recognition subsequence and the additional 4–6 terminal nucleotides, and has, therefore, a length of at least from 8 to 12 nucleotides and preferably has a length of at least 10 nucleotides. This longer effective target subsequence is then used in the QEA™ analysis methods as described in Sec. 5.4.5 ("QEA™ Analysis and Design Methods") which involve searching a database of sequences to identify the sequence or gene from which the fragment derived. The longer effective target subsequence increases the capability of these methods to determine a unique source sequence for a fragment.

In this section, for ease of description and not by ay of limitation, first shall be described Type IIS REs, next the specially constructed primers, and then the additional method steps of a SEQ-QEA™ method used to recognize the additional nucleotides.

Figure 23A:
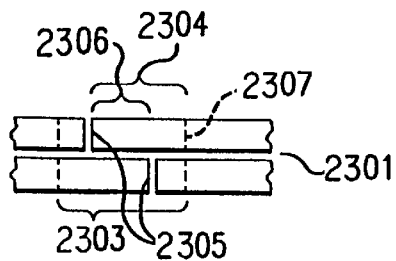
Figure 23B:
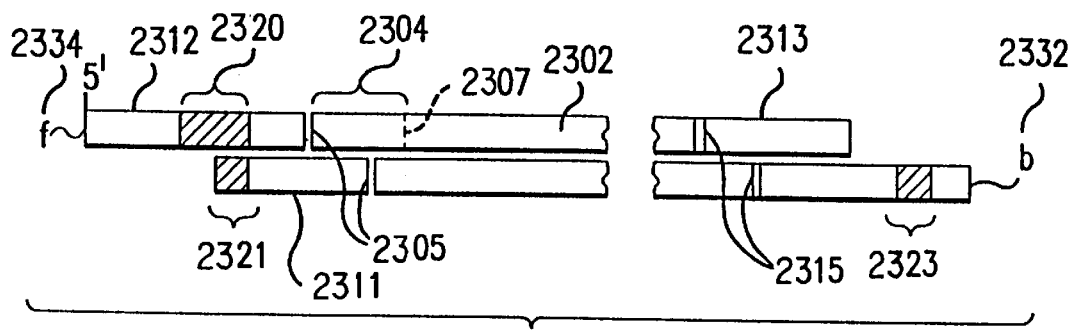
Figure 23C:
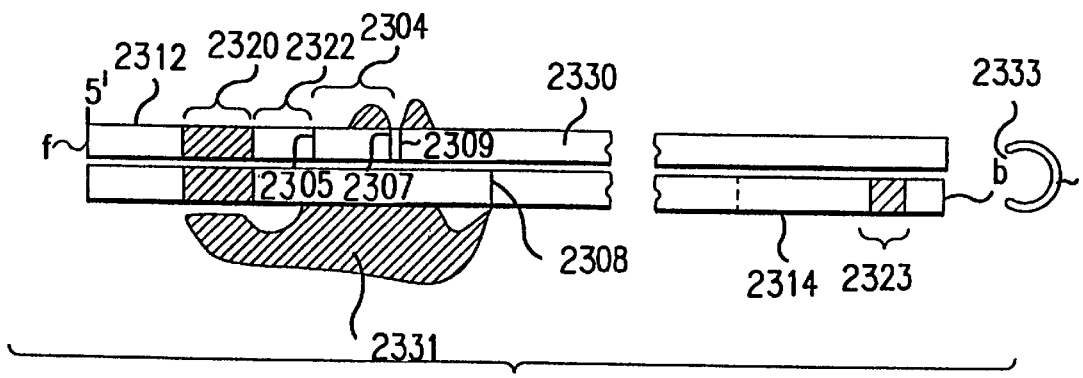

A Type IIS RE is a restriction endonuclease enzyme which cuts a dsDNA molecule at locations outside of the recognition site of the Type IIS RE (Szybalski et al., 1991, Gene 100:13–26). FIG. 23C illustrates Type IIS RE 2331 cutting dsDNA 2330 outside of its recognition site, which is recognition subsequence 2320, at locations 2308 and 2309. The Type IIS RE preferably generates an overhang by cutting the two dsDNA strands at locations differently displaced away on the two strands from the recognition subsequence. Although the recognition subsequence and the displacement(s) to the cutting site(s) are determined by the RE and are known, the sequence of the generated overhang is determined by the dsDNA cut, in particular by its nucleotide sequence outside of the Type IIS recognition region, and is, at first, unknown. Thus, in a SEQ-QEA™ embodiment, the overhangs generated by the Type IIS REs are sequenced. Table 9 in Sec. 6.1.12.5 ("Preferred Reactants for SEQ-QEA™ Methods") lists several Type IIS REs adaptable for use in a SEQ-QEA™ method and their relevant characteristics, including their recognition subsequences on both DNA strands and the displacements from these recognition subsequences to the respective cutting sites. It is preferable to use REs of high specificity and generating an overhang of at least 4 bp displaced at least 4 or 5 bp beyond the recognition subsequence in order to span the remaining recognition subsequence of the RE that initially cut the fragment. FokI and BbvI are most preferred Type IIS REs for a SEQ-QEA™ method.

Next, the special primers, and the special linkers if needed, which hybridize to form the adapters for SEQ-QEA™ have, in additional to the structure previously described in Sec. 5.4.3 ("RE Embodiments Of a QEA™ Method"), a Type IIS recognition subsequence whose placement is important in order that the overhang generated by the Type IIS enzyme be contiguous to the initial target end subsequence. The placement of this additional subsequence is described with reference to FIGS. 23A–E, which illustrate steps in a SEQ-QEA™ embodiment. FIG. 23B schematically illustrates dsDNA 2302, which is a fragment cut from an original sample sequence on one end by a first initial RE and on the other end by a different second initial RE, with adapters fully hybridized but prior to primer ligation. Thus, linker strand 2311 has hybridized to primer strand 2312 and to the 5' overhang generated by the first initial RE, and now fixes primer 2312 adjacent to fragment 2302 for subsequent ligation. Primer 2312 has recognition subsequence 2320 for Type IIS RE 2321. Linker 2311, to the extent it overlaps and hybridizes with recognition subsequence 2320, has complementary recognition subsequence 2321. Additionally, primer 2312 preferably has a conjugated label moiety 2334, e.g. a fluorescent FAM moiety. Similarly, linker strand 2313 has hybridized to primer strand 2314 and to the 5' overhang generated by the second initial RE. Primer 2314 preferably has a conjugated capture moiety 2332, e.g. a biotin moiety, and a release means represented by subsequence 2323 (to be described subsequently). Primer 2312 is also called the "cut primer," and primer 2314 the "capture primer."

Subsequence 2304 terminating at nucleotide 2307 in FIG. 23B is the portion of the recognition subsequence of the first initial RE remaining after its cutting of the original sample sequence. The placement of the Type IIS RE recognition subsequence is determined by the length of this subsequence. FIG. 23A schematically illustrates how the length of subsequence 2304 is determined by properties of the first initial RE. The first RE is chosen to be of a type that recognizes subsequence 2303, terminating with nucleotide 2307, of sample dsDNA 2301, and that cuts the two strands of dsDNA 2301 at locations 2305 that are located within recognition subsequence 2303. In order that the first RE recognize a known target subsequence, it is highly preferable that subsequence 2303 be entirely determined by the first RE and be without indeterminate nucleotides. As a result of this cutting, overhang subsequence 2306 is generated and has a known sequence, since it is entirely within the determined recognition subsequence 2303. Thereby, subsequence 2304, the portion of the recognition subsequence 2303 remaining on a fragment cut by the first RE, has a length not less than the length of overhang 2306 and is typically longer. Typically and preferably, subsequence 2303 is of length 6 and is palindromic; locations 2305 are symmetrically placed in subsequence 2303; and overhang 2306 is of length 4. Therefore, the typical length of the remaining portion 2304 of the recognition subsequence 2303 is of length 5. In cases where shorter recognition subsequences 2303 are preferably, the remaining portion 2304 will have a corresponding length.

The preferred placement of Type IIS recognition sequence 2320 is now described with reference to FIG. 23C, which schematically illustrates dsDNA 2330, which derives from dsDNA 2302 of FIG. 23B after the further steps of primer ligation, PCR amplification with primers 2312 and 2314, binding of capture moiety 2332 to binding partner 2333 affixed to a solid-phase substrate, and then binding of Type IIS RE 2331 to its recognition subsequence 2320. Subsequence 2322 is the subsequence between recognition subsequence 2320 and the end of primer 2312 at location 2305. Type IIS RE is illustrated cutting dsDNA 2330 at nucleotide locations 2308 and 2309 and, thereby, generating an exemplary 5' overhang 2324 between these locations. For this overhang to be contiguous with the remaining portion 2304 of initial target end subsequence 2303, nucleotide 2309 is adjacent to nucleotide 2307 terminating subsequence 2304. Therefore, Type IIS recognition sequence 2320 is preferably placed on primer 2312 such that the length of subsequence 2304 plus the length of subsequence 2322 equals the distance of closest cutting of Type IIS RE 2331. For example, in the case of FokI, since the closest cutting distance is 9 and the typical length of subsequence 2304 is 5, its recognition sequence is preferably placed 4 bp from the end of primer 2312. In the case of BbvI, since the closest cutting distance is 8, its recognition sequence is preferably placed 3 bp from the end of primer 2312.

Figure 23D:
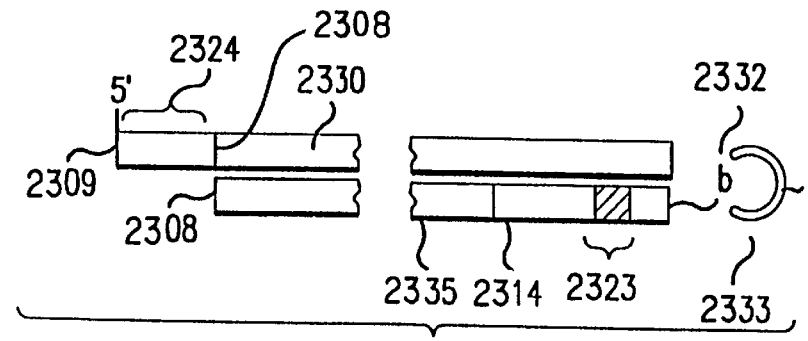

Finally, FIG. 23D schematically illustrates dsDNA 2330 after cutting by Type IIS RE 2331. dsDNA has 5' overhang 2324 between and including nucleotides 2308 and 2309, where the Type IIS RE cut dsDNA 2330 of FIG. 23C. This overhang is contiguous with former subsequence 2304, the remaining portion of the recognition subsequence of the first RE, which has been cut off. The shorter strand has primer 2314 including release means represented by subsequence 2323. dsDNA 2330 remains bound to the solid-phase support through capture moiety 2332 and binding partner 2324. The absence of label moiety 2334 can be used to monitor the completeness of cutting by Type IIS RE 2331. The label moiety also advantageously assists in the determination of the length of dsDNA 2330.

The QEA™ method is also adaptable to other less preferable placements of recognition sequence 2320. If recognition sequence 2320 is placed closer to the 3' end of primer 2312 than the optimal and preferable distance, the overhang produced by Type IIS RE 2331 is not contiguous with recognition subsequence 2303 of the first RE, and a contiguous effective target subsequence is not generated. In this case, optionally, the determined sequence of the Type IIS RE generated overhang can be used as third internal subsequence information in QEA™ experimental analysis methods in order to further resolve the source sequence of fragment 2302, if necessary. If recognition sequence 2320 is placed further from the 3' end of the cut primer than the optimal and preferable distance, the overhang produced by Type IIS RE overlaps with recognition subsequence 2303 of the first RE. In this case, the length of the now contiguous effective target subsequence is less than the sum of the lengths of the Type IIS overhang and the first RE recognition subsequence. Effective target end subsequence information is, thereby, lost. In case recognition sequence 2310 is placed further from the 3' end than the distance of furthest cutting, no additional information is obtained.

Primer 2314 also has certain additional structure. First additional structure is capture moiety 2332 conjugated near or to the 5' end of primer 2314. The capture moiety cooperates with a corresponding binding partner affixed to a solid support, an attachment means, to immobilize dsDNA 2330. Biotin/streptavidin are the preferred capture moiety/binding partner pair, which are used in the following description without limitation to this invention. This embodiment is adaptable to any operating pair of capture moiety and binding partner that remain bound under DNA denaturing conditions. Several such pairs have been previously described.

A second additional structure is a release means represented as subsequence 2323 of primer 2314. The release means allows controlled release of strand 2335 of FIG. 23D from the capture moiety/binding partner complex. This alternative is adaptable to any such controlled release means. Two such means are preferable. First, subsequence 2323 can be one or more uracil nucleotides. In this case, digestion with uracil DNA glycosylase (UDG) and subsequent hydrolysis of the sugar backbone at an alkaline pH releases strand 2335. Second, subsequence 2323 can be the recognition subsequence of an RE which cuts extremely rarely if at all in the sequences of the sample. A preferred RE of this sort is AscI, which has an 8 bp recognition sequence that rarely, if ever, occurs in mammalian DNA, and is active at the ends of molecules. In this case, digestion with the RE, i.e. AscI, releases strand 2335. These release means are particularly useful in the case of biotin-streptavidin, which form a complex that is difficult to dissociate.

Table 10 of Sec. 6.1.12.5 ("Preferred Reactants for SEQ-QEA™ Methods") lists exemplary primers, linkers, and associated REs, for the preferred implementation of SEQ-QEA™ in which contiguous effective target end subsequences are formed. This description has illustrated the generation of a 5' Type IIS generated overhang. Primers can equally be constructed to generate a less preferable 3' overhang by using a Type IIS whose closest cutting distance is on the 3' strand, rather than on the 5' strand.

Finally, the method steps of SEQ-QEA™ are now described. SEQ-QEA™ comprises, first, practicing the RE/ligase embodiment of QEA™ using the special primers and linkers previously described followed, second, by certain additional steps specific to SEQ-QEA™. More detailed exemplary reaction protocols are found in the accompanying examples in Sec. 6 ("Examples"). The protocols of Sec. 6.1.12.1 ("Preferred QEA™ RE Method") are preferred for performing a QEA™ method, and the protocols of Sec. 6.1.12.2 ("Preferred Methods Of A SEQ-QEA™ Embodiment") are preferred for performing the additional steps specific to SEQ-QEA™. FIGS. 23B–E illustrate various steps in a SEQ-QEA™ method. FIG. 23B illustrates a fragment from a sample sequence digested by two different REs and just prior to primer ligation. FIG. 23C illustrates a sample sequence after primer ligation, chain blunt-ending, and PCR amplification. These QEA™ steps are preferably performed according to the alternative described in Sec. 5.4.3 ("RE Embodiments Of a QEA™ Method"), but can alternatively be performed by any RE/ligase alternative. The additional steps unique to SEQ-QEA™ include, first, binding the amplified fragments to a solid-phase support, also illustrated in FIG. 23C, second, washing the bound fragments, and third, digesting the bound fragments by the Type IIS RE corresponding to primer 2312 used. The Type IIS digestion is preferably performed with reaction conditions suitable to achieve complete digestion, which can be checked by insuring the absence of optional label moiety 2334 after washing the bound, digested sequences. FIG. 23D illustrates dsDNA fragments 2330 remaining after complete digestion by the Type IIS RE. Before Type IIS digestion, an aliquot of the bound, amplified RE/ligase reaction products is denatured and the supernatant, containing the labeled 5' strands, are separated according to length by, e.g., gel electrophoresis, in order to determine the length of each fragment doubly cut by different REs as in the previous QEA™ embodiments.

Figure 23E:
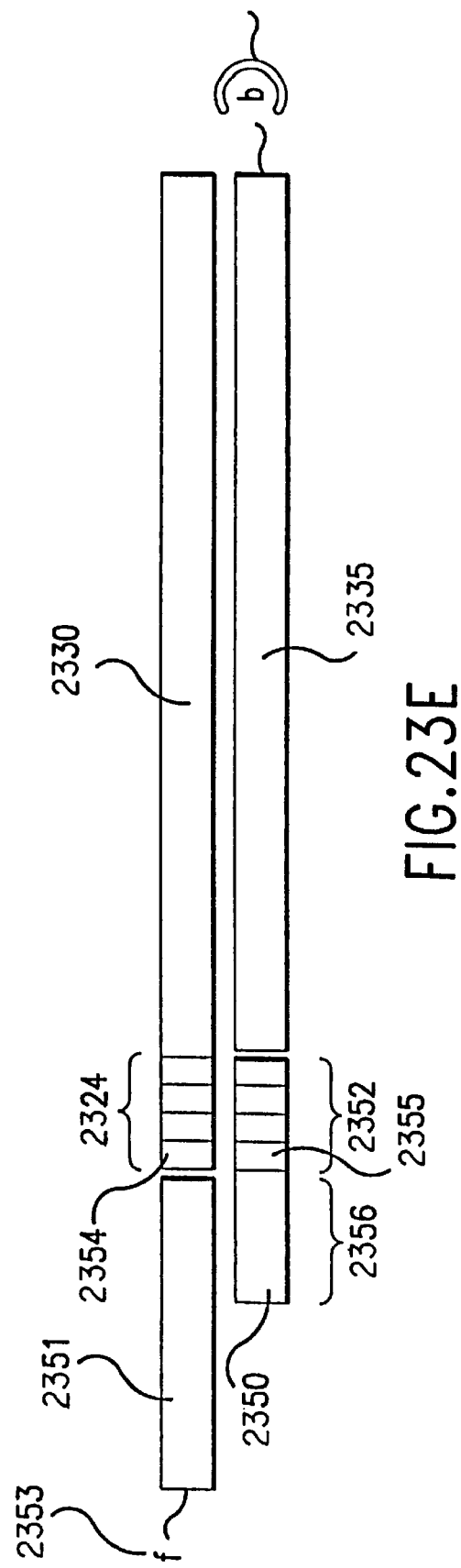

The subsequent additional SEQ-QEA™ step is sequencing of overhang 2324. This can be done in any manner known in the art. In a preferred embodiment suitable for lower fragment quantities, an alternative, herein called phasing QEA™, can be used to sequence this overhang. A phasing QEA™ method depends on the precise sequence specificity with which RE/ligase reactions recognize short overhangs, in this case the Type IIS generated overhang. FIG. 23E illustrates a first step of this alternative in which a QEA™ method adapter, which is comprised of primer 2351 with label moiety 2353 and linker 2350, has hybridized to overhang 2324 in Type IIS digested fragment 2330 bound to a solid-phase support. By way of example only, overhang 2324 is here illustrated as being 4 bp long. In this alternative, special phasing linkers are used. For each nucleotide position of overhang 2324, e.g. position 2354, 4 pools of linkers 2350 are prepared. All linkers in each pool have one fixed nucleotide, i.e. one of either A, T, C, or G, at that position, e.g. position 2355, while random nucleotides in all combinations are present at the other three positions. For each nucleotide position of the overhang, four RE/ligase reactions are performed according to QEA™ protocols, one reaction using linkers from one of the four corresponding pools.

Linkers from only one pool, that having a nucleotide complementary to overhang 2324 at position 2354, hybridize without error, and only these linkers can cause ligation of primer 2351 to the 5' strand of fragment 2330. When the results of the four RE/ligase reactions are denatured and separated according to length, only one reaction of the four can produce labeled products at a length corresponding to the length of fragment 2330, namely the reaction with linkers complementary to position 2354 of overhang 2324. Thereby, by performing four RE/ligase reactions for each nucleotide position of overhang 2324, this overhang can be sequenced. Optionally, the products of these four RE/ligase reactions can be further PCR amplified. In a further option, if linkers 2350 comprise subsequence 2356 that is uniquely related to the fixed nucleotide in subsequence 2352 and if four separately and distinguishably labeled primers 2351 complementary to these unique subsequences are used, all four RE/ligase for one overhang position reactions can be simultaneously performed in one reaction tube. With this overhang sequencing alternative, release means 2323 can be omitted from primer 2314.

In an alternate embodiment, sequencing of a 5' overhang can be done by standard Sanger reactions. Thus strand 2335 is elongated by a DNA polymerase in the presence of labeled ddNTPs at a relatively high concentration to dNTPs in order to achieve frequent incorporation in the short 4–6 bp elongation. Partially elongated strands 2335 are released by denaturing fragment 2330, washing, and then by causing release means 2323 to release strands 2335 from the capture moiety bound to the solid phase support. The released, partially elongated strands are then separated by length, e.g., by gel electrophoresis, and the chain terminating ddNTP is observed at the length previously observed for that fragment. In this manner, the 4–6 bp overhang 2324 of each fragment can be quickly sequenced.

The effective target subsequence information, formed by concatenating the sequence of the Type IIS overhang to the sequence of the recognition subsequence of the first RE, is then input into QEA™ Experimental Analysis methods, and is used as a longer target subsequence in order to determined the source of the fragment in question. This longer effective target subsequence information preferably permits exact and unique sample sequence identification.

5.4.5. QEA™ ANALYSIS AND DESIGN METHODS

Described hereinbelow are two groups of computer methods: first, methods for the QEA™ method experimental design; and second, methods for the QEA™ method experimental analysis. Although, logically, design precedes analysis, the methods of experimental design depend on basic methods described herein as part of experimental analysis. Consequently, experimental analysis methods are described first.

In the following, descriptions are often cast in terms of the preferred QEA™ method embodiment, in which REs are used to recognize target subsequences. However, such description is not limiting, as all the methods to be described are equally adaptable to all QEA™ method embodiments.

Further, the following descriptions are directed to the currently preferred embodiments of these methods. However, it will be readily apparent to those skilled in the computer and simulation arts that many other embodiments of these methods are substantially equivalent to those described and can be used to achieve substantially the same results. The QEA™ methods comprise such alternative implementations as well as its currently preferred implementation.

5.4.5.1. QEA™ EXPERIMENTAL ANALYSIS METHODS

The analysis methods comprise, first, selecting a database of DNA sequences representative of the DNA sample to be analyzed, second, using this database and a description of the experiment to derive the pattern of simulated signals, contained in a database of simulated signals, which will be produced by DNA fragments generated in the experiment, and third, for any particular detected signal, using the pattern or database of simulated signals to predict the sequences in the original sample likely to cause this signal. Further analysis methods present an easy to use user interface and permit determination of the sequences actually causing a signal in cases where the signal may arise from multiple sequences, and perform statistical correlations to quickly determine signals of interest in multiple samples.

The first analysis method is selecting a database of DNA sequences representative of the sample to be analyzed. In one use of a QEA™ method, the DNA sequences to be analyzed will be derived from a tissue sample, typically a human sample examined for diagnostic or research purposes. In this use, database selection begins with one or more publicly available databases which comprehensively record all observed DNA sequences. Such databases are GenBank from the National Center for Biotechnology Information (Bethesda, Md.), the EMBL Data Library at the European Bioinformatics Institute (Hinxton Hall, UK) and databases from the National Center for Genome Research (Santa Fe, N.Mex.). However, as any sample of a plurality of DNA sequences of any provenance can be analyzed by QEA™ methods, any database containing entries for the sequences likely to be present in such a sample to be analyzed is usable in the further steps of the computer methods.

Figures 13A, 13B:
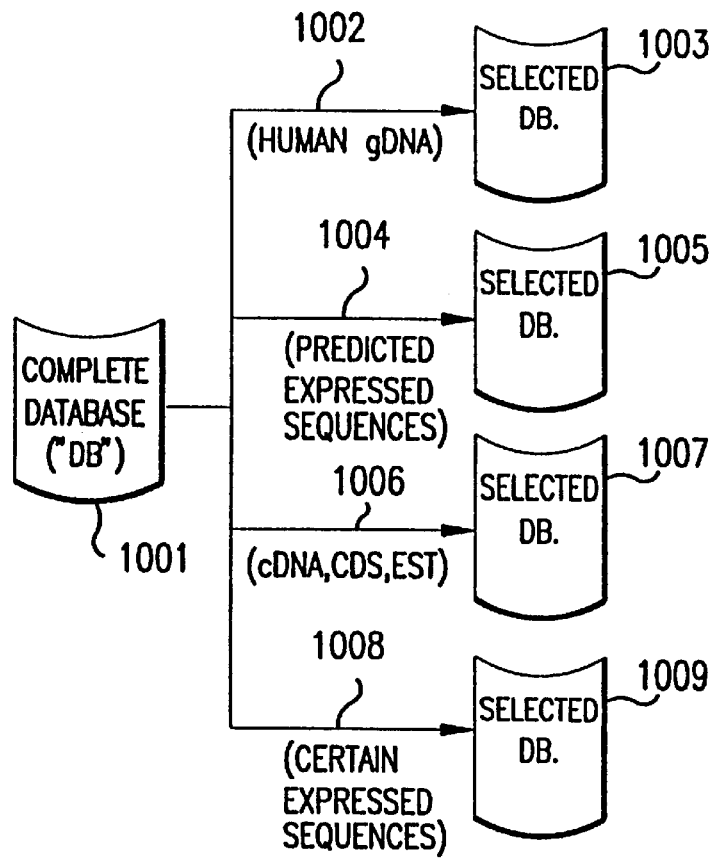
FIGS. 13A and 13B show a method for DNA sequence database selection according to a QEA™ method.

FIG. 13A illustrates the preferred database selection method starting from a comprehensive tissue derived database. Database 1001 is the comprehensive input database, having the exemplary flat-file or relational structure 1010 shown in FIG. 13B, with one row, or record, 1014 for each entered DNA sequence. Column, or field, 1011 is the accession number field, which uniquely identifies each sequence in database 1001. Most such databases contain redundant entries, that is multiple sequence records are present that are derived from one biological sequence. Column 1013 is the actual nucleotide sequence of the entry. The plurality of columns, or fields, represented by 1012 contain other data identifying this entry including, for example whether this is a cDNA or gDNA sequence, if cDNA, whether this is a full length coding sequence or a fragment, the species origin of the sequence or its product, the name of the gene containing the sequence, if known, etc. Although shown as one file, DNA sequence databases often exits in divisions and selection from all relevant divisions is contemplated by a QEA™ method. For example, GenBank has 15 different divisions, of which the EST division and the separate database, dbEST, that contain expressed sequence tags ("EST") are of particular interest, since they contain expressed sequences.

From the comprehensive database, all records are selected which meet criteria for representing particular experiments on particular tissue types. This is accomplished by conventional techniques of sequentially scanning all records in the comprehensive database, selecting those that match the criteria, and storing the selected records in a selected database.

The following are exemplary selection methods. To analyze a genomic DNA sample, database 1001 is scanned against criteria 1002 for human gDNA to create selected database 1003. To analyze expressed genes (cDNA sequences), several selection alternatives are available. First, a genomic sequence can be scanned in order to predict which subsequences (exons) will be expressed. Thus selected database 1005 is created by making selections according to expression predictions 1004. Second, observed expressed sequences, such as cDNA sequences, coding domain sequences ("CDS"), and ESTs, can be selected 1006 to create selected database 1007 of expressed sequences. Additionally, predicted and observed expressed sequences can be combined into another, perhaps more comprehensive, selected database of expressed sequences. Third, expressed sequences determined by either of the prior methods may be further selected by any available indication of interest 1008 in the database records to create more targeted selected database 1009. Without limitation, selected databases can be composed of sequences that can be selected according to any available relevant field, indication, or combination present in sequence databases.

The second analysis method uses the previously selected database of sequences likely to be present in a sample and a description of an intended experiment to derive a pattern of the signals which will be produced by DNA fragments generated in the experiment. This pattern can be stored in a computer implementation in any convenient manner. In the following, without limitation, it is described as being stored as a table of information. This table may be stored as individual records or by using a database system, such as any conventionally available relational database. Alternatively, the pattern may simply Be stored as the image of the in-memory structures which represent the pattern.

A QEA™ method experiment comprises several independent recognition reactions applied to the DNA sample sequences, where in each of the reactions labeled DNA fragments are produced from sample sequences the fragments lying between certain target subsequences in a sample. sequence. The target subsequences can be recognized and the fragments generated by the preferred RE embodiments of the QEA™ method. The following description is focused on the RE embodiments.

Figure 14:
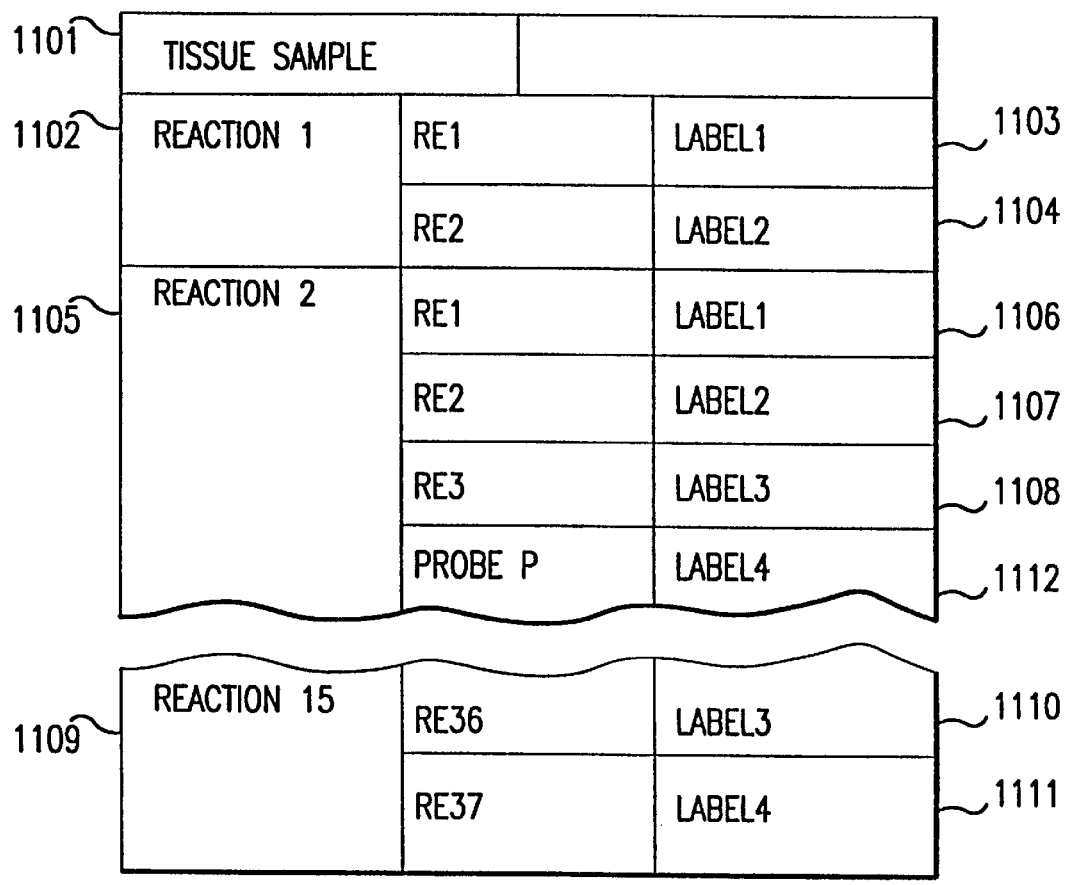
FIG. 14 shows an exemplary experimental description for an embodiment of a QEA™ method.

FIG. 14 illustrates an exemplary description 1100 of a preferred QEA™ method embodiment. Field 1101 contains a description of the tissue sample which is the source of the DNA sample. For example, one experiment could analyze a normal prostate sample; a second otherwise identical experiment could analyze a prostate sample with premalignant changes; and a third experiment could analyze a cancerous prostate sample. Differences in gene expression between these samples, particularly among interacting proteins detected according to the method of the invention, then relate to the progress of the cancer disease state. Such samples could be drawn from any other human cancer or malignancy.

Major rows 1102, 1105, and 1109 describe the separate individual recognition reactions to which the DNA from tissue sample 1101 is subjected. Any number of reactions may be assembled into an experiment, from as few as one to as many as there are pairs of available recognition means to recognize subsequences. FIG. 14 illustrates 15 reactions. For example, reaction 1 specified by major row 1102 generates fragments between target subsequences which are the recognition sites of restriction endonucleases 1 and 2 described in minor rows 1103 and 1104. Further, the RE1 cut end is recognized by a labeling moiety labeled with LABEL1, and the RE2 end is recognized by LABEL2. Similarly, reaction 15, 1109, utilizes restriction endonucleases 36 and 37 labeled with labels 3 and 4, minor rows 1110 and 1111, respectively.

Major row 1105 describes a variant QEA™ method reaction using three REs and a separate probe. As described, many REs can be used in a single recognition reaction as long as a useful fragment distribution results. Too many REs results in a compressed length distribution. Further, probes for target subsequences that are not intended to be labeled fragment ends, but rather occur within a fragment, can be used. For a further example, a labeled probe added after the QEA™ method PCR amplification step (if present in a given embodiment), a post PCR probe, can recognize subsequences internal to a fragment and thereby provide an additional signal which can be used to discriminate between two sample sequences which produce fragments of the same length and end sequence which otherwise have differing internal sequences. For another example, a probe added before a QEA™ method PCR step and which cannot be extended by DNA polymerase will prevent PCR amplification of those fragment containing the probe's target subsequences. If PCR amplification is necessary to generate detectable signals (in a given embodiment), such a probe will prevent the detection of such a fragment. The absence of a fragment may make a previously ambiguous detected band now unambiguous. Such PCR disruption probes can be PNA oligomers or degenerate sets of DNA oligomers, modified to prevent polymerase extension (e.g., by incorporation of a dideoxynucleotide at the 3' end).

In certain QEA™ method embodiments an effective target subsequence is available that is longer than the recognition subsequence of the cutting RE. In these cases, the effective target subsequence is to be used in the analysis and design methods in place of the cutting RE recognition subsequence in order to obtain extra specificity. One such embodiment is a SEQ-QEA™ method, wherein an overhang generated by a Type IIS RE is sequenced to obtain a longer target end subsequence. Another such embodiment involves the use of alternative phasing PCR primers. In this case, their extra recognition subsequences and labeling are described in rows dependent to the RE/ligase reaction whose products they are used to amplify.

Next, FIG. 15A illustrates, in general, that from the database selected to best represent the likely DNA sequences in the sample analyzed, 1201, and the description of the QEA™ method experiment, 1202, the simulation methods, 1203, determine a pattern of simulated signals stored in a simulated database, 1204, that represents the results of the QEA™ method experiment. The experimental simulation generates the same fragment lengths and end subsequences from the input database that will be generated in an actual experiment performed on the same sample of DNA sequences.

Alternately, the simulated pattern or database may not be needed, in which case the DNA database is searched sequence by sequence, mock digestions are performed and compared against the input signals. A simulated database is preferable if several signals need to be searched or if the same QEA™ method experiment is run several times. Conversely, the simulated database can be dispensed with when few signals from a few experiments need to searched. A quantitative statement of when the simulated database is more efficient depends upon an analysis of the costs of the various operations and the size of DNA database, and can be performed as is well known in the computer arts. Without limitation, in the following the simulated database is described.

FIG. 15B illustrates an exemplary structure for the simulated database. Here, the simulated results of all the individual recognition reactions defined for the experiment are gathered into rectangular table 1210. The QEA™ method is equally adaptable to other database structures containing equivalent information; such an equivalent structure would be one, for example, where each reaction was placed in a separate table. The rows of table 1210 are indexed by the lengths of possible fragments. For example, row 1211 contains fragments of length 52. The columns of table 1210 are indexed by the possible end subsequences and probe hits, if any, in a particular experimental reaction. For example, columns 1212, 1213, and 1214 contain all fragments generated in reaction 1, R1, which have both end subsequences recognized by RE1, one end subsequence recognized by RE1 and the other by RE2, and both end subsequences recognized by RE2, respectively. Other columns relate to other reactions of the experiment. Finally, the entries in table 1210 contain lists of the accession numbers of sequences in the database that give rise to a fragment with particular length and end subsequences. For example, entry 1215 indicates that only accession number A01 generates a fragment of length 52 with both end subsequences recognized by RE1 in R1. Similarly, entry 1216 indicates that accession numbers A01 and S003 generate a fragment of length 151 with both end subsequences recognized by RE3 in reaction 2.

In alternative embodiments, the contents of the table can be supplemented with various information. In one aspect, this information can aid in the interpretation of results produced by the separation and detection means used. For example, if separation is by electrophoresis, then the detected electrophoretic DNA length can be corrected to obtain the true physical DNA length. Such corrections are well known in the electrophoretic arts and depend on such factors as average base composition and fluorochrome labels. One commercially available package for making these corrections is Gene Scan Software from Applied Biosystems, Inc. (Foster City, Calif.). In this case, each table entry for a fragment can contain additionally average base composition, perhaps expressed as percent G+C content, and the experimental definition can include primer average base composition and fluorochrome label used. For a further example, if separation is by mass spectroscopy or similar method, the additional information can be the molecular weight of each fragment and perhaps a typically fragmentation pattern. Use of other separation and detection means can suggest the use of other appropriate supplemental data.

Where phasing primers are used, supplemental columns are used with RE pairs in order to further identify the effective target subsequence. A similar method can be employed to take account of the SEQ-QEA™ method additional subsequence information. In this latter case, the additional information is not available until after the QEA™ method experiment is performed.

Before describing how this simulated database is generated, it is useful first to describe how this database is used to predict experimental results. Returning to FIG. 14, labels are used to detect binding reaction events by subsequence recognition means to the target DNA, to allow detection after separation of the fragments by length. In an embodiment using fluorescent detection means, these labels are fluorochromes covalently attached to the primer strands of the adapters, as previously described, or to hybridization probes, if any. Typically, all the fluorochrome labels used in one reaction are simultaneously distinguishable so that fragments with all possible combinations of target subsequences can be fluorescently distinguished. For example, fragments at entry 1217 in table 1210 (FIG. 15B) occur at length 175 and present simultaneous fluorescent signals LABEL1 and LABEL2 upon stimulation, since these are the labels used with adapters which recognize ends cuts by RE1 and RE2 respectively. For a further example, in reaction 2, major row 1105 of experimental definition 1100 (FIG. 14), a fragment with ends cut by RE2 and RE3 and hybridizing with probe P will present simultaneous signals LABEL2, LABEL3, and LABEL4. Where effective target subsequences are constructed with the SEQ-QEA™ method or alternative phasing primers, this lookup is appropriately modified.

Other labelings are within the scope of the QEA™ method. For example, a certain group of target subsequences can be identically labeled or not labeled at all, in which case the corresponding group of fragments are not distinguishable. In this case, if RE1 and RE3 end subsequences were identically labeled in table 1210 (FIG. 15B), a fragment of length 151 may be generated by sequence T163, A01, or S003, or any combination of these sequences. In the extreme, if silver (Ag) staining of an electrophoresis gel is used in an embodiment to detect separated fragments, then all bands will be identically labeled and only band lengths can be distinguished within one electrophoresis lane.

Thus the simulated database together with the experimental definition can be used to predict experimental results. If a signal is detected in a recognition reaction, say Rn, whose end labelings are LABEL1 and LABEL2 and whose representation of length is corrected to physical length in base pairs of L, the length L row of the simulated database is retrieved and it is scanned for Rn entries with the detected subsequence labeling, by using the column headings indicating observed subsequences and the experimental definition indicating how each subsequence is labeled. If no match is found, this fragment represents a new gene or sequence not present in the selected database. If a match is found, then this fragment, in addition to possibly being a new gene or sequence, can also have been generated by those candidate sequences present in the table entry(ies) found.

The simulated database lookup is described herein as using the physical length of a detected fragment. In cases where the separation and detection means returns an approximation to the true physical fragment length, lookup is augmented to account for such as approximation. For example, electrophoresis, when used as the separation means, returns the electrophoretic length, which depending on average base composition and labeling moiety is typically within 10% of the physical length. In this case database lookup can search all relevant entries whose physical length is within 10% of the reported electrophoretic length, perform corrections to obtain electrophoretic length, and then check for a match with the detected signal. Alternative lookup implementations are apparent, one being to precompute the electrophoretic length for all predicted fragments, construct an alternate table index over the electrophoretic length, and then directly lookup the electrophoretic length. Other separation and detection means can require corresponding augmentations to lookup to correct for their particular experimental biases and inaccuracies. It is understood that where database lookup is referred to subsequently, either simple physical lookup or augmented lookup is meant as appropriate.

If matched candidate database sequences are found, then the selected database can be consulted to determine other information concerning these sequences, for example, gene name, tissue origin, chromosomal location, etc. If an unpredicted fragment is found, this fragment can be optionally retrieved from the length separation means, cloned or sequenced, and used to search for homologues in a DNA sequence database or to isolate or characterize the previously unknown gene or sequence. In this manner, the QEA™ method can be used to rapidly discover and identify new genes.

The QEA™ computer methods are also adaptable to other formats of an experimental definition. For example, the labeling of the target subsequence recognition moieties can be stored in a table separate from the table defining the experimental reactions.

Now turning to the methods by which the simulated database is generated, FIG. 16 illustrates a basic method, termed herein mock fragmentation, which takes one sequence and the definition of one reaction of an experiment and produces the predicted results of the reaction on that sequence. Generation of the entire simulated database requires repetitive execution of this basic method.

Turning first to a description of mock fragmentation, the method commences at 1301 and at 1302 it inputs the sequence to be fragmented and the definition of the fragmentation reaction, in the following terms: the target end subsequences RE1 . . . REn, where n is typically 2 or 3, and the subsequences to be recognized by third subsequence probes, P1 . . . Pn, where n is typically 0 or 1. Note that post PCR disruption probes act as unlabeled end subsequences and are so treated for input to this method. The operation of the method is illustrated by example in FIG. 17A–F for the case RE1, RE2 and P1.

At step 1303, for each target end subsequence, the method makes a "vector of ends", which has elements which are pairs of nucleotide positions along the sequence, each pair being labeled by the corresponding end subsequence. For embodiments where end subsequences are recognized by hybridizing oligonucleotides, the first member of each pair is the beginning of a target end subsequence and the second member is the end of a target end subsequence. For embodiments where target end subsequences are recognized by restriction endonucleases, the first member of each pair is the beginning of the overhang region that corresponds to the RE recognition subsequence and the second member is the end of that overhang region. It is preferred to use REs that generate 4 bp overhangs. The actual target end subsequences are the RE recognition sequences, which are preferably 4–8 bp long.

This vector is generated by a string operation which compares the target end subsequence in a 5' to 3' direction against the input sequence and seeks string matches, that is the nucleotides match exactly. Where effective target subsequences are formed by using the SEQ-QEA™ method or alternative phasing primers, it is the effective subsequences that are compared. This can be done by simply comparing the end subsequence against the input sequence starting at one end and proceeding along the sequence one base at time. However, it is preferable to use a more efficient string matching algorithm, such as the Knuth-Morris-Pratt or the Boyer-Moore algorithms. These are described with sample code in Sedgewick, 1990, *Algorithms in C*, chap. 19, Addison-Wesley, Reading, Mass.

In embodiments of the. QEA™ method wherein target subsequence are recognized with accuracy, such as the RE embodiments, the comparison of target subsequence against input sequence should be exact, that is the bases should match in a one-to-one manner. In embodiments where target subsequences are less accurately recognized, the string match should be done in a less exact, or fuzzy, manner. In this case the string operation, which generates the vector of ends, should accept partial T-n matches as well as exact matches. In this, the string operations generate the false positive matches expected from the experiments and permit these fragments to be identified. Ambiguity in the simulated database, however, increases, since more fragments leads to a greater chance of fragments of identical length and end labels.

FIG. 17A illustrates end vectors 1401 and 1402, comprising three and two ends, respectively, generated by RE1 and RE2, which are for this example assumed to be REs with a 4 bp overhang. The first overhang in vector 1401 occurs between nucleotide 10 and 14 in the input sequence.

Step 1304 of FIG. 16 merges all the end vectors for all the end subsequences and sorts the elements on the position of the end. Vector 1404 of FIG. 17B illustrates the result of this step for example end vectors 1401 and 1402.

Step 1305 of FIG. 16 then creates the fragments generated by the reaction by selecting the parts of the full input sequence that are delimited by adjacent ends in the merged and sorted end vector. Since the experimental conditions in conducting the QEA™ method should be selected such that target end subsequence recognition is allowed to go to completion, all possible ends are recognized. For the restriction endonuclease embodiments, the cutting and ligase reactions should be conducted such that all possible RE cuts are made and to each cut end a labeled primer is ligated. These conditions insure that no fragments contain internal unrecognized target end subsequences and that only adjacent ends in the merged and sorted vector define generated fragments.

Where additional information is needed for simulated database entries to adapt to inaccuracies in particular separation and detection means, such information can be collected at this step. For example, in the case of electrophoretic separation, fragment sequence can be determined and percent G+C content computed and entered in the database along with the fragment accession number.

For the PCR embodiments, the fragment length is the difference between the end position of the second end subsequence and the start position of the first end subsequence. For RE embodiments, the fragment length is the difference between the start position of the second end subsequence and the start position of the first end subsequence plus twice the primer length (48 in the preferred primer embodiment).

FIG. 17C illustrates the exemplary fragments generated, each fragment being represented by a 4 member tuple comprising: the two end subsequences, the length, and an indicator whether the third subsequence probe binds to this fragment. In FIG. 17C the position of this indicator is indicated by a '*'. Fragment 1408 is defined by ends 1405 and 1406, and fragment 1409 by ends 1406 and 1407. There is no fragment defined by ends 1405 and 1407 because the intermediate end subsequence is recognized and either fully cut in an RE embodiment or used as a fragment end priming position in a PCR embodiment. For simplicity, the fragment lengths are illustrated for the RE embodiment without the primer length addition.

Step 1306 of FIG. 16 checks if a hybridization probe is involved in the experiment. If not, the method skips to step 1309. If so, step 1307 determines the sequence of the fragment defined in step 1305. FIG. 17D illustrates that the fragment sequences for this example are the nucleotide sequences within the input sequence that are between the indicated nucleotide positions. For example, the first fragment sequence is the part of the input sequence between positions 10 and 62. Step 1308 then checks each third subsequence probe subsequence against each fragment sequence to determine whether there is any match (i.e., whether the probe has a sequence complementary enough to the fragment sequence sufficient for it to hybridize thereon).

If a match is found, an indication is made in the fragment 4 member tuple. This match is done by string searching in a similar manner to that described for generation of the end vectors.

Next at step 1309 of FIG. 16, all the fragment are sorted on length and assembled into a vector of sorted fragments, which is output from the mock fragmentation method at step 1310. This vector contains the complete list of all fragments, with probe information, defined by their end subsequences and lengths that the input reaction will generate from the input sequence.

FIG. 17E illustrates the fragment vector of the example sorted according to length. For illustrative purposes, third subsequence probe P1 was found to hybridize only to the third fragment 1412, where a 'Y' is marked. 'N' is marked in all the other fragments, indicating no probe binding.

The simulated database is generated by iteratively applying the basic mock fragmentation method for each sequence in the selected database and each reaction in the experimental definition. FIG. 18 illustrates a simulated database generation method. The method starts at 1501 and at 1502 inputs the selected representative database and the experimental definition with, in particular, the list of reactions and their related subsequences. Step 1503 initializes the digest database table so that lists of accession numbers may be inserted for all possible combinations of fragment length and target end subsequences. Step 1504, a DO loop, causes the iterative execution of steps 1505, 1506, and 1507 for all sequences in the input selected database.

Step 1505 takes the next sequence in the database, as selected by the enclosing DO loop, and the next reaction of the experiment and performs the mock fragmentation method of FIG. 16, on these inputs. Step 1506 adds the sorted fragment vector to the simulated database by taking each fragment from the vector and adding the sequence accession number to the list in the database entry indexed by the fragment length and end subsequences and probe (if any). FIG. 17F represents the simulated database entry list additions that would result for the example mock fragmentation reaction of FIGS. 17A–E. For example, accession number A01 is added to the accession number list in the entry 1412 at length 151 and with both end subsequences RE2.

Finally, step 1507 tests whether there is another reaction in the input experiment that should be simulated against this sequence. If so, step 1505 is repeated with this reaction. If not, the DO loop is repeated to select another database sequence. If all the database sequences have been selected, the step 1508 outputs the simulated database and the method ends at 1509.

5.4.5.2. QEA™ EXPERIMENTAL DESIGN METHODS

The goal of the experimental design methods is to optimize each experiment in order to obtain the maximum amount of quantitative information. An experiment is defined by its component recognition reactions, which are in turn defined by the target end subsequences recognized, third subsequences recognized, if any, and labels assigned. If the SEQ-QEA™ method or alternative phasing primers are used, effective target subsequences are used. Any of several criteria can be used to ascertain the amount of information obtained, and any of several algorithms can be used to perform the reaction optimization.

A preferred criteria for ascertaining the amount of information uses the concept of "good sequence." A good sequence for an experiment is a sequence for which there is at least one reaction in the experiment that produces a unique signal from that sequence, that is, a fragment is produced from that good sequence, by at least one recognition reaction, that has a unique combination of length and labeling. For example, returning to FIG. 15B, the sequence with accession number A01 is a good sequence because reaction 1 produces signal 1215, with length 52 and with both target end subsequences recognized by RE1, uniquely from sequence A01. However, sequence S003 is not a good sequence because there are no unique signals produced only from S003: reaction R2 produces signal 1216 from both A01 and S003 and signal 1219 from both Q012 and S003. Using the amount of good sequences as an information measure, the greater the number of good sequences in an experiment the better is the experimental design. Ideally, all possible sequences in a sample would be good sequences.

Further, a quantitative measure of the expression of a good sequence can simply be determined from the detected signal intensity of the fragment uniquely produced from the good sequence. Relative quantitative measures of the expression of different good sequences can be obtained by comparing the relative intensities of the signal uniquely produced from the good sequences. An absolute quantitative measure of the expression of a good sequence can be obtained by including a concentration standard in the original sample. Such a standard for a particular experiment can consist of several different good sequences known not to occur in the original sample and which are introduced at known concentrations. For example, exogenous good sequence 1 is added at a $1:10^3$ concentration in molar terms; exogenous good sequence 2 at a $1:10^4$ in molar terms, etc. Then comparison of the relative intensity of the unique signal of a good sequence in the sample with the intensities of the unique signal of the standards allows determination of the molar concentrations of the sample sequence. For example, if the good sequence has a unique signal intensity half way between the unique signal intensities of good sequences 1 and 2, then it is present at a concentration half way between the concentrations of good sequences 1 and 2.

Another preferred measure for ascertaining the amount of information produced by an experiment is derived by limiting attention to a particular set of sequences of interest, for example a set of known oncogenes or a set of receptors known or expected to be present in a particular tissue sample. An experiment is designed according to this measure to maximize the number of sequences of interest that are good sequences. Whether other sequences possibly present in the sample are good sequences is not considered. These other sequences are of interest only to the extent that the sequences of interest produce uniquely labeled fragments without any contribution from these other sequences.

The QEA™ method experimental design is adaptable to other measures for ascertaining information from an experiment. For example, another measure is to minimize on average the number of sequences contributing to each detected signal. A further measure is, for example, to minimize for each possible sequence the number of other sequences that occur in common in the same signals. In that case each sequence is linked by common occurrences in fragment labelings to a minimum number of other sequences. This can simplify making unambiguous signal peaks of interest (see infra).

Having chosen an information measure, for example the number of good sequences, for an experiment, the optimization methods choose target subsequences, and possibly probes, which optimize the chosen measure. One possible optimization method is exhaustive search, in which all subsequences in lengths less than approximately 10 are tested in all combinations for that combination which is optimum. This method requires considerable computing power, and the upper bound is determined by the computational facilities available and the average probability of occurrence of subsequences of a given length. With adequate resources, it is preferable to search all sequences down to a probability of occurrence of about 0.005 to 0.01. Upper bounds may range from 8 to 11 or 12.

A preferred optimization method is known as simulated annealing. See Press et al., 1986, *Numerical Recipes—The Art of Scientific Computing*, § 10.9, Cambridge University Press, Cambridge, U.K. Simulated annealing attempts to find the minimum of an "energy" function of the "state" of a system by generating small changes in the state and accepting such changes according to a probabilistic factor to create a "better" new state. While the method progresses, a simulated "temperature", on which the probabilistic factor depends and which limits acceptance of new states of higher energy, is slowly lowered.

In the application to the methods of the QEA method experimental design, a "state", denoted by S, is the experimental definition, that is the target end subsequences and hybridization probes, if any, in each recognition reaction of the experiment. The "energy", denoted E, is taken to be 1.0 divided by the information measure, so that when the energy is minimized, the information is maximized. Alternatively, the energy can be any monotonically decreasing function of the information measure. The computation of the energy is denoted by applying the function E( ) to a state.

The preferred method of generating a new experiment, or state, from an existing experiment, or state, is to make the following changes, also called moves to the experimental definition: (1) randomly change a target end subsequence in a randomly chosen recognition reaction; (2) add a randomly chosen target end subsequence to a randomly chosen reaction; (3) remove a randomly chosen target end subsequence from a randomly chosen reaction with three or ore target subsequences; (4) add a new reaction with two randomly chosen target end subsequences; and (5) remove a randomly chosen reaction. All target end subsequences are to be chosen from available RE recognition sequences. If the SEQ-QEA™ method or alternative phasing primers are used to generate effective target subsequences, all subsequences must be chosen from among such effective target subsequences that can be generated from available REs. In the case of the SEQ-QEA™ method, the extra subsequence information is not known until the QEA™ method experiment is performed. To generate a new experimental definition, one of these moves is randomly selected and carried out on the existing experimental definition. Alternatively, the various moves can be unequally weighted. In particular, if the number of reactions is to be fixed, moves (4) and (5) are skipped. The QEA™ method is further adaptable to other moves for generating new experiments. Preferable generation methods will generate all possible experiments.

Several additional subsidiary choices are needed in order to apply simulated annealing. The "Boltzman constant" is taken to be 1.0, so that the energy equals the temperature. The minimum of the energy and temperature, denoted $E_0$ and $T_0$, respectively, are defined by the maximum of the information measure. For example, if the number of good sequences of interest is G and is used as the information measure, then $E_0$, which equals $T_0$, equals $1/G$. An initial temperature, denoted $T_1$, is preferably chosen to be 1. An initial experimental definition, or state, is chosen, either randomly or guided by prior knowledge of previous experimental optimizations. Finally, two execution parameters are chosen. These parameters define the "annealing schedule", that is the manner in which the temperature is decreased during the execution of the simulated annealing method. They are the number of iterations in an epoch, denoted by N, which is preferably taken to be 100 and the temperature decay factor, denoted by f, which is preferably taken to be 0.95. Both N and f may be systematically varied case-by-case to achieve a better optimization of the experiment definition with a lower energy and a higher information measure.

With choices for the information measure or energy function, the moves for generating new experiments, an initial state or experiment, and the execution parameters made as above, the general application of simulated annealing to optimize an experimental definition is illustrated in FIG. 20A. The information measure used in this description is the number of good sequences of interest. Any information measure, such as those previously described, may be used alternately.

The method begins at step 1701. At step 1702 the temperature is set to the initial temperature; the state to the initial state or experimental definition; and the energy is set to the energy of the initial state. At step 1703 the temperature and energy are checked to determine whether either is less than or equal to the minima for the information measure chosen, as the result of either a fortuitous initial choice or subsequent computation steps. If the energy is less than or equal to the minimum energy, no further optimization is possible, and the final experimental definition and its energy is output. If the temperature is less than or equal to the minimum temperature, the optimization is stopped. Then the inverse of the energy is the number of good sequences of interest for this experimental definition.

Step 1706 is a DO loop which executes an epoch, or N iterations, of the simulated annealing algorithm. Each iteration consists of steps 1707 through 1711. Step 1707 generates a new experimental definition, or state, $S_{new}$, according to the described generation moves. Step 1708 ascertains or determines the information content, or energy, of $S_{new}$. Step 1709 tests the energy of the new state, and, if it is lower than the energy of the current state, at step 1711, the new state and new energy are accepted and replace the current state and current energy. If the energy of the new state is higher than the energy of the current state, step 1710 computes the following function.

$$\text{EXP}[-(E-E_{new})/T] \quad (4)$$

This function defines the probabilistic factor controlling acceptance. If this function is less than a random chosen number uniformly distributed between 0 and 1, then the new state is accepted at step 1711. If not, then the newly generated state is discarded. These steps are equivalent to accepting a new state if the energy is not increased by an amount greater than that determined by function (4) in conjunction with the selection of a random number. Or in other-words, a new state is accepted if the new information measure is not decreased by an amount greater than indirectly determined by function (4).

Finally, after an epoch of the algorithm, at step 1712 the temperature is reduced by the multiplicative factor f and the method loops back to the test at step 1703.

Using this algorithm, starting from an initial experimental definition which has certain information content, the algorithm produces a final experimental definition with a higher information content, or lower energy, by repetitively and randomly altering the experimental definition in order to search for a definition with a higher information content.

The computation of the energy of an experimental definition, or state, in step 1708 is illustrated more detail in FIG. 20B. This method starts at step 1720. Step 1721 inputs the current experimental definition. Step 1722 determines a complete digest database from this definition and a particular selected database by the method of FIG. 18. Step 1723 scans the entire digest database and counts the number of good sequences of interest. If the total number of good sequences is the measure used, the total number of good sequences can be counted. Alternatively, other information measures may be applied to the digest database. Step 1724 computes the energy as the inverse of the information measure. Alternatively, another decreasing function of the information content may be used as the energy. Step 1725 outputs the energy, and the method ends at step 1726.

5.4.5.3. THE QEA™ METHOD AMBIGUITY RESOLUTION

In one utilization of the QEA™ method, DNA from two related tissue samples can be subject to the same experiment, perhaps consisting of only one recognition reaction, and the outcomes compared. The two tissue samples may be otherwise identical except for one being normal and the other diseased, perhaps by infection or a proliferative process, such as hyperplasia or cancer. One or more signals may be detected in one sample and not in the other sample. Such signals might represent genetic aspects of the pathological process in one tissue. These signals are of particular interest.

The candidate sequences that can produce a signal of interest are determined, as previously described, by lock-up in the digest database. The signal may be produced by only one sequence, in which case it is unambiguously identified. However, even if the experiment has been optimized, the signal may be ambiguous in that it may be produced by several candidate sequences from the selected database. A signal of interest may be made unambiguous in several manners which are described herein.

In a first manner of making unambiguous assume the signal of interest is produced by several candidate sequences all of which are good sequences for the particular experiment. Then which sequences are present in the signal of interest can be ascertained by determining the quantitative presence of the good sequences from their unique signals. For example, referring to FIG. 15B, if the signal 1217 of length 175 with the labeling 1213 is of interest, the sequences actually present in the signal can be determined from the quantitative determination of the presence of signals 1215 and 1218. Here, both the possible sequences contributing to this signal are good sequences for this experiment.

The first manner of making unambiguous can be extended to the case where one of the sequences possibly contributing to a signal is not a good sequence. The quantitative presence of all the possible good sequences can be determined from the quantitative strength of their unique signals. The presence of the remaining sequence which is not a good sequences can be determined by subtracting from the quantitative presence of the signal of interest the quantitative presences of all the good sequences.

Further extensions of the first manner can be made to cases where more than one of the possible sequences is not a good sequences if the sequences which are not good appear as contributors to further signals involving good sequences in a manner which allows their quantitative presences to be determined. For example, suppose signal 1219 is of interest, where both possible sequences are not good sequences. The quantitative presence of sequence Q012 can be determined from signals 1220 and 1218 in the manner previously outlined. The quantitative presence of sequence S003 can be determined from signals 1216 and 1215. Thereby, the sequences contributing to signal 1219 can be determined. More complex combinations can be similarly made unambiguous.

An alternative extension of the first manner of making unambiguous is by designing a further experiment in which the possible sequences contributing to a signal of interest are good sequences even if they were not originally so. Since there are approximately 50 suitable REs that can be used in the RE embodiment of the QEA™ method (Section 6.2), there are approximately 600 RE reaction pairs that can be performed, assuming that half of the theoretical maximum of 1,250 (50×50/2=1,250) are not useable. Since most RE pairs produce on the average of 200 fragments and standard electrophoretic techniques can resolve at least approximately 500 fragment lengths per lane, the RE QEA™ method embodiment has the potential of generating over 100,000 signals (500×200=100,000). The number of possible signals is further increased by the use of reactions with three or more REs and by the recognition of third subsequences. Further, since the average complex human tissue, for example brain, is estimated to express no more than approximately 25,000 genes, there is a 4 fold excess of possible signals over the number of possible sequences in a sample. Thus it is highly likely that for any signal of interest, a further experiment can be designed and optimized for which all possible candidates of the signal of interest are good sequences. This design can be made by using the prior optimization methods with an information measure the sequences of interest in the signal of interest and starting with an extensive initial experimental definition including many additional reactions. In that manner, any signal of interest can be made unambiguous.

A second manner of making unambiguous is by automatically ranking the likelihood that the sequences possibly present in a signal of interest are actually present using information from the remainder of the experimental reactions. FIG. 21 illustrates a preferred ranking method. The method begins at step 1801 and at step 1802 inputs the list of possible accession numbers in a signal of interest, the experimental definition, and the actual experimental results. DO-loop 1803 iterates once for each possible accession number. Step 1804 performs a simulated experiment by the method illustrated in FIG. 11 in which, however, only the current accession number is acted on. The output is a single sequence digest table, such as illustrated in FIG. 17F.

Step 1805 determines a numerical score of ranking the similarity of this digest table to the experimental results. One possible scoring metric comprises scanning the digest table for all fragment signals and adding 1 to the score if such a signal appears also in the experimental results and subtracting 1 from the score if such signal does not appear in the experimental results. Alternate scoring metrics are possible. For example, the subtraction of 1 may be omitted.

Step 1806 sorts the numerical scores of the likelihood that each possible accession number is actually present in the sample. Step 1807 outputs the sorted list and the method ends at step 1808.

By this method likelihood estimates of the presence of the various possible sequences in a signal of interest can be determined.

5.4.6. APPARATUS FOR PERFORMING THE QEA™ METHODS

An apparatus for the QEA™ method includes means for performing the computer implemented QEA™ experimental analysis and design methods and optionally for performing the QEA™ method recognition reactions in a preferably automated fashion, for example by the protocols of § 6.1.12.1 (entitled "QEA™ Preferred RE Method"). In the embodiment herein presented both elements are described. In an alternative embodiment, the laboratory methods can be performed by other means, for example manually, and the apparatus needed is limited to the computer apparatus described for performing the experimental design and analysis methods.

FIG. 19A illustrates an exemplary apparatus for the QEA™ method embodiments. Computer 1601 can be, alternatively, a UNIX based work station type computer, an MS-DOS or Windows based personal computer, a Macintosh personal computer, or another equivalent computer. In a preferred embodiment, computer 1601 is a PowerPC™ based Macintosh computer with software systems capable of running both Macintosh and MS-DOS/Windows programs.

FIG. 19B illustrates the general software structure in RAM memory 1650 of computer 1601 in a preferred embodiment. At the lowest software level is Macintosh operating system 1655. This system contains features 1656 and 1657 for permitting execution of UNIX programs and MS-DOS or Windows programs alongside Macintosh programs in computer 1601. At the next higher software level are the preferred languages in which the QEA™ computer methods are implemented. LabView 1658, from National Instruments (Dallas, Tex.), is preferred for implementing control routines 1661 for the laboratory instruments, exemplified by 1651 and 1652, which perform the recognition reactions and fragment separation and detection. C or C++ languages 1659 are preferred for implementing experimental routines 1662, which are described in § ? (entitled "QEA™ Analysis And Design Methods"). Less preferred but useful for rapid prototyping are various scripting languages known in the art. PowerBuilder 1660, from Sybase (Denver, Col.), is preferred for implementing the user interfaces to the computer implemented routines and methods. Finally, at the highest software level are the programs implementing the described computer methods. These programs are divided into instrument control routines 1661 and experimental analysis and design routines 1662. Control routines 1661 interact with laboratory instruments, exemplified by 1651 and 1652, which physically perform the QEA™ method and CC protocols. Experimental routines 1662 interact with storage devices, exemplified by devices 1654 and 1653, which store DNA sequence databases and experimental results.

Returning to FIG. 19A, although only one processor is illustrated, alternatively, the computer methods and instrument control interface can be performed on a multiprocessor or on several separate but linked processors, such that instrument control methods 1661, computational experimental methods 1661, and the graphical interface methods can be on different processors in any combination or sub-combination.

Input/output devices include color display device 1620 controlled by a keyboard and standard mouse 1603 for output display of instrument control information and experimental results and input of user requests and commands. Input and output data are preferably stored on disk devices such as 1604, 1605, 1624, and 1625 connected to computer 1601 through links 1606. The data can be stored on any combination of disk devices as is convenient. Thereby, links 1606 can be either local attachments, whereby all the disks can be in the computer cabinet(s), LAN attachments, whereby the data can be on other local server computers, 6r remote links, whereby the data can be on distant servers.

Instruments 1630 and 1631 exemplify laboratory devices for performing, in a partly or wholly automatic manner, the QEA™ method recognition reactions. These instruments can be, for example, automatic thermal cyclers, laboratory robots, and controllable separation and detection apparatus, such as is found in the applicants' copending U.S. patent application Ser. No. 08/438,231 filed May 9, 1995, incorporated by reference herein in its entirety. Links 1632 exemplify control and data links between computer 1601 and controlled devices 1631 and 1632. They can be special buses, standard LANs, or any suitable link known in the art. These links can alternatively be computer readable medium or even manual input exchanged between the instruments and computer 1601. Outline arrows 1634 and 1635 exemplify the physical flow of samples through the apparatus for performing experiments 1607 and 1613. Sample flow can be either automatic, manual, or any combination as appropriate. In alternative embodiments there may be fewer or more laboratory devices, as dictated by the current state of the laboratory automation art.

On this complete apparatus, a QEA™ method experiment is designed, performed, and analyzed, preferably in a manner as automatic as possible. First, a QEA™ method experiment is designed, according to the methods specified in § 5.4.5 (entitled "QEA™ Analysis And Design Methods") as implemented by experimental routines 1662 on computer 1601. Input to the design routines are databases of DNA sequences, which are typically representative selected database 1605 obtained by selection from input comprehensive sequence database 1604, as described in § 5.4.5 (entitled "QEA™ Analysis And Design Methods"). Alternatively, comprehensive DNA databases 1604 can be used as input. Database 1604 can be local to or remote from computer 1601. Database selection performed by processor 1601 executing the described methods generates one or more representative selected databases 1605. Output from the experimental design methods are tables, exemplified by 1609 and 1615, which, for a QEA™ method RE embodiment, specify the recognition reaction and the REs used for each recognition reaction.

Second, the apparatus optionally performs the designed experiment. Exemplary experiment 1607 is defined by tissue sample 1608, which may be normal or diseased, experimental definition 1609, and physical recognition reactions 1610 as defined by 1609. Where instrument 1630 is a laboratory robot for automating reaction, computer 1601 commands and controls robot 1630 to perform reactions 1610 on cDNA samples prepared from tissue 1608. Where instrument 1631 is a separation and detection instrument, the results of these reactions are then transferred, automatically or manually, to 1631 for separation and detection. Computer 1601 commands and controls performance of the separation and receives detection information. The detection information is input to computer 1601 over links 1632 and is stored on storage device 1624, along with the experimental design tables and information on the tissue sample source for processing. Since this experiment uses, for example, fluorescent labels, detection results are stored as fluorescent traces 1611.

Experiment 1613 is processed similarly along sample pathway 1633, with robot 1630 performing recognition reactions 1616 on cDNA from tissue 1608 as defined by definition 1615, and device 1631 performing fragment separation and detection. Fragment detection data is input by computer 1601 and stored on storage device 1625. In this case, for example, silver staining is used, and detection data is image 1617 of the stained bands.

During experimental performance, instrument control routines 1661 provide the detailed control signals needed by instruments 1630 and 1631. These routines also allow operator monitoring and control by displaying the progress of the experiment in process, instrument status, instrument exceptions or malfunctions, and such other data that can be of use to a laboratory operator.

Third, interactive experimental analysis is performed using the database of simulated signals generated by analysis and design routines 1662 as described in § 5.4.5 (entitled "QEA™ Analysis And Design Methods"). Simulated database 1612 for experiment 1607 is generated by the analysis methods executing on processor 1601 using as input the appropriate selected database 1605 and experimental definition 1609, and is output in table 1612. Similarly table 1618 is the corresponding simulated database of signals for experiment 1613, and is generated from appropriate selected database 1605 and experimental definition 1615. A signal is made unambiguous by experimental routines 1662 that implement the methods described in § 5.4.5 (entitled "QEA™ Analysis And Design Methods").

Display device 1602 presents an exemplary user interface for the QEA™ method data. This user interface is programmed preferably by using the Powerbuilder display front end. At 1620 are selection buttons which can be used to select the particular experiment and the particular reaction of the experiment whose results are to be displayed. Once the experiment is selected, histological images of the tissue source of the sample are presented for selection and display in window 1621. These images are typically observed, digitized, and stored on computer 1601 as part of sample preparation. The results of the selected reaction of the selected experiment are displayed in window 1622. Here, a fluorescent trace output of a particular labeling is made available. Window 1622 is indexed by marks 1626 representing the possible locations of DNA fragments of successive integer lengths.

Window 1623 displays contents from simulated database 1612. Using, for example, mouse 1603, a particular fragment length index 1626 is selected. The processor then retrieves from the simulated database the list of accession numbers that could generate a peak of that length with the displayed end labeling. This window can also contain further information about these sequences, such as gene name, bibliographic data, etc. This further information may be available in selected databases 1605 or may require queries to the complete sequence database 1604 based on the accession numbers. In this manner, a user can interactively inquire into the possible sequences causing particular results and can then scan to other reactions of the experiment by using buttons 1620 to seek other evidence of the presence of these sequences.

It is apparent that this interactive interface has further alternative embodiments specialized for classes of users of differing interests and goals. For a user interested in determining tissue gene expression, in one alternative, a particular accession number is selected from window 1623 with mouse 1603, and processor 1601 scans the simulated database for all other fragment lengths and their recognition reactions that could be produced by this accession number. In a further window, these lengths and reactions are displayed, and the user allowed to select further reactions for display in order to confirm or refute the presence of this accession number in the tissue sample. If one of these other fragments are generated uniquely by this sequence (a "good sequence", see supra), that fragment can be highlighted as of particular interest. By displaying the results of the generating reaction of that unique fragment, a user can quickly and unambiguously determine whether or not that particular accession number is actually present in the sample.

In another interface alternative, the system displays two experiments side by side, displaying two histological images 1621 and two experimental results 1622. This allows the user to determine by inspection signals present in one sample and not present in the other. If the two samples were diseased and normal specimens of the same tissue, such signals would be of considerable interest as perhaps reflecting differences due to the pathological process. Having a signal of interest, preferably repeatable and reproducible, a user can then determine the likely accession numbers causing it by invoking the previously described interface facilities. In a further elaboration of this embodiment, system 1601 can aid the determination of signals of interest by automating the visual comparison by performing statistical analysis of signals from samples of the same tissue in different states. First, signals reproducibly present in tissue samples in the same state are determined, and second, differences in these reproducible signals across samples from the several states are compared. Display 1602 then shows which reproducible signals vary across the states, thereby guiding the user in the selection of signals of interest.

This apparatus has been described above in an embodiment adapted to a single site implementation, where the various devices are substantially local to computer 1601 of FIG. 19A, although the various links shown could also represent remote attachments. Alternative, explicitly distributed embodiments of this apparatus are possible as is apparent to those of ordinary skill in the computer arts.

All the computer implemented QEA™ methods can be recorded for storage and transport on any computer readable memory devices known in the art. For example, these include, but are not limited to, semiconductor memories—such as ROMs, PROMs, EPROMs, EEPROMS, etc., of whatever technology or configuration—magnetic memories—such as tapes, cards, disks, etc of whatever density or size—optical memories—such as optical read-only memories, CD-ROM, or optical writable memories—and any other computer readable memory technologies.

6. EXAMPLES

The following examples further illustrate the different features of the invention but do not in any way limit the scope of the invention which is defined by the appended claims. This section describing examples has been divided into a section describing protocols that are common to several of the examples and another section that is a description of the examples themselves.

6.1. DESCRIPTION OF PROTOCOLS

The following sections describe protocols for use.

6.1.1. MATING PROTOCOL

Mating is performed as per standard protocols (Sherman et al., eds., 1991, *Getting started with yeast*, Vol. 194, Academic Press, New York). Briefly, cells are grown until mid to late log phase on solid or liquid media that select for the appropriate plasmids. The two mating strains, a and α, are then mixed together as a paste onto a rich solid media like YPAD (Sherman et al., eds., 1991, *Getting started with yeast*, Vol. 194, Academic Press, New York) and incubated at 30° C. for 6–8 hr. The cells are then transferred to selective media appropriate for the desired diploids.

In a preferred embodiment, $1 \times 10^8$ cells/ml of each mating type are mixed for 30 minutes at room temperature and then plated onto a 150 mm diameter YPAD plate and incubated at 30° C. for 6–8 hours. Then, the contents of the plate are harvested in a volume of 1–2 ml in the appropriate selective media and transferred to a 150 mm diameter plate that has the selective medium for selecting interactions. Alternatively, the YPAD plate with the mating mix can be replica-plated onto another 15 cm diameter plate that has the selective medium for selecting interactions.

6.1.2. TRANSFORMATION PROTOCOL

Yeast transformations are performed by the lithium acetate procedure (Ito et al., 1983, J. Bacteriol. 153:163–168) and the transformants are selected by plating on appropriate selective media that are usually Synthetic Complete (SC) media that lack the appropriate nutrients (Sherman et al., eds., 1991, *Getting started with yeast*, Vol. 194, Academic Press) New York).

6.1.3. RNA EXTRACTION

The tissue to be extracted is weighed and a 10-fold volume/weight of Triazol reagent (Life Technologies) is added and the tissue ground with a Polytron homogenizer (Brinkman Instruments, Westbury, N.Y.). Example: 100 mg in 1 ml, 1 g in 10 ml. 0.2 volumes of chloroform are added and vortexed for 15 seconds, and phases separated by centrifugation (5000×g, 15 min). The aqueous phase is precipitated with 0.6 volumes of 2-propanol. The precipitated RNA is pelleted at 10,000×g for 15 min, rinsed with 70% ethanol and dried. The RNA pellet is resuspended in water to give a final concentration of 100 ng/$\mu$l.

6.1.4. DNASE TREATMENT 0.2 volumes of 5×reverse transcriptase buffer (Life Technologies), 0.1 volumes of 0.1 M DTT, and 5 units RNAguard/100 mg starting tissue (Pharmacia Biotech, Uppsala, Sweden) are added to the RNA extracted according to Section 6.1.3. One unit RNase-free DNase I (Pharmacia Biotech)/100 mg starting tissue is added, and the mixture is incubated at 37° C. for 20 min. 10 volumes of Triazol is added and RNA extraction by addition of chloroform and precipitation is repeated.

6.1.5. MESSENGER RNA PURIFICATION

RNA concentration is estimated by measuring $OD_{260}$ of a 100-fold dilution of extracted RNA mixture after DNase treatment. The Dynal oligo(dT) magnetic beads have a capacity of 1 $\mu$g poly(A+) per 100 $\mu$g of beads (1 mg/ml concentration). Assuming that 2% of the total RNA is poly(A+), 5 volumes of Lysis/Binding buffer (Dynal) and sufficient beads to bind poly(A+) are added. This mixture is heated at 65° C. for 2 min and then incubated at room temperature for 5 min. The beads are first washed with 1 ml washing buffer/LiDS (Dynal), then with 1 ml washing buffer (Dynal) twice. The poly(A+) RNA is eluted with 1 $\mu$l water/$\mu$g beads twice.

6.1.6. cDNA SYNTHESIS AND CONSTRUCTION OF FUSION-LIBRARIES cDNA synthesis is performed using the Hybrizap Two-Hybrid cDNA synthesis and Gigapack cloning kit cDNA synthesis kit (Stratagene) according to the manufacturer's protocol with the following modifications. The cDNA synthesis is performed substantially as per the Gubler-Hoffman method (Gubler and Hoffman, 1983, Gene 25:263–269). In the first strand synthesis step, MoMuLV reverse transcriptase is used for reverse transcription. The primer (from the kit) (GAGAGAGAGAGAGAGAGAGAACTA GTCTCGAGTTTTTTTTTTTTTTTTTT) (SEQ ID NO:36) used in the first strand synthesis also adds an XhoI site near the 3' end. After the second strand synthesis, EcoRI adapters (also from the kit) are ligated to the cDNAs using standard linker ligation conditions according to manufacturer's (Stratagene's) protocols. The identities of the EcoRI adapters are AATTCGGCACGAG (SEQ ID NO:37) and CTCGT-GCCG (SEQ ID NO:38). Following this, the cDNA is digested with EcoRI and XhoI and cloned into the EcoRI and XhoI sites of the Hybrizap vector (Stratagene), which is a lambda phage vector, using the manufacturer's protocols. The phagemid pAD-GAL4 bearing the cDNA inserts is removed by in vivo excision using the reagents and protocols provided in the Hybrizap Gigapack cloning kit. This creates a cDNA library, containing plasmid pAD-GAL4, with the sense strand being in frame with the GAL4 activation domain of the plasmid pAD-GAL4 (Stratagene). Plasmid pAD-GAL4 contains LEU2 to facilitate selection in media lacking leucine.

In a different embodiment, the activation domain fusion library is created in the vector pACT2 (Clontech). The EcoRI-XhoI linked cDNA is cloned between the EcoRI and SalI sites in pACT2. This creates a cDNA library with the sense strand being in frame with the GAL4 activation domain in the plasmid pACT2 (Clontech). Plasmid pACT2 contains LEU2 to facilitate selection in media lacking leucine.

In the case of cloning into pAS2-1 (Clontech) to create a library of DNA-binding domain fusion genes, the EcoRI-XhoI linked cDNA is cloned between the EcoRI and SalI sites in pAS2-1 to create a cDNA library in plasmid pAS2-1, with the sense strand being in frame with the GAL4 DNA-binding domain. Statistically, one in every three clones will represent a true open reading frame. Plasmid pAS2-1 contains TRP1 to facilitate selection in media lacking tryptophan.

6.1.7. TRANSFORMATION OF THE REPORTER STRAINS WITH THE BINDING DOMAIN FUSION cDNA LIBRARY AND ACTIVATION DOMAIN cDNA LIBRARY TO CREATE "M" AND "N" POPULATIONS

The strains YULH and N106' (see Sections 6.3.2 and 6.3.4) are transformed with the pAS2-1 and the pAD-GAL4 or pACT2 cDNA libraries, respectively, by lithium acetate protocol (Section 6.1.2; Ito et al., 1983, J. Bacteriol. 153:163–168). One $\mu$g of library DNA generally yields a maximum of $1\times10^6$ transformants. The transformants are selected on either media lacking leucine (for pAD-GAL4/pACT2) or lacking tryptophan and containing 5-FOA (for pAS2-1). In the latter case, all GAL4 DNA-binding domain (GBD)-fusions that fortuitously activate transcription on their own will be eliminated since 5-FOA kills the URA+ cells. The transformants are harvested in the appropriate media (SC-Leu for pAD-GAL4/pACT2 and SC-TRP for pAS2-1) to a final cell density of $1\times10^8$ cells/ml and stored in aliquots at −70° C. after making them 10% in DMSO or glycerol.

6.1.8. WHOLE CELL PCR

After mating (Section 6.1.1), whole cell PCR is performed on the cells positive for interaction under the following conditions:

Reaction volume: 100 $\mu$l

10×PC2 Buffer for Klentaq polymerase: 10 $\mu$l (1×PC2 Buffer=20 mm Tris-HCl pH 8.55, 16 mM ammonium sulfate, 2.5 mM $MgCl_2$, 150 $\mu$g/ml BSA)

10 mM dNTPs: 3 $\mu$l 50 pmoles of each primer pair 1.0 $\mu$l of Klentaq polymerase (a thermostable DNA polymerase sold by AB Peptides Inc., St. Louis, Mo.).

2–5 µl of saturated culture of yeast in water. PCR is performed at 94° C. for 30 sec, 45–55° C. for 30 sec and 72° C. for 2 min, with each being repeated for 20–30 cycles. The annealing temperature (i.e., the 45–55° C. for 30 sec step) depends on the melting temperature of the primers used. The PCR primers are designed in such a way that the melting temperature usually lies between 45–55° C. A primer pair suitable for use can be selected from among those described below.

To amplify the fusion gene insert from pAS2, pAS2-1, pASSfiI, pBD-GAL4, and other related vectors such as pAS1 (collectively referred to herein as "pAS-like-vectors") (pAS1 is a parental GAL4-DNA binding domain vector; see Durfee et al., 1993, Genes Dev. 7:555–569), one of the following primer pairs can be used:

pACTBAC+pASFOR
PASSEQI+pASSEQII
PASSEQIA+pASSEQII pASFOR, pASSEQI, and pASSEQIA are interchangeable. pASSEQII and pACTBAC are interchangeable.

To amplify the fusion gene insert from pACT, pACT2, pACTSfiI, pAD-GAL4 and other related vectors (collectively referred to herein as "pACT-like vectors"), one of the following primer pairs can be used:

pACTBAC+pACTFOR
pACTBAC+pACTFORII
pACTSEQI+pACTSEQII
pACTSEQI+pACTBAC
pACTSEQII+pACTFOR
pACTSEQII+pACTFORII pACTBAC and pACTSEQII are interchangeable.
pACTFOR, pACTFORII, and pACTSEQI are interchangeable.

The identities of the above-listed primers are as follows:

pACTSEQII=5'-CGA TGC ACA GTT GAA GTG AAC-3' (SEQ ID NO:1)
pACTFORII=5'-CGC GTT TGG AAT CAC TAC AGG GAT G-3' (SEQ ID NO:2)
pACTBAC=5'-CTA CCA GAA TTC GGC ATG CCG GTA GAG GTG TGG TCA-3' (SEQ ID NO:3)
pASFOR=5'-ATG AAG CTA CTG TCT TCT ATC GAA C-3' (SEQ ID NO:4)
pACTFOR=5'-ATGGATGATGTATATAACTATCTATTC-3' (SEQ ID NO:23)
pACTSEQI=5'-TTGGAATCACTACAGGGATG-3' (SEQ ID NO:49).
pASSEQI=5'-GAATTCATGGCTTACCCATAC-3' (SEQ ID NO:50)
pASSEQII=5'-AACCTGACCTACAGGAAAGAGTTAC-3' (SEQ ID NO:51)
pASSEQIA=5'-CCTCTAACATTGAGACAGCATAG-3' (SEQ ID NO:52) The primers can be used in sequencing as well as in PCR.

6.1.9. RECOVERY OF COLONIES POSITIVE FOR PROTEIN-PROTEIN INTERACTION

Colonies that are URA+, HIS+, 3-AT$^r$ and lacZ+ are selected as positive for protein-protein interactions and arrayed onto 96-well plates in which each well contains 100 µl of the appropriate selective media like SC-URA-HIS-TRP-LEU+3-AT (SC medium lacking uracil, histidine, tryptophan, leucine, and containing 3-amino-1,2,4-triazole). Thus, each column or row in a 96-well plate now serves as a pool of interactants. Cells are grown at 30° C. until late log phase ($OD_{600}$ of 1.5–2). These cells are processed further or stored frozen at –80° C. after making them 10% in DMSO or glycerol.

6.1.10. PRODUCTION OF PCR POOLS FOR CREATION OF PROTEIN INTERACTION MAPS

If the total number of positive colonies is less than 1500 then they are readily pooled according to a two-dimensional pooling scheme. 10 µl of each well in a given column or row are combined into a single pool and mixed well. The mix is centrifuged at 1000 g for 2 minutes, resuspended in 100 µl of water, centrifuged again as described above, and the supernatant discarded. The PCR mix is added directly to the pellet and mixed well. PCR is performed wherein DNA-binding (pAS-specific) and activation domain fusion specific primers (pAD-GAL4/pACT-specific) amplify the genes encoding the two interacting proteins directly from yeast (Section 6.1.8). Thus, each PCR reaction refers to the "M" population or the "N" population. Primers that can be used are described in Section 6.1.8.

6.1.11. β-GALACTOSIDASE ASSAYS

Filter-lift β-galactosidase assays are performed as modified from the protocol of Breeden and coworkers (Breeden and Nasmyth, 1985, Cold Spring Harb. Symp. Quant. Biol. 50:643–650). The URA+, HIS+ and 3-AT$^r$ colonies are patched onto SC-TRP-LEU-URA-HIS+3-AT plates, grown overnight and replica plated onto Whatman no. 1 filter papers overlayed onto SC-TRP-LEU plates and again grown overnight at 30° C. The filters with the grown colonies of yeast are then assayed for β-galactosidase activity. Colonies positive for β-galactosidase activity turn blue. Quantitative β-galactosidase assays on yeast are performed as described previously by Coney and Roeder (Coney and Roeder, 1988, Mol. Cell. Biol. 8:4009–4017). Chemiluminescent β-galactosidase assays are performed by using the Galacto-Light and Galacto-Light Plus Chemiluminescent reporter assay system for the detection of β-galactosidase (Tropix, Inc.) according to the manufacturer's protocols. Fluorescent β-galactosidase assays are performed using the FluoReporter lacZ/Galactosidase Quantitation kit (Molecular Probes) according to the manufacturer's protocols.

6.1.12. PROTOCOLS FOR QEA™ METHODS AND SEQ-QEA™ METHODS 6.1.12.1. PREFERRED QEA™ RE METHOD

A DNA (preferably cDNA) population is input to the QEA™ method protocols described in this section. This DNA population can be pooled DNAs, each DNA encoding an interactant protein identified according to the methods of the invention, or can be, or can be derived from, one or both of two DNA populations encoding the initial protein populations between which (in fusion form) protein interactions are detected according to the invention.

This protocol is designed to keep the number of individual manipulations down, and thereby raise the reproducibility of the QEA™ method procedure. In a preferred method, no buffer changes, precipitations or organic (phenol/chloroform) extractions are used, all of which lower the overall efficiency of the process and reduce its utility for general use and more specifically for its use in automated or robotic procedures.

The protocol is described in terms of cDNA, but can be used with any DNA.

6.1.12.1.1. cDNA PREPARATION

Terminal phosphate removal from cDNA is illustrated with the use of Barents sea shrimp alkaline phosphatase ("SAP") (U.S. Biochemical Corp.) and 2.5 µg of cDNA. Substantially less (<10 ng) or more (>20 µg) of cDNA can be prepared at a time with proportionally adjusted amounts of enzymes. Volumes are maintained to preserve ease of handling. The quantities necessary are consistent with using the method to analyze small tissue samples from normal or diseased specimens.

1. Mix the following reagents 2.5 µl 200 mM Tris-HCL

23 µl cDNA

2 µl 2 units/µl Shrimp alkaline phosphatase

The final resulting cDNA concentration is 100 ng/µl.

2. Incubate at 37° C. for 1 hour

3. Incubate at 80° C. 15 minutes to inactivate the SAP.

6.1.12.1.2. PREFERRED RE/LIGASE AND AMPLIFICATION REACTIONS

Once the cDNA has been prepared, including terminal phosphate removal, it is separated into a number of batches of from 10 ng to 200 ng each, equal to the desired number of individual samples that need to be analyzed and the extent of the analysis. For example, if six RE/ligase reactions and six analyses are needed to generate all necessary signals, six batches are made. Shown by example are 50 ng fractions.

RE/ligase reactions are performed as digestions by, preferably, a pair of REs; alternatively, one or three or more REs can be used provided the four base pair overhangs generated by each RE differ and can each be ligated to a uniquely adapter and a sufficiently resolved length distribution results. The amount of RE enzyme specified is sufficient for complete digestion while minimizing any other exo- or endo-nuclease activity that may be present in the enzyme.

Adapters are chosen that are unique to each RE in a reaction. Thus, one uses a linker complementary to each unique RE sticky overhang and a primer which uniquely hybridized with that linker. The primer/linker combination is an adapter, which will preferably be uniquely and distinguishably labeled.

Adapter Annealing

Pairs of 12-mer linkers and 24-mer primers are pre-annealed to form adapters before they are used in the QEA™ method reactions, as follows:

1. Add to water linker and primer in a 2:1 concentration ratio (12-mer:24-mer) with the primer at a total concentration of 5 pM per µl.

2. Incubate at 50° C. for 10 minutes.

3. Cool slowly to room temperature and store at −20° C.

Restriction-Digestion/Ligation Reaction

Reactions are prepared for use in a 96 well thermal cycler. Add per reaction:

1. 1 U of appropriate REs (New England Biolabs, Beverly, Mass.) (preferred RE pair listing in § 6.1.12.3 (entitled "Preferred QEA™ Method Adapters and RE Pairs"))

2. 1 µl of appropriate annealed adapter 3. 1 µl of Ligase/ATP (0.2 µl T4 DNA ligase [1 U/µl]/0.8 µl 10 mM ATP from Life Technologies (Gaithersburg, Md.))

4. 0.5 µl 50 mM MgCl$_2$ 5. 10 ng of subject prepared cDNA 6. 1 µl 10×NEB2 buffer from New England Biolabs (Beverly, Mass.)

7. Water to bring total volume to 10 µl

Figure 22A:
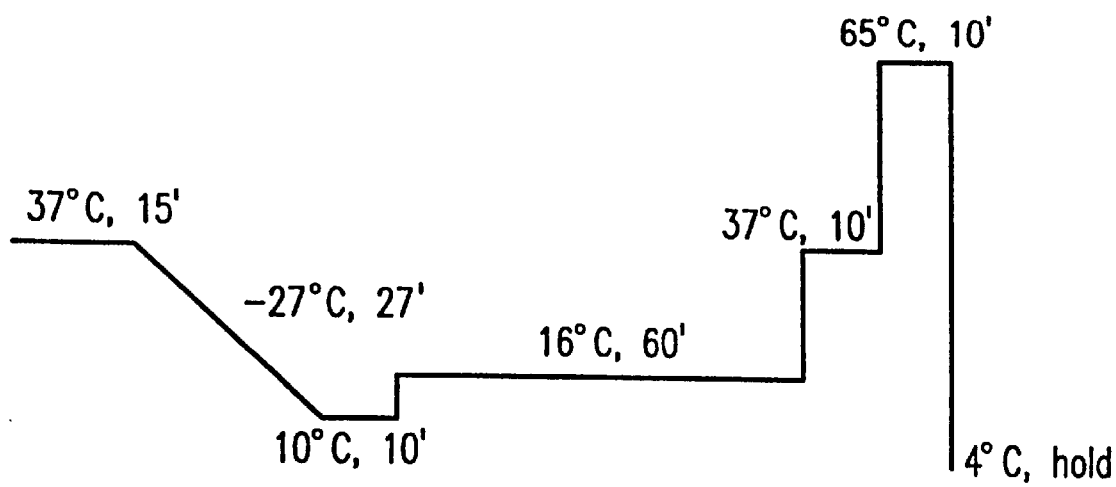

Then perform the RE/ligation reaction by following the thermal profile in FIG. 22A using a PTC-100 Thermal Cycler from MJ Research (Watertown, Mass.).

Amplification Reaction

Prepare the PCR reaction mix by combining:

1. 10 µl 5×E-Mg (300 mM Tris-Hcl pH 9.0, 75 mM (NH$_4$)$_2$SO$_4$, no Mg ions))

2. 100 pm of appropriate fluorescently labeled 24-mer primers 3. 1 µl 10 mM dNTP mix (Life Technologies, Gaithersburg, Md.)

4. 2.5 U of 50:1 Taq polymerase (Life Technologies, Gaithersburg, Md.): Pfu polymerase (Stratagene, La Jolla, Calif.)

5. Water to bring volume to 40 µl per PCR reaction

Then perform the following steps:

1. Add 40 µl of the PCR reaction mix to each RE/ligation reaction

2. Perform the PCR temperature profile of FIG. 22B using a PTC-100 thermal cycler (MJ Research, Watertown, Mass.)

6.1.12.1.3. PREFERRED AUTOMATED RE/LIGASE REACTIONS

The reactions of the preceding section can be automated according to the following protocol which requires intermediate reagent additions or by a protocol note requiring such additions.

Single Tube Protocol With Reagent Additions

Reactions are preformed in a standard 96 well thermal cycler format using a Beckman Biomek 2000 robot (Beckman, Sunnyvale, Calif.). Typically 4 cDNA samples are analyzed in duplicate with 12 different RE pairs, for a total of 96 reactions. All steps are performed by the robot, including solution mixing, from user provided stock reagents, and temperature profile control.

Pre-annealed adapters are prepared as in the preceding section.

Restriction-Digestion/Ligation Reaction

Mix per reaction:

1. 1 U of appropriate RE (New England Biolabs, Beverly, Mass.)

2. 1 µl of appropriate annealed adapter (10 pmoles)

3. 0.1 µl T4 DNA ligase [1 U/µl] (Life Technologies (Gaithersburg, Md.)

4. 1 µl ATP (Life Technologies, Gaithersburg, Md.)

5. 5 ng of subject prepared cDNA 6. 1.5 µl 10×NEB2 buffer from New England Biolabs (Beverly, Mass.)

7. 0.5 µl of 50 mM MgCl$_2$

8. Water to bring total volume to 10 µl and transfer to thermal cycler

The robot requires 23 minutes total time to set up the reactions. Then it performs the RE/ligation reaction by following the temperature profile of FIG. 22C using a PTC-100 Thermal Cycler equipped with a mechanized lid from MJ Research (Watertown; Mass.).

Amplification Reaction

Prepare the PCR reaction mix by combining:

1. 10 µl 5×E-Mg (300 mM Tris-HCl pH 9.0, 75 mM (NH$_4$)$_2$SO$_4$)

2. 100 pm of appropriate fluorescently labeled 24-mer primer 3. 1 µl 10 mM dNTP mix (Life Technologies, Gaithersburg, Md.)

4. 2.5 U of 50:1 Taq polymerase (Life Technologies, Gaithersburg, Md.): Pfu polymerase (Stratagene, La Jolla, Calif.)

5. Water to being volume to 35 µl per PCR reaction

Preheat the PCR mix to 72° C. and transfer 35 µl of the PCR mix to each digestion/ligation reaction and mix. The robot requires 6 minutes for the transfer and mixing.

Figure 22B:
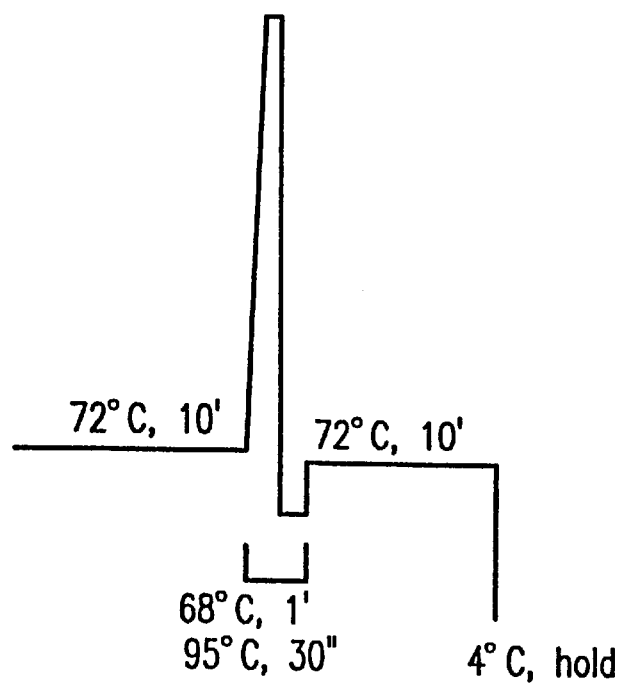
Figure 22C:
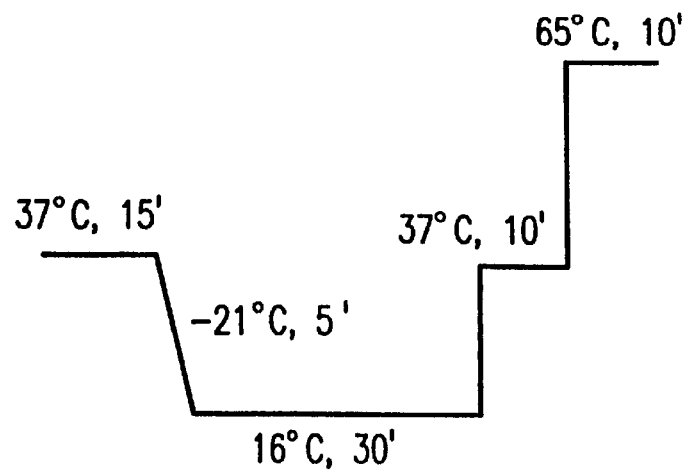
Figure 22D:
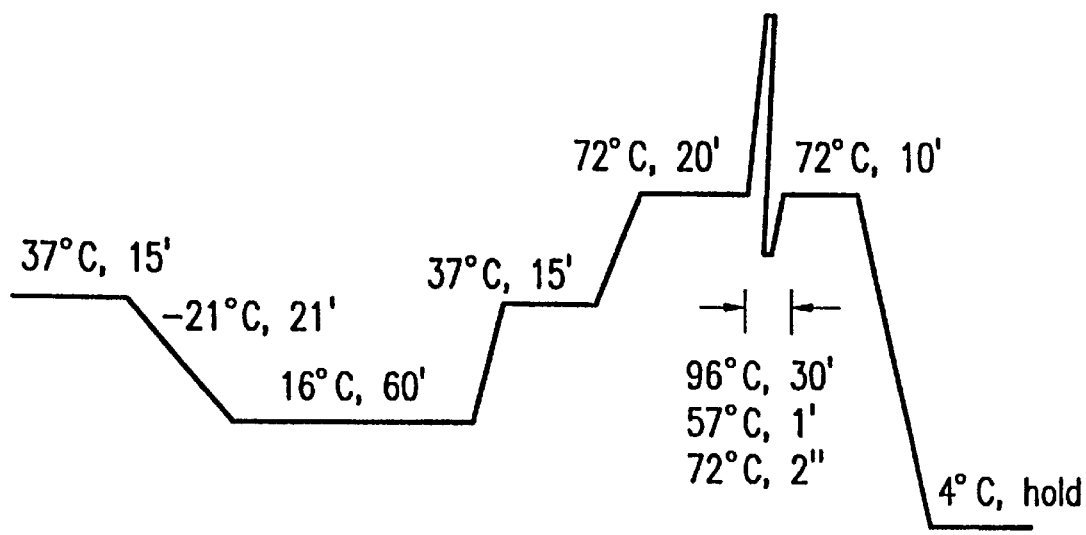

Then the robot performs the PCR amplification reaction by following the temperature profile of FIG. 22B using a PTC-100 thermal cycler equipped with a mechanized lid (MJ Research, Watertown, Mass.).

The total elapsed time for the digestion/ligation and PCR amplification reactions is 179 minutes. No user intervention is required after initial experimental design and reagent positioning.

Single Tube Protocol Without Reagent Additions

First, add the PCR reaction mix by combining in the reaction tube:
1. 10 µl 5×E-Mg (300 mM Tris-HCl pH 9.0, 75 mM $(NH_4)_2SO_4$)
2. 100 pm of appropriate fluorescently labeled 24-mer primer
3. 2 µl 10 mM dNTP mix (Life Technologies, Gaithersburg, Md.)
4. 2.5 U of 50:1 Taq polymerase (Life Technologies, Gaithersburg, Md.): Pfu polymerase (Stratagene, La Jolla, Calif.)
5. Water to bring volume to 40 µl per PCR reaction Second, add a bead of wax melting approximately at 72° C. (Ampliwax, Perkin-Elmer, Norwalk, Conn.). Melt the wax at 75° C. for 5 minutes, and let the wax solidify at 25° C. for 10 minutes with the lid open.

Third, add the RE/ligase reaction mix by combining in the reaction tube:
1. 0.1 µl of the REs (New England Biolabs, Beverly, Mass.)
2. 1 µl of appropriate annealed adapter (2:1 of 12:24 mer at 50 pmoles/ml)
3. 0.2 µl T4 DNA ligase [1 U/µl] (Life Technologies (Gaithersburg, Md.)
4. 1 µl of 0.1 M ATP (Life Technologies, Gaithersburg, Md.)
5. 1 µl of subject prepared cDNA (0.1–10 ng)
6. 0.1 µl 10×NEB 2 buffer from New England Biolabs (Beverly, Mass.)
7. 0,5 µl of 50 mM $MgCl_2$
8. Water to bring total volume to 10 µl and transfer to thermal cycler Then perform the RE/ligation and PCR reactions by following the thermal profile in FIG. 22D using, for example, a PTC-100 Thermal Cycler from MJ Research (Watertown, Mass.).

6.1.12.1.4. ALTERNATIVE RE/LIGASE AND AMPLIFICATION REACTIONS

Once the cDNA has been prepared it is separated into a number of batches of from 20 ng to 200 ng each equal to the desired number of individual samples that need to be analyzed and the extent of the analysis. For example, if six RE/ligase reactions and six analyses are needed to generate all necessary signals, six batches are made. Shown by example are 50 ng fractions.

RE/ligase reactions are performed as digestions by, preferably, a pair of REs; alternatively, one or three or more REs can be used provided the four base pair overhangs generated by each RE differ and can each be ligated to a uniquely adapter and a sufficiently resolved length distribution results. The amount of RE enzyme specified is sufficient for complete digestion while minimizing any other exo- or endo-nuclease activity that may be present in the enzyme.

RE Digestion
Digest (with 50 ng of cDNA)
1. Mix the following reagents

| | |
|---|---|
| 0.5 µl | prepared cDNA (100 ng/µl) mixture |
| 10 µl | New England Biolabs Buffer No. 2 |
| 3 Units | RE enzyme |

2. Incubate for 2 hours at 37° C. Larger size digests with higher concentrations of cDNA can be used and fractions of the digest saved for additional sets of experiments.

Adapter Ligation

Since it is important to remove unwanted ligation products, such as concatamers of fragments from different cDNAs resulting from hybridization of RE sticky ends, the restriction enzyme is left active during ligation. This leads to a continuing cutting of unwanted concatamers and end ligation of the desired end adapters.

The majority of restriction enzymes are active at the 16° C. ligation temperature. Ligation profiles consisting of optimum ligation conditions interspersed with optimum digestion conditions can also be used to increase efficiency of this process. An exemplary profile comprises periodically cycling between 37° C. and 10° C. and 16° C. at a ramp of 1° C./min.

One linker complementary to each 5 minutes overhang generated by each RE is required. 100 pico moles ("pm") is a sufficient molar excess for the protocol described. For each linker a complementary uniquely labeled primer is added for ligation to the cut ends of cDNAs. 100 pm is a sufficient molar excess for the protocol described. If the amounts of RE cDNA is changed the linker and primer amounts should be proportionately changed.

Ligation Reaction
(per 10 µl and 50 ng cDNA)
1. Mix the following reagents

| Component | Volume |
|---|---|
| RE digested cDNA mixture | 10 µl |
| 100 pM/µl each primer | 1 µl |
| 100 pM/µl each linker | 1 µl |

2. Thermally cycle from 50° C. to 10° C. (−1° C./minute) then back to 16° C.
3. Add 2 µl 10 mM ATP with 0.2 µl T4 DNA ligase (Premix 0.1 µl ligase 1 U/µl per 1 µl ATP) (E. Coli ligase is a less preferred alternative ligase.)
4. Incubate 12 hours at 16° C. This step can be shortened to less than 2 hours with proportionately higher ligase concentration. Alternately the thermal cycling protocol described can be used here.
5. Incubate 2 hours 37° C.
6. Incubate 20 minutes at 65° C. to heat inactivate the ligase (last step should be RE cutting).
7. Hold at 4° C.

Amplification Of Fragments With Ligated Adapters

This step amplifies the fragments that have been cut twice and ligated with adapters unique for each RE cut end. It is designed for a very high amplification specificity. Multiple amplifications are performed, with an increasing number of amplification cycles. Use the minimum number of cycles to get the desired signal. Amplifications above 20 cycles are not generally reliably quantitative.

Mix the following to form the ligation mix:

| Component | Volume |
|---|---|
| RE/Ligase cDNA mixture | 5 µl |
| 10X PCR Buffer | 5 µl |
| 25 mM MgCl$_2$ | 3 µl |
| 10 mM dNTPs | 1 µl |
| 100 pM/µl each primer | 1 µl |

Mix the following to form 150 µl PCR-Premix

| | |
|---|---|
| 30 µl | Buffer E (ligation mix will contribute 0.3 mM MgCl) |
| 1 µl | (300 pmoles/µl Rbuni24 Flour) 24 mer primer strand (50 pmoles/µl NBuni24 Tamra) |
| 0.6 µl | Taq polymerase (per 150 µl) |
| 3 µl | dNTP (10 mM) |
| 106 µl | H$_2$O |

Amplification of fragments is more specific if the small linker dissociates from the ligated primer-cDNA complex prior to amplification. The following is an exemplary method for amplification of the results of six RE/ligase reactions.

1. Place three strips of six PCR tubes, marked 10, 15, and 20 cycles, into three rows on ice as shown.

| | | | | | | |
|---|---|---|---|---|---|---|
| 20 cycles | 1 | 2 | 3 | 4 | 5 | 6- Add 140 µl PCR-premix |
| 15 cycles | 1 | 2 | 3 | 4 | 5 | 6 |
| 10 cycles | 1 | 2 | 3 | 4 | 5 | 6- Add 10 µl ligation mix |

2. Place 10 µl ligation mix in each tube in 10 cycle row
3. Place 140 µl PCR premix in each tube in 20 cycle row
4. Place into cycler and incubate for 5 minutes at 72° C. This melts linker which was not covalently ligated to the second strand of a cDNA fragment and allows the PCR premix to come to temperature.
5. Move the 140 µl PCR premix into the tubes in the 10 cycle row containing the 10 µl ligation mix, then place 50 µl of result into corresponding tubes each in other rows.
6. Incubate for 5 minutes at 72° C. This finishes incompletely double stranded cDNA ends into complete dsDNA, the top primer being used as template for second strand completion.

The amplification cycle is designed to raise specificity and reproducibility of the reaction. High temperature and long melting times are used to reduce bias of amplification due to high G+C content. Long extension times are used to reduce bias in favor of smaller fragments.

7. Thermally cycle 95° C. for 1 minute followed by 68° C. for 3 minutes. Long denaturing times reduce PCR bias due to melting rates of fragments, and long extension time reduces PCR bias on fragment sizes.
8. Incubate at 72° C. for 10 minutes at end of reaction.

6.1.12.1.5. OPTIONAL POST-AMPLIFICATION STEPS

Several optional steps can improve the signal from the detected bands. First, single strands produced as a result of linear amplification from singly cut fragments can be removed by the use of single strand specific exonuclease. Exo I is the preferred nuclease.

1. Incubate 2 units of nuclease with the product of each PCR reaction for 60 minutes at 37° C.

Second, the amplified products can be concentrated prior to detection either by ethanol precipitation or column separation with a hydroxyapatite column.

Several labeling methods are usable, including fluorescent labeling as has been described, silver staining, radiolabelled end primers, and intercalating dyes. Fluorescent end labeling is preferred for high throughput analysis with silver staining preferred if the individual bands are to be removed from the gel for further processing, such as sequencing.

Finally, fourth, use of two primers allows direct sequencing of separated strands by standard techniques. Also separated strands can be directly cloned into vectors for use in RNA assays such as in situ analysis. In that case, it is more preferred to use primers containing T7 or other polymerase signals.

6.1.12.2. PREFERRED METHODS OF A SEQ-QEA™ EMBODIMENT

6.1.12.2.1. QEA™ METHOD PREFERRED FOR USE IN A SEQ-QEA™ METHOD

The following single tube RE/ligase and PCR rotocol is the most preferred embodiment of a QEA™ method, not only when employing a SEQ-QEA™ method.

Initially 10 ng of each pooled PCR product (e.g., binding domain fusion proteins; activation domain fusion proteins) is digested with two restriction enzymes that each recognize a 4 nucleotide restriction site (like Sau3AI, BsaWI, or Tsp509I). After that, the restriction enzymes are destroyed either by heat inactivation or by extraction with phenol and chloroform. The restriction digestion is done in a volume of 50 µl and the digested DNA is extracted and precipitated. The digested DNA is then used as input to a QEA™ method reaction.

Reagents Used:

RE enzymes (RE1 and RE2)

primer set 1 and primer set 2 cDNA 10 mM ATP

10×NEB Buffer 2 (10 mM Tris HCl pH 7.9, 10 mM MgCl$_2$, 50 mM NaCl, 1 mM DTT (dithiothreitol))

T4 DNA ligase

5 M betaine 10 mm DNTP (equimolar mixture of all 4 dNTPs)

10×TB2.0 buffer (50 mM Tris pH 9.15, 16 mM (NH$_4$)$_2$SO$_4$, 2 mM MgCl$_2$)

16 units Klentaq (Ab Peptides, Inc.): 1 unit Pfu polymerase (Stratagene, Inc.)

wax(90:10 Parafin:Chillout PCR wax)

water

A pair of RE enzymes, RE1 and RE2, to perform the QEA™ method are selected according to Sec. 6.1.12.3. For RE1 (or RE2), primer set 1 (or primer set 2) comprising a primer and a linker are also selected according to Sec. 6.1.12.3, specifically, Table 10.

The following components are mixed in a 1.5 ml tube to form QPCR mix, quantities as shown:

| Reagent | 1 rxn |
| --- | --- |
| TB 2.0 | 5 µl |
| dNTP | 2 µl |
| Klentaq | 0.25 µl |
| water | 32.75 µl |

The solutions are mixed by tapping and/or inverting the solution. Pre-waxed PCR tubes are used where 90:10 Paraffin:Chillout wax had been melted and added to the tubes in such a way that the wax solidified on the sides of the upper half of the tube. 40 µl QPCR mix is added to the prewaxed PCR tubes, avoiding the sides and wax in the tubes. The tubes are placed in a thermal cycler without lids and the wax is melted onto the liquid layer by incubating at 75° C. for 2 min, followed by decreasing increments of 5° C. for every 2 min until 25° C. is reached.

The following components are mixed as shown, to form the Qlig mix:

| Reagent | 1 rxn |
| --- | --- |
| Primer set 1 | 1 µl |
| Primer set 2 | 1 µl |
| ATP | 0.8 µl |
| NEB Buffer 2 | 1 µl |
| Betaine | 2 µl |
| Digested DNA | 1 µl |
| T4 DNA Ligase | 0.2 µl |
| $H_2O$ | 3 µl |

The Q-lig mixes are added to the top of the wax layer in the PCR tubes containing the Q-PCR mix. Caps are applied gently to the PCR tubes and PCR is performed under the following conditions: 37° C. for 30 minutes, followed by a decrease to 16° C. with a decrease of 1° C. every minute. This is followed by an incubation at 16° C. for 1 hr, followed by an incubation at 37° C. for 10 minutes. This is followed by an incubation at 65° C. for 10 minutes, followed by an incubation at 72° C. for 20 minutes. After this, 20 cycles of the following conditions are repeated: 96° C. for 30 seconds, 57° C. for 1 minute and 72° C. for 2 minutes. This is followed by an incubation at 72° C. for 10 minutes and then the QEA™ method reactions are stored at −20° C. until processed further.

QEA™ Method Post-Processing Protocol ("Biotin bead clean-up")

In the case where one of the primers in either primer set 1 or primer set 2 has an attached biotin capture moiety at its 5' end, this post-processing protocol purifies the QEA™ method reaction products and denatures the DNA strands for analysis of the strand not captured via the biotin moiety.

Reagents Used:
QEA™ method reaction samples
Dynal Magnetic Streptavidin Beads
Binding Buffer: 5M NaCl, 10 mM Tris, pH 8.0, 1 mM EDTA
Wash Buffer I: 10 mM Tris, pH 8.0
Wash Buffer II: 10 mM EDTA
Loading Buffer: Deionized formamide, 25 mM EDTA (pH 8.0), 50 mg/ml Blue dextran (1000 µl formamide is mixed with 200 µl EDTA/dextran)
Ladder Loading Buffer: 100 µl GeneScan 500 ROX ladder (molecular weight makers) (Applied Biosciences, Inc. (ABI), Norwalk, Conn.) with 900 µl Loading Buffer The magnetic streptavidin beads are washed with 3 volumes of binding buffer and then resuspended in an equal volume of binding buffer. An equal volume of beads is added to the QEA™ method reaction to be processed (e.g., 5 µl beads for 5 µl QEA™ method sample). Purifications are done in a 96 well Costar PCR plate. The QEA™ method products are added to the beads and incubated at room temperature for 15 minutes. These are then placed on a Tecan magnetic holder and the magnetic beads are allowed to migrate down. The supernatant is discarded and washed with 200 µl of wash buffer I, followed by a 200 µl wash with wash buffer II. When a SEQ-QEA™ method is to be done, then the additional procedures starting with digestion with Type IIS restriction enzymes described in Section 6.1.12.2.2 are inserted here, prior to air drying and resuspension in loading buffer. If a SEQ-QEA™ method is not to be done, the beads are then air-dried and resuspended in loading buffer (5 µl for 5 µl of beads). In the loading buffer the GeneScan 500 ROX ladder may be mixed in a one-tenth dilution. The processed QEA™ method samples are then analyzed by electrophoresis on an ABI 377 (Applied Biosystems, Inc.) automated sequencer using the GeneScan software (ABI) for analysis.

6.1.12.2.2. SEQ-QEA™ METHOD STEPS

When a SEQ-QEA™ method is to be done, the QEA™ method is carried out through the washing and purification procedures involving wash buffer II of the biotin bead clean-up, except that the QEA™ method primer pairs (primer set 1 and primer set 2) are replaced by SEQ-QEA™ method primer pairs. One of these SEQ-QEA™ method primers has a Type IIS restriction enzyme (e.g., Fok I) recognition site and a fluorescent tag, (e.g., FAM (carboxy-fluoroscein) (ABI)) attached at the 5' end. The other primer has a biotin tag ("Bio") used for QEA™ method processing and comprises either a uracil residue or a site for a rare-cutting restriction enzyme like AscI. Sec. 6.1.12.5 and Table 18 has a list of exemplary primers and linkers for the SEQ-QEA™ methods.

The following are preferable primers and linkers to be used together with the REs BglII and BspHI.

| SEQ-QEA ™ method primer pairs | Type-IIS Enzyme | Method of Bead Release |
| --- | --- | --- |
| 1) KA5/KA24-FAM + RC9/UC24-Bio | FokI | UDG |
| 2) BA5/BA24-FAM + RC9/UC24-Bio | BbvI | UDG |
| 3) KA5/KA24-FAM + RC9/SC24-Bio | FokI | AscI |
| 4) BA5/BA24-FAM + RC9/SC24-Bio | BbvI | AscI |

Using the above REs and primer pairs, the QEA™ method reaction products obtained fall into the following three categories:

a) A double-stranded DNA with a 5' FAM label with nearby sequence containing a recognition site for FokI or. BbvI on one strand, and a 3' biotin label with nearby sequence containing a uracil residue or an AscI recognition site on the other strand (in the case where different REs cut at each end)

b) A double-stranded DNA with a 5' biotin label with nearby sequence containing a uracil residue or an AscI recognition site on one strand, and a 3' biotin label with nearby sequence containing a uracil residue or an AscI recognition site on the other strand (in the case where same RE cuts at both ends)

c) A double-stranded DNA with a 5' FAM label with nearby sequence containing a recognition site for FokI or BbvI on one strand, and a 3' FAM label with nearby sequence containing a recognition site for FokI or BbvI on the other strand (in the case where same RE cuts at both ends)

After the biotin bead clean-up, that is, washing and purification procedures using magnetic streptavidin beads as described above through the use of wash buffer II, only category "a" will be visible to fluorescent analysis. Typically, after the reaction is completed, 45 µl out of 50 µl is processed (the rest is saved). These 45 µl of the QEA™ method reaction are bound to the magnetic streptavidin beads as described above. Subsequently, the DNA bound to the beads is digested with the Type IIS restriction enzyme in a volume of 100 ml with about 10 units of the enzyme for 3 hours at 37° C. Type IIS restriction enzymes cleave DNA at a location outside their recognition sites, thus producing overhangs of unknown sequences (Szybalski et al., 1991, *Gene* 100:13–26). The Type IIS digestion thus releases the FAM label and creates a fragment-specific overhang that acts as a template for sequencing. The supernatant is then removed and the beads are washed with wash buffer I followed by a wash with wash buffer II.

The end-sequencing reaction is essentially a fill-in reaction using the overhang generated by the Type-IIS restriction enzyme as a template. Dideoxy chain terminators labeled with different ABI fluorescent dyes are mixed at high ratios with dNTPs to ensure high frequency of incorporation, and the DNA polymerase enzyme used (e.g., Sequenase (T7 DNA polymerase), Taquenase (Taq polymerase)) has high affinity. for the labeled dideoxynucleotides. A sequencing mix totalling 20 µl containing the appropriate 1× buffer, 1 µl dNTPs diluted 1/200 from stock (3 mM dATP, 1.2 mM dCTP, 4.5 mM dGTP, 1.2 mM dTTP), 0.5 µl each ABI dye-labeled terminator solution (containing ddATP, ddCTP, ddGTP and ddTTP, respectively), (and 1 µl 0.1 M DTT for Sequenase) is made. The beads are resuspended in the sequencing mix and 0.1 µl Taquenase is added and the reaction is incubated at 65° C. for 15 minutes. If Sequenase is to be used, 0.1 µl Sequenase is added instead of taquenase and the reaction is incubated at 37° C. for 15 minutes. After this, the reaction mix is transferred to a magnet and the supernatant is removed. The beads are washed twice with wash buffer I.

The above-described end-sequencing reaction incorporates dye labeled nucleotides into the strand that contains biotin. Since biotin-streptavidin binding is nearly irreversible, the labeled strands must be cleaved for analysis by electrophoresis. This is achieved by treating UMP-containing fragments with Uracil DNA Glycosylase (UDG), or cleaving AscI-site-containing fragments with Asc I. UDG removes the Uracil residue from dsDNA; the phosphate backbone is subsequently hydrolyzed at temperatures above room temperature and at pH>8.3.

For UDG treatment, the beads are resuspended in 20 µl UDG buffer (30 mM Tris-HCl pH 7.5, 50 mM KCl, 5 mM MgCl$_2$), 0.2 units of UDG are added and the reaction is incubated at room temperature for 30 minutes. The reaction is then transferred to a magnet and the supernatant removed. The biotinylated strand, which is the strand that is being filled in during end-sequencing, is still attached to the beads as UDG does not destroy the backbone, but makes it very susceptible to hydrolysis.

The beads are resuspended in 5 µl formamide loading buffer. These are then split into 2 tubes of 2.5 µl each. Another 2.5 µl formamide loading buffer is added to one and 2.5 µl formamide loading buffer with 20% GS500 ROX ladder (ABI) is added to the other. These are heated at 95° C. for 5 minutes to effect hydrolysis and denaturation and analyzed by electrophoretic separation.

In case of the biotinylated primer having an Asc I site, the following is performed. The beads are resuspended in 20 µl of Asc I buffer and 5 units of Asc I is added and incubated at 37° C. for 1 hour. The beads are separated on a magnet and the supernatant that contains the digestion products is precipitated with three volumes of ethanol after the addition of 5 µg of glycogen. The pellet is resuspended in 5 µl formamide loading buffer and split into 2 tubes of 2.5 µl each. Another 2.5 µl formamide loading buffer is added to one and 2.5 µl formamide loading buffer with 20% GS500Rox ladder is added to the other. These are heated at 95° C. for 5 minutes and analyzed by electrophoretic separation.

Sequencing is completed by gel electrophoretic separation of released and sequenced strands. The overhang sequence is the order of partially filled in fragments observed.

6.1.12.3. PREFERRED QEA™ METHOD ADAPTERS AND RE PAIRS

Table 2 lists preferred primer-linker pairs that may be used as adapters for the preferred RE embodiment of a QEA™ method. The primers listed cover all possible double-digest RE combinations involving approximately 56 available RE having a 5' 4 bp overhang. There are 40 such REs available from New England Biolabs. For each QEA™ method double digest, one primer and one linker from the "R" series and one primer and one linker from the "J" series are used together. This choice satisfies all adapter constraints previously described. Two pairs from the same series are not compatible during amplification.

TABLE 2

SAMPLE ADAPTERS

| series | Adapter:<br>Primer (Longer strand)<br>Linker (shorter strand) | RE |
|---|---|---|
| RA24 | (SEQ ID NO:53) 5' AGC ACT CTC CAG CCT CTC ACC GAA 3' | |
| RA1 | (SEQ ID NO:54) 3' AG TGG CTT TTA | Tsp509I<br>MfeI<br>EcoRI |
| RA5 | (SEQ ID NO:55) 3' AG TGG CTT GTAC | NcoI<br>BspHI |
| RA6 | (SEQ ID NO:56) 3' AG TGG CTT GGCC | XmaI<br>NgoMI<br>BspEI |
| RA7 | (SEQ ID NO:57) 3' AG TGG CTT GCGC | BssHII<br>AscI |

TABLE 2-continued

SAMPLE ADAPTERS

| Adapter: series | Primer (Longer strand) Linker (shorter strand) | RE |
|---|---|---|
| RA8 | (SEQ ID NO:58) 3' AG TGG CTT GATC | AvrII<br>NheI<br>XbaI |
| RA9 | (SEQ ID NO:59) 3' AG TGG CTT CTAG | DpnII<br>BamHI<br>BclI |
| RA10 | (SEQ ID NO:60) 3' AG TGG CTT CGCG | KasI |
| RA11 | (SEQ ID NO:61) 3' AG TGG CTT CCGG | EagI<br>Bspl20I<br>NotI<br>EaeI |
| RA12 | (SEQ ID NO:62) 3' AG TGG CTT CATG | BSiWI<br>Acc651<br>BsrGI |
| RA14 | (SEQ ID NO:63) 3' AG TGG CTT AGCT | XhoI<br>SalI |
| RA15 | (SEQ ID NO:64) 3' AG TGG CTT ACGT | ApaLI |
| RA16 | (SEQ ID NO:65) 3' AG TGG CTT AATT | AflII |
| RA17 | (SEQ ID NO:66) 3' AG TGG CTT AGCA | BssSI |
| RC24 | (SEQ ID NO:67) 5' AGC ACT CTC CAG CCT CTC ACC GAC 3' | |
| RC1 | (SEQ ID NO:68) 3' AG TCG CTG TTAA | Tsp509I<br>EcoRI<br>ApoI |
| RC3 | (SEQ ID NO:69) 3' AG TCG CTG TCGA | HindIII |
| RC5 | (SEQ ID NO:70) 3' AG TCG CTG GTAC | BspHI |
| RC6 | (SEQ ID NO:71) 3' AG TCG CTG GGCC | AgeI<br>NgoMI<br>BspEI<br>SgrAI<br>BsrFI<br>BsaWI |
| RC7 | (SEQ ID NO:72) 3' AG TCG CTG GCGC | MluI<br>BssHII<br>AscI |
| RC8 | (SEQ ID NO:73) 3' AG TCG CTG GATC | SpeI<br>NheI<br>XbaI |
| RC9 | (SEQ ID NO:74) 3' AG TCG CTG CTAG | DpnII<br>BglII<br>BamHI<br>BclI<br>BstYI<br>SauIIIA |
| RC10 | (SEQ ID NO:75) 3' AG TCG CTG CGCG | KasI |
| RC11 | (SEQ ID NO:76) 3' AG TCG CTG CCGG | Bspl20I<br>NotI |
| RC12 | (SEQ ID NO:77) 3' AG TCG CTG CATG | ACC56I<br>BsrGI |
| RC14 | (SEQ ID NO:78) 3' AG TCG CTG AGCT | SalI |
| RC15 | (SEQ ID NO:79) 3' AG TCG CTG ACGT | Ppul0I<br>ApaLI |
| JA24 | (SEQ ID NO:80) 5' ACC GAC GTC GAC TAT CCA TGA AGA 3' | |
| JA1 | (SEQ ID NO:81) 3' GT ACT TCT TTAA | Tsp509I<br>MfeI<br>EcoRI |
| JA5 | (SEQ ID NO:82) 3' GT ACT TCT GTAC | NcoI<br>BspHI |
| JA6 | (SEQ ID NO:83) 3' GT ACT TCT GGCC | XmaI<br>NgoMI<br>BspEI |
| JA7 | (SEQ ID NO:84) 3' GT ACT TCT GCGC | BssHII<br>AscI |
| JA8 | (SEQ ID NO:85) 3' GT ACT TCT GATC | AvrII<br>NheI<br>XbaI |
| JA9 | (SEQ ID NO:86) 3' GT ACT TCT CTAG | DpnII<br>BamHI<br>BclI |
| JA10 | (SEQ ID NO:87) 3' GT ACT TCT CGCG | KasI |
| JA11 | (SEQ ID NO:88) 3' GT ACT TCT CCGG | EagI<br>Bsp120I<br>NotI<br>EaeI |

TABLE 2-continued

SAMPLE ADAPTERS

| Adapter series | Primer (Longer strand) Linker (shorter strand) | RE |
|---|---|---|
| JA12 | (SEQ ID NO:89) 3' GT ACT TCT CATG | BsiWI |
| | | Acc65I |
| | | BsrGI |
| JA14 | (SEQ ID NO:90) 3' GT ACT TCT AGCT | XhoI |
| | | SalI |
| JA15 | (SEQ ID NO:91) 3' GT ACT TCT ACGT | ApaLI |
| JA16 | (SEQ ID NO:92) 3' GT ACT TCT AATT | AflII |
| JA17 | (SEQ ID NO:93) 3' GT ACT TCT AGCA | BssSI |
| JC24 | (SEQ ID NO:94) 5' ACC GAC GTC GAC TAT CCA TGA AGC 3' | |
| JC1 | (SEQ ID NO:95) 3' GT ACT TCG TTAA | Tsp509I |
| | | EcoRI |
| | | ApoI |
| JC3 | (SEQ ID NO:96) 3' GT ACT TCG TCGA | HindIII |
| JC5 | (SEQ ID NO:97) 3' GT ACT TCG GTAC | BspHI |
| JC6 | (SEQ ID NO:98) 3' GT ACT TCG GGCC | AgeI |
| | | NgoMI |
| | | BspEI |
| | | SgrAI |
| | | BsrFI |
| | | BsaWI |
| JC7 | (SEQ ID NO:99) 3' GT ACT TCG GCGC | MluI |
| | | BssHII |
| | | AscI |
| JC8 | (SEQ ID NO:100) 3' GT ACT TCG GTAC | SpeI |
| | | NheI |
| | | XbaI |
| JC9 | (SEQ ID NO:101) 3' GT ACT TCG CTAG | DpnII |
| | | BglII |
| | | BamHI |
| | | BclI |
| | | BstYI |
| JC10 | (SEQ ID NO:102) 3' GT ACT TCG CGCG | KasI |
| JC11 | (SEQ ID NO:103) 3' GT ACT TCG CCGG | Bsp120I |
| | | NotI |
| JC12 | (SEQ ID NO:104) 3' GT ACT TCG CATG | Acc56I |
| | | BsrGI |
| JC14 | (SEQ ID NO:105) 3' GT ACT TCG AGCT | SalI |
| JC15 | (SEQ ID NO:106) 3' GT ACT TCG ACGT | Ppul0I |
| | | ApaLI |

Tables 3 and 4 list the RE combinations that have been tested in QEA™ method experiments on human placental and glandular cDNAs samples. The preferred double digests are those that give more than approximately 50 bands in the range 100 to 700 bp. Table 11 lists the preferred RE combinations for human cDNA analyses.

TABLE 3

PREFERRED RE COMBINATIONS FOR HUMAN cDNA ANALYSIS

| | | |
|---|---|---|
| Acc56I & HindIII | Acc65I & NgoMI | BamHI & EcoRI |
| BglII & HindIII | BglII & NgoMI | BsiWI & BspHI |
| BspHI & BstYI | BspHI & NgoMI | BsrGI & EcoRI |
| EagI & EcoRI | EagI & HindIII | EagI & NcoI |
| HindIII & NgOMI | NGOMI & NheI | NgoMI & SpeI |
| BglII & BspHI | Bsp120I & NcoI | BssHII & NgoMI |
| EcoRI & HindIII | NgoMI & XbaI | |

Table 4 lists other RE combinations tested and that can be used for human cDNA analyses.

TABLE 4

OTHER RE COMBINATIONS FOR HUMAN cDNA ANALYSIS

| | | |
|---|---|---|
| AvrII & NgoMI | BamHI & Bsp120I | BamHI & BspHI |
| BamHI & NcoI | BclI & BspHI | BclI & NcoI |

TABLE 4-continued

OTHER RE COMBINATIONS FOR HUMAN cDNA ANALYSIS

| | | |
|---|---|---|
| BglII & BspEI | BglII & EcoRI | BglII & NcoI |
| BssHII & BsrGI | BstYI & NcoI | BamHI & HindIII |
| BglII & Bsp120I | BspHI & HindIII | |

Tables 5 and 6 list the RE combinations that have been tested in QEA™ method experiments on mouse cDNA samples. The preferred double digests are those that give more than approximately 50 bands in the range of 100 to 700 bp. Table 5 lists the preferred RE combinations for mouse cDNA analyses.

TABLE 5

PREFERRED RE COMBINATIONS FOR MOUSE cDNA ANALYSIS

| | | |
|---|---|---|
| Acc56I & HindIII | Acc65I & NgoMI | AscI & HindIII |
| AvrII & NgoMI | BamHI & BspHI | BamHI & HindIII |
| BamHI & NcoI | BclI & NcoI | BglII & BspHI |
| BglII & HindIII | BglII & NcoI | BglII & NgoMI |
| Bsp120I & NcoI | Acc65I & BspHI | BspHI & Bsp120I |
| BspHI & BsrGI | BspHI & EagI | BspHI & NgoMI |

TABLE 5-continued

PREFERRED RE COMBINATIONS
FOR MOUSE cDNA ANALYSIS

| | | |
|---|---|---|
| BspHI & NotI | BssHII & HindIII | BstYI & HindIII |
| HindIII & NcoI | HindIII & NgoMI | NcoI & NotI |
| NgOMI & NheI | NgoMI & SpeI | NgoMI & XbaI |
| BclI & HindIII | | |

Table 6 lists other RE combinations tested and that can be used for mouse cDNA analyses.

TABLE 6

OTHER RE COMBINATIONS FOR MOUSE cDNA ANALYSIS

| | | |
|---|---|---|
| Acc65I & NcoI | BclI & BspHI | BsiWI & BspHI |
| BsiWI & NcoI | BspHI & HindIII | BsrGI & NcoI |
| BssHII & NgoMI | BstYI & BspHI | EagI & NcoI |
| HindIII & MluI | | |

Table 7 lists the data obtained from various RE combinations using mouse cDNA samples. The number of bands was observed from silver stained acrylamide separation gels.

TABLE 7

MOUSE cDNA RE DIGESTION RESULTS

| RE Combination | Number of Bands |
|---|---|
| Acc65I & HindIII | 200 |
| Acc65I & NgoMI | 150 |
| AscI & HindIII | 100 |
| AvrII & NgoMI | 50 |
| BamHI & BspHI | 200 |
| BamHI & HindIII | 150 |
| BamHI & NcoI | 150 |
| BclI & BspHI | 5 |
| BclI & HindIII | 150 |
| BclI & NcoI | 50 |
| BglII & BspHI | 50 |
| BglII & HindIII | 150 |
| BglII & NcoI | 50 |
| BglII & NgoMI | 50 |
| Bsp120I & NcoI | 50 |
| BspHI & Acc65I | 150 |
| BspHI & Bsp120I | 50 |
| BspHI & BsrGI | 200 |
| BspHI & EagI | 150 |
| BspHI & HindIII | 0 |
| BspHI & NgoMI | 150 |
| BspHI & NotI | 150 |
| BsrGI & NcoI | 10 |
| BssHII & HindIII | 100 |
| BssHII & NgoMI | 20 |
| BstYI & BspHI | 20 |
| BstYI & HindIII | 200 |
| EagI & NcoI | 10 |
| HindIII & MluI | 25 |
| HindIII & NcoI | 50 |
| HindIII & NgoMI | 150 |
| NcoI & NotI | 200 |
| NgoMI & NheI | 50 |
| NgOMI & SpeI | 200 |
| NgOMI & XbaI | 50 |
| TOTAL # BANDS | 3490 |

31 available REs that recognize a 6 bp recognition sequence and generate a 4 bp 5' overhang are: Acc65I, AflII, AgeI, ApaLI, ApoI, AscI, AvrI, BamHI, BclI, BglII, BsiWI, Bsp120I, BspEI, BspHI, BsrGI, BssHII, BstYI, EagI, EcoRI, HindIII, MfeI, MluI, NcoI, NgoMI, NheI, NotI, Ppu10I, SalI, SpeI, XbaI, and XhoI.

All of these enzymes have been tested in QEA™ method protocols with the specified buffer conditions with the exception of AflII. All were useable except for MfeI, Ppu10I, SalI, and XhoI. All the other 26 enzymes have been tested and are usable in the RE implementation of QEA™ method.

However certain pairs of these enzymes are less informative due to the fact that they produce identical overhangs, and thus their recognition sequences cannot be distinguished by the QEA™ method adapters. These pairs are Acc65I and (BsiWI or BsrGI); AgeI and (BspEI or NcoMI); ApoI and EcoRI; AscI and (BssHII or MluI); AvrI and (NheI, SpeI, or XbaI); BamHI and (BclI, BglII, or BstYI); BclI and (BgLII or BstYI); BglII and BstYI; BsiWI aid BsrGI; Bsp120I and EagI; BspEI and NcoMI; BspHI and NcoI; BssHII and MluI; NheI and (SpeI or XbaI); and SpeI and XbaI.

Thus, 301 RE pairs have been tested and are useable in the RE embodiments of the QEA™ method.

6.1.12.4. FLUORESCENT LABELS FOR QEA™ METHODS

Fluorochromes labels that can be used in QEA™ methods include the classic fluorochromes as well as more specialized fluorochromes. The classic fluorochromes include bimane, ethidium, europium (III) citrate, fluorescein, La Jolla blue, methylcoumarin, nitrobenzofuran, pyrene butyrate, rhodamine, terbium chelate, and tetramethylrhodamine. More specialized fluorochromes are listed in Table 8 along with their suppliers.

TABLE 8

FLUORESCENT LABELS

| Fluorochrome | Vendor | Absorption Maximum | Emission Maximum |
|---|---|---|---|
| Bodipy 493/503 | Molecular Probes | 493 | 503 |
| Cy2 | BDS | 489 | 505 |
| Bodipy FL | Molecular Probes | 508 | 516 |
| FTC | Molecular Probes | 494 | 518 |
| FluorX | BDS | 494 | 520 |
| FAM | Perkin-Elmer | 495 | 535 |
| Carboxyrhodamine | Molecular Probes | 519 | 543 |
| EITC | Molecular Probes | 522 | 543 |
| Bodipy 530/550 | Molecular Probes | 530 | 550 |
| JOE | Perkin-Elmer | 525 | 557 |
| HEX | Perkin-Elmer | 529 | 560 |
| Bodipy 542/563 | Molecular Probes | 542 | 563 |
| Cy3 | BDS | 552 | 565 |
| TRITC | Molecular Probes | 547 | 572 |
| LRB | Molecular Probes | 556 | 576 |
| Bodipy LMR | Molecular Probes | 545 | 577 |
| Tamra | Perkin-Elmer | 552 | 580 |
| Bodipy 576/589 | Molecular Probes | 576 | 589 |
| Bodipy 581/591 | Molecular Probes | 581 | 591 |
| Cy3.5 | BDS | 581 | 596 |
| XRITC | Molecular Probes | 570 | 596 |
| ROX | Perkin-Elmer | 550 | 610 |
| Texas Red | Molecular Probes | 589 | 615 |
| Bodipy TR (618?) | Molecular Probes | 596 | 625 |
| Cy5 | BDS | 650 | 667 |
| Cy5.5 | BDS | 678 | 703 |
| DdCy5 | Beckman | 680 | 710 |
| Cy7 | BDS | 443 | 767 |
| DbCy7 | Beckman | 790 | 820 |

The suppliers listed in Table 8 are Molecular Probes (Eugene, Oreg.), Biological Detection Systems ("BDS") (Pittsburgh, Pa.) and Perkin-Elmer (Norwalk, Conn.).

Means of utilizing these fluorochromes by attaching them to particular nucleotide groups are described in Kricka et al., 1995, Molecular Probing, Blotting, and Sequencing, chap. 1, Academic Press, New York. Preferred methods of attachment are by an amino linker or phosophoramidite chemistry.

6.1.12.5. PREFERRED REACTANTS FOR SEQ-QEA™ METHODS

Table 9 lists exemplary Type IIS REs adaptable to a SEQ-QEA™ method and their important characteristics. For each RE, the table lists the recognition sequence on each strand of a dsDNA molecule and the distance in bp from the recognition sequence to the location of strand cutting. Also listed is the net overhang generated.

TABLE 9

SAMPLE TYPE IIS REs

| RE | Recog. Seqs. | Dist. to cutting Site (bp) | Over-Hang (bp) | Comment |
|---|---|---|---|---|
| FokI | GGATG | 9 | 4 | |
| | CCTAC | 13 | | |
| HgaI | GACGC | 5 | 5 | |
| | CTGCG | 10 | | |
| BbvI | GCAGC | 8 | 4 | |
| | CGTCG | 12 | | |
| BsmFI | GGGAC | 10 | 4 | Lower recognition site specificity |
| | CCCTG | 14 | | |
| BspMI | ACCTGC | 4 | 4 | |
| | TGGACG | 8 | | |

TABLE 9-continued

SAMPLE TYPE IIS REs

| RE | Recog. Seqs. | Dist. to cutting Site (bp) | Over-Hang (bp) | Comment |
|---|---|---|---|---|
| SfaNI | GCATC | 5 | 4 | |
| | CGTAG | 9 | | |

Table 10 lists exemplary primer and linker combinations adaptable to a SEQ-QEA™ method. They satisfy the previously described requirements on primers and linkers. Except for the indicated differences, they are the-same as the primers and linkers of similar names in Table 10. RA24-U and RC24-U have a 5' biotin capture moiety and a uracil release means as indicated, and are adaptable to the same linkers and REs as are RA24 and RC24 of Table 10. RA24-S and RC24-S also have a 5' biotin capture moiety with a AscI recognition site release means as indicated, and are adaptable to the same linkers and REs as are RA24 and RC24 of Table 10. JA24-K has an internal FokI recognition site as indicated and a 5' FAM label moiety (see Table 16). Linkers KA5, KA6, and KA9 with the indicated REs function with this primer. JC24-B has an internal BbvI recognition site, a 5' FAM label, and functions with linkers BA5 and BA9.

TABLE 10

SAMPLE ADAPTERS

| Adapter Series | Primer (longer strand) Linker (shorter strand.) | | RE |
|---|---|---|---|
| RA24-U | (SEQ ID NO:107) | 5' b-AGC ACT CTC CAG CCU CTC ACC GAA 3' | |
| RA24-S | (SEQ ID NO:108) | 5' b-AGC ACT CTG GCG CGC CTC ACC GAA 3' | |
| RC24-U | (SEQ ID NO:109) | 5' b-AGC ACT CTC CAG CCUCTC ACC GAC 3' | |
| RC24-S | (SEQ ID NO:110) | 5' b-AGC ACT CTG GCG CGC CTC ACC GAC 3' | |
| A24-K | (SEQ ID NO:111) | 5' f-ACC GAC GTC GAC TAT GGA TGA AGA 3' | FokI (9) |
| KA9 | (SEQ ID NO:112) | 3'CT ACT TCT CTAG | DpnII BglII BamHI BclI BstYI |
| KA5 | (SEQ ID NO:113) | 3' CT ACT TCT GTAC | NcoI BspHI |
| KA6 | (SEQ ID NO:114) | 3' CT ACT TCT GGCC | AgeI NgoMI BspEI SgrAI BsrFI BsaWI |
| JC24-B | (SEQ ID NO:115) | 5' f-ACC GAC GTC GAC TAT CGC AGC AGC 3' | BbvI (8) |
| BA9 | (SEQ ID NO:116) | 3' CG TCG TCT CTAG | DpnII BglII BamHI BclI BstYI |
| BA5 | (SEQ ID NO:117) | 3' CG TCG TCT GTAC | NcoI BspHI |

Notes:
'b' signifies a biotin moiety
'f' signifies a FAM label moiety

6.2. LIBRARIES

Libraries in pAD-GAL and in pAS2-1 of ~1×10⁶ clones were made from 1–10 μg of cDNA from a colon cancer cell line by the methods described above in Section 6.1.6. The libraries were propagated in the *E. coli* strain XL1Blue (Stratagene) and plasmid DNA was extracted by standard procedures.

6.3. CONSTRUCTION OF YEAST STRAINS

Construction of Reporter Systems

The Reporter System is binary in nature and consists of two halves with each half containing a reporter strain. Each half is of the opposite mating type, i.e., a or α. In a preferred embodiment, the mating type a reporter strain contains an intrachromosomal URA3 Reporter Gene under the control of the GAL1 promoter and its native GAL4 DNA binding sites; and the mating type α reporter strain contains both an intrachromosomal HIS3 Reporter Gene and an intrachromosomal lacZ Reporter Gene, each under the control of the GAL1 promoter and its native GAL4 DNA binding sites.

The a strain YULH contains the URA3 Reporter Gene under the control of a promoter that contains GAL4 binding sites.

The α strain N106' contains two reporters: a HIS3 Reporter Gene under the control of a HIS3 promoter that has been engineered to contain GAL4 binding sites, and a lacZ Reporter Gene under the control of a GAL1 promoter.

The a strain N105' contains two reporters: a HIS3 Reporter Gene under the control of a HIS3 promoter that has been engineered to contain GAL4 binding sites, and a lacZ Reporter Gene under the control of a GAL1 promoter.

The a strain N105 contains two reporters: a HIS3 Reporter Gene under the control of a HIS3 promoter that has been engineered to contain GAL4 binding sites, and a lacZ Reporter Gene under the control of a GAL1 promoter. The strain is not deficient in LYS2 or URA3.

The α strain N106 contains two reporters: a HIS3 Reporter Gene under the control of a HIS3 promoter that has been engineered to contain GAL4 binding sites, and a lacZ Reporter Gene under the control of a GAL1 promoter. The strain is not deficient in LYS2 or URA3.

In one embodiment of the invention, the two reporter strains are N105' (mating type a) and N106' (mating type α).

In another embodiment of the invention, the two reporter strains are YULH (mating type a) and N106' (mating type α). In another embodiment, N203 is used as mating type a. N105 (which is not ura3 or lys2) can be used as an alternative to YULH if uracil selection is not desired for use. Details of the methods used to construct these strains are presented in the subsections below.

6.3.1. CONSTRUCTION OF STRAINS N105 AND N106

Strains N105 and N106 were derived from the strain Y190 (available from Clontech; Harper et al., 1993, Cell 75:805–816). The a strain Y190 contains two reporters: a HIS3 Reporter Gene under the control of a HIS3 promoter that has been engineered to contain GAL4 binding sites, and a lacZ Reporter Gene under the control of a GAL1 promoter. Y190 (a gift of Stephen J. Elledge, Baylor College of Medicine) was diploidized by transforming it with a plasmid bearing a copy of the HO gene (Herskowitz and Jensen, 1991, Meth. Enzymol. 194:132–146). The HO gene switches the mating type of the strain and thus, when two opposite mating types exist, they mate to form diploids. The diploids were then transferred to sporulating medium on plates (Sherman et al., eds., 1991, *Getting started with yeast*, Vol. 194, Academic Press, New York) and left to sporulate at 30° C. for 2 days. The haploids were isolated by dissection of tetrads and the two mating types were determined by mating to tester a and α strains, a will not mate with a, and α will not mate with α. These two strains, with the exception of being opposite mating types, are truly isogenic and the genotype includes leu2, trp1, his3, URA3::GAL-lacZ, LYS2::GAL-HIS3.

6.3.2. CONSTRUCTION OF THE REPORTER STRAIN N106'

The strain N106 was made deficient in ura3 by selection of ura minus cells on 5-FOA plates. Then, these cells were made lys2 (lysine minus) by a two-step gene-disruption method (Rothstein, 1983, Methods. Enzymol. 101:202–211), so that, if desired, a LYS2 Reporter Gene or a plasmid containing LYS2 can be selected for in the strain. A mutant version of the lys2 gene was used for this purpose. This-mutant lys2-ΔNheI (a gift of Albert Smith, Yale University) was generated by deleting the NheI fragment that is internal to the LYS2 coding region (Fleig et al., 1986, Gene 46:237–245). This gene is in a plasmid that was linearized with XbaI and the linearized DNA was used to transform N102 by the lithium acetate transformation protocol of Section 6.1.2. This plasmid is also marked with URA3 and so cells in which the plasmid had integrated were selected on ura minus plates. These transformants were then patched out onto 5-FOA plates and ura minus cells were recovered. These ura minus cells were patched out simultaneously onto lysine minus plates and YPAD plates, and cells that did not grow on the lysine minus plates were chosen. In this manner, cells that were lys2 were recovered and the strain was named N106'. The genotype of this strain is MATα, ura3, his3, lys2, ade2, trp1, leu2, ga14, gal80, cyh', lys2::GAL1$_{UAS}$-HIS$_{TATA}$-HIS3, ura3::GAL1$_{UAS}$-GAL$_{TATA}$-lacZ.

6.3.3. CONSTRUCTION OF THE REPORTER STRAIN N105'

The strain N105 was made deficient in ura3 by selection of ura minus cells on 5-FOA plates. Then, these cells were made lys2 (lysine minus) by a two-step gene-disruption method (Rothstein, 1983, Methods. Enzymol. 101:202–211), so that, if desired, a LYS2 Reporter Gene or a plasmid containing LYS2 can be selected for in the strain. A mutant version of the LYS2 gene was used for this purpose. This mutant lys2-ΔNheI (a gift of Albert Smith, Yale University) was generated by deleting the NheI fragment that is internal to the LYS2 coding region (Fleig et al., 1986, Gene 46:237–245). This gene is in a plasmid that was linearized with XbaI and the linearized DNA was used to transform N101 by the lithium acetate transformation protocol of Section 6.1.2. This plasmid is also marked with URA3 and so cells in which the plasmid had integrated were selected on ura minus plates. These transformants were then patched out onto 5-FOA plates and ura minus cells were recovered. These ura minus cells were patched out simultaneously onto lysine minus plates and YPAD plates, and cells that did not grow on the lysine minus plates were chosen. In this manner, cells that were lys2 were recovered and the strain was named N105'. The genotype of this strain is MATa, ura3, his3, lys2, ade2, trp1, leu-2, gal4, gal80, cyh', lys2::GAL1$_{UAS}$-HIS3$_{TATA}$-HIS3, ura3::GAL1$_{UAS}$-GAL$_{TATA}$-lacZ.

6.3.4. CONSTRUCTION OF THE REPORTER STRAIN YULH

The strain Y166 (a gift of Stephen J. Elledge, Baylor College of Medicine) was made lys2 (lysine minus) by a two-step gene-disruption method (Rothstein, 1983, Methods. Enzymol. 101:202–211), so that, if desired, a LYS2 Reporter Gene or a plasmid containing LYS2 can be selected for in the strain. A mutant version of the LYS2 gene was used for this purpose. This mutant lys2-ΔNheI (a gift of Albert Smith, Yale University) was generated by deleting the NheI fragment that is internal to the LYS2 coding region. (Fleig et al., 1986, Gene 46:237–245). This gene is in a plasmid that was linearized with XbaI and the linearized DNA was used to transform N101 by the lithium acetate transformation protocol of Section 6.1.2. This plasmid is also marked with URA3 and so cells in which the plasmid had integrated were selected on ura minus plates. These transformants were then patched out onto 5-FOA plates and ura minus cells were recovered. These ura minus cells were patched out simultaneously onto lysine minus plates and YPAD plates, and cells that did not grow on the lysine minus plates were chosen. In a similar manner, these cells that were lys2 were also made his3 (histidine minus) by a two-step gene disruption method. A mutant his3-NdeI (a gift of Petra RossMacDonald, Yale University) was used for this purpose. This mutant his3-Nde I was generated by digesting the HIS3 gene in the plasmid pRS303. (Sikorski and Heiter, 1989, Genetics 122:19–27) and filling in the NdeI site with Klenow DNA Polymerase I and dNTPs. Then the URA3 gene was removed as a EagI-SmaI fragment from the plasmid YiP5 (Struhl et al., 1979, Proc. Natl. Acad. Sci. 72:1035–1039) and cloned in between the same sites in pRS303. This plasmid was linearized with NheI and the linearized DNA was used to transform the Y166 derivative that is lys2, by the lithium acetate transformation protocol of Section 6.1.2. This plasmid is also marked with URA3 and so cells in which the plasmid had integrated were selected on ura minus plates. These transformants were then patched out onto 5-FOA plates and ura minus cells were recovered. These ura minus cells were patched out simultaneously onto histidine minus plates and YPAD plates, and cells that did not grow on the histidine minus plates were chosen. In this manner, cells that were his3 were recovered and the strain was named YULH. The genotype of this strain is MATa, ura3, his3, lys2, ade2, trp1, leu2, gal4, gal80, GAL1-URA3.

6.3.5. CONSTRUCTION OF THE YEAST STRAIN N203

This section describes methods for the construction of a yeast strain, termed N203, bearing a URA3 Reporter Gene under the control of a GAL1-10 promoter (driven by GAL4 DNA binding sites), that can be used in place of strain YULH for detecting protein-protein interactions.

Construction of the GAL1-10::URA3 fusion gene

The GAL1-10 promoter (Yocum et al. 1984, Mol. Cell. Biol. 4:1985–1998) is used to create the GAL1-10::URA3 fusion gene. The GAL1-10 promoter is isolated by PCR from yeast genomic DNA by using the following oligonucleotides:

```
G1

5'-GAGAGAGAGAGGGTACCGAACCAATGTATCCAGCACCACCTGTAACC-3'     (SEQ ID NO:39)
               KpnI

G2

5'-GAGAGAGAGAGAATTCCATTATAGTTTTTTCTCCTTGACGTTAAAGTATAGAGG-3' (SEQ ID NO:40)
              EcoRI
```

The two primers flank the entire GAL1-10 promoter (Yocum et al., 1984, Mol. Cell. Biol. 4:1985–1998). The two primers also donate the restriction sites KpnI and EcoRI. The GAL1-10-specific sequences are italicized. The primer G1 contains the sequences of the GAL10 coding region from position +74 to +44, with +1 being the start of the coding region. The primer G2 contains the ATG codon of the GAL1 gene and the 35 nucleotides upstream to it. The PCR products are digested with KpnI and EcoRI and cloned between the same sites in the plasmid SK+ (Stratagene) to yield the plasmid GAL1-SK.

The URA3 gene is amplified by PCR using the following oligonucleotides and yeast genomic DNA as template:

```
5'-GAGAGAGAGAATTCTCGAAAGCTACATATAAGGAACGTGCTGC-3'      (SEQ ID NO:41)
             EcoRI

5'-GAGAGAGACGGCCGCGTCATTATAGAAATCATTACGACCGAG-3'       (SEQ ID NO:42)
           EagI
```

The URA3-specific sequences are italicized and the URA3 sequences extend from the second codon to the 3' end of the gene. The PCR products are digested with EcoRI and EagI and cloned between the same sites in GAL1-SK. This creates a GAL1-10::URA3 fusion that contains all of the URA3 protein except the first ATG and also contains the ATG of GAL1. Two amino acids (glutamate and phenylalanine) are added at the junction of GAL1 and URA3 by the cloning protocol (i.e., by the addition of the EcoRI recognition site). The GAL1-10::URA3 fusion has GAL$_{UAS}$ in its promoter and so can be activated by the GAL4 protein.

Construction of the Yeast Strain Bearing the GAL1-10::URA3 Reporter Gene

The GAL1-10::URA3 is amplified using the following oligonucleotides:

U1

5'-GATTCGGTAATCTCCGAACAGAAGGAAGAACGAAGGAAGGAGCACAGACTTAGATTGGTAGAACCAATGTATCCAGCACCACCTGTAACC-3' (SEQ ID NO:43)

U2

5'-ACATCAAAAGGCCTCTAGGTTCCTTTGTTACTTCTTCCG-3' (SEQ ID NO:44)

The oligonucleotide U1 contains the 60 nucleotides (+67 to +126) of the URA3 sequence upstream of the promoter (Rose et al., 1984, Gene 29:113–124) fused to the 30 nucleotides of the GAL1-10 promoter (italicized; Yocum et al. 1984, Mol. Cell. Biol. 4:1985–1998). The oligonucleotide U2 contains sequences from within the coding region (+632 to 670; Rose et al., 1984, Gene 29:113–124). GAL1-10::URA3 is used as the template for the PCR reaction.

The strain N201 contains copies of the RAS-GBD and RAF-GAD plasmids described in Section 6.4 and is derived by the transformation of the strain N200 that is itself a derivative of the strain CG-1945 (Clontech Laboratories, Inc., Palo Alto, Calif.) with the RAS-GBD and RAF-GAD plasmids. The genotype of the CG-1945 strain is MATa, ura3-52, his3-200, lys2-801, ade2-101, trp1-901, leu2-3, 112, gal4-542, gal80-538, cyh'2, LYS2::GAL1$_{UAS}$-GAL1$_{TATA}$-HIS3, URA3::GAL1$_{UAS}$ 17mers $_{x(3)}$-CYC1$_{TATA}$-lacZ. N200 is obtained by selecting ura minus cells by 5-FOA resistance selection. This is performed by patching cells onto 5-FOA plates. The RAS-GBD and RAF-GAD transformants of N200 are selected on SC-TRP and. SC-LEU plates respectively, as the RAS-GBD and the RAF-GAD plasmids are marked with TRP1 and LEU2 genes, respectively.

The PCR products from a reaction using the oligonucleotides U1 and U2 are used to transform the yeast strain N201, and the transformants are selected on SC-TRP-LEU-URA medium. The GAL1-10::URA3 gene is inserted at the ura3-52 locus by a double reciprocal recombination event (Rothstein, 1983, Methods. Enzymol. 101:202–211). The interaction of the RAS-GBD and RAF-GAD plasmids reconstitutes the transcriptional activator GAL4 that activates transcription from the GAL1-10::URA3 gene, thereby expressing the GAL1::URA3 fusion reporter gene and thus, enabling the cells to grow in the absence of uracil. The dependence of the +URA phenotype on the reconstitution of GAL4 is confirmed by the inability of cells, that have lost the RAS-GBD and RAF-GAD plasmids, to grow in the absence of uracil. This derivative of N201 bearing the GAL1-10::URA3 gene and the RAS-GBD and RAF-GAD plasmids is named N202.

The strain N202 is streaked out on YPAD plates and individual colonies that have lost both the RAS-GBD and the RAF-GAD plasmids are selected by their inability to grow on media lacking either tryptophan or leucine, respectively. This strain is named N203 and is a strain bearing the GAL1-10::URA3 Reporter Gene that can be used for detecting protein-protein interactions.

The strain N203 can be transformed with both the GBD and GAD plasmids to detect protein-protein interactions. Alternatively, this strain bearing just one of the plasmids (GBD or GAD) can be mated to another strain like N106' that bears the other kind of plasmid (GBD or GAD). Since the N2C3 strain has the URA3 Reporter Gene, it can be used for counterselection on 5-FOA plates to eliminate the false positives that may arise from the activation of the URA3 reporter gene by the GBD plasmid alone.

Counter Selection of N203 Transformants on 5-FOA Plates to Eliminate False-Positives The strain N203 is transformed with the pAS2-1 library and selected with 5-FOA as described in Section 6.1.7.

6.4. CONSTRUCTION OF FUSION GENES

The pairs of interacting proteins, against which peptide inhibitors are to be screened, we reintroduced into the reporter strains as fusion genes. RAS was introduced as a GAL4 DNA-Binding Domain fusion (GBD), termed RAS-GBD, RAF was-introduced as a GAL4 Activation Domain fusion (GAD) termed RAF-GAD, Vascular Endothelial Growth Factor (VEGF) was introduced both as a GAL4 DNA-Binding domain fusion protein (VEGF-GBD) and GAL4 activation domain fusion protein (VEGF-GAD), and KDR (receptor for VEGF) was introduced as a GAL4 activation domain fusion protein (KDR-GAD). The complete RAS protein was used in making the fusion (Miura et al., 1986, Jpn. J. Cancer Res. 77:45–51), the RAF sequences extend from amino acids 1 to 257 of the RAF protein (Bonner. et al., 1986, Nucleic Acids Res. 14:1009–1015), the VEGF sequences extend from amino acids 32 to the C terminus of the protein of the VEGF-165 protein (Leung et al., 1989, Science 246:1306–1309), and the KDR sequences extend from amino acids 19 to 757 of the KDR protein (Terman et al., 1992, Biochem. Biophys. Res. Comm. 187:1579–1586).

The plasmid vectors for the GBD fusions and the GAD fusions, pAS2 and pACT2, respectively (Clontech) were each modified to introduce two SfiI sites to facilitate cloning of insert DNAs. These plasmids are yeast E. coli shuttle vectors and are marked with β-lactamase for selection in E. coli using ampicillin and a 2μ circle DNA for replication in yeast. The pAS2 plasmid (Clontech; also known as pAS1-CYH, Harper et al., 1993, Cell 75:805–816) is marked with the TRP1 gene for selection in yeast (in medium lacking tryptophan) whereas the pACT2 is marked with the LEU2 gene for the same (in medium lacking leucine). The resulting plasmids with the two SfiI sites were called pASSfiI and pACTSfiI, respectively. The polylinkers of the plasmids are as follows:

```
pASSfiI:
            Sfii                    Sfii
5'-CAT ATG GCC GAG GTG GCC TAG GGC CTC CTG GGC CTC CCT TAG GGA TCC-3'    (SEQ ID NO:5)
   NdeI                                                         BamHI pACTSfiI:
         SfiI                    SfiI
5'-GAG GCC GAG GTG GCC TAG GGC CTC CTG GGC CTC TAG AAT TCC-3'            (SEQ ID NO:6)
                                                  EcoRI
```

SfiI sites were introduced at the beginning and end of H-RAS genes by use of PCR and oligonucleotides such that when cloned in pASSfiI the RAS coding region was in frame with the GAL4 DNA-Binding Domain, thus creating a fusion protein RAS-GBD. In an identical manner VEGF was cloned into pASSfiI. A RAF fusion gene with the GAL4 Activation Domain was constructed and cloned into pACTSfiI to create RAF-GAD. Similarly VEGF and KDR were also cloned into pACTSfiI. The oligonucleotides used for amplification of RAS were as follows:

5'-G GAC TAG GCC GAG GTG GCC GGT ATG ACG GAA TAT AAG CTG GTG-3' (SEQ ID NO:7)

5'-G GAC TAG GCC GAG GTG GCC GGA GAG CAC ACA CTT GCA GCT-3' (SEQ ID NO:8)

The oligonucleotides used for amplification of RAF were as follows:

5'-G GAC TAG GCC GAG GTG GCC ATG GAG CAC ATA CAG GGA GCT-3' (SEQ ID NG:9)

5'-G GAC TAG GCC GAG GTG GCC CGA CCT CTG CCT CTG GGA GAG-3' (SEQ ID NO:10)

The oligonucleotides used for amplification of VEGF were as follows:

5'-G GAC TAG GCC GAG GTG GCC GGA GGA GGG CAG AAT CAT CAC-3' (SEQ ID NO:11)

5'-G GAC TAG GCC TCC TGG GCC ACG CCT CGG CTT GTC ACA TCT GC-3' (SEQ ID NO:12)

The oligonucleotides used for amplification of KDR were as follows:

5'-G GAC TAG GCC GAG GTG GCC CTC TCT GTG GGT TTG CCT AGT GTT TC-3' (SEQ ID NO:13)

5'-G GAC TAG GCC TCC TGG GCC CTC CTT TGA AAT GGG ATT GGT AAG-3' (SEQ ID NO:14)

The reporter strains YULH and N106' were transformed with each of the plasmids containing the fusion genes (RAS-GBD, RAF-GAD, VEGF-GBD, VEGF-GAD, KDR-GAD etc.) to yield YULH(RAS-GBD), YULH(VEGF-GBD), N106'(RAF-GAD), N106'(VEGF-GAD), and N106' (KDR-GAD). When two are mated together (e.g., YULH (RAS-GBD)×N106'(RAF-GAD)), then the interaction between RAS-GBD and RAF-GAD reconstitutes the GAL4 transcription factor, thus activating the URA3, HIS3 and the lacZ reporter genes which are under the control of the GAL promoter.

6.5. CONSTRUCTION OF cDNA LIBRARIES IN pASSfiI

Following cDNA synthesis from human placental tissue as described above in Section 6.1.6, SfiI adapters were ligated to the cDNA under standard linker ligation conditions. The SfiI adapters used for linker ligation have the sequence:

5'-A G G C C G G A G G C-3' (SEQ ID NO:15)

5'-T C C T C C G G C C T C C G-3' (SEQ ID NO:16)

The SfiI linked cDNA was amplified by a PCR of 20 cycles and the primer used in the amplification was: 5'-AGGTGCAAGGCCCAGGAGGCCGGAGGC-3' (SEQ ID NO:17)

The first 5 cycles of PCR had the following profile:
94° C. for 30 sec
37° C. for 30 sec
72° C. for 30 sec The next 15 cycles of PCR had the following profile:
94° C. for 30 sec
65° C. for 30 sec
72° C. for 30 sec The amplified cDNA was digested with SfiI and cloned into pASSfiI that had been digested with SfiI. This created a cDNA library with cDNA fused to the DNA-binding domain of GAL4. A library was of $2.5 \times 10^4$ clones was made by this method. The library was propagated in the E. coli strain XL1Blue (Stratagene) and plasmid DNA was extracted by standard procedures.

6.6. TRANSFORMATION OF THE REPORTER STRAINS WITH THE pASSfiI AND pACT cDNA LIBRARIES TO CREATE "M" AND "N" POPULATIONS

Plasmid pACT differs from pACT2 in the polylinker region (Durfee et al., 1993, Genes Dev. 7:555–569). The strains YULH and N106' were transformed with the pASSfiI and pACT cDNA libraries by the lithium acetate protocol (Section 6.1.2; Ito et al., 1983, J. Bacteriol. 153:163–168). 1 µg of library DNA generally yields a maximum of about $1 \times 10^6$ transformants. The pACT cDNA library (gift of Stephen J. Elledge; Baylor College of Medicine) (Durfee et al., 1993, Genes Dev. 7:555–569) consists of human peripheral T lymphocyte cDNA and the pASSfiI cDNA library consists of human placental cDNA as described in Section 6.5. The transformants were selected on either media lacking leucine (for pACT) or lacking tryptophan and containing 5-FOA (for pASSfiI). In the latter case, all GBD-fusions that fortuitously activate transcription on their own are eliminated as the URA+cells will be killed. The transformants were harvested in the appropriate media (SC-LEU for pACT and SC-TRP for pASSfiI) to a final cell density of $1 \times 10^8$ cells/ml and stored in aliquots at –70° C. after making them 10% in DMSO or glycerol.

6.7. CONSTRUCTION OF YEKST STRAINS WITH INTEGRATED COPIES OF RAF-GAD

As an alternative to bearing RAF on a replicating plasmid, the RAF-GAD fusion gene was integrated into the yeast genome. This method has the advantage of creating stable strains of yeast that express RAF-GAD which do not require growth on selective media for the maintenance of the fusion gene.

The RAF-GAD fusion gene was amplified by PCR from the RAF-GAD plasmid, using the following oligonucleotides:

```
                 Eag I
5'-GGG ACA AAC GGC CGC ACC GAA ACG CGC GAG GCA GCA AC-3'    (SEQ ID NO:18)

Sph I
5'-GGG AGT TGC ATG CGC CGG TAG AGG TGT GGT CAA TAA G-3'     (SEQ ID NO:19)
```

These oligonucleotides also introduced unique restriction sites (EagI and SphI) that facilitate the cloning of the amplified DNA fragments into the integration vector R1400. The R1400 plasmid vector consists of two yeast genes LYS2 (Fleig et al., 1986, Gene 46:237–245) and MER2 (Engebrecht et al., 1991, Cell 66:1257–1268). The LYS2 marker is used for the selection of integration events, while the MER2 gene is used for integration of the entire plasmid into the yeast genome. MER2 is a gene that is not essential for the vegetative growth of yeast. The RAF-GAD gene was cloned into the R1400 plasmid to yield RAF-INT. This plasmid was then digested with the restriction enzyme PstI that has a site in the MER2 gene. The restriction was done in a partial manner as there are other PstI sites in the plasmid vector. The restriction digestion was allowed to proceed only for 1 minute and then the enzyme was inactivated by extracting with phenol-chloroform and the DNA was then precipitated. This linearized DNA was used to transform the YULH strain to yield YULH-RAFINT. Integration occurs at the MER2 locus, and the integration events were selected by growing the transformants on media lacking lysine. The N106' strain was transformed with the RAS-GBD plasmid to form N106' (RAS-GBD). The proper functioning of the RAF-GAD fusion was confirmed by mating YULH-RAFINT and N106' (RAS-GBD) and observing the resultant activation of the URA3 and the lacZ Reporter Genes.

6.8. CONSTRUCTION OF PEPTIDE EXPRESSION VECTORS (PEVS)

The PEVs serve to express and localize peptides (or proteins) in the nucleus of the yeast cell where their potential to inhibit specific protein-protein interactions is tested. This inhibitory activity of the peptides is monitored by their ability to inhibit the activity of the reporter genes like URA3, HIS3 and lacZ.

Figure 7:
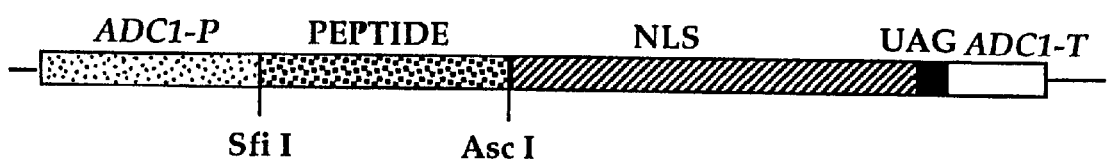

The PEVs comprise the following operably linked components (FIG. 7): an ADC1 promoter (ADC1-P) for supporting transcription in yeast (Ammerer, 1983, Meth. Enymol. 101:192–201); a nucleotide sequence encoding an SV40 Nuclear Localization Signal (NLS) for transporting the peptide to the nucleus (Dingwal and Laskey, 1991, Trends. Biochem. Sci. 16:478); followed by a stop codon (UAG) for terminating translation; means for inserting a DNA sequence encoding a candidate inhibitor peptide into the PEV in such a manner that the candidate inhibitor peptide is capable of being expressed as part of a fusion protein containing the NLS; and an ADC1 transcription termination signal. The NLS from SV40 large T comprises a 7 amino acid stretch (PKKKRKV) (SEQ ID NO:20) that has been successfully used in targeting proteins into the yeast nucleus (Benton et al., 1990, Mol. Cell. Biol. 10:353–360). The ADC1 promoter and the sequence encoding the NLS are separated by two restriction sites for Sfi I and Asc I, respectively, that facilitate cloning of insert DNAs encoding the peptides. These sites can also be used for introducing a polypeptide backbone into which the inhibitory peptide can then be fused; this can facilitate the proper folding and presentation of the peptide. The PEVs also containing 2μ DNA for replication in yeast, a LEU2 gene for selection in yeast, and a β-lactamase gene for selection in *E.coli*.

pPEV1 is constructed in the following manner. Synthetic oligonucleotides that introduce SfiI and AscI sites, the NLS and a stop codon are-cloned into the HindIII site in pAAH5 (Ammerer, 1983, Meth. Enzymol. 101:192–201). pAAH5 has the ADC1 promoter that supports transcription of genes in yeast and is marked with LEU2 for selection of transformants. The sequences of the two oligonucleotides are as follows:

ADCNLS-S
  5'-AGC TTG GCC TCC CAG GCC ACA GAC AGG CGC GCC CCC AAA GAA GAG AAA GGT TTA GA-3' (SEQ ID NO:21)

ADCNLS-A
  5'-AGC TTC TAA ACC TTT CTC TTC TTC TTT GGG GGC GCG CCT GTC TGT GGC CTG GGA GGC CA-3' (SEQ ID NO:22)

6.9. SELECTION OF PROTEIN-PROTEIN INTERACTIONS FROM A NON-INTERACTING BACKGROUND

A. Selection of SNF1-SNF4 interactions: Mating assay SNF1 and SNF4 are a pair of interacting proteins in the yeast *Saccharomyces cerevisiae* (Celenza and Carlson, 1986, Science 233:1175–1180). The following example describes the selection of these two interacting proteins SNF1 and SNF4, from a background of cells that do not contain any DNA-binding or activation domain fusion proteins. This experiment provides an example of the selection of cells expressing interacting proteins from a population. The yeast strains expressing these two interacting proteins as fusions to the DNA-binding and activation domains of GAL4 were mated in the presence of varying quantities of yeast strains that were not expressing any fusion protein. As evidenced from the results below, selection of SNF1-SNF4 interaction occurs even at a 100 to 1000-fold excess of background (cells that do not contain interacting proteins).

The reporter strains N105 and N106 were transformed with the SNF4-GAD (called pSE1111, a gift from Stephen J. Elledge, Baylor College of Medicine; Fields and Song, 1989, Nature 340:245–246) and SNF1-GBD (called pSE1112, a gift from Stephen J. Elledge, Baylor College of Medicine; Fields and Song, 1989, Nature 340:245–246) to yield N105 (SNF4-GAD) and N106 (SNF1-GBD), respectively.

N105 (SNF4-GAD) and N106 (SNF1-GBD), were grown in the appropriate selective media to a cell density of $1\times10^8$ cells per ml. The SNF1-GBD and SNF4-GAD transformants were mixed with the a and α reporter strains, transformed with the vector pAS2 (in N105) and the vector pACT2 (in N106) respectively, in the following dilutions:

$2.5\times10^5$ cells of SNF1-GBD and SNF4-GBD strains each mixed with $2.5\times10^5$ cells each of an a strain bearing pAS2 and an α strain bearing pACT2.

$2.5\times10^4$ cells of SNF1-GBD and SNF4-GBD strains each mixed with $2.5\times10^5$ cells each of an a strain bearing pAS2 and an α strain bearing pACT2.

$2.5\times10^3$ cells of SNF1-GBD and SNF4-GBD strains each mixed with $2.5\times10^5$ cells each of an a strain bearing pAS2 and an α strain bearing pACT2.

$2.5\times10^2$ cells of SNF1-GBD and SNF4-GBD strains each mixed with $2.5\times10^5$ cells each of an a strain bearing pAS2 and an α strain bearing pACT2.

The mixtures were plated in a volume of 500 μl onto YPAD plates and incubated at 30° C. for 8 hours. (During this incubation, one or two cell divisions may occur resulting in duplication of events.) After this, the cells were harvested by the addition of 500 μl of SC-LEU-TRP medium and plated onto media lacking leucine, tryptophan, histidine and containing 40 mM 3-aminotriazole (3-AT).

After three to six days, the number of TRP+, LEU+, HIS+ and 3-AT resistant colonies were counted. Results from our completion of this protocol are shown in Table 11.

TABLE 11

| No. of cells of SNF1-GBD and SNF4-GAD each | No. of cells of pAS2 and pACT2 each | No. of TRP+, LEU+, HIS+, 3-AT$^r$ colonies |
|---|---|---|
| $2.5 \times 10^5$ | $2.5 \times 10^5$ | Confluent growth (>10,000 colonies) |
| $2.5 \times 10^4$ | $2.5 \times 10^5$ | 458 |
| $2.5 \times 10^3$ | $2.5 \times 10^5$ | 7 |
| $2.5 \times 10^2$ | $2.5 \times 10^5$ | 1 |
| 0 | $2.5 \times 10^5$ | 0 |

Confirmation of Interaction by Whole Cell PCR

Whole cell PCR was performed on the cells positive for interactions as described under the protocols section (Section 6.1.8):

Reaction volume: 100 μl
  10×PC2 Buffer for Klentaq: 10 μl 10 mM dNTPs: 3 μl 50 pmoles of each primer pair 1.0 μl of Klentaq polymerase A few yeast cells from the colony (a swipe of the colony that is positive for interaction with a plastic tip). PCR was performed at 94° C. for 30 sec, 55° C. for 30 sec and 72° C. for 2 min with each being repeated for 20–30 cycles. Two separate PCR reactions were performed in parallel on the colonies that were TRP+, LEU+, HIS+ and 3-AT resistant. One PCR with the pASFOR (ATGAAGCTACTG TCTTCTATCGAAC-3') (SEQ ID NO:4) and pACTBAC (5'-CTACCAGAATTCGGCATGCCGGTAGAG GTGTGGTCA) (SEQ ID NO:3) primers (for pAS2) amplifies the insert from the GAL4 binding domain fusion (GBD) plasmid, and the other PCR with the pACTFOR (5'-ATGGATGATGTATATAACTATCTATTC-3') (SEQ ID NO:23) and pACTBAC primers (for pACT or pACT2) amplifies the insert from the GAL4 activation domain fusion (GAD) plasmid. As controls, PCR reactions were performed on cells that harbored the GBD and GAD plasmids that did not contain any insert DNA.

"Real positives," in which the pAS2 and pACT2 vectors are replaced by analogous vectors containing for example, cDNA inserts, should yield PCR products for both the GBD and GAD plasmids that are bigger than that of the respective controls. pAS2 and pACT2 specific primers are used in a yeast whole cell PCR assay on these colonies. In a trial, PCR products whose sizes corresponded to SNF1- and SNF4- fusion proteins were obtained.

B. Selection of VEGF-VEGF Interactions: Mating Assay

The following example describes the optimum plating conditions for the selection of interacting proteins from a mating assay. The yeast strains expressing two interacting proteins, both VEGF in this case, as fusions to the DNA-binding and activation domains of GAL4, were mated in the presence of varying quantities of yeast strains that were not expressing any fusion protein. The effect of increasing the total cell density on the efficiency of selecting the VEGF-VEGF interaction was studied as described below.

YULH(VEGF-GBD) and N106'(VEGF-GAD), made as described in Section 6.4, were grown to saturation in media (SC-TRP-LEU) that selects for both of these plasmids in which VEGF is encoded. VEGF dimerizes to form homodimers (Potgens et al., 1994, J. Biol. Chem. 269:32879–32885; Claffey et al., 1995, Biochem. Biophys. Acta 1246:1–9), and thus the interaction between two VEGF molecules can be monitored in the mating interaction assay. Simultaneously, YULH and N106' were grown to saturation in YPAD medium. The VEGF-GBD and VEGF-GAD transformants were mixed with the YULH and N106' reporter strains, in the following dilutions:

$6.6 \times 10^4$ cells of YULH(VEGF-GBD) and N106'(VEGF-GBD) strains each mixed with $6.6 \times 10^7$ cells each of YULH and N106' strain in a total volume of 0.5 ml.

$1.3 \times 10^5$ cells of YULH(VEGF-GBD) and N106'(VEGF-GBD) strains each mixed with $1.3 \times 10^8$ cells of YULH and N106' strain in a total volume of 1 ml.

$2.6 \times 10^5$ cells of YULH(VEGF-GBD) and N106'(VEGF-GBD) strains each mixed with $2.6 \times 10^8$ cells each of YULH and N106' strain in a total volume of 2 ml.

$5.3 \times 10^5$ cells of YULH(VEGF-GBD) and N106'(VEGF-GBD) strains each mixed with $5.3 \times 10^8$ cells of YULH and N106' strain in a total volume of 4 ml.

The mixtures were transferred onto one YPAD plate each, each plate 150 mm in diameter, and incubated at 30° C. for 6–8 hours. (During this incubation one or two cell divisions may occur resulting in duplication of events). After this, the cells were harvested by the addition of 1–2 ml of SC-LEU-TRP-URA-HIS medium and plated onto plates lacking leucine, tryptohan, histidine, uracil and containing 40 mM 3-aminotriazole (3-AT). The contents of one YPAD plate went into one selective media plate.

After three-six days, the number of TRP+, LEU+, HIS+, URA+ and 3-AT resistant colonies were counted. In an exemplary trial, the following results shown in Table 12 were obtained:

TABLE 12

| No. of YULH and N106 cells each | No. of VEGF (GBD) and VEGF (GAD) cells each | No. of HIS+, URA+ and 3-AT$^r$ colonies[1] |
|---|---|---|
| $6.6 \times 10^7$ | $6.6 \times 10^4$ | 71 |
| $1.3 \times 10^8$ | $1.3 \times 10^5$ | 137 |
| $2.6 \times 10^8$ | $2.6 \times 10^5$ | 233 |
| $5.3 \times 10^8$ | $5.3 \times 10^5$ | * |

*The paste representing the mixture of cells was so thick that the emerging colonies could not be clearly differentiated from the background.
[1]These values represent averages of duplicates.

VEGF-VEGF interactions were detected. The optimum. cell density required for mating to yield interacting colonies was $1-2 \times 10^8$ cells/150 mm diameter plate, since at cell densities higher than this, the number of interactants detected decreased. At cell densities higher than $1-2 \times 10^8$ cells/plate, doubling the individual interacting cells did not double the yield of HIS+, URA+ and 3-AT$^R$ cells.

6.10. SELECTION OF SPECIFIC PROTEIN-PROTEIN INTERACTIONS FROM A BACKGROUND OF OTHER INTERACTING PROTEINS

Mating Assay

This example describes the selection of a pair of interacting proteins from a background of other interacting proteins. The interaction between the RAS-GAL4 DNA binding domain fusion and RAF-GAL4 activation domain fusion proteins was selected in the presence of other GAL4 DNA-binding and activation domain fusion proteins. This example demonstrates that specific interactors can be selected when present in a background of other interacting proteins.

YULH(RAS-GBD) and N106'(RAF-GAD) transformants made as described in Section 6.4 were grown in the appropriate selective media to a cell density of $2 \times 10^8$ cells/ml. RAS and RAF are members of signal transduction pathway leading to mitogenesis and have been demonstrated to interact with each other (Vojtek et al., 1993, Cell 74:205–214). The RAS-GBD and RAF-GAD transformants were mixed with the M and N cells in the following dilutions:

$2.5 \times 10^5$ cells of RAS-GBD and RAF-GBD strains each mixed with $2.9 \times 10^8$ cells each of M and N.

$2.9 \times 10^8$ cells each of M and N.

The 'M' cells in this example are YULH cells bearing a library of human placental cDNA fused to GBD in pASSfi. The 'N' cells in this example are N106' cells bearing a library of cDNA of human peripheral T lymphocytes fused to GAD in pACT.

The M and N cells represent 1000 transformants each. That is, in $10^8$ cells each transformant is represented $10^5$ times.

These mixtures were vortexed very gently and then pelleted by centrifugation and then resuspended in 0.2 ml of YPAD medium and then spread on YPAD plates and incubated at 30° C. for 6–8 hours. (During this incubation one or two cell divisions may occur resulting in duplication of events.) At this stage, cells of the M (and RAS-GBD) and N (and RAF-GAD) strains have mated to yield diploids.

The mating mixes were harvested from the plates by adding 1 ml of SC-URA-LEU-TRP media and scraping. The harvested cells were then plated onto SC-URA-LEU-TRP-HIS+3-AT agar plates. The -TRP and -LEU select for the GBD and GAD plasmids (encoding trp and leu, respectively), while the -URA and -HIS and presence of 3-AT selects for the interaction between the two fusion proteins (by selecting for the expression of the URA3 and HIS3 Reporter Genes). Thus, cells that are URA+, HIS+, 3-AT resistant, TRP+ and LEU+ contain GAD and GBD fusion proteins that interact with each other.

The URA+ cells were picked and patched onto SC-LEU-TRP plates and incubated at 30° C. for 12–24 hours. These patches were then replica-plated onto SC-URA, SC-HIS and SC-TRP-LEU plates. Growth on -URA and -HIS plates confirmed interaction of the two fusion proteins. The patches from the SC-LEU-TRP plates were transferred onto a Whatman no. 1 filter and assayed for β-galactosidase activity (Section 6.1.11). The patches turned blue, indicating β-galactosidase activity as a result of the activation of the lacZ Reporter Gene due to interaction between RAS-GBD and RAF-GAD.

Confirmation of Interaction by Whole Cell PCR

Two PCR reactions were performed in parallel on the colonies that were TRP+, LEU+, and URA+ (as in the case of Section 6.3.): one with the RAFSfiS (5'-G GAC TAG GCC GAG GTG GCC GGT ATG ACG GAA TAT AAG CTG GTG-3') (SEQ ID NO:23) and RAFSfiA (5'-G GAC TAG GCC GAG GTG GCC GGA GAG CAC ACA CTT GCA GCT-3') (SEQ ID NO:24) that amplify the RAF insert from the GAD plasmid, and the other with primers specific for the RAS sequences, RASSfiS (5'-G GAC TAG GCC GAG GTG GCC ATG GAG CAC ATA CAG GGA GCT-3') (SEQ ID NO:25) and RASSfiA (5'-G GAC TAG GCC GAG GTG GCC CGA CCT CTG CCT CTG GGA GAG-3') (SEQ ID NO:26).

RAF-RAS interactors yield PCR products for the GAD plasmid with the RAF specific primers and a RAS-specific PCR product with the RAS specific primers. The ratios of the RAS-RAF interactors to the total cells in each mating, shown in Table 13, were obtained:

TABLE 13

| No. of RAS-GBD and RAF-GAD cells each in the mating mix | No. of M and N cells each in the mating mix | Total no. of RAS-RAF interactants |
|---|---|---|
| 0 | $2.9 \times 10^8$ | 0 |
| $2.5 \times 10^5$ | $2.9 \times 10^8$ | 200[a] |

[a]This value represents average of duplicates.

6.11. SELECTION OF INTERACTING PROTEINS FROM AN M×N SCREEN

6.11.1. MATING ASSAY

The M and N cells (as described in Section 6.10) were mixed together and 0.5 ml of the mix (a total cell density of $2.5 \times 10^9$ cells /ml) was spread onto YPAD plates and incubated at 30° C. for 8 hours for mating. The M and N cells represent 5,000 transformants each. That is, in $10^8$ cells each transformant is represented 20,000 times. The mating mixes were then harvested in 1 ml of the appropriate selective media and plated onto SC-URA-LEU-TRP-HIS plates that contain 40 mM 3-AT and incubated at 30° C. until colonies emerge. In a trial, this analysis was performed in duplicate.

Cells that were URA+, HIS+ and 3-AT resistant were patched onto separate SC-TRP-LEU plates and assayed for β-galactosidase activity. Cells that were URA+, HIS+, 3-AT resistant and positive for 6-galactosidase activity were classified as positive for protein-protein interactions (Sections 6.1.8 and 6.1.10). These colonies were then grown to saturation in 100 μl each of SC-LEU-TRP medium in a 96 well plate and an aliquot was stored frozen after making it 10% in DMSO. These cultures represent the interactive population from an M×N screen.

6.11.2. WHOLE CELL PCR OF THE POSITIVE COLONIES

From the patches of the positive colonies, whole cell PCR was performed as described under Section 6.1.8 with the modification that a tiny amount of the colony was taken with the help of a plastic tip and transferred to the PCR mix for amplification of the inserts from the GBD (in pASSfiI) and GAD (in pACT) plasmids. Two PCR reactions are performed in parallel for each colony: one with the pASFOR (SEQ ID NO:4) and pACTBAC (SEQ ID NO:3) primers that amplify the insert from the GBD plasmid, and one with the pACTFORII (SEQ ID NO:2) and pACTBAC (SEQ ID NO:3) primers that amplify the insert from the GAD plasmid.

The primers can be used for sequencing as well as PCR.

6.11.3. QEA™ METHOD OF THE PCR PRODUCTS

The pASSfiI and pACT specific PCR products were pooled separately and a 4-mer and 5-mer QEA™ method were performed as described in in Section 6.1.12.2.1. 10 μl of each PCR reaction were used in pooling. The pooled PCR products were then purified with the GeneClean II DNA purification kit (Bios 101) according to the manufacturer's instructions. The GeneClean II kit uses a glassmilk-based DNA purification protocol. 10 ng of the pooled PCR products were used in a QEA™ method reaction. The enzymes Sau3A I and BsaW I were used in the QEA™ method process. The primer pairs for QEA™ method were as follows:

```
For Sau3A I,  5'-AGCACTCTCCAGCCTCTCACCGAC-3'    (SEQ ID NO:27)
                         3'-AGTGGCTGCTAG-5'    (SEQ ID NO:28)

For BsaW I,   5'-AGCACTCTCCAGCCTCTCACCGAC-3'    (SEQ ID NO:29)
                         3'-AGTGGCTGGGCC-5'    (SEQ ID NO:30)
```

Figure 8:
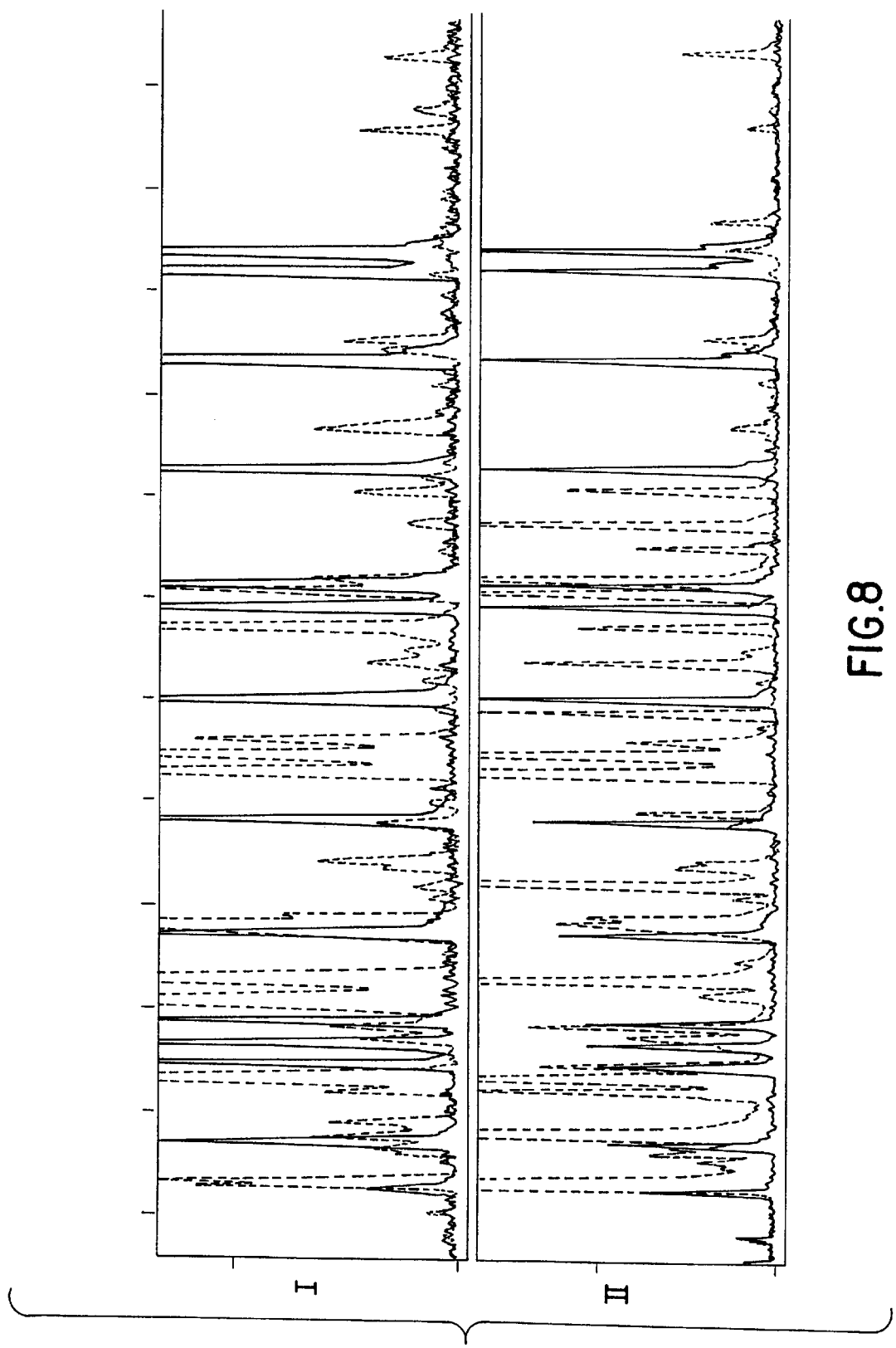

The QEA™ method products were then analyzed on a ABI 377 automated sequencer by denaturing gel electrophoresis. In a trial, the QEA™ method patterns obtained from duplicate N×M screens were very similar (FIG. 8).

6.11.4. CREATION OF TWO-DIMENSIONAL POOLS

Two-dimensional pools were created as per Section 6.1.9. 5 μl of saturated culture from each well in a row or in a column were combined to create a pool which was given a particular designation (like Pool 1, 2, 3 . . . for columns and Pool A, B, C . . . for rows). Each of these pools then served as starting material for further analysis by PCR. A duplicate of the two-dimensional pool was made in which an additional well, that consisted of diploids resulting from the mating of YULH(RAS-GBD) and N106' (RAF-GAD), was added to this array.

6.11.5. WHOLE CELL PCR OF THE POOLED CELLS

Whole cell PCR was performed on the pooled rows and columns arising from the two-dimensional pools as described under the protocols section (Section 6.1.8). Two PCR reactions were performed in parallel for each pool: one with the pASFOR (SEQ ID NO:4) and pACTBAC (SEQ ID NO:3) primers that amplify the insert from the GBD plasmid, and one with the pACTFORII (SEQ ID NO:2) and pACTSEQII (SEQ ID NO:1) primers that amplify the insert from the GAD plasmid. Thus, each PCR reaction represents genes from a particular pool for either the "M" or the "N" population. The PCR products served as templates for further analysis by the QEA™ method and SEQ-QEA™ method.

6.11.6. QEA™ METHOD OF THE PCR DERIVED FROM POOLED CULTURES

PCR products (10 μl out of 100 μl) from each row or column (in the case of two-dimensional pools) were all combined and subjected to the QEA™ method as described above. The QEA™ method was also performed on the PCR products from the individual rows and columns. Four base-pair recognition site restriction enzymes like Sau3A I, BsaW I and Tsp 509 I were used and after restriction-digestion for 120 min, the enzymes were either heat-inactivated at 65° C. for 20 min or inactivated by phenol extraction. Combinations of four-base recognizing enzymes (Sau3A I) and six-base recognition enzymes (Hind III) were also used in the QEA™ method.

For Tsp 509 I, the QEA™ method primer pair (adapter) used in a trial was:

5'-AGCACTCTCCAGCCTCTCACCGAC-3' (SEQ ID NO:31)

3'-AGTGGCTGAATT-5' (SEQ ID NO:32)

For Hind III, the QEA™ method primer pair (adapter) used in a trial was:

5'-AGCACTCTCCAGCCTCTCACCGAC-3' (SEQ ID NO:33)

3'-AGTGGCTGTCGA-5' (SEQ ID NO:34) SEQ ID NO:31 and NO:33 had the fluorescent dye Fam affixed to the 5' end.

For Sau3AI, the QEA™ method primer pair (adapter) used in a trial was

```
Primer RC24: 5'-AGCACTCTCCAGCCTCTCACCGAC-3'    (SEQ ID NO:67)
                        3'-AGTGGCTGCTAG-5' (SEQ ID NO:74)
                        Primer RC9.
```

Primer RC24 had biotin attached at its 5' end. After this, T4 DNA ligase was added and the QEA™ method was performed as described in Section 6.1.12.2.1.

The QEA™ method was carried out with Sau3AI and HindIII, using the above primer pairs listed for each enzyme.

Figure 9:
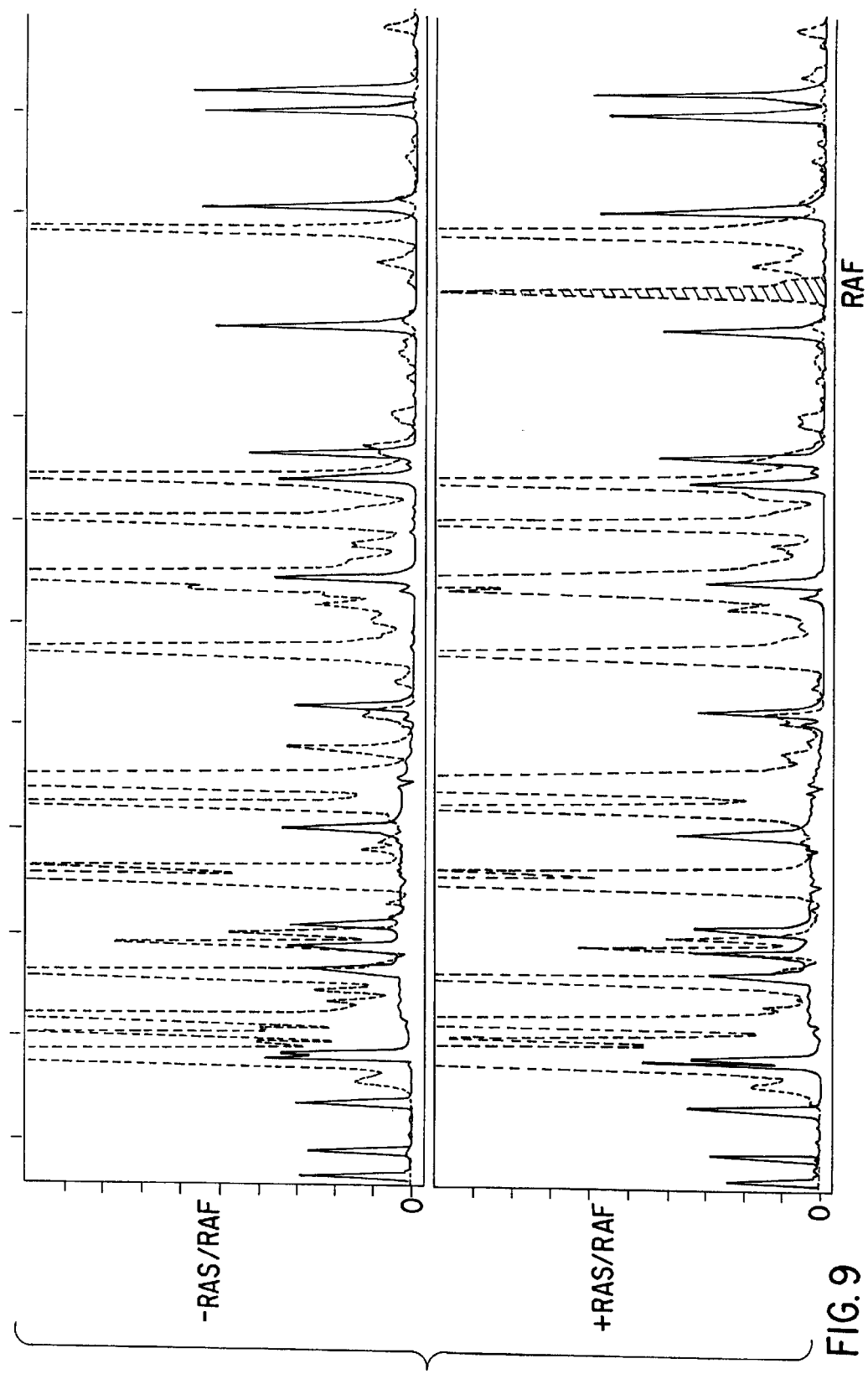

The QEA™ method products were analyzed on denaturing polyacrylamide gels as described above. Each QEA™ method band is a representative of protein present in the interactive population. The QEA™ method patterns obtained from duplicate N×M screening trials were very similar. This was observed with both pAS-and pACT-specific PCR products. A RAF-specific band was clearly seen, at the expected position, in the QEA™ method of the pool that contained the RAS-RAF diploid, while this band was absent in the pool that did not contain the RAS-RAF diploid (FIG. 9).

Furthermore, by comparing the QEA™ method patterns of each row and column, it was possible to identify the well from which the RAS-RAF diploid originated. This is exemplary of deconvolution of the QEA™ method results from the two-dimensional pool to arrive at source of genes that contribute to differential QEA™ method patterns.

Thus, by analyzing multiple replicates of the QEA™ method of one interactive population with multiple replicates of the QEA™ method of another interactive population, it is possible to identify genuine differences identify and isolate protein-protein interactions that are unique to any particular tissue/cell type, stage of development, or disease state.

6.11.7. THE SEQ-QEA™ METHOD OF THE PCR DERIVED FROM POOLED CULTURES

The QEA™ method products from the pooled pASSfiI and pACT PCR products are subjected to the SEQ-QEA™ method separately as described in Section 6.1.12.2.2. The SEQ-QEA™ method gives the additional information about each QEA™ method-product in that it provides the identity of the terminal 4 bases immediately downstream of the restriction site that is used in the QEA™ method. With this additional information, gene identification is possible even with 4-base recognizing restriction enzymes. Comparison of the QEA™ method and the SEQ-QEA™ method patterns between the rows and columns of the pooled interactants (see FIG. 3) permits the deconvolution of the pools and thus reveals the location of each interacting pair in the original master plate that contains all the interacting pairs. Gene identification through the SEQ-QEA™ method thus reveals the identity of each pair of interacting proteins in an interacting population and thus helps in the identification of unique interactors specific to a particular population.

6.12. IDENTIFICATION OF SPECIFIC PAIRS OF INTERACTING PROTEINS FROM A QEA™ METHOD OF THE INTERACTIVE POPULATION AND BY THE USE OF GENE-SPECIFIC PRIMERS

Based on the sequence information obtained from the SEQ-QEA™ method, gene-specific primers are synthesized and are used as PCR primers to screen the interactive population. PCR is performed on all the pools of PCR products (that are derived from the interactive population from the pAS-like vectors and from the pACT-like vectors using the gene specific primers; see Section 6.1.8). Decoding the PCR results identifies the original colony that gives rise to the QEA™ method band. The pAS-like-vector and pACT-like-vector primer-derived PCR products from these colonies are then sequenced to reveal the identities of both the interacting proteins. The identity of one of the genes encoding the interacting proteins is given by the sequence obtained from the QEA™ method band.

6.13. CREATION OF INTERACTIVE GRIDS

As an alternative to the above PCR-based strategy to identify interacting proteins from an interactive population, a hybridization-based strategy is used. As a first step in this process an "Interactive Grid" is created in the following manner. A portion (25 µl) of the pooled PCR products (derived using the pAS-like-vector-specific and PACT-like-vector-specific primer pairs) are used to create an interactive grid. The interaction grids are created by spotting a pair of PCR products onto a nylon membrane with the same dimensions as the 96-well plate from which the whole-cell PCR was done. The DNA is denatured according to standard protocols before spotting onto a nylon membrane. Spotting of DNA is done as per standard dot-blotting protocols for RNA, except with prior denaturation (in Current Protocols in Molecular Biology, 1995, Chapter 2.9B, Dot and Slot Blotting of DNA onto uncharged nylon and nitrocellulose membranes, Frederick M. Ausubel et al. (eds.), John Wiley & Sons, New York). Thus, each spot on the interactive grid corresponds to the original well containing the culture harboring the two interacting proteins.

6.14. ISOLATION OF STAGE-SPECIFIC PAIRS OF INTERACTING PROTEINS

The QEA™ method stage/tissue-specific bands are excised from gels and amplified by PCR using the same primer sets that are used in the QEA™ method. These PCR products are then labeled either with radiolabeled nucleotides (e.g., $^{32}$P-dCTP) or biotinylated nucleotides (e.g., Bio-dCTP) or fluorescently tagged nucleotides, and used to probe the interaction grids. Labeling and hybridization are done according to standard protocols (Sambrook et al., 1989, Molecular Cloning: A Laboratory Manual, Second Edition, Cold Spring Harbor Laboratory Press, Cold Spring Harbor, New York). Spots that hybridize to the probe represent the pair of interacting proteins from which the QEA™ method band arose. By relating this signal to the original master plate, the original cell culture harboring the two interacting proteins can be identified.

To sequence the pAS-like vector and pACT-like vector clones from these cells, the stored PCR products (50 µl each) are sequenced by standard protocols and the sequence identity is obtained.

6.15. EXPRESSION OF PEPTIDE INHIBITORS IN PEV AND INHIBITION OF PROTEIN-PROTEIN INTERACTIONS

To test the functionality of pPEV1 (described in Section 6.8), the RAS effector peptide (amino acids 17–40) is cloned between the Sfi I and Asc I sites to yield pPEVRAS-E, which is used to transform the yeast strain YULH-RAFINT by the lithium acetate protocol (Section 6.1.2). The RAS effector peptide arises from a region in the RAS protein that is important for its interaction with RAF (Chuang et al., 1994, Mol. Cell. Biol. 14:5318–5325; Zhang et al., 1993, Nature 384:308–313). The resulting strain, YULH2RAS, is then. mated to the N106'(RAS-GBD) strain. The mated cells are transferred to the appropriate selective media. The resulting diploids are ura- (unable to grow on media lacking uracil) and lacz- (negative for β-galactosidase activity). These diploids also grow on medium containing 5-FOA, a chemical that kills URA+ cells (Rothstein, 1983, Meth. Enzymol. 101:167–180). The control N106'(RAS-GBD) diploids are URA+ and LACZ+, but are unable to grow on medium containing 5-FOA.

Thus, pPEV1 can be successfully used to introduce a polypeptide into the nucleus where this polypeptide successfully competes with and inhibits a specific protein-protein interaction. In the above instance the RAS-E peptide inhibits the interaction between the RAF-GAD and RAS-GBD proteins. Furthermore, the presence of the inhibitory peptide enables the cells to grow in the presence of an agent (like 5-FOA) that would kill or select against cells displaying interaction between the two proteins. Thus, this general method has use as a device to screen for and isolate peptides or other inhibitors that can specifically inhibit protein-protein interactions.

6.16. IDENTIFICATION OF CELLS CONTAINING AN INHIBITOR OF PROTEIN-PROTEIN INTERACTION USING THE 5-FOA ASSAY

The above method described for the isolation of inhibitor peptides can also be used to screen and isolate inhibitors that are not genetically encoded. In other contexts, for example, a yeast-based transcription-inhibition assay has been used to screen for inhibitors of the HIV-1 proteinase (Murray et al., 1993, Gene 134:123–128). The reporter strains YULH(R4-GBD) and N106' (FKBP-12-GAD), that harbor the reporter gene-systems and the two interacting proteins are grown in a 96-well format with each well containing 200 µl of media that selects for both the GBD and GAD plasmids (SC-LEU-TRP).

After a growth period. (24–36 hours) that is sufficient for early log-phase growth (a cell density of $1 \times 10^7$ cells/ml), the cells are exposed to an RNA inhibitor at a concentration of 100 nM for 1–2 hours. This RNA inhibitor is of the sequence 5'-CCCUGAUGGUAGACCGGGGUG-3' (SEQ ID NO:35). The pyrimidines in this RNA are modified with 2'-amino-2-deoxypyrimidines that causes the RNA to be resistant to nucleases. This RNA binds with high affinity to VEGF (Green et al., 1995, Current Biol. 2:683–695). After treating the cells with the RNA inhibitor, a 1:10 dilution of the cells is transferred to a 96-well plate containing 200 µl media same as above except that it lacks uracil, and incubated for 4–6 hours. This medium requires that cells express the URA3 gene product. As the expression of the URA3 gene is dependent on the interaction between the two hybrid proteins, only those cells where inhibition is not occurring will express the URA3 gene product. In other words, cells where inhibition occurs do not express the URA3 gene and hence are ura minus.

After treating the cells with the RNA inhibitor in a medium that lacks uracil, a 1:10 dilution of the cells is transferred to a 96-well plate containing 200 µl media same as above except that it contains 5-FOA, uracil and the RNA at a concentration of 100 nanomolar. FOA kills the URA+ cells (i.e., cells in which inhibition did not occur); uracil allows the ura minus cells to grow back (i.e., cells where inhibition occurred), and the presence of RNA inhibitor ensures that there is no reversion of inhibition.

Growth is evident only in those instances where the RNA inhibitor is present. The cells are able to grow in the absence of 5-FOA but in the presence of the inhibitor in SC-TRP-LEU, indicating that absence of growth in 5-FOA is due to inhibition. In the absence of the RNA inhibitor, cells are not able to grow in 5-FOA. The activity of the lacZ reporter genes is also assayed enzymatically. The activity of the lacZ gene is determined by assaying the β-galactosidase activity of the cells as mentioned in Section 6.1.11. Thus, by selecting for growth in a inhibitor-dependent fashion, a robust and high throughput assay for the selection of inhibitor drugs that inhibit protein-protein interactions is achieved.

6.17. 5-FOA INHIBITION ASSAY FOR SELECTING INHIBITION OF THE INTERACTION BETWEEN R4 AND FKBP-12

6.17.1. DEVELOPMENT OF EXPERIMENTAL PARAMETERS

Construction of R4-GBD and FKBP-12-GAD Fusion Genes:

The cytoplasmic domain of R4 (also known as ALK5; Frazen et al. 1993, Cell, 75:681) is a Type I receptor for the Transforming Growth Factor β (TGFβ) that has been demonstrated to bind to the immunophilin FKBP-12 (Standaert et al. 1990, Nature 346:671) in the yeast two-hybrid assay (Wang et al. 1994, Science 265:674–676; Wang et al. 1996, Science 271:1120–1123). This interaction is blocked by the immunosuppressant drug FK506 in the yeast two-hybrid assay (Wang et al. 1994, Science 265:674–676; Wang et al. 1996, Science, 271:1120–1123).

The interaction between R4 and FKBP-12 is monitored according to the invention by the ability to activate the lacZ Reporter Gene, and the inhibition of the interaction by FK506 is monitored by a reduction in the activity of the lacZ Reporter Gene in the presence of FK506.

The DNA encoding the cytoplasmic domain of R4 was obtained by PCR amplification using total peripheral T-lymphocyte cDNA as template. The primers used for amplification were:

ALK5SfiI-S

5'-GGACTAGGCCGAGGTGGCCTGCCACAACCG CACTGTCATTCAC-3' (SEQ ID NO:45)

ALK5SfiI-A

5'-GGACTAGGCCTCCTGGGCCTTACATTTTGA TGCCTTCCTGTTGACTGAG-3' (SEQ ID NO:46)

These primers flank the region from amino acid 148 to carboxyl terminus of the protein (Frazen et al., 1993, Cell 75:681). The PCR products were digested with Sfi I and cloned at the Sfi I site in pASSfiI to yield R4-GBD, wherein the R4 cytoplasmic domain is fused in frame to the DNA-binding domain of GAL4.

The FKBP gene was amplified from total peripheral T lymphocyte cDNA by PCR using the following primers:

FKBPSfiI-S

5'-GGACTAGGCCGAGGTGGCCATGGGAGTGCA GGTGGAAACCATC-3' (SEQ ID NO:47)

FKBPSfiI-A

5'-GGACTAGGCCTCCTGGGCCTCATTCCAGTT TTAGAAGCTCCAC-3' (SEQ ID NO:48)

These primers flank the entire coding region of the FKBP-12 protein (Standaert et al., 1990, Nature 346:671). The PCR products were digested with Sfi I and cloned at the Sfi I site in pACTSfiI to yield FKBB-12-GAD, wherein the FKBP-12 protein is fused in frame to the activation domain of GAL4.

6.17.2. INHIBITION OF R4-FKBP-12 INTERACTION BY FK506 AND THE SELECTION OF THESE INHIBITION EVENTS USING THE 5-FOA ASSAY

Step I. Interaction of R4-GBD with FKBP-GAD:

The R4-GBD and FKBP-12-GAD plasmids were transformed into the yeast strains YULH and N106', respectively, to yield YULH(R4-GBD) and N106'(FKBP-12-GAD). These strains are then mated as described in the mating protocol (Section 6.1.1). The resulting diploids are patched onto SC-URA-TRP-LEU-HIS+3-AT media. This media is selective for the interaction between the two fusion proteins. Growth in this media demonstrates the interaction between the R4-GBD and FKBP-12-GAD-fusion proteins.

Step II. Growth of R4-GBD::FKBP-12-GAD Diploids in Non-inducing Media:

The R4-GBD::FKBP-12-GAD diploids are inoculated into media that contains instead of glucose, a carbon source like lactate that does not induce the expression from the ADH promoter (Denis et al., 1983, J. Biol. Chem. 258:1165) that is driving transcription of the two fusion genes. The medium also lacks tryptophan and leucine to maintain the two plasmids R4-GBD and FKBP-12-GAD. This is repeated in the presence or absence of FK506 at a final concentration of 1 μM. This concentration of FK506 has been demonstrated to inhibit the interaction of R4 with FKBP-12 in the yeast two-hybrid system (Wang et al., 1994, Science, 265:674–676). These cells may or may not be mixed with the VEGF-GBD::VEGF-GAD diploids (described in Section 6.9.B).

The different experiments are summarized below in Table 14.

TABLE 14

| Experiment | R4-GBD: FKBP-12-GAD | VEGF-GBD:: VEGF-GAD | FK506 (1 μM) | Carbon Source |
|---|---|---|---|---|
| 1 | + | + | + | Lactate |
| 2 | + | + | − | Lactate |
| 3 | + | − | − | Lactate |
| 4 | − | + | − | Lactate |
| 5 | + | − | + | Lactate |
| 6 | − | + | + | Lactate |

Step III. Growth of R4-GBD::FKBP-12-GAD Diploids in Inducing Media:

The cells are grown in the lactate medium for 24–36 hours and then the cell suspensions corresponding to each individual experiment are then diluted-at 1:100 ratio in SC-URA-LEU-TRP-HIS+FK506(1 μM) liquid media and grown for 8–24 hours. The carbon source in this medium is glucose that supports the induction of transcription from the ADH promoter (Holland and Holland, 1978, Biochemistry 17:4900). Growth in all the experiments is monitored by measuring $OD_{600}$.

TABLE 15

| Experiment | R4-GBD: FKBP-12-GAD | VEGF-GBD:: VEGF-GAD | FK506 (1 μM) | Carbon Source |
|---|---|---|---|---|
| 1 | + | + | + | Glucose |
| 2 | + | + | − | Glucose |
| 3 | + | − | − | Glucose |
| 4 | − | + | − | Glucose |
| 5 | + | − | + | Glucose |
| 6 | − | + | + | Glucose |

Growth in this media should be evident in Experiments 1, 2, 3, 4 and 6 and should be inhibited only in Experiment 5 due to the inhibition of the R4-FKBP-12 interaction in the presence of FK506, thereby resulting in the non-activation of the URA3 reporter gene. Growth in Experiments 1 and 6 should occur due to the interaction of VEGF-GBD with VEGF-GAD that is not inhibited by FK506.

Step IV. Monitoring Inhibition of R4-FKBP12 Interaction Enzymatically by β-galactosidase Assays:

As described above, the cells are allowed to grow for 8–24 hours (in Step III) after which the β-galactosidase activity is measured in a fraction of the cells using the FluoReporter lacZ/Galactosidase Quantitation kit (Molecular Probes) according to the manufacturer's protocols. Alternatively, chemiluminescent β-galactosidase assays are performed by using the Galacto-Light and Galacto-Light Plus Chemiluminescent reporter assay system for the detection of β-galactosidase (Tropix, Inc., Bedford, Mass.). β-galactosidase activity is measured in a fraction of the cells using the FluoReporter lacZ/Galactosidase Quantitation kit (Molecular Probes) according to the manufacturer's protocols and a decrease in β-galactosidase activity should be observed in Experiment 5 (+FK506) in comparison to Experiment 3 (−FK506) of Table 15, above.

Step V. Selecting R4-FKBP Inhibition by FK506 Using the 5-FOA Assay

In parallel, the individual experiments (from Step III) are also diluted in a 1:100 ratio in SC-LEU-TRP-HIS+FK506(1 μM)+5-FOA liquid media and incubated at 30° C. for 8–48 hr. The experimental setup is shown in Table 16.

TABLE 16

| Experiment | R4-GBD: FKBP-12-GAD | VEGF-GBD:: VEGF-GAD | 5-FOA | FK506 (1 μM) | Carbon Source |
|---|---|---|---|---|---|
| 1 | + | + | + | + | Glucose |
| 2 | + | + | + | − | Glucose |
| 3 | + | − | + | − | Glucose |
| 4 | − | + | + | − | Glucose |
| 5 | + | − | + | + | Glucose |
| 6 | − | + | + | + | Glucose |

In this instance, growth should be evident in all the experiments of Table 16 except in experiment 3 where the growth should be inhibited. This is because in experiment 3 the R4-GBD::FKBP-12-GAD interaction activates the URA3 gene and this event is toxic to yeast in the presence of 5-FOA. β-galactosidase activity is measured in a fraction of the cells using the FluoReporter lacZ/Galactosidase Quantitation kit (Molecular Probes) according to the manufacturer's protocols and a decrease in β-galactosidase activity should be observed in Experiment 3 in comparison to Experiment 5.

Alternatively, dilutions of the individual treatments are plated on SC-LEU-TRP-HIS+FK506(1 μM)+5-FOA plates and after a growth period of 8–48 hours ten colonies from each dilution of each treatment are picked up and whole cell PCR (Section 6.1.8) is performed in parallel with VEGF-(SEQ ID NO. 11 and 12 from Section 6.4) and R4-specific primers (ALK5SfiI S (SEQ ID NO:45) and ALK5SfiI A (SEQ ID NO:46)). In this manner, the selection of either VEGF-VEGF or R4-FKBP diploids is monitored by the presence of the specific PCR product. Experiment 5 (R4-FKBP+FK506) should give rise to greater numbers of colonies than Experiment 3 (R4-FKBP-FK506). From Experiment 1 at lower dilutions predominantly R4 PCR product should be obtained indicating the presence of R4-FKBP diploids, and in the higher dilutions VEGF-specific PCR product should be seen very rarely and the R4-specific PCR product should be almost always obtained.

The results should indicate a selection of the R4-FKBP diploids due to the inhibition of their interaction by FK506 and thereby the non-activation of the URA3 Reporter Gene, allowing the R4-FKBP diploids to survive in the 5-FOA media. On the other hand, the VEGF-VEGF interaction is not inhibited by FK506 and as a result this interaction should activate the URA3 Reporter Gene and thus the VEGF-VEGF diploids should be killed in the 5-FOA media.

6.17.3. SELECTION OF R4-GBD::FKBP-12-GAD BY THE 5-FOA ASSAY FROM AN M×N ANALYSIS

Isolation of R4-FKBP Interactants in a Background of Interacting Proteins from an M×N Analysis:

As described in Section 6.1.7, the strains YULH and N106' are transformed with the pAS2-1 and the pAD-GAL4 or pACT2 cDNA libraries, respectively, by the lithium acetate protocol (Section 6.1.2; Ito et al., 1983, J. Bacteriol. 153: 163–168) to yield M and N populations. 1 μg of library DNA generally yields a maximum of 1×10$^6$ transformants. The transformants are selected on either media lacking leucine (for pAD-GAL4/pACT2) or lacking tryptophan and containing 5-FOA (for pAS2-1). In the latter case all GBD-fusions that fortuitously activate transcription on their own will be eliminated as 5-FOA kills the URA+cells. The transformants are harvested in the appropriate media (SC-LEU for pAD-GAL4/pACT2 and SC-TRP for pAS2-1) to a final cell density of 1×10$^8$ cells/ml.

A thousand independent transformants each of M and N cells are mixed together with YULH(R4-GBD) and N106' (FKBP-12-GAD) in the following cell to cell ratios: 1.3×10$^5$ cells each of YULH(R4-GBD) and N106'(FKBP-12-GBD) strains mixed with 1.3×10$^8$ cells each of M (YULH with GBD fusions) and N (N106' with GAD fusions) in a total volume of 1 ml. This is done in duplicate.

The mixtures are subjected to the mating protocol described in Section 6.1.1. The mating mixtures are transferred onto one YPAD plate each, each plate 15 mm in diameter, and incubated at 30° C. for 6–8 hours. (During this incubation one or two cell divisions may occur resulting in duplication of events). After this, the cells are harvested by the addition of 1–2 ml of SC-LEU-TRP-URA-HIS medium and plated onto plates lacking leucine, tryptophan, histidine, uracil and containing 40 mM 3-aminotriazole (3-AT). The contents of one YPAD plate go into one selective media plate.

After three-six days the number of TRP+, LEU+, HIS+, URA+ and 3-AT resistant colonies are picked and patched onto SC-LEU-TRP-URA-HIS+3AT (40 mM) plates.

Selecting Inhibition of R4-FKBP Interaction by FK506 Using the 5-FOA Assay

The diploids isolated from the M×N analysis are pooled and inoculated, into a medium that contains, instead of glucose, a carbon source like lactate that does not induce the expression from the ADH promoter (Denis et al., 1983, J. Biol. Chem. 258:1165) that is driving transcription of the two fusion genes. The medium also lacks tryptophan and leucine, to maintain the GBD and GAD plasmids. This is repeated in the presence or absence of FK506 at a final concentration of 1 μM. This concentration of FK506 has been demonstrated to inhibit the interaction of R4 with FKBP-12 in the yeast two-hybrid system (Wang et al., 1994, Science 265:674–676).

The cells are grown in the Lactate medium (that also lacks tryptophan and leucine) for 24–48 hours and then diluted at a 1:100 ratio in SC-URA-LEU-TRP-HIS+FK506(1 μM) liquid media and grown for 8–24 hours. The carbon source in this medium is glucose that supports the induction of transcription from the ADH promoter (Holland and Holland, 1978, Biochemistry 17:4900). Growth is monitored by measuring OD$_{600}$.

Dilutions of the culture are plated on SC-LEU-TRP-HIS+ FK506(1 μM)+5-FOA plates and after a growth period of 24–48 hours, fifty colonies from each dilution are picked up and whole cell PCR is performed in parallel with R4-specific primers (ALK5SfiI S (SEQ ID NO:45) and ALK5Sfi A (SEQ ID NO:46)) and FKBP-12-specific primers (FKBPSfiI-A (SEQ ID NO:48) and FKBPSfiI-S (SEQ ID NO:47)). In this manner, the selection of R4-FKBP diploids is monitored by the presence of the specific PCR product. The ratio of R4-FKBP diploids to the total number of diploids obtained indicates the degree of enrichment of the FK506 inhibition of R4-FKBP interaction due to 5-FOA selection.

The entire protocol is outlined in FIG. 24.

6.18. SELECTION OF NOVEL INTERACTING PROTEINS AND INHIBITORS OF THESE INTERACTING PROTEINS

The above example in Section 6.17 provides a means to select for those yeast cells in which the interaction between two proteins is inhibited by an inhibitor. A mixture of cells that bear interacting proteins, that have risen from an 'M×N' screen can be subjected to the-above assay with many inhibitors being screened against the mixture of cells bearing pairs of interacting proteins (FIG. 6). Only those cells will survive in the 5-FOA media in which the inhibitors successfully inhibit the protein-protein interaction and thereby do not activate the URA3 reporter gene. This process can be iterative to enrich for a population of cells representing interacting pairs of proteins that are inhibited by specific inhibitors. The individual inhibition events can be sorted by diluting the cultures from 5-FOA media and single colony purifying each diploid representing a -pair of interacting proteins whose identity is confirmed by sequencing.

Isolation of Interacting Proteins from an M×N Analysis

The M (YULH transformed with GBD fusions in pAS2-1) and N cells (N106' transformed with GAD fusions in pAD-GAL4) are mixed together and 1.0 ml of the mix (a total cell density of $1.5 \times 10^8$ cells/ml) is spread onto YPAD plates and incubated at 30° C. for 6–8 hours for mating. A total of $1.7 \times 10^9$ cells representing $5 \times 10^5$ yeast transformants are present in the entire mating mix. The $5 \times 10^5$ yeast transformants arise from a library of $1 \times 10^6$ individual GBD or GAD fusion plasmids. These populations are sufficient to screen for interacting proteins form genes that are expressed at a level of 1 in a 1000. The mating mixes are then harvested in 1 ml of SC-URA-LEU-TRP media and plated onto SC-URA-LEU-TRP-HIS plates that contain 40 mM 3-AT and incubated at 30° C. until colonies emerge.

Cells that are URA+, HIS+ and 3-AT resistant are patched onto separate SC-TRP-LEU plates and assayed for β-galactosidase activity by the filter-lift assay. Cells that are URA+, HIS+, 3-AT resistant and positive for β-galactosidase activity are classified as positive for protein-protein interactions.

Selecting Inhibitors of Novel Protein-protein Interactions Using the 5-FOA Assay Step I:

The diploids isolated from the M×N analysis are pooled and inoculated into a medium that contains, instead of glucose, a carbon source like lactate that does not induce the expression from the ADH promoter (Denis et al., 1983, J. Biol. Chem. 258:1165) that is driving transcription of the two fusion genes. The medium also lacks tryptophan and leucine to maintain the GBD and GAD plasmids. The cells are inoculated in a a 96-well plate containing 150 μl of media. Each well in the 96-well plate receives a unique inhibitor compound. Each 96-well plate is repeated in triplicate with each replicate receiving one particular concentration (1–100 μM) of the inhibitor compound.

Step II:

The cells are grown in the lactate medium for 24–48 hours at 30° C. and then diluted at a 1:100 ratio in SC-URA-LEU-TRP-HIS liquid media and grown for 8–24 hours. The carbon source in this medium is glucose that supports the induction of transcription from the ADH promoter (Holland and Holland, 1978, Biochemistry 17:4900). Growth is monitored by measuring $OD_{600}$. As described above, the cells are inoculated in a a 96-well plate containing 150 μl of media. Each well in the 96-well plate receives a unique inhibitor compound. Each 96-well plate is repeated in triplicate with each replicate receiving one particular concentration (1–100 μM) of the inhibitor compound.

Step III:

After this, a 1 to a 100 dilution of the cells is transferred to similar 96-well plates that contain SC-LEU-TRP+5-FOA liquid media (150 μl). The chemicals (identity and concentration) present in each well are identical to that present in Step II. The cells are incubated at 30° C. for 8–48 hours.

Step IV:

After proper mixing, 5 μl of cells from each well is spotted onto a plate with the same dimensions as the 96-well plate and containing SC-URA-LEU-TRP-HIS agar and incubated at 30° C. After 2–4 days, colonies of yeast grow up and these are picked and patched onto SC-LEU-TRP media.

Step V:

A confirmation of the inhibition of the pooled interactants by the particular inhibitor is performed by inoculating, in parallel, the colonies from each patch in Step IV to a well containing SC-URA-LEU-TRP-HIS liquid media and SC-URA-LEU-TRP-HIS liquid media with the same inhibitor at an identical concentration (i.e., as in Step III) that gave rise to 5-FOA resistant colonies. The cultures are incubated at 30° C. for 24–48 hours, and growth is monitored by measuring $OD_{600}$. Inhibition of growth should be observed in the presence of the inhibitor, while none should be evident in the absence of the inhibitor. β-galactosidase activity is measured in a fraction of the cells using the FluoReporter, lacZ/Galactosidase Quantitation kit (Molecular Probes) according to the manufacturers protocols and a decrease in β-galactosidase activity should be observed in the presence of the inhibitor in comparison to the cells grown in the absence of the inhibitor.

Identification of the Pairs of Interacting Proteins that are Inhibited by Specific Inhibitors Whole cell PCR is performed, as described in Section 6.1.8, on the colonies that are isolated as a result of the 5-FOA selection. This is done in parallel with both the GBD-fusion plasmid specific and GAD-fusion plasmid specific primer pairs. If more than one PCR product is observed from one patch of cells, it indicates that more than one pair of interacting proteins are inhibited by the same inhibitor. Then, the patch of colonies are streak-purified to yield clonal colonies and the whole cell PCR procedure is repeated. The presence of a single PCR product confirms the clonal nature of the colony. The PCR products are identified to reveal the identity of the genes encoding the pair of interacting proteins.

Thus the above method (outlined in FIG. 25) provides a high throughput mechanism for isolation of inhibitors against all possible pairs of interacting proteins that are characteristic to a particular population, be it a cell-type, disease-state or stage of development.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of detecting one or more protein-protein interactions comprising:
   (a) recombinantly expressing within a population of host cells a first population of first fusion proteins, each said first fusion protein comprising a first protein sequence and a DNA binding domain in which the DNA binding domain is the same in each said first fusion protein, in which said host cells comprise at least one polynucleotide operably linked to a promoter driven by one or more DNA binding sites recognized by said DNA binding domain of said first fusion protein such that an interaction of a first fusion protein with a second fusion protein, said second fusion protein comprising a transcriptional regulatory domain which is an activation domain, results in activation of transcription of said at least one polynucleotide by said activation domain, and in which said first population of first fusion proteins has a complexity of at least 10;
   (b) negatively selecting to eliminate those host cells expressing said first population of first fusion proteins in which said activation of transcription of said at least one polynucleotide occurs in the absence of a second fusion protein, said negatively selecting being performed by a method comprising incubating said host cells expressing said first population of first fusion proteins in an environment in which substantial death of said host cells occurs if said activation of transcription occurs;
   (c) after step (b), recombinantly co-expressing with said population of host cells a second population of second fusion proteins, each said second fusion protein comprising a second protein sequence and an activation domain of a transcriptional regulator, in which the activation domain is the same in each said second fusion protein, and in which said second population of second fusion proteins has a complexity of at least 10; and
   (d) detecting said activation of transcription of said at least one polynucleotide, thereby detecting cells in which an interaction between a first protein and a second protein has occurred, wherein the first and second populations of fusion proteins comprise first and second protein sequences, respectively, that are encoded by DNA sequences which are drawn from different DNA populations.

2. A method of detecting one or more protein-protein interactions comprising
   (a) recombinantly expressing in a first population of yeast cells of a first mating type, a first population of first fusion proteins, each first fusion protein comprising a first protein sequence and a DNA binding domain, in which the DNA binding domain is the same in each said first fusion protein; wherein said first population of yeast cells contains a first polynucleotide operably linked to a promoter driven by one or more DNA binding sites recognized by said DNA binding domain such that an interaction of a first fusion protein with a second fusion protein, said second fusion protein comprising a transcriptional activation domain results in increased transcription of said first polynucleotide, and in which said first population of first fusion proteins has a complexity of at least 100;
   (b) negatively selecting to eliminate those yeast cells expressing said first population of first fusion proteins in which said increased transcription of said first polynucleotide occurs in the absence of said second fusion protein, said negatively selecting being carried out by a method comprising incubating said first population of yeast cells expressing said first population of first fusion proteins in an environment in which substantial death of said first population of yeast cells occurs if said increased transcription occurs;
   (c) recombinantly expressing in a second population of yeast cells of a second mating type different from said first mating type, a second population of said second fusion proteins, each second fusion protein comprising a second protein sequence and an activation domain of a transcriptional activator, in which the activation domain is the same in each said second fusion protein, and in which said second population of second fusion proteins has a complexity of at least 100;
   (d) mating said first population of yeast cells that has been negatively selected with said second population of yeast cells to form a population of diploid yeast cells, wherein said population of diploid yeast cells contains a second polynucleotide operably linked to a promoter driven by a DNA binding site recognized by said DNA binding domain such that an interaction of a first fusion protein with a second fusion protein results in increased transcription of said second polynucleotide, in which the first and second polynucleotide can be the same or different; and
   (e) detecting said increased transcription of said first and/or second polynucleotide, thereby detecting colonies in which an interaction between a first protein and a second protein has occurred, wherein the first and second populations of fusion proteins comprise first and second protein sequences, respectively, that are encoded by DNA sequences which are drawn from different DNA populations.

3. The method described in claim 1 wherein said first population of first fusion proteins has a complexity of at least 100 and said second population of second fusion proteins has a complexity of at least 100.

4. The method described in claim 1 or 2 wherein at least one of said populations of fusion proteins comprise protein sequences that are encoded by cDNA sequences.

5. The method described in claim 4 wherein the cDNA sequences are provided by a cDNA library that has been normalized or subtracted.

6. The method described in claim 1 or 2 wherein at least one of the DNA populations is cDNA library obtained from a cell sample or a tissue sample, wherein said sample originates from a particular species, a particular cell type, a particular age of individual, a particular tissue type, a disease state, a disorder, a stage of a disease state or disorder, or a stage of development.

\* \* \* \* \*

SEQUENCE LISTING

<160> NUMBER OF SEQ ID NOS: 118

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 1
cgatgcacag ttgaagtgaa c                                          21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 2
cgcgtttgga atcactacag ggat                                       24

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 3
ctaccagaat tcggcatgcc ggtcgaggtg tggtca                          36

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
atgaagctac tgtcttctat cgaa                                       24

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: linker

<400> SEQUENCE: 5
catatggccg aggtggccta gggcctcctg ggcctccctt aggatcc              48

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: linker

<400> SEQUENCE: 6
gaggccgagg tggcctaggg cctcctgggc tctagaatt cc                    42

<210> SEQ ID NO 7
<211> LENGTH: 43

```
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
ggactaggcc gaggtggccg gtatgacgga atataagctg gtg              43

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ggactaggcc gaggtggccg gagagcacac acttgcagct                  40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ggactaggcc gaggtggcca tggagcacat acagggagct                  40

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
ggactaggcc gaggtggccc gacctctgcc tctgggagag                  40

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
ggactaggcc gaggtggccg gaggagggca gaatcatcac                  40

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ggactaggcc tcctgggcca cgcctcggct tgtcacatct gc               42

<210> SEQ ID NO 13
<211> LENGTH: 45
<212> TYPE: DNA
```

<213> ORGANISM: Artificial Sequence
<220> FEATURE:
<223> OTHER INFORMATION: Description of Artificial Sequence:
      oligonucleotide

<400> SEQUENCE: 13
ggactaggcc gaggtggccc tctctgtggg tttgcctagt gtttc         45

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 14
ggactaggcc tcctgggccc tcctttgaaa tgggattggt aag         43

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: adapter

<400> SEQUENCE: 15
aggccggagg c         11

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: adapter

<400> SEQUENCE: 16
tcctccggcc tccg         14

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 17
aggtgcaagg cccaggaggc cggaggc         27

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
gggacaaacg gccgcaccga aacgcgcgag gcagcaac         38

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
gggagttgca tgcgccggta gaggtgtggt caataa                     36

<210> SEQ ID NO 20
<211> LENGTH: 7
<212> TYPE: PRT
<213> ORGANISM: yeast

<400> SEQUENCE: 20

Pro Lys Lys Lys Arg Lys Val
 1               5

<210> SEQ ID NO 21
<211> LENGTH: 56
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
agcttggcct cccaggccac agacaggcgc gccccaaag aagagaaagg tttaga     56

<210> SEQ ID NO 22
<211> LENGTH: 59
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
agcttctaaa cctttctctt cttctttggg ggcgcgcctg tctgtggcct gggaggcca    59

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 23
ggactaggcc gaggtggccg gtatgacgga atataagctg gtg             43

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 24
ggactaggcc gaggtggccg gagagcacac acttgcagct          40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 25
ggactaggcc gaggtggcca tgagcacat acagggagct          40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: primer

<400> SEQUENCE: 26
ggactaggcc gaggtggccc gacctctgcc tctgggagag                    40

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 27
agcactctcc agcctctcac cgac                                    24

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: primer

<400> SEQUENCE: 28
gatcgtcggt ga                                                 12

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 29
agcactctcc agcctctcac cgac                                    24

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: primer

<400> SEQUENCE: 30
ccgggtcggt ga                                                 12

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 31
agcactctcc agcctctcac cgac                                    24

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: primer

```
<400> SEQUENCE: 32
ttaagtcggt ga                                                    12

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 33
agcactctcc agcctctcac cgac                                       24

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: primer

<400> SEQUENCE: 34
agctgtcggt ga                                                    12

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: RNA
      inhibitor

<400> SEQUENCE: 35
cccugauggu agaccggggu g                                          21

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 36
gagagagaga gagagagaga actagtctcg agttttttttt tttttttttt          50

<210> SEQ ID NO 37
<211> LENGTH: 13
<212> TYPE: DNA
<213> ORGANISM: Artificial Sequence
<220> FEATURE:
<223> OTHER INFORMATION: Description of Artificial Sequence: adapter

<400> SEQUENCE: 37
aattcggcac gag                                                   13

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: adapter

<400> SEQUENCE: 38 ctcgtgccg                                                         9

<210> SEQ ID NO 39
```

```
<211> LENGTH: 47
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 39
gagagagaga gggtaccgaa ccaatgtatc cagcaccacc tgtaacc                    47

<210> SEQ ID NO 40
<211> LENGTH: 52
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 40
gagagagaga attccattat agttttttct ccttgacgtt aaagtataga gg              52

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 41
gagagagaga attctcgaaa gctacatata aggaacgtgc tgc                        43

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 42
gagagagacg gccgcgtcat tatagaaatc attacgaccg ag                         42

<210> SEQ ID NO 43
<211> LENGTH: 90
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 43
gattcggtaa tctccgaaca gaaggaagaa cgaaggaagg agcacagact tagattggta      60
gaaccaatgt atccagcacc acctgtaacc                                       90

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 44
acatcaaaag gcctctaggt tcctttgtta cttcttccg                             39
```

```
<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 45
ggactaggcc gaggtggcct gccacaaccg cactgtcatt cac            43

<210> SEQ ID NO 46
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 46
ggactaggcc tcctgggcct tacattttga tgccttcctg ttgactgag      49

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 47
ggactaggcc gaggtggcca tgggagtgca ggtggaaacc atc            43

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 48
ggactaggcc tcctgggcct cattccagtt ttagaagctc cac            43

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 49
ttggaatcac tacagggatg                                      20

<210> SEQ ID NO 50
<211> LENGTH: 21
<212> TYPE: DNA
<213> ORGANISM: Artificial Sequence

<400> SEQUENCE: 50
gaattcatgg cttacccata c                                    21

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 51
```

-continued aacctgacct acaggaaaga gttac         25

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 52
cctctaacat tgagacagca tag         23

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 53
agcactctcc agcctctcac cgaa         24

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 54
aattttcggt ga         12

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 55
catgggcggt ga         12

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 56
ccggttcggt ga         12

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 57
cgcgttcggt ga         12

<210> SEQ ID NO 58
<211> LENGTH: 12
<212> TYPE: DNA
<213> ORGANISM: Artificial Sequence

```
<220> FEATURE:
<223> OTHER INFORMATION: Description of Artificial Sequence: linker

<400> SEQUENCE: 58
ctagttcggt ga                                                              12

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 59
gatcttcggt ga                                                              12

<210> SEQ ID NO 60
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 60
gcgcttcggt ga                                                              12

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 61
ggccttcggt ga                                                              12

<210> SEQ ID NO 62
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 62
gtacttcggt ga                                                              12

<210> SEQ ID NO 63
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 63
tcgattcggt ga                                                              12

<210> SEQ ID NO 64
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 64
tgcattcggt ga                                                              12
```

<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 65
ttaattcggt ga                                                        12

<210> SEQ ID NO 66
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 66
acgattcggt ga                                                        12

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 67
agcactctcc agcctctcac cgac                                           24

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 68
aattgtcgct ga                                                        12

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 69
agctgtcgct ga                                                        12

<210> SEQ ID NO 70
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 70
catggtcgct ga                                                        12

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 71
ccgggtcgct ga                                                         12

<210> SEQ ID NO 72
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 72
cgcggtcgct ga                                                         12

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 73
ctaggtcgct ga                                                         12

<210> SEQ ID NO 74
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 74
gatcgtcgct ga                                                         12

<210> SEQ ID NO 75
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 75
gcgcgtcgct ga                                                         12

<210> SEQ ID NO 76
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 76
ggccgtcgct ga                                                         12

<210> SEQ ID NO 77
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 77
gtacgtcgct ga                                                         12

<210> SEQ ID NO 78

```
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 78
tcgagtcgct ga                                                           12

<210> SEQ ID NO 79
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 79
tgcagtcgct ga                                                           12

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 80
accgacgtcg actatccatg aaga                                              24

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 81
aatttcttca tg                                                           12

<210> SEQ ID NO 82
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 82
catgtcttca tg                                                           12

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 83
ccggtcttca tg                                                           12

<210> SEQ ID NO 84
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 84
```
cgcgtcttca tg                                                    12

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 85
ctagtcttca tg                                                    12

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 86
gatctcttca tg                                                    12

<210> SEQ ID NO 87
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 87
gcgctcttca tg                                                    12

<210> SEQ ID NO 88
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 88
ggcctcttca tg                                                    12

<210> SEQ ID NO 89
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 89
gtactcttca tg                                                    12

<210> SEQ ID NO 90
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 90
tcgatcttca tg                                                    12

<210> SEQ ID NO 91
<211> LENGTH: 12
<212> TYPE: DNA

```
<213> ORGANISM: Artificial Sequence
<220> FEATURE:
<223> OTHER INFORMATION: Description of Artificial Sequence: linker

<400> SEQUENCE: 91
tgcatcttca tg                                                              12

<210> SEQ ID NO 92
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 92
ttaatcttca tg                                                              12

<210> SEQ ID NO 93
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 93
acgatcttca tg                                                              12

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 94
accgacgtcg actatccatg aagc                                                 24

<210> SEQ ID NO 95
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 95
aattgcttca tg                                                              12

<210> SEQ ID NO 96
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 96
agctgcttca tg                                                              12

<210> SEQ ID NO 97
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 97
catggcttca tg                                                              12
```

<210> SEQ ID NO 98
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 98
ccgggcttca tg                                                              12

<210> SEQ ID NO 99
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 99
cgcggcttca tg                                                              12

<210> SEQ ID NO 100
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 100
catggcttca tg                                                              12

<210> SEQ ID NO 101
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 101
gatcgcttca tg                                                              12

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 102
gcgcgcttca tg                                                              12

<210> SEQ ID NO 103
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 103
ggccgcttca tg                                                              12

<210> SEQ ID NO 104
<211> LENGTH: 12
<212> TYPE: DNA
<213> ORGANISM: Artificial Sequence
<220> FEATURE:

```
<223> OTHER INFORMATION: Description of Artificial Sequence: linker

<400> SEQUENCE: 104
gtacgcttca tg                                                           12

<210> SEQ ID NO 105
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 105
tcgagcttca tg                                                           12

<210> SEQ ID NO 106
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 106
tgcagcttca tg                                                           12

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 107
agcactctcc agccuctcac cgaa                                              24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 108
agcactctgg cgcgcctcac cgaa                                              24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 109
agcactctcc agccuctcac cgac                                              24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 110
agcactctgg cgcgcctcac cgac                                              24
```

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 111
accgacgtcg actatggatg aaga                                      24

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 112
gatctcttca tc                                                   12

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 113
catgtcttca tc                                                   12

<210> SEQ ID NO 114
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 114
ccggtcttca tc                                                   12

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 115
accgacgtcg actatcgcag cagc                                      24

<210> SEQ ID NO 116
<211> LENGTH: 12
<212> TYPE: DNA
<213> ORGANISM: Artificial Sequence
<220> FEATURE:
<223> OTHER INFORMATION: Description of Artificial Sequence: linker

<400> SEQUENCE: 116
gatctctgct gc                                                   12

<210> SEQ ID NO 117
<211> LENGTH: 12
<212> TYPE: DNA
<213> ORGANISM: Artificial Sequence
<220> FEATURE:
<223> OTHER INFORMATION: Description of Artificial Sequence: linker

```
-continued

<400> SEQUENCE: 117
catgtctgct gc                                                                12

<210> SEQ ID NO 118
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 118
atggatgatg tatataacta tctattc                                                27
```